US009963716B2

(12) United States Patent
Bradley et al.

(10) Patent No.: US 9,963,716 B2
(45) Date of Patent: May 8, 2018

(54) CHIMAERIC SURROGATE LIGHT CHAINS (SLC) COMPRISING HUMAN VPREB

(71) Applicant: Kymab Limited, Cambridge, Cambridgeshire (GB)

(72) Inventors: Allan Bradley, Cambridge (GB); E-Chiang Lee, Cambridge (GB); Qi Liang, Cambridge (GB); Dominik Spensberger, Cambridge (GB); Nicholas England, Cambridge (GB)

(73) Assignee: Kymab Limited, Cambridge (GB)

(*) Notice: Subject to any disclaimer, the term of this patent is extended or adjusted under 35 U.S.C. 154(b) by 439 days.

(21) Appl. No.: 14/226,698

(22) Filed: Mar. 26, 2014

(65) Prior Publication Data

US 2014/0359797 A1 Dec. 4, 2014

Related U.S. Application Data

(63) Continuation of application No. PCT/GB2012/052380, filed on Sep. 26, 2012.

(30) Foreign Application Priority Data

Sep. 26, 2011 (GB) .................................. 1116495.1
Nov. 28, 2011 (GB) .................................. 1120423.7

(51) Int. Cl.
*A01K 67/00* (2006.01)
*C12N 15/85* (2006.01)
*C12N 5/10* (2006.01)
*A01K 67/02* (2006.01)
*A01K 67/027* (2006.01)

(52) U.S. Cl.
CPC .............. *C12N 15/85* (2013.01); *A01K 67/02* (2013.01); *A01K 67/0278* (2013.01); *C12N 5/10* (2013.01); *C12N 15/8509* (2013.01); *A01K 2217/07* (2013.01); *A01K 2217/077* (2013.01); *A01K 2227/10* (2013.01); *A01K 2227/105* (2013.01); *A01K 2267/01* (2013.01); *C12N 2015/8518* (2013.01)

(58) Field of Classification Search
None
See application file for complete search history.

(56) References Cited

U.S. PATENT DOCUMENTS

| 4,720,449 | A | 1/1988 | Borror et al. |
| 5,169,939 | A | 12/1992 | Gefter et al. ............... 530/387.3 |
| 5,545,807 | A | 8/1996 | Surani et al. |
| 5,565,321 | A | 10/1996 | Spriggs et al. |
| 5,633,425 | A | 5/1997 | Lonberg et al. |
| 5,770,429 | A | 6/1998 | Lonberg et al. |
| 5,789,215 | A | 8/1998 | Berns et al. ............... 435/172.3 |
| 5,939,598 | A | 8/1999 | Kucherlapati et al. ......... 800/25 |
| 5,948,600 | A | 9/1999 | Roschger et al. |
| 6,130,364 | A | 10/2000 | Jakobovits et al. |
| 6,162,963 | A | 12/2000 | Kucherlapati et al. |
| 6,319,906 | B1 | 11/2001 | Bennett et al. |
| 6,395,487 | B1 | 5/2002 | Bradley et al. |
| 6,461,818 | B1 | 10/2002 | Bradley et al. |
| 6,596,541 | B2 | 7/2003 | Murphy et al. ............... 435/463 |
| 6,673,986 | B1 | 1/2004 | Kucherlapati et al. |
| 6,713,610 | B1 | 3/2004 | Kucherlapati et al. .. 530/388.23 |
| 6,833,268 | B1 | 12/2004 | Green et al. ............... 435/320.1 |
| 6,914,128 | B1 | 7/2005 | Salfeld et al. ............. 530/387.3 |
| 6,992,235 | B2 | 1/2006 | Bode et al. |
| 6,998,514 | B2 | 2/2006 | Brüggemann ................. 800/18 |
| 7,105,348 | B2 | 9/2006 | Murphy et al. |
| 7,119,248 | B1 | 10/2006 | Rajewsky et al. ................ 800/6 |
| 7,205,140 | B2 | 4/2007 | Gottschalk et al. |
| 7,205,148 | B2 | 4/2007 | Economides et al. ........ 435/462 |
| 7,294,754 | B2 | 11/2007 | Poueymirou et al. |
| 7,435,871 | B2 | 10/2008 | Green et al. .................... 800/18 |
| 7,501,552 | B2 | 3/2009 | Lonberg et al. .................. 800/6 |
| 7,605,237 | B2 | 10/2009 | Stevens et al. |
| 7,605,238 | B2 | 10/2009 | Korman et al. |
| 7,910,798 | B2 | 3/2011 | Tanamachi et al. |
| 7,932,431 | B2 | 4/2011 | Bruggemann |
| 8,158,419 | B2 | 4/2012 | Lonberg et al. |

(Continued)

FOREIGN PATENT DOCUMENTS

| CA | 2 307 503 A1 | 11/2001 | ............ A61K 39/42 |
| DE | 10251918 A1 | 5/2004 | |

(Continued)

OTHER PUBLICATIONS

Donohoe et al. J Immunol 2000;164:5269-76.*
Sabbattini et al. Mole Cell Biol 1999;19:671-9.*
Mullins et al. Journal of Clinical Investigation, 1996.*
Pera et al. Journal of Cell Science 2000; 113: 5-10.*
Tong et al. Nature. Sep. 9, 2010; 467: 211-213.*
Kawakasi et al. Genome Res. Mar. 1997;7(3):250-61.*
Adams, D., et al., "A Genome-Wide, End-Sequenced 129Sv BAC Library Resource for Targeting Vector Construction," Genomics, vol. 86, pp. 753-758, 2005.

(Continued)

*Primary Examiner* — Janice Li
(74) *Attorney, Agent, or Firm* — Sunstein Kann Murphy & Timbers LLP

(57) ABSTRACT

The present invention relates inter alia to improvements in the production of chimaeric antibodies in non-human transgenic vertebrates such as mice and rats bearing one or more chimaeric antibody transgenes. In particular, the invention provides for improved non-human vertebrates and cells in which VpreB has been species-matched with the variable region of the chimaeric antibodies. Also, embodiments also provide for species-matching of the entire surrogate light chain for efficient pairing with chimaeric heavy chains during B-cell development in vivo in a non-human transgenic vertebrate setting.

38 Claims, 5 Drawing Sheets

(56) References Cited

U.S. PATENT DOCUMENTS

| | | | |
|---|---|---|---|
| 8,502,018 B2 | 8/2013 | Murphy et al. | 800/18 |
| 8,592,644 B2 * | 11/2013 | Harriman | A01K 67/0278 800/13 |
| 8,642,835 B2 | 2/2014 | MacDonald et al. | |
| 8,697,940 B2 | 4/2014 | MacDonald et al. | |
| 8,754,287 B2 | 6/2014 | MacDonald et al. | |
| 8,791,323 B2 | 7/2014 | Murphy et al. | |
| 8,877,901 B2 | 11/2014 | Govindan | |
| 9,253,965 B2 | 2/2016 | Liang et al. | |
| 9,434,782 B2 | 9/2016 | Bradley et al. | |
| 9,445,581 B2 | 9/2016 | Bradley et al. | |
| 9,504,236 B2 | 11/2016 | Bradley et al. | |
| 9,505,827 B2 | 11/2016 | Bradley et al. | |
| 2002/0088016 A1 | 7/2002 | Bruggemann | 800/18 |
| 2002/0183275 A1 | 12/2002 | Murphy et al. | |
| 2003/0108925 A1 | 6/2003 | Dix et al. | |
| 2003/0217373 A1 | 11/2003 | Green et al. | 800/6 |
| 2004/0231012 A1 | 11/2004 | Bruggemann | |
| 2005/0048621 A1 | 3/2005 | Grasso et al. | 435/69.1 |
| 2006/0015949 A1 | 1/2006 | Lonberg et al. | |
| 2006/0015957 A1 | 1/2006 | Lonberg et al. | 800/18 |
| 2006/0021074 A1 | 1/2006 | Kellermann et al. | 800/18 |
| 2006/0199204 A1 | 9/2006 | Dix et al. | |
| 2007/0280945 A1 | 12/2007 | Stevens et al. | 424/145.1 |
| 2008/0098490 A1 | 4/2008 | Jakobovits et al. | |
| 2009/0083870 A1 | 3/2009 | Horn et al. | 800/13 |
| 2009/0083879 A1 | 3/2009 | Dhugga | |
| 2009/0093059 A1 | 4/2009 | Baszczynski et al. | |
| 2009/0196112 A1 | 8/2009 | Cho | 365/200 |
| 2009/0209036 A1 | 8/2009 | Reynaud et al. | 435/455 |
| 2009/0307787 A1 | 12/2009 | Grosveld et al. | |
| 2010/0011450 A1 | 1/2010 | Garcia et al. | |
| 2010/0069614 A1 | 3/2010 | Houtzager et al. | 530/387.1 |
| 2010/0146647 A1 | 6/2010 | Logtenberg et al. | 800/4 |
| 2010/0196367 A1 | 8/2010 | Day | 424/130.1 |
| 2010/0330676 A1 * | 12/2010 | Horowitz | C07K 16/00 435/455 |
| 2011/0119779 A1 | 5/2011 | Shizuya et al. | |
| 2011/0138489 A1 | 6/2011 | Tanamachi et al. | |
| 2011/0145937 A1 | 6/2011 | MacDonald et al. | 800/6 |
| 2011/0195454 A1 † | 8/2011 | McWhirter | |
| 2011/0236378 A1 | 9/2011 | Green et al. | 424/133.1 |
| 2011/0283376 A1 | 11/2011 | Murphy et al. | |
| 2012/0070861 A1 | 3/2012 | Macdonald et al. | 435/91.1 |
| 2012/0073004 A1 | 3/2012 | MacDonald et al. | |
| 2012/0096572 A1 | 4/2012 | MacDonald et al. | |
| 2012/0167237 A1 | 6/2012 | Bradley et al. | 800/9 |
| 2012/0204278 A1 | 8/2012 | Bradley et al. | 800/18 |
| 2012/0233715 A1 | 9/2012 | Kuroiwa et al. | 800/3 |
| 2012/0322108 A1 | 12/2012 | Macdonald et al. | 435/69.6 |
| 2013/0039850 A1 | 2/2013 | Lonberg et al. | 424/1.49 |
| 2013/0096287 A1 | 4/2013 | MacDonald et al. | |
| 2013/0102031 A1 | 4/2013 | King et al. | 435/69.6 |
| 2013/0160153 A1 | 6/2013 | MacDonald et al. | |
| 2013/0198879 A1 * | 8/2013 | McWhirter | A01K 67/0278 800/18 |
| 2013/0212719 A1 | 8/2013 | MacDonald et al. | |
| 2013/0247235 A1 | 9/2013 | McWhirter et al. | |
| 2013/0254911 A1 | 9/2013 | MacDonald et al. | |
| 2013/0323790 A1 | 12/2013 | MacDonald et al. | |
| 2013/0323791 A1 | 12/2013 | MacDonald et al. | |
| 2013/0326647 A1 | 12/2013 | MacDonald et al. | |
| 2013/0333057 A1 | 12/2013 | MacDonald et al. | |
| 2014/0017228 A1 | 1/2014 | MacDonald et al. | |
| 2014/0041067 A1 | 2/2014 | Bradley et al. | |
| 2014/0120582 A1 | 5/2014 | Bradley et al. | |
| 2014/0130193 A1 | 5/2014 | MacDonald et al. | |
| 2014/0130194 A1 | 5/2014 | MacDonald et al. | |
| 2014/0137275 A1 | 5/2014 | MacDonald et al. | |
| 2014/0150125 A1 | 5/2014 | Bradley et al. | |
| 2014/0150126 A1 | 5/2014 | Bradley et al. | |
| 2014/0182003 A1 | 6/2014 | Bradley et al. | |
| 2014/0201854 A1 | 7/2014 | Bradley et al. | |
| 2014/0201856 A1 | 7/2014 | Bradley et al. | |
| 2014/0212416 A1 | 7/2014 | Friedrich et al. | |
| 2014/0213773 A1 | 7/2014 | MacDonald et al. | |
| 2014/0283150 A1 | 9/2014 | Bradley et al. | |
| 2014/0323327 A1 | 10/2014 | Bradley et al. | |
| 2014/0325690 A1 | 10/2014 | Bradley et al. | |
| 2014/0331339 A1 | 11/2014 | Bradley et al. | |
| 2014/0331343 A1 | 11/2014 | Bradley et al. | |
| 2014/0331344 A1 | 11/2014 | Friedrich et al. | |
| 2014/0359797 A1 | 12/2014 | Bradley et al. | |
| 2015/0033369 A1 | 1/2015 | Bradley et al. | |
| 2015/0033372 A1 | 1/2015 | Bradley et al. | |
| 2015/0037337 A1 | 2/2015 | Friedrich et al. | |
| 2015/0040250 A1 | 2/2015 | Bradley et al. | |
| 2015/0082466 A1 | 3/2015 | Clube | |
| 2015/0113669 A1 | 4/2015 | Bradley et al. | |
| 2015/0133641 A1 | 5/2015 | Germaschewski et al. | |
| 2015/0196015 A1 | 7/2015 | MacDonald et al. | |
| 2015/0334998 A1 | 11/2015 | Bradley et al. | |
| 2016/0044900 A1 | 2/2016 | Bradley et al. | |
| 2016/0150768 A1 | 6/2016 | Bradley et al. | |
| 2016/0219846 A1 | 8/2016 | Liang | |
| 2016/0249592 A1 | 9/2016 | Bradley et al. | |
| 2016/0345551 A1 | 12/2016 | Bradley et al. | |
| 2016/0345552 A1 | 12/2016 | Bradley et al. | |
| 2016/0353719 A1 | 12/2016 | Friedrich et al. | |
| 2017/0051045 A1 | 2/2017 | Bradley et al. | |
| 2017/0071174 A1 | 3/2017 | Bradley et al. | |
| 2017/0081423 A1 | 3/2017 | Bradley et al. | |
| 2017/0094956 A1 | 4/2017 | Bradley et al. | |
| 2017/0096498 A1 | 4/2017 | Bradley et al. | |
| 2017/0099815 A1 | 4/2017 | Bradley et al. | |
| 2017/0099816 A1 | 4/2017 | Bradley et al. | |
| 2017/0099817 A1 | 4/2017 | Bradley et al. | |
| 2017/0101482 A1 | 4/2017 | Bradley et al. | |
| 2017/0101483 A1 | 4/2017 | Bradley et al. | |
| 2017/0105396 A1 | 4/2017 | Bradley et al. | |
| 2017/0135327 A1 | 5/2017 | Lee | |

FOREIGN PATENT DOCUMENTS

| | | | |
|---|---|---|---|
| EP | 1780272 A1 | 5/2007 | C12N 15/00 |
| EP | 2550363 | 10/2012 | C12N 15/85 |
| GB | 2398784 A | 9/2004 | A01K 67/027 |
| GB | 2403475 A | 1/2005 | |
| JP | 2004524841 A | 8/2004 | |
| JP | 2005510253 A | 4/2005 | |
| JP | 2008507257 A | 3/2008 | |
| JP | 2012521211 A | 9/2012 | |
| KR | 20050042792 A | 5/2005 | |
| WO | WO-9004036 A1 | 4/1990 | |
| WO | WO-9100906 A1 | 1/1991 | |
| WO | WO 1991/10741 | 7/1991 | C12P 21/06 |
| WO | WO-9312227 A1 | 6/1993 | |
| WO | WO-9402602 A1 | 2/1994 | |
| WO | WO-9404667 A1 | 3/1994 | |
| WO | WO-9425585 A1 | 11/1994 | |
| WO | WO-9630498 A1 | 10/1996 | |
| WO | WO 1998/24884 | 6/1998 | C12N 5/00 |
| WO | WO-9824893 A2 | 6/1998 | |
| WO | WO-9945962 A1 | 9/1999 | |
| WO | WO 2002/08409 A2 | 1/2002 | C12N 15/00 |
| WO | WO-0236789 A2 | 5/2002 | |
| WO | WO 2002/043478 | 6/2002 | A01K 67/027 |
| WO | WO 2002/053596 A2 | 7/2002 | C07K 16/28 |
| WO | 02/066630 A1 † | 8/2002 | |
| WO | WO 2002/059263 A2 | 8/2002 | |
| WO | WO 2002/066630 A1 | 8/2002 | C12N 15/00 |
| WO | WO 2002/070648 A2 | 9/2002 | |
| WO | WO 2003/006639 A1 | 1/2003 | C12N 5/10 |
| WO | WO 2003/047336 A2 | 6/2003 | |
| WO | WO 2003/061363 A2 | 7/2003 | |
| WO | WO 2004/050838 A2 | 6/2004 | |
| WO | WO 2005/003364 A2 | 1/2005 | C12N 15/90 |
| WO | WO-2005004592 A2 | 1/2005 | |
| WO | WO 2005/019463 A1 | 3/2005 | C12N 15/85 |
| WO | WO-2005058815 A2 | 6/2005 | |
| WO | WO-2005092926 A2 | 10/2005 | |
| WO | WO-2006008548 A2 | 1/2006 | |
| WO | WO 2006/044492 | 4/2006 | C12N 15/52 |
| WO | WO-2006055704 A2 | 5/2006 | |

(56) References Cited

FOREIGN PATENT DOCUMENTS

| WO | WO-2006068953 A2 | 6/2006 | |
|---|---|---|---|
| WO | WO 2006/122442 A1 | 11/2006 | ............... C12N 9/22 |
| WO | WO 2007/096779 A2 | 8/2007 | |
| WO | WO-2007085837 A1 | 8/2007 | |
| WO | WO 2007/117410 A2 | 10/2007 | ........... A01K 67/027 |
| WO | WO-2007143168 A2 | 12/2007 | |
| WO | WO-2008022391 A1 | 2/2008 | |
| WO | WO 2008/054606 A2 | 5/2008 | ............. C07K 16/00 |
| WO | WO 2008/070367 A2 | 6/2008 | ............. C12N 15/09 |
| WO | WO 2008/076379 A2 | 6/2008 | ............. C07K 16/18 |
| WO | WO-2008081197 A1 | 7/2008 | |
| WO | WO 2008/094178 A2 | 8/2008 | ............... C12Q 1/68 |
| WO | WO 2008/103474 A1 | 8/2008 | ............. C12N 15/13 |
| WO | WO 2008/118970 A2 | 10/2008 | ............. A61K 48/00 |
| WO | WO 2008/122886 A2 | 10/2008 | ............. C12N 15/85 |
| WO | WO 2008/151081 A1 | 12/2008 | ............. C12N 15/13 |
| WO | 2009/013620 A2 † | 1/2009 | |
| WO | WO 2009/013620 A2 | 1/2009 | |
| WO | WO 2009/018411 A1 | 2/2009 | ............. C07K 16/28 |
| WO | WO 2009/023540 A1 | 2/2009 | ........... A61K 39/395 |
| WO | WO 2009/076464 A2 | 6/2009 | ............. C12N 15/09 |
| WO | WO 2009/080254 A1 | 7/2009 | ............. C07K 16/46 |
| WO | WO 2009/094178 A2 | 7/2009 | ............. C09B 67/08 |
| WO | WO-2009097006 A2 | 8/2009 | |
| WO | WO-2009118524 A2 | 10/2009 | |
| WO | WO-2009129247 A2 | 10/2009 | |
| WO | WO 2009/143472 A2 | 11/2009 | ............. C07K 16/46 |
| WO | WO 2009/157771 A2 | 12/2009 | ........... A01K 67/027 |
| WO | 2010/039900 A2 † | 4/2010 | |
| WO | WO 2010/039900 A2 | 4/2010 | ............. C12N 15/13 |
| WO | WO 2010/070263 A1 | 6/2010 | ............. C12N 15/85 |
| WO | WO-2010077854 A1 | 7/2010 | |
| WO | WO 2010/097385 A1 | 9/2010 | ............. C07K 16/24 |
| WO | WO-2010109165 A2 | 9/2010 | |
| WO | WO 2010/113039 A1 | 10/2010 | ............... C12N 5/00 |
| WO | WO 2011/004192 A1 | 1/2011 | ............. C07K 16/46 |
| WO | WO 2011/008093 A1 | 1/2011 | ............. C07K 16/00 |
| WO | WO 2011/056864 A1 | 5/2011 | ............. C12P 21/06 |
| WO | WO-2011062206 A1 | 5/2011 | |
| WO | WO-2011062207 A1 | 5/2011 | |
| WO | 2011/071957 A1 † | 6/2011 | |
| WO | WO-2011071957 A1 | 6/2011 | |
| WO | WO-2011072204 A1 | 6/2011 | |
| WO | WO 2011/097603 A1 | 8/2011 | ............. C12N 15/85 |
| WO | WO-2011146121 A1 | 11/2011 | |
| WO | WO 2011/158009 A1 | 12/2011 | ........... A01K 67/027 |
| WO | WO 2011/163311 A1 | 12/2011 | ............. C12N 15/85 |
| WO | WO 2011/163314 A1 | 12/2011 | ............. C12N 15/85 |
| WO | WO 2012/018764 A1 | 2/2012 | ............. C12N 15/85 |
| WO | WO 2012/023053 A2 | 2/2012 | |
| WO | WO 2012/141798 A1 | 10/2012 | ............. C12N 15/85 |
| WO | WO 2012/148873 A2 | 11/2012 | ........... A01K 67/027 |
| WO | WO 2013/022782 A1 | 2/2013 | ............. C12N 15/85 |
| WO | WO 2013/041844 A1 | 3/2013 | ............. C12N 15/85 |
| WO | WO 2013/041845 A2 | 3/2013 | ............. C12N 15/85 |
| WO | WO 2013/059230 A1 | 4/2013 | ............. C12N 15/85 |
| WO | WO 2013/061098 A2 | 5/2013 | ............. C12N 15/85 |
| WO | WO 2013/096142 | 6/2013 | ........... A01K 67/027 |
| WO | WO 2013/116609 A1 | 8/2013 | ........... A01K 67/027 |
| WO | WO-2013134263 A1 | 9/2013 | |
| WO | WO-2013176772 A1 | 11/2013 | |
| WO | WO-2014093622 A2 | 6/2014 | |

OTHER PUBLICATIONS

Askew, R., et al., "Site-Directed Point Mutations in Embryonic Stem Cells: a Gene-Targeting Tag-and-Exchange Strategy," Molecular and Cellular Biology, pp. 4115-4124, Jul. 1993.

Auerbach, et al., "Establishment and chimera analysis of 129/SvEv- and C57BL/6-derived mouse embryonic stem cell lines," Biotechniques, vol. 29: pp. 1024-1032 (Nov. 2000).

Baker et al., "Homologous Recombination between Transferred and Chromosomal Immunoglobulin k Genes," Mol. Cell. Biology, pp. 4041-4047, Oct. 1988.

Barreto et al., "AID from bony fish catalyzes class switch recombination," Journal of Experimental Medicine, pp. 1-6, Sep. 12, 2005.

Bates et al., "Chromosomal position of a VH gene segment determines its activation and inactivation as a substrate for V(D)J recombination," The Journal of Experimental Medicine, vol. 204, No. 13, pp. 3247-3256, Dec. 24, 2007.

Beard, et al., "Efficient method to generate single-copy transgenic mice by site-specific integration in embryonic stem cells," Genesis (2006), vol. 44, pp. 23-28.

Beck et al., "Nucleotide sequence and exact localization of the neomycin phosphotransferase gene from transposon Tn5". Gene, vol. 19, pp. 327-336, Oct. 1982.

Berg et al., "Inverted repeats of Tn5 are transposable elements". PNAC USA, Genetics, Vo. 79, pp. 2632-2635, Apr. 1982.

Bethke et al., "Segmental genomic replacement by Cre-mediated recombination: genotoxic stress activation of the p53 promoter in single-copy transformants," Nucleic Acids Research, vol. 25, No. 14, pp. 2828-2834, 1997.

Billiard, et al., "Ongoing Dll4-Notch signaling is required for T-cell homeostasis in the adult thymus," European Journal of Immunology, Aug. 4, 2011, vol. 41, pp. 2207-2216.

Bolland et al., "Antisense Intergenic Transcription Precedes IghD-to-J Recombination and is Controlled by the Intronic Enhancer Eμ," Mol. Cell. Biology, vol. 27, No. 15, pp. 5523-5533, Aug. 2007.

Bonin et al., "Isolation, Microinjection, and Transfer of Mouse Blastocysts" Methods in Molecular Biology, vol. 158, Gene Knockout Protocols, pp. 121-134.

Bottaro et al., "Deletion of the IgH intronic enhancer and associated matrix-attachment regions decreases, but does not abolish, class switching at the μ locus," Int. Immunol Vo. 10, No. 6, pp. 799-806, 1998.

Bradley et al., "Formation of germ-line chimaeras from embryo-derived teratocarcinoma cell lines," Nature Publishing Group, pp. 255-256, vol. 309, 1984.

Breden et al., "Comparison of Antibody Repertoires Produced by HIV-1 Infection, Other Chronic and Acute Infections, and Systemic Autoimmune Disease," PloS One. vol. 6, Issue 3, pp. 1-11, Mar. 2011.

Brocker et al., "Evolutionary divergence and functions of the ADAM and ADAMTS gene families" Human Genomics, vol. 4, No. 2, pp. 43-55, Oct. 2009.

Brüggemann, et al., "Human antibody production in transgenic mice: expression from 100 kb of the human lgH locus*," European Journal of Immunology, vol. 21, Issue 5, pp. 1323-1326, May 1991.

Brüggemann, "Human Antibody Expression in Transgenic Mice," Archivum Immunologiae et Therapiae Experimentalis, vol. 49, pp. 203-208, 2001.

Brüggemann et al., "Immunoglobulin heavy chain locus of the rat: Striking homology to mouse antibody genes," Proc. Natl. Acad. Sci. USA, Immunology, vol. 83, pp. 6075-6079, Aug. 1986.

Brüggemann et al., "A repertoire of monoclonal antibodies with human heavy chains from transgenic mice," Proc. Natl. Acad. Sci. USA, Immunology, vol. 86, pp. 6709-6713, Sep. 1989.

Buehr et al., "Capture of Authentic Embryonic Stem Cells from Rat Blastocysts," Cell, vol. 135, pp. 1287-1298, Dec. 26, 2008.

Cadinanos et al., "Generation of an inducible and optimized 10iggyback transposon system," Nucleic Acids Research, vol. 35, No. 12, Jun. 18, 2007.

Carstea, et al., "Germline competence of mouse ES and iPS cell lines: Chimera technologies and genetic background," World Journal of Stem Cells, Dec. 31, 2009; 1(1): pp. 22-29.

Chen et al., "B cell development in mice that lack one or both immunoglobulin χ light chain genes," The EMBO Journal, Vo. 12, No. 3, pp. 821-830, 1993.

Chen et al., "Immunoglobulin Heavy Chain Gene Replacement: A Mechanism of Receptor Editing" Immunity, vol. 3, pp. 747-755, Dec. 1995.

Cho, "Testicular and epididymal ADAMs: expression and function during fertilization," Nature, vol. 9, pp. 550-560, Oct. 2012.

Choi et al., "Characterization and comparative genomic analysis of intronless Adams with testicular gene expression," Genomics 83, pp. 636-646, Aug. 2003.

(56) References Cited

OTHER PUBLICATIONS

Clark et al., "Trends in Antibody Sequence Changes During the Somatic Hypermutation Process," The Journal of Immunology, vol. 177, pp. 333-340, 2006.
Clark et al., "A Future for Transgenic Livestock," Nature Reviews, Genetics, vol. 4, pp. 825-833, Oct. 2003.
Colbere Garapin et al., "A New Dominant Hybrid Selective Marker for Higher Eukaryotic Cells". J Mol. Biol., vol. 150, No. 1, pp. 1-14, Jul. 25, 1981.
Collins, et al., "A mouse for all reasons," Cell, vol. 128, Issue 1, pp. 9-13 (Jan. 2007).
Combriato, et al., "Regulation of human Igλ light chain gene expression by NF-κB1," Journal of Immunology, Issue 168, vol. 3, pp. 1259-1266, Feb. 1, 2002.
Conrath, et al., "Camel Single-domain Antibodies as Modular Building Units in Bispecific and Bivalent Antibody Constructs," The Journal of Biological Chemistry, vol. 276, No. 10, pp. 7346-7350, Mar. 9, 2001.
Copeland et al., "Recombineering: A Powerful New Tool for Mouse Functional Genomic," Nature Reviews, Genetics, vol. 2, pp. 769-869, Oct. 2001(10):769-79.
Corti et al., "A Neutralizing Antibody Selected from Plasma Cells That Binds to Group 1 and Group 2 Influenza A Hemagglutinins" Science, vol. 333, pp. 850-856, 2011.
Cuesta et al., "Multivalent antibodies: when design surpasses evolution," Trends Biotechnology, vol. 28, pp. 355-362, 2010.
De Saint Vincent et al., "Homologous recombination in mammalian cells mediates formation of a functional gene from two overlapping gene fragments," Proc. Natl. Acad. Sci., USA, Genetics, vol. 80, pp. 2002-2006, Apr. 1983.
DeChiara et al., "VelociMouse: Fully ES Cell-Derived FO-Generation Mice Obtained from the Injection of ES Cells into Eight-Cell-Stage Embryos," Gene Knockout Protocols: Second Edition, vol. 530, pp. 311-324, 2009.
DeChiara et al., "Producing Fully ES Cell-Derived Mice From Eight-Cell Stage Embryo Injections," Methods in Enzymology, vol. 476, Chapter 16, pp. 285-294, Jan. 2010.
Denome et al., "Patterns of polyadenylation site selection in gene constructs containing multiple polyadenylation signals," Mol. Cell Biol., vol. 8, No. 11, pp. 4829-4839, Nov. 1988.
Diez-Roux et al., "A High-Resolution Anatomical Atlas of the Transcriptome in the Mouse Embryo," PloS Biology, vol. 9, Issue 1, pp. 1-13, Jan. 2011.
Ding, et al., "Generation of high-affinity fully human anti-interleukin-8 antibodies from its cDNA by two-hybrid screening and affinity maturation in yeast," Protein Science, Oct. 2010; vol. 19, pp. 1957-1966.
DiNoia et al., "Molecular Mechanism of Antibody Somatic Hypermutation," Annu. Rev. Biochem, vol. 76, No. 1, pp. 1-22, 2007.
Doetschman et al., "Establishment of Hamster Blastocyst-Derived Embryonic Stem (ES) Cells," Developmental Biology, vol. 127, pp. 224-227, 1988.
Doetschman, et al., "Targeted mutation of the Hprt gene in mouse embryonic stem cells," Proceedings of the National Academy of Sciences of the United States of America, vol. 85, No. 22, pp. 8583-8587 Nov. 1988.
Doyle, et al., "The construction of transgenic and gene knockout/knockin mouse models of human disease," Transgenic Research, Apr. 2012; 21(2): pp. 327-349.
Durbin, "A map of human genome variation from population-scale sequencing," Nature, vol. 467, pp. 1061-1074, Oct. 28, 2012.
Durdik et al., "Isotype switching by a microinjected μ immunoglobulin heavy chain gene in transgenic mice," PNAS USA Immunol, vol. 86, pp. 2346-2350, Apr. 1989.
Eisener-Dorman, et al., "Cautionary insights on knockout mouse studies: The gene or not the gene?," Brain, Behavior, and Immunity, vol. 23, No. 3, pp. 318-324, (Sep. 2009).

Ekiert et al., "A Highly Conserved Neutralizing Epitope on Group 2 Influenza A Viruses," Science, vol. 333, pp. 843-850, Aug. 12, 2011.
Evans, "Fertilin B and other ADAMs as integrin ligands: insights into cell adhesion and fertilization," BioEssays 23.7, pp. 628-639, 2001.
Featherstone et al., "The Mouse Immunoglobulin heavy Chain V-D Intergenic Sequence Contains Insulators That May Regulate Ordered V(D)J Recombination," The Journal of Biological Chemistry, vol. 285, No. 13, pp. 9327-9338, Mar. 26, 2010.
Feeney, "Genetic and Epigenetic Control of V Gene Rearrangement Frequency," V(D)J Recombination Advances in Experimental Medicine and Biology, 2009, vol. 650, pp. 73-81.
Fell et al., "Homologous recombination in hybridoma cells: heavy chain chimeric antibody produced by gene targeting," PNAS USA Immunology, vol. 86, pp. 8507-8511, Nov. 1989.
Feschotte et al., "DNA Transposons and the Evolution of Eukaryotic Genomes.," Annu Rev Genet., vol. 41, pp. 331-368, 2007.
Folger et al., "Patterns of Integration of DNA Microinjected into Cultured Mammalian Cells: Evidence for Homologous Recombination Between Injected Plasmid DNA Molecules," Mol. Cell Biol., vol. 2, No. 11, pp. 1372-1387, 1982.
Forconi et al., "The normal IGHV1-69-derived B-cell repertoire contains stereotypic patterns characteristic of unmutated CLL," vol. 115, pp. 71-77, 2010.
Fukita et al., "Somatic Hypermutation in the Heavy Chain Locus Correlates with Transcription," Immunity, vol. 9, pp. 106-114, Jul. 1998.
Gefter et al., "Expression of a VHC kappa chimaeric protein in mouse myeloma cells," Nature, pp. 364-367, May 24-30, 1984 (Abstract only).
Gerdes et al., "Physical Map of the mouse λ light chain and related loci," Immunogenetics, vol. 54, pp. 62-65, 2002.
Gerstein, et al., "Isotype switching of an immunoglobulin heavy chain transgene occurs by DNA recombination between different chromosomes," Cell, vol. 63, No. 3, pp. 537-548, Nov. 1990.
Geurts et al., "Knockout Rats via Embryo Microinjection of Zinc-Finger Nucleases," Science, vol. 325, p. 433, Jul. 24, 2009.
Gluzman, "SV40-Transformed Simian Cells Support the Replication of Early SV40 Mutants". Cell, vol. 23, pp. 175-182, Jan. 1981.
Goodhart, et al., "Rearrangement and expression of rabbit immunoglobulin kappa light chain gene in transgenic mice," Proceedings of the National Academy of Sciences (USA), vol. 84, No. 12, pp. 4229-4233, Jun. 1987.
Gorman et al., "The IgK 3' enhancer influences the ratio of Ig? Versus Ig? B lymphocytes" Immunity, vol. 5, pp. 241-252, Sep. 1996.
Gorny et al., "Human Anti-V3 HIV-1 Monoclonal Antibodies Encoded by the VH5-51/VL Lambda Genes Define a Conserved Antigenic Structure," PloSone, vol. 6, Issue 12, pp. 1-10, Dec. 2011.
Goyenechea et al., "Cells strongly expressing Ig(kappa) transgenes show clonal recruitment of hypermutation: a role for both MAR and the enhancers" The EMBO Journal, vol. 16, No. 13, pp. 3987-3994, 1997.
Gu et al., Independent Control of Immunoglobulin Switch Recombination at Individual Switch Regions Evidenced through Cre-loxP-Mediated Gene Targeting. Cell, vol. 73, pp. 1155-1164, Jun. 18, 1993.
Guerrero et al., "The bleomycin resistance gene of transposon Tn5 is an excellent marker for transformation of corynebacteria," Applied Microbiology Biotechnology, vol. 36, pp. 759-762, 1992.
Guntaka, "Transcription Termination and Polyadenylation in Retroviruses" Microbiological Reviews, vol. 57, No. 3, pp. 511-521, Sep. 1993.
Green, "Antibody Engineering via Genetic Engineering of the Mouse: XenoMouse Strains are a Vehicle for the Facile Generation of Therapeutic Human Monoclonal Antibodies," Journal of Immunological Methods, Dec. 10, 1999, vol. 231, Issues 1-2, pp. 11-23.
Han et al., "Comprehensive Analysis of Reproductive ADAMs: Relationship of ADAM4 and ADAM6 with an ADAM Complex Required for Fertilization in Mice," Biology of Reproduction 80, pp. 1001-1008, Jan. 7, 2009.

(56) References Cited

OTHER PUBLICATIONS

Hasty et al., "Target frequency and integration pattern for insertion and replacement vectors in embryonic stem cells," Molecular Cellular Biology, vol. 11, No. 9, pp. 4509-4517, Sep. 1991.
Hagiwara, Transgenic expression of VpreB-3 under the control of the immunoglobulin heavy chain enhancer and SV40 promoter, Kobe Journal of Medical Sciences, Feb. 1996, vol. 42, No. 1, pp. 43-59 (English Abstract).
Houvila et al., "Shedding light on ADAM metalloproteinases," Trends in Biochemical Sciences, vol. 30, No. 7, pages, Jul. 2005.
Hudziak et al., "Establishment of Mammalian Cell Lines Containing Multiple Nonsense Mutations and Functional Suppressor tRNA Genes," Cell, vol. 31, pp. 137-146, Nov. 1982.
Huang, et al., "Structural Basis of Tyrosine Sulfation and VH-Gene Usage in Antibodies that Recognize the HIV Type 1 Coreceptor-Binding Site on gp120," PSNA, Mar. 2, 2004, vol. 101, No. 9, pp. 2706-2711.
Iglesias-Ussel, et al., "Forced expression of AID facilitates the isolation of class switch variants from hybridoma cells," Journal of Immunological Methods, Oct. 2006; 316(1-2), pp. 59-66.
Ivics et al., "The expanding universe of transposon technologies for gene and cell engineering," Mobile DNA, pp. 1-25, 2010.
Ivics et al., "The Sleeping Beauty Transposable Element: Evolution, Regulation and Genetic Applications," Curr. Issues Mol. Biol., vol. 6, pp. 43-56, 2004.
Izsvak et al., "Sleeping Beauty Transposition: Biology and Applications for Molecular Therapy," Molecular Therapy, vol. 9, No. 2, pp. 147-156, Feb. 2, 2004.
Jacob et al., "Gene targeting in the rat: advances and opportunities," Trends in Genetics, vol. 26, No. 12, pp. 510-518, Dec. 2010.
Jakobovits, et al., "From XenoMouse technology to panitumumab, the first fully human antibody product from transgenic mice," Nature Biotechnology, vol. 25, No. 10, pp. 1134-1143, Oct. 2007.
Janssens, et al., "Generation of heavy-chain-only antibodies in mice," Proceedings of the National Academy of Sciences (USA), Oct. 10, 2006, vol. 103, No. 41, pp. 15130-15135.
Jendreyko, et al., "Intradiabodies, Bispecific, Tetravalent Antibodies for the Simultaneous functional knockout of two cell surface receptors," The Journal of Biological Chemistry, vol. 278, pp. 47812-47819, Nov. 28, 2003.
Jung, et al., "Mechanism and Control of V(D)J Recombination at the Immunoglobulin Heavy Chain Locus," Annual Review of Immunology, Apr. 2006, vol. 24, pp. 541-570.
Kaminski, et al., "Antibody class switching differs among SJL, C57BL/6 and 129 mice," International Immunology, vol. 19, No. 4, pp. 545-556 (2007).
Kellerman, et al, "Developing the Xenomouse technology for evaluating immunogenicity ," AntibOZ 2 Conference, Australia, 2004.
Kim et al., "CHO cells in biotechnology for production of recombinant proteins: current state and further potential" Appl. Microbiology Biotechnology, vol. 93, pp. 917-930, Dec. 9, 2011.
Kingzette et al., "Trans-chromosomal recombination within the Ig heavy chain switch region in B lymphocytes," Proc. Natl. Acad. Sci., vol. 95, pp. 11840-11845, Sep. 1998.
Kitamura et al., "A B cell-deficient mouse by targeted disruption of the membrane exon of the immunoglobulin chain gene," Nature, vol. 350, pp. 423-426, Apr. 1991.
Kohrer et al., "Import of amber and ochre suppressor tRNAs into mammalian cells: A general approach to site-specific insertion of amino acid analogues into proteins," PNAS USA, vol. 98, No. 25, pp. 214310-14315, Dec. 4, 2001.
Kostenuik, et al., Denosumab, a fully human monoclonal antibody to RANKL, inhibits bone resorption and increases BMD in knock-in mice that express chimeric (Murine/Human) RANKL, Journal of Bone and Mineral Research, vol. 24, No. 2, pp. 182-195, 2009.
Kotzamaris et al., Recombining overlapping BACs into a single larger BAC, BMC Biotechnology, pp. 1-10, 2004.
Krause, Epitope-Specific Human Influenza Antibody Repertoires Diversify by B Cell Intraclonal Sequence Divergence and Interclonal Convergence, The Journal of Immunology, pp. 3704-3711, Aug. 31, 2011.
Kruif et al., "Human Immunoglobulin Repertoires against Tetanus Toxoid Contain a Large and Diverse Fraction of High-Affinity Promiscuous Vh Genes," Journal of Molecular Biology, vol. 387, pp. 548-558, Feb. 11, 2009.
Krutskikh et al., "Epididymal protein Rnase10 is required for post-testicular sperm maturation and male fertility," The FASEB Journal, pp. 4198-4209, 2012.
Kucherlapati et al., "Homologous recombination between plasmids in mammalian cells can be enhanced by treatment of input DNA," PNAS USA Genetics, vol. 81, pp. 3135-3157, May 1984.
Kuroiwa et al., "Sequential targeting of the genes encoding immunoglobulin and prion protein in cattle," Nature Genetics, vol. 36, No. 7, pp. 775-780, Jul. 2004.
Laventie, et al., "Heavy chain-only antibodies and tetravalent bispecific antibody neutralizing *Staphylococcus aureus* leukotoxins," Proceedings of the National Academy of Sciences (USA), Sep. 27, 2011; vol. 108, No. 39, pp. 16404-16409.
Lee et al, "Human C5aR knock-in mice facilitate the production and assessment of anti-inflammatory monoclonal antibodies," Nature Biotechnology, vol. 24, No. 10, pp. 1279-1284, Oct. 2006.
Li et al., "Transgenic mice with a diverse human T cell antigen receptor repertoire," Nature Medicine, vol. 16, No. 9, pp. 1029-1035, Sep. 2010.
Li et al., "The minimum Internal and external sequence requirements for transposition of the eukaryotic transformation vector 17iggyback," Mol. Genet. Genomics, vol. 266, pp. 190-198, 2001.
Li et al., "Crafting rat genomes with zinc fingers," Nature Biotechnology, vol. 29, No. 1, pp. 39-41, Jan. 2011.
Li et al., "Germline Competent Embryonic Stem Cells Derived from Rat Blastocysts," Cell, vol. 135, pp. 1299-1310, Dec. 26, 2008.
Liao et al., "Generation of Induced Pluripotent Stem Cell Lines from Adult Rat Cells," Cell Stem Cell Brief Report, vol. 4, pp. 11-15, Jan. 9, 2009.
Luciw et al., "Location and Function of Retroviral and SV40 Sequences that Enhance Biochemical Transformation after Microinjection of DNA," Cell., vol. 33, pp. 705-176, Jul. 1983.
Luo et al., "Chromosomal transposition of a Tc1/mariner-like element in mouse embryonic stem cells," Proc. Natl. Acad. Sci. USA, Genetics, vol. 95, pp. 10769-10773, Sep. 1998.
Liu, et al., "Potent and Broad Anti-HIV-1 Activity Exhibited by a Glycosyl-Phosphatidylinositol-Anchored Peptide Derived from the CDR H3 of Broadly Neutralizing Antibody PG16," Journal of Virology, Sep. 2011, vol. 85, No. 17, pp. 8467-8476.
Lonberg, "Human antibodies from transgenic animals," Nature Biotechnology, vol. 23, No. 9, pp. 1117-1125, Sep. 2005.
Loveslati, et al., "A study of Gm allotypes ad immunoglobulin heavy gamma IGHG genes in Berbers, Arabs and sub-Saharan Africans from Jerba Island, Tunisia" Blackwell Science Ltd., Europran journal of Immunogenetics, vol. 28, pp. 531-538, 2001.
Luby, et al., "The µ switch region tandem repeats are important, but not required, for antibody class switch recombination," The Journal of Experimental Medicine, Jan. 15, 2001; 193(2): pp. 159-168.
Mack et al., "A small bispecific antibody construct expressed as a functional single-chain molecule with high tumor cell cytotoxicity," Proc. Natl. Acad. Sci. USA, Immunology, vol. 92, pp. 7021-7025, Jul. 1995.
Makris et al., "Mutational analysis of insertion sequence 50 (IS50) and transposon 5 (Tn5) ends," Proc. Natl. Acad. Sci. USA, Genetics, vol. 85, pp. 2224-2228, Apr. 1988.
Mallender et al., "Construction, Expression, and Activity of a Bivalent Bispecific Single-chain Antibody," The Journal of Biological Chemistry, vol. 269, No. 1, pp. 199-206, 1994.
Manis, et al., "Mechanism and control of class-switch recombination," Trends in Immunology, Jan. 2002, vol. 23, Issue 1, pp. 31-39.
Marcello et al., Lack of Tyrosylprotein Sulfotransferase-2 Activity Results in Altered Sperm-Egg Interactions and Loss of ADAM3 and ADAM6 in Epididymal Sperm, The Journal of Biological Chemistry, vol. 286, No. 15, pp. 13060-13070, Apr. 15, 2011.

(56) References Cited

OTHER PUBLICATIONS

Martensson et al., "Role of the surrogate light chain and the pre-B-cell receptor in mouse B-cell development," Immunology, vol. 101, pp. 435-441, 2000.
Maitta, et al., "Immunogenicity and Efficacy of *Cryptococcus neoformans* Capsular Polysaccharide Glucuronoxylomannan Peptide Mimotope-Protein Conjugates in Human Immunoglobulin Transgenic Mice," Infection and Immunity, vol. 72, No. 1, pp. 196-208, Jan. 2004.
Maul et al., "AID and Somatic Hypermutation," Advances in Immunology, vol. 105, pp. 159-191, 2010.
McCreath et al., "Production of gene-targeted sheep by nuclear transfer from cultured somatic cells," Nature, vol. 405, pp. 1066-1070, Jul. 29, 2000.
Mejia et al., "The Assembly of Large BACs by in Vivo Recombination," Genomics, vol. 70, pp. 165-170, 2000.
Mendez et al., "Functional Transplant of Megabase Human Immunoglobulin Loci Recapitulates Human Antibody Response in Mice," Nature Genetics, Feb. 1997, vol. 15, pp. 146-156.
Milner, et al., "Polymorphism and utilization of Human $V_h$ Genes," Annals of the New York Academy of Sciences, vol. 764,, pp. 50-61, Sep. 1995.
Mir, "Sequencing Genomes: From Individuals to Populations," Briefings in Functional Genomics Proteomics, vol. 8, No. 5, pp. 367-378, 2009.
Moreau et al., "The SV40 72 base repair repeat has a striking effect on gene expression both in SV40 and other chimeric recombinants," Nuclear Acids Research, vol. 9, No. 22, pp. 6047-6068, 1981.
Moreno et al., "The emerging role of matrix metalloproteases of the ADAM family in male germ cell apoptosis," Spermatogenesis, vol. 1, No. 3, pp. 195-208, Jul./Aug./Sep. 2011.
Mouellic et al., "Pattern of transcription of the homeo gene Hox-3.1 in the mouse embryo," Denes Dev., vol. 2, pp. 125-135, 1988.
Mortuza et al., "Immunoglobulin heavy-chain gene rearrangement in adult acute lymphoblastic leukemia reveals preferential usage of JH-proximal variable gene segments," Blood, vol. 97, No. 9, pp. 2716-2726, May 2001.
Murphy, "VelocImmune: immunoglobulin variable region humanized mice," Recombinant Antibodies for Immunotherapy. $1^{st}$ ed. Cambridge: Cambridge University Press, pp. 100-108, 2009.
Murphy, et al., "Mice with megabase humanization of their immunoglobulin genes generate antibodies as efficiently as normal mice," PNAS, vol. 111, No. 14, pp. 5153-5158, Apr. 8, 2014.
Nadel, et al., "Sequence of the Spacer in the Recombination Signal Sequence Affects V(D)J Rearrangement Frequency and Correlates with Nonrandom Vκ Usage In Vivo," J. Exp. Med., May 4, 1998, vol. 187, No. 9, pp. 1495-1503.
Nagle, "Regeneron helps make Sanofi VelocImmune to its 'weak' pipeline," Outsourcing-Pharmac.com, 2 pages, Dec. 3, 2007.
Nandi et al., "Regulated expression of genes inserted at the human chromosomal B-globin locus by homologous recombination," Proc. Natl. Sci. USA, Cell Biology, vol. 85, pp. 3845-3849, Jun. 1998.
Narayanan et al., "Bacterial Artificial Chromosome Mutagenesis Using Recombineering" Journal of Biomedicine and Biotechnology, vol. 2011, Article ID 971296, 10 pages, Dec. 9, 2010.
Nelson et al., "Development trends for human monoclonal antibody therapeutics," Nature Reviews, Drug Discovery, vol. 9, pp. 767-774, Oct. 2010.
Neuberger et al., "Somatic hypermutation," Current Opinion in Immunology, vol. 7, pp. 248-254, 1995.
Nicholson, et al., "Antibody Repertoires of Four- and Five-Feature Translocus Mice Carrying Human Immunoglobulin Heavy Chain and κ and λ Light Chain Yeast Artificial Chromosomes," The Journal of Immunology, Dec. 15, 1999, vol. 163, No. 12, pp. 6898-6906.
Niemann et al., "Transgenic farm animals: present and future," Rev. Sci Tech Off. Int Epiz., vol. 24, pp. 285-298, 2005.
Oancea et al., "Expression of the (Recombinant) Endogenous Immunoglobulin Heavy-Chain Locus requires the Intronic Matrix Attachment Regions," Molecular and Cellular Biology, vol. 17, No. 5, pp. 2658-2668, May 1997.
Oberdoerffer et al., "Unidirectional Cre-mediated genetic inversion in mice using the mutant loxP pair lox66/lox71," Nucleic Acids Research, vol. 31, No. 22, pp. 1-7, 2003.
Ohlin, et Al., "The human antibody repertoire to infectious agents: implications for disease pathogenesis," Molecular Immunology, vol. 40, Issue 1, pp. 1-11, Sep. 2003.
Osborn et al., "High-Affinity IgG Antibodies Develop Naturally in Ig-Knockout Rats Carrying Germline Human IgH/Ig k/Igλ Loci Bearing the Rat Ch Region," The Journal of Immunology, pp. 1481-1490, Feb. 15, 2013 (E Pub Jan. 9, 2013).
Osoegawa et al., "Bacterial Artificial Chromosome Libraries for Mouse Sequencing and Functional Analysis," Genome Research, pp. 16-28, 2000.
Pavlicek et al., "Ancient Transposable Elements, Processed Pseudogenes, and Endogenous Retroviruses," Genomic Disorders, pp. 57-72, 2006.
Pelham et al., "Expression of a *Drosophila* Heat Shock Protein in Mammalian Cells: Transient Association with Nucleoli after Heat Shock," Philosophical Transactions of the Royal Society, pp. 301-307, 1984.
Perlot et al., "Antisense transcripts from immunoglobulin heavy-chain locus V(D)J and switch regions," PNAS, vol. 105, No. 10, pp. 3843-3848, Mar. 11, 2008.
Perlot et al., "Cis-Regulatory Elements and Epigenetic Changes Control Genomic Rearrangements of the IgH Locus," Advances in Immunology, vol. 99, pp. 1-32, 2008.
Pettitt, et al., "Agouti C57BL/6N embryonic stem cells for mouse genetic resources," Nature Methods, vol. 6, No. 7, pp. 493-495 (Jul. 2009).
Plasterk et al., "Resident aliens: The Tcl/mariner superfamily of transposable elements," YIG, vol. 15, No. 8, pp. 326-333, Aug. 1999.
Ponsel, et al., "High Affinity, Developability and Functional Size: The Holy Grail of Combinatorial Antibody Library Generation," Molecules, vol. 16, No. 5, pp. 3675-3700, 2011.
Popov et al., "A Human Immunoglobulin λ Locus Is Similarly Well Expressed in Mice and Humans," Journal of Experimental Medicine, vol. 189, No. 10, pp. 1611-1619, May 17, 1999.
Pramanik, et al., Segmental duplication as one of the driving forces underlying the diversity of the human immunoglobulin heavy chain variable gene region, BMC Genomics, vol. 12, No. 78, 2011.
Primakoff et al., "Penetration, Adhesion, and Fusion in Mammalian Sperm-Egg Interaction," Science, vol. 296, pp. 2183-2185, Jun. 21, 2002.
Primakoff et al., "The ADAM Gene Family: surface proteins with adhesion and protease activity," Trends in Genetics, vol. 16, No. 2, pp. 83-87, Feb. 2000.
Puente et al., "Comparative genomic analysis of human and chimpanzee proteases," Genomics, vol. 86, pp. 638-647, 2005.
Prosser, et al., "Mosaic complementation demonstrates a regulatory role for myosin VIIa in actin dynamics of stereocilia," Molecular and Cellular Biology, Mar. 2008, vol. 28, No. 5, pp. 1702-1712.
Prosser, et al., "A resource of vectors and ES cells for targeted deletion of microRNAs in mice," Nature Biotechnology, vol. 29, No. 9, pp. 840-845, Sep. 2011.
Qu et al., "Gene Targeting of ErbB3 Using a Cre-Mediated Unidirectional DNA Inversion Strategy," Technology Report, Genesis, vol. 44, pp. 477-486, 2006.
Raynard et al., "Cis-acting regulatory sequences promote high-frequency gene conversion between repeated sequences in mammalian cells," Nucleic Acids Research, vol. 32, No. 19, pp. 5916-5927, Nov. 4, 2004.
Reddy et al., "Monoclonal antibodies isolated without screening by analyzing the variable-gene repertoire of plasma cells," Nature Biotechnology, vol. 28, No. 9, pp. 965-971, Sep. 2010.
Regeneron, "Big pharma vies for mice," Nature Biotechnology, Jun. 2007,vol. 25, No. 6, p. 613.

(56) References Cited

OTHER PUBLICATIONS

Retter, "Sequence and Characterization of the Ig Heavy Chain Constant and Partial Variable Region of the Mouse Strain 129S1," The Journal of Immunology, vol. 179, pp. 2419-2427, 2007.
Rivera, et al., "Genetic background and the dilemma of translating mouse studies to humans," Immunity, vol. 28, No. 1, pp. 1-4, Jan. 28, 2008.
Rodriguez, et al., "High-efficiency deleter mice show that FLPe is an alternative to Cre-loxP," Nature Genetics, vol. 25, pp. 139-140, Jun. 2000.
Rogozin et al., "Cutting Edge: DGYW/WRCH Is a Better Predictor of Mutability at G:c Bases in Ig Hypermutation Than the Widely Accepted RGYW/WRCY Motif and Probably Reflects a Two-Step Activation-Induced Cytidine Deaminase-Triggered Process," Journal of Immunology, vol. 172, pp. 3382-3384, 2004.
Sakai et al., "Recombination and transcription of the endogenous Ig heavy chain locus is effected by the Ig heavy chain intronic enhancer core region in the absence of the matrix attachment regions," Proc. Natl. Acad. Sci., vol. 96, pp. 1526-1531, Feb. 1999.
Sarkar et al., "Molecular evolutionary analysis of the widespread piggyBac transposon family and related "domesticated" sequences," Mol. Gen. Genomics, vol. 270, pp. 173-180, 2003.
Sasso et al., "Expression of the Immunoglobulin Vh Gene 51p1 Is Proportional to Its Germline Gene Copy Number," J. Clin. Invest., vol. 97, No. 9, pp. 2074-2080, May 1996.
Sasso, et al., "Ethnic differences in Polymorphism of an Immunoglobulin $V_h3$ gene," Journal of Clinical Investigation, vol. 96, No. 3, pp. 1591-1600, Sep. 1995.
Sauer, "Functional Expression of the cre-lox Site-Specific Recombination System in the Yeast *Saccharomyces cerevisiae*," Molecular and Cellular Biology, vol. 7, No. 6, pp. 2087-2096, Jun. 1987.
Sauer et al., "Cre-stimulated recombination at loxP-containing DNA sequences placed into the mammalian genome," Nucleic Acids Research, vol. 17, No. 1, pp. 147-161, 1989.
Sauer et al., "Site-specific DNA recombination in mammalian cells by the Cre recombinase of bacteriophage P1," Proc. Natl. Acad. Sci. USA, Genetics, vol. 85, pp. 5166-5170, 1988.
Schnutgen et al., "A directional strategy for monitoring Cre-mediated recombination at the cellular level in the mouse", Nature Biotechnology, vol. 21, pp. 562-565, May 2003.
Schlake et al., "Use of Mutated FLP Recognition Target (FRT) Sites for the Exchange of Expression Cassettes at Defined Chromosomal Loci," Biochemistry, vol. 33, pp. 12746-12751, 1994.
Schrock et al., "Comparative Genomic Hybridization (CGH)—Detection of Unbalanced Genetic Aberrations Using Conventional Micro-Array Techniques," Molecular Cytogenetics, Unit 8.12.1, Supplement 18, 30 pages, 2001.
Schroeder, et al., "Preferential utilization of conserved immunoglobulin heavy chain variable gene segments during human fetal life," Proc. Natl. Acad. Science USA, vol. 87, pp. 6146-6150, Aug. 1990.
Schweinfest et al., "A heat-shock-inducible eukaryotic expression vector," Gene. 71, pp. 207-210, 1988.
Scott, "Mice with a human touch," Nature Biotechnology, vol. 25, pp. 1075-1077, Dec. 2007.
Seed et al., "Purification of genomic sequences from bacteriophage libraries by recombination and selection in vivo," Nucleic Acids Research, vol. 11, No. 8, pp. 2427-2445, 1983.
Sen, et al., "Multiple nuclear factore interact with the immunoglobulin enhancer sequences," Cell, vol. 46, pp. 705-716, Aug. 29, 1986.
Seong, et al., "To knockout in 129 or in C57BL/6: that is the question," Trends in Genetics, vol. 20, No. 2, pp. 59-62, Feb. 2004.
Serwe et al., "V(D)J recombination in B cells is impaired but not blocked by targeted deletion of the immunoglobulin heavy chain intron enhancer," The EMBO Journal, vol. 12, No. 6, pp. 2321-2327, 1993.
Shaul, et al, "Homologous recombination between a defective virus and a chromosomal sequence in mammalian cells," Proceedings of the National Academy of Sciences (USA), vol. 89, pp. 3781-3784, Jun. 1985.
Shimizu et al., "Immunoglobulin double-isotype expression by trans-mRNA in a human immunoglobulin transgenic mouse," Proc. Natl. Acad. Sci. USA, Immunology, vol. 86, pp. 8020-8023, Oct. 1989.
Shultz, et al., "Humanized mice in translational biomedical research," The Journal of Immunology, Feb. 2007, vol. 7, No. 2, pp. 118-130.
Sirac, et al., "Role of the monoclonal κ chain V domain and reversibility of renal damage in a transgenic model of acquired Fanconi syndrome," Blood, Jul. 15, 2006, vol. 108, No. 2, pp. 536-543.
Skarnes, et al., "A conditional knockout resource for the genome-wide study of mouse gene function," Nature, vol. 474, pp. 337-342, Jun. 16, 2011.
Simpson, et al., "Genetic variation among 129 substrains and its importance for targeted mutagenesis in mice," Nature Genetics, vol. 16, pp. 19-27.
Skoultchi et al., "Expression of Genes Inserted at the Human B-Globin Locus by Homologous Recombination," Developmental Control of Globin Gene Expression, pp. 581-594, 1987.
Smithies, "Direct Alteration of a Gene in the Human Genome," J. Inher. Metab., Dis. 9, Suppl. 1, pp. 92-97, 1986.
Smithies et al., "Insertion of DNA sequences into the human chromosomal B-globin locus by homologous recombination," Nature, vol. 317, No. 19, pp. 230-234, Sep. 1985.
Sohn et al., "Somatic Hypermutation of an Immunoglobulin µ Heavy Chain Transgene," J. Exp. Med., vol. 177, pp. 493-504, Feb. 1993.
Song et al., "Accurate modification of a chromosomal plasmid by homologous recombination in human cells," Proc. Natl. Acad. Sci. USA, Genetics, vol. 84, pp. 6820-6824, Oct. 1987.
Sonoda et al., "B Cell Development under the Condition of Allelic Inclusion," Immunology, vol. 6, pp. 225-233, Mar. 1997.
Storb et al., "Physical Linkage of Mouse Genes by Pulsed-Field Gel Electrophoresis Suggests that the Rearrangement Process Favors Proximate Target Sequences," Molecular and Cellular Biology, vol. 9, No. 2, pp. 711-718, Feb. 1989.
Stevens et al., "Human Antibody Discovery, VelocImmune—A novel platform," Pharma Focus Asia, Clinical Trials Issue 8, pp. 1-5, 2008.
Taki et al., "Targeted Insertion of a Variable Region Gene into the Immunoglobulin Heavy Chain Locus," Science, vol. 262, pp. 1268-1271, Nov. 19, 1993.
Talbot et al., "Cell Adhesion and Fertilization: Steps in Oocyte Transport, Sperm-Zona Pellucida Interactions, and Sperm-Egg Fusion," Biology of Reproduction 68, pp. 1-9, 2003.
Te Riele, et al., "Highly efficient gene targeting in embryonic stem cells through homologous recombination with isogenic DNA constructs," Proceedings of the National Academy of Sciences (USA), vol. 89, pp. 5128-5132, Jun. 1992.
Thomas et al., "High Frequency Targeting of Genes to Specific Sites in the Mammalian Genome," Cell, vol. 44, pp. 419-428, Feb. 14, 1986.
Thomas et al., "Introduction of homologous DNA sequences into mammalian cells induces mutations in the cognate gene" Nature, vol. 324, Nov. 1986.
Thomas et al., "Site-Directed Mutagenesis by Gene Targeting in Mouse Embryo-derived stem cells," Cell, vol. 51, pp. 503-512, Nov. 6, 1987.
Tomizuka, et al., "Double trans-chromosomic mice: Maintenance of two individual human chromosome fragments containing Ig heavy and k loci and expression of fully human antibodies," Proceedings of the National Academy of Sciences (USA), Jan. 18, 2000, vol. 97, No. 2, pp. 722-727.
Torres et al., "Laboratory protocols for conditional gene targeting", Institute for Genetics, University of Cologne, pp. 37-40, 1997.
Ungrin et al., "Strict control of telomerase activation using Cre-mediated inversion", BMC Biotechnology, vol. 6, pp. 1-9, 2006.

(56) References Cited

OTHER PUBLICATIONS

Valenzuela, et al., "High-throughput engineering of the mouse genome coupled with high-resolution expression analysis," Nature Biotechnology vol. 21, No. 6, p. 652-659 and vol. 21, No. 7, p. 822, (2003).

Van Spriel, et al., "Immunotherapeutic perspective for bispecific antibodies," Immunology Today, vol. 21, No. 8, pp. 391-397, Aug. 1, 2000.

Vassilieva et al., "Establishment of SSEA-1- and Oct-4 expressing rat embryonic stem-like cell lines and effects of cytokines of the IL-6 family on clonal growth," Experimental Cell Research, vol. 258, pp. 361-373, 2000.

Vasicek, et al., Structure and expression of the human Immunoglobulin λ genes, J. Exp. Med., vol. 172, pp. 609-620, Aug. 1990.

Venken et al., "P[acman]: A BAC Transgenic Platform for Targeted Insertion of Large DNA Fragments in *D. melanogaster*," Science, vol. 314, pp. 1747-1751, Dec. 15, 2006.

Vora et al., "Altering the Antibody Repertoire via Transgene Homologous Recombination: Evidence for Global and Clone-autonomous Regulation of Antigen-driven B Cell Differentiation," J. Exp. Med., vol. 181, pp. 271-281, Jan. 1995.

Wallace et al., "Manipulating the Mouse Genome to Engineer Precise Functional Syntenic Replacements with Human Sequence," Cell, vol. 18, pp. 197-209, Jan. 12, 2007.

Wang et al., "AID upmutants isolated using a high-throughput screen highlight the immunity/cancer balance limiting DNA deaminase activity," Nature Structural & Molecular Biology, vol. 16, No. 7, Jul. 2009.

Wang et al., "Altering the spectrum of immunoglobulin V gene somatic hypermutation by modifying the active site of AID," J. Exp. Med., vol. 207, No. 1, pp. 141-153, 2010.

Wang et al., "Catching a Moving Target," Science, Biochemistry, vol. 333, pp. 834-835, Aug. 21, 2011.

Wang, et al., "Chromosomal transposition of PiggyBac in mouse embryonic stem cells," Proceedings of the National Academy of Sciences (USA), (2008) vol. 105, No. 27, pp. 9290-9295.

Wang, et al., "Many human immunoglobulin heavy-chain IGHV gene polymorphisms have been reported in error," Immunology and Cell Biology, vol. 86, No. 2, pp. 111-115, Feb. 2008.

White, et al, "Genome-wide generation and systematic phenotyping of knockout mice revels new roles for many genes," Cell, vol. 154, Issue 2: pp. 452-464, Jul. 18, 2013.

Wilkie et al., "Analysis of the Integrant in MyK-103 Transgenic Mice in which Males Fail to Transmit the Integrant," Molecular and Cellular Biology, pp. 1646-1655, May 1987.

Williams et al., "Unequal VH Gene Rearrangement Frequency Within the Large Vh7183 Gene Family is not Due to Recombination Signal Sequence Variation, and Mapping of the Genes Shows a Bias of Rearrangement Base on Chromosomal Location," The Journal of Immunology, pp. 257-263, 2001.

Xu, et al., "Combinatorial surrobody libraries," Proceedings of the National Academy of Sciences (USA), (2008) vol. 105, No. 31, pp. 10756-10761.

Yancopoulous et al., "Preferential utilization of the most JH-proximal VH gene segments in pre-B-cell lines," Nature, vol. 311, pp. 727-733, 1984.

Yu, et al., Differential Usage of VH Gene Segments Is Mediated by cis Elements, The Journal of Immunology, Oct. 1, 1998, vol. 161, No. 7, pp. 3444-3454.

Zheng et al., Engineering Mouse Chromosomes with Cre-loxP: Range, Efficiency, and Somatic Applications, Molecular and Cellular Biology, vol. 20, No. 2, pp. 648-655, Jan. 2000.

Zou et al., "Cre-loxP-mediated gene replacement: a mouse strain producing humanized antibodies," Current Biology, vol. 4, No. 12, pp. 1099-1104, 1994.

Kling, "News in Brief," Nature Biotechnology, vol. 25, No. 6, p. 613, Jun. 2007.

GenBank Accession No. X97051 564822, accessed Aug. 6, 2014, 29 pages.

Nucleotide Sequence RID Y55HBK1W114, accessed Aug. 6, 2014, 2 pages.

Macdonald, et al., "Precise and in situ genetic humanization of 6Mb of mouse immunoglobulin genes," Proceedings of the National Academy of Sciences (USA), vol. 111, No. 14, pp. 5147-5152, Apr. 8, 2014.

2006 MUGEN Conference (Abstracts 1-52), 52 pages.

Adams D.J. et al., "Contemporary approaches for modifying the mouse genome," *Physiological Genomics*, vol. 34, 2008, pp. 225-238.

Adams D.J. et al., "Mutagenic Insertion and Chromosome Engineering Resource (MICER)," *Nature Genetics*, vol. 36 (8), Aug. 2004, pp. 867-871.

Affidavits Evidencing Murphy Slides as Printed Publication, 84 pages, dated Jun. 20, 2016.

Aguilera R.J. et al., "Characterization of immunoglobulin enhancer deletions in murine plasmacytomas," *The EMBO Journal*, 1985, vol. 4 (13B), pp. 3689-3693.

Ahmed T., "Sanofi-aventis and Regeneron Extend Therapeutic Antibody Agreement," *PharmaDeals Review*, Nov. 2009, vol. 11, p. 115.

Arnaout R., et al., "High-Resolution Description of Antibody Heavy-Chain Repertoires in Humans," *PLOS One*, 2011, vol. 6 (8), pp. e22365-1-e22365-8.

Arthur J.S. et al., "Gene-Targeting Vectors," Chapter 9, *Transgenesis Techniques, Principles and Protocols*, Third edition, 2009 (24 pages, including cover sheet, copyright and preface pages and table of contents), pp. 127-144.

Asenbauer H. et al., "The immunoglobulin lambda light chain enhancer consists of three modules which synergize in activation of transcription," *European Journal of Immunology*, 1999, vol. 29, pp. 713-724.

Atlas of Genetics and Cytogenetics in Oncology and Haematology, VPREB1 (pre-B lymphocyte 1), 5 pages. [online at http://atlasgeneticsoncology.org/Genes/GC_VPREB1.html] (Retrieved from the Internet on May 25, 2015).

Avery S., Attorney for Applicant, Third-Party Pre-Issuance Submission Under 37 CFR Section 1.290 in U.S. Appl. No. 14/517,755, dated Jun. 26, 2015, 16 pages.

Baer A. et al., "Coping with kinetic and thermodynamic barriers: RMCE, an efficient strategy for the targeted integration of transgenes," *Current Opinions in Biotechnology*, Oct. 2001, vol. 12 (5), pp. 473-480.

Baker A.M., et al., "Adaptation of TCR Expression Vectors for the Construction of Mouse-Human Chimeric MBP-Specific TCR Transgenes," *Journal of Neuroscience Research*, 1996, vol. 45 (4), pp. 487-491.

Beerli R.R., et al., "Mining Human Antibody Repertoires," *mAbs*, Jul./Aug. 2010, vol. 2 (4), pp. 365-378.

Bhattacharya P., et al., "Switch Region Identity Plays an Important Role in Ig Class Switch Recombination," *Journal of Immunology*, 2010, vol. 184 (11), pp. 6242-6248.

Birling M.C. et al., "Site-Specific Recombinases for Manipulation of the Mouse Genome," Chapter 16, *Transgenesis Techniques, Principles and Protocols*, Third edition, 2009 (25 pages, including cover sheet, copyright and preface pages and table of contents), pp. 245-263.

Blankenstein T. et al., "Immunoglobulin $V_H$ Region Genes of the Mouse are Organized in Overlapping Clusters," *European Journal of Immunology*, 1987, vol. 17 (9), pp. 1351-1357.

Board of Appeal of the European Patent Office, Datasheet for the Decision of Nov. 9, 2015 for Application No. 02709544.7, Case T 2220/14-3.3.08, 83 pages.

Bode J., et al., "The Transgeneticist's Toolbox: Novel Methods for the Targeted Modification of Eukaryotic Genomes," *Biological Chemistry*, Sep./Oct. 2000, vol. 381 (9-10), pp. 801-813.

Bogen B., et al., "A Rearranged λ2 Light Gene Chain Retards but does not Exclude $_x$ and $\lambda_1$ Expression," *European Journal of Immunology*, 1991, vol. 21 (10), pp. 2391-2395.

Bransteitter R., et al., "Activation-Induced Cytidine Deaminase Deaminates Deoxycytidine on Single-Stranded DNA but Requires the Action of RNase," *Proceedings of the National Academy of Sciences of the U.S.A.*, 2003, vol. 100 (7), pp. 4102-4107.

(56) References Cited

OTHER PUBLICATIONS

Brezinschek H.P., et al., "Analysis of the Human $V_H$ Gene Repertoire," *Journal of Clinical Investigation*, 1997, vol. 99 (10), pp. 2488-2501.
Brüggemann M., et al., "The Immunogenicity of Chimeric Antibodies," *The Journal of Experimental Medicine*, 1989, vol. 170 (6), pp. 2153-2157.
Brüggemann M., et al., "Strategies for Expressing Human Antibody Repertoires in Transgenic Mice," *Immunology Today*, 1996, vol. 17 (8), pp. 391-397.
Briney B.S., et al., "Human Peripheral Blood Antibodies with Long HCDR3s are Established Primarily at Original Recombination using a Limited Subset of Germline Genes," *PLOS One*, 2012, vol. 7 (5), pp. e36750-1-e36750-13.
Brüggemann M., et al., "Human Monoclonal Antibodies from Translocus Mice," *Molecular Biology of B Cells*, Chapter 34, 2003, pp. 547-561.
Butler J.E., et al., "Immunoglobulin Diversity, B-Cell and Antibody Repertoire Development in Large Farm Animals," *Revue scientifique et technique* (International Office of Epizootics), 1998, vol. 17 (7), pp. 43-70.
Casrouge A., et al., "Size Estimate of the TCR Repertoire, of Naive Mouse Splenocytes," *The Journal of Immunology*, 2000, vol. 164 (11), pp. 5782-5787.
Chan A.C., et al., "Therapeutic Antibodies for Autoimmunity and Inflammation," *Nature Reviews Immunology*, 2010, vol. 10 (5), pp. 301-316.
Chen Y., "PiggyBac Transposon-Mediated, Reversible Gene Transfer in Human Embryonic Stem Cells," *Stem Cells and Development*, Nov. 2010, vol. 19 (6), 9 pages.
Chinese Patent Office, First Office Action for Chinese Application No. 201180039668.1, dated Jan. 3, 2014, 6 pages.
Chinese Patent Office, English Translation of First Office Action for Chinese Application No. 201180039668.1, dated Jan. 3, 2014, 6 pages.
Chinese Patent Office, Office Action for Chinese Patent Application No. 201380029744.1, dated Nov. 10, 2016, 2 pages.
Chinese Patent Office, English Translation of Office Action for Application No. 201380027944.1, dated Nov. 10, 2016, 5 pages.
Chinese Patent Office, Search Report, Chinese Application No. 201180039668.1, dated Jan. 3, 2014, 2 pages.
Chinese Patent Office, Search Report (English Translation), Chinese Patent Application No. 201180039668.1, dated Jan. 3, 2014, 1 page.
Clark M.R., "IgG Effector Mechanisms," *Chemical Immunology*, 1997, vol. 65, pp. 88-110.
Corbett S.J., et al., "Sequence of the Human Immunoglobulin Diversity (D) Segment Locus: A Systematic Analysis Provides No Evidence for the Use of DIR Segments, Inverted D Segments, "Minor" D Segments or D-D Recombination," *Journal of Molecular Biology*, 1997, vol. 270 (4), pp. 587-597.
Crouch E.E., et al., "Regulation of AID expression in the Immune Response," *Journal of Experimental Medicine*, 2007, vol. 204 (5), pp. 1145-1156.
Davies N.P., et al., "Creation of Mice Expressing Human Antibody Light Chains by Introduction of a Yeast Artificial Chromosome Containing the Core Region of the Human Immunoglobulin κ Locus," *Nature Biotechnology*, 1993, vol. 11 (8), pp. 911-914.
De Bono B., et al., "$V_H$ Gene Segments in the Mouse and Human Genomes," *Journal of Molecular Biology*, 2004, vol. 342 (1), pp. 131-143.
De Wildt R.M. et al., "Analysis of Heavy and Light Chain Pairings Indicates that Receptor Editing Shapes the Human Antibody Repertoire," *Journal of Molecular Biology*, 1999, vol. 285, pp. 895-901.
Declerck P. et al., "Generation of Monoclonal Antibodies against autologous Proteins in Gene-inactivated Mice," *The Journal of Biological Chemistry*, Apr. 1995, vol. 270 (15), pp. 8397-8400.
Deftos, M., et al., "Defining the Genetic Origins of Three Rheumatoid Synovium-derived IgG Rheumatoid Factors," *Journal of Clinical Investigations*, Jun. 1994, vol. 93, pp. 2545-2553.
Deng C., et al., "Reexamination of Gene Targeting Frequency as a Function of the Extent of Homology Between the Targeting Vector and the Target Locus," *Molecular and Cellular Biology*, 1992, vol. 12 (8), pp. 3365-3371.
Ebert A., et al., "The Distal $V_H$ Gene Cluster of the Igh Locus Contains Distinct Regulatory Elements with Pax5 Transcription Factor-Dependent Activity in Pro-B Cells," *Immunity*, 2011, vol. 34 (2), pp. 175-187.
Edwards D.R., et al., "The ADAM Metalloproteinases," *Molecular Aspects of Medicine*, 2008, vol. 29 (5), pp. 258-289.
European Patent Office, Alessando Brero, Authorized officer, International Search Report for Application No. PCT/GB2012/052297, dated Jun. 19, 2013, 24 pages, together with the Written Opinion of the International Searching Authority.
European Patent Office, Alessandro Brero, Authorized Officer, International Search Report for Application No. PCT/GB2012/052298, dated Jun. 13, 2013, 21 pages, together with the Written Opinion of the International Searching Authority.
European Patent Office, Examination Report for Application No. 12762378.3, dated Jun. 8, 2016, 5 pages.
European Patent Office, Extended European Search Report for Application No. 16189625.3, dated Nov. 23, 2016, 8 pages.
European Patent Office, Alessandro Brero, Authorized officer, International Search Report for Application No. PCT/GB2012/052296, dated May 17, 2013, 30 pages, together with the Written Opinion of the International Searching Authority.
European Patent Office, Communication pursuant to Rule 114(2) EPC regarding 14772198.9, dated Mar. 30, 2016, 16 pages.
European Patent Office, European Search Report for Application No. 12194977.0, dated Jul. 5, 2013, 4 pages.
European Patent Office, Extended European Search Report for Application No. 12171791.2, dated Jun. 18, 2013, 5 pages.
European Patent Office, Extended European Search Report for Application No. 12171793.8 dated Jun. 21, 2013, 8 pages.
European Patent Office, Extended European Search Report for Application No. 12194970.5, dated Jan. 23, 2013, 9 pages.
European Patent Office, Extended European Search Report for Application No. 12194977.0, dated Jul. 17, 2013, 8 pages.
European Patent Office, Extended European Search Report for Application No. 12195041.4, dated Nov. 18, 2013, 8 pages.
European Patent Office, Extended European Search Report for Application No. 14170196.1, dated Oct. 8, 2014, 8 pages.
European Patent Office, Extended European Search Report for Application No. 14176740.0, dated Oct. 15, 2014, 7 pages.
European Patent Office, Extended European Search Report for Application No. 15188522.5 dated Feb. 2, 2016, 15 pages.
European Patent Office, F. Chambonnet, Authorized officer, International Search Report for Application No. PCT/GB2012/052380, dated Jan. 3, 2013, 17 pages, together with the Written Opinion of the International Searching Authority.
European Patent Office, Gaby Brouns, Authorized officer, International Search Report for Application No. PCT/GB2012/052956, dated Mar. 1, 2013, 14 pages, together with the Written Opinion of the International Searching Authority.
European Patent Office, Gaby Brouns, Authorized officer, International Search Report for Application No. PCT/GB2012/052960, dated Apr. 29, 2013, 19 pages, together with the Written Opinion of the International Searching Authority.
European Patent Office, Gaby Brouns, Authorized officer, International Search Report for Application No. PCT/GB2013/050682, dated Sep. 25, 2013, 16 pages, together with the Written Opinion of the International Searching Authority.
European Patent Office, Gaby Brouns, Authorized officer, International Search Report for Application No. PCT/GB2013/050683, dated Jul. 9, 2013, 11 pages, together with the Written Opinion of the International Searching Authority.
European Patent Office, Gaby Brouns, Authorized officer, International Search Report for Application No. PCT/GB2013/051280, dated Nov. 15, 2013, 19 pages, together with the Written Opinion of the International Searching Authority.
European Patent Office, Examination Report for Application No. 12795841.1, dated Feb. 12, 2016, 5 pages.

(56) References Cited

OTHER PUBLICATIONS

European Patent Office, Examination Report for Application No. 13711119.1, dated Dec. 17, 2015, 6 pages.
European Patent Office, Examination Report for Application No. 13711119.1, dated Jul. 13, 2016, 6 pages.
European Patent Office, International Searching Authority, Examiners Report on Allowable Claims for Application No. PCT/GB2010/051122, dated Jan. 2004, 1 page.
European Patent Office, Examination Report for Application No. 12778780.2, dated Oct. 14, 2016, 3 pages.
European Patent Office, Extended European Search Report for Application No. 14196645.7, dated Jun. 26, 2015, 12 pages.
European Patent Office, Julien Landré, Authorized officer, International Search Report for Application No. PCT/GB2012/052670, dated Feb. 14, 2013, 12 pages, together with the Written Opinion of the International Searching Authority.
European Patent Office, Laurent Deleu, Authorized Officer, International Preliminary Report on Patentability Chapter II for Application No. PCT/GB2010/051122, date of completion Nov. 2, 2011, 33 pages.
European Patent Office, Laurent Deleu, Authorized officer, International Search Report for Application No. PCT/GB2010/051122, dated Sep. 29, 2010, 9 pages, together with the Written Opinion of the International Searching Authority.
European Patent Office, Laurent Deleu, Authorized officer, International Search Report for Application No. PCT/GB2011/050019, dated May 16, 2011, 12 pages, together with the Written Opinion of the International Searching Authority.
European Patent Office, Examination Report for Application No. 12194970.5, dated Sep. 23, 2013, 6 pages.
European Patent Office, Examination Report for Application No. 14176740.0, dated Jun. 6, 2016, 5 pages.
European Patent Office, Examination Report for Application No. 14176740.0, dated Oct. 23, 2015, 5 pages.
European Patent Office, Notice of opposition to a European patent, pertaining to Application No. 10734546.4, dated Jan. 23, 2013, 41 pages.
European Patent Office, Opposition against EP2421357 Animal Models and Therapeutic Molecules in the name of Kyrnab Limited pertaining to Application No. 10734546.4, dated Oct. 23, 2013, 44 pages.
European Patent Office, Statement of Fact and Arguments in Support of Opposition pertaining to Application No. 10734546.4, dated Oct. 22, 2013, 41 pages.
European Patent Office, Invitation to Pay Additional Fees and, Where Applicable, Protest Fee, Application No. PCT/GB2012/052296, mailed on Jan. 24, 2013, 9 pages.
Feng Y.Q., et al., "Site-Specific Chromosomal Integration in Mammalian Cells: Highly Efficient CRE Recombinase-Mediated Cassette Exchange," *Journal of Molecular Biology*, 1999, vol. 292 (4), pp. 779-785.
Fleischer B., et al., "Reactivity of Mouse T-Cell Hybridomas Expressing Human Vβ Gene Segments With Staphylococcal and Streptococcal Superantigens," *Infection and Immunity*, Mar. 1996, vol. 64 (3), pp. 987-994.
Friedrich G., Statement of Dr. Glenn Friedrich, Mar. 3, 2016, 4 pages.
Fujieda S., et al., "Multiple Types of Chimeric Germ-Line Ig Heavy Chain Transcripts in Human B Cells: Evidence for Trans-Splicing of Human Ig RNA," *Journal of Immunology*, 1996, vol. 157 (8), pp. 3450-3459.
Gallo M.L., et al., "The Human Immunoglobulin Loci Introduced into Mice: V (D) and J Gene Segment Usage Similar to that of Adult Humans," *European Journal of Immunology*, 2000, vol. 30 (2), pp. 534-540.
Gama Sosa M.A., et al., "Animal Transgenesis: An Overview," *Brain Structure and Function*, 2010, vol. 214 (2-3), pp. 91-109.
Gavilondo J.V., et al., "Antibody Engineering at the Millennium," *BioTechniques*, 2000, vol. 29 (1), pp. 128-145.

Genbank (D. Muzny et al.), "Rattus norvegicus clone CH230-30N12, * Sequencing in Progress *, 6 unordered pieces," Accession No. AC111740, Nov. 9, 2002, 24 pages. [Retrieved from the Internet: http://www.ncbi.nlm.nih.gov/nuccore/AC111740 on Feb. 28, 2013].
Genbank, "DNA Sequence of the Human Immunoglobulin D Segment Locus," Accession No. x97051.1 S64822, Aug. 6, 2014, 29 pages. (URL: http://www.ncbi.nlm.nih.gov/nuccore/X97051).
Genbank, "DNA Sequence of the Human Immunoglobulin D Segment Locus," Accession No. x97051.1 S64822, updated Mar. 3, 2015, 26 pages.
Genbank, "*Homo sapiens* immunoglobulin heavy-chain (IGHV2-5) gene, IGHV2-5*10 allele, partial sequence," Accession No. KF698731.1, dated Nov. 18, 2013, 1 page.
Genbank, "Mus musculus strain 129S1/SvImJ chromosome 12 genomic sca locus group 129S1/SvImJ_MMCHR12_CTG1," NCBI Reference Sequence No. NT_114985.3, dated May 5, 2014, 1 page.
Giallourakis C.C., et al., "Elements Between the IgH Variable (V) and Diversity (D) Clusters Influence Antisense Transcription and Lineage-Specific V(D)J Recombination," *Proceedings of the National Academy of Sciences of the U.S.A.*, 2010, vol. 107 (51), pp. 22207-22212.
Giraldo P., et al., "Size Matters: Use of YACs, BACs and PACs in Transgenic Animals," *Transgenic Research*, 2001, vol. 10 (2), pp. 83-103.
Giusti A.M., et al., "Hypermutation is Observed only in Antibody H Chain V Region Transgenes that have Recombined with Endogenous Immunoglobulin H DNA: Implications for the Location of cis-Acting Elements Required for Somatic Mutation," *The Journal of Experimental Medicine*, Mar. 1993, vol. 177 (3), pp. 797-809.
Glanville J., et al., "Naive Antibody Gene-Segment Frequencies are Heritable and Unaltered by Chronic Lymphocyte Ablation," *Proceedings of the National Academy of Sciences of the U.S.A*, 2011, vol. 108 (50), pp. 20066-20071.
Glaser S. et al., "Current issues in mouse genome engineering," *Nature Genetics*, Nov. 2005, Vo. 37 (11), pp. 1187-1193.
Goldman I.L., et al., "Transgenic Animals in Medicine: Integration and Expression of Foreign Genes, Theoretical and Applied Aspects," *Medical Science Monitor*, 2004, vol. 10 (11), pp. RA274-RA285.
Gratz S. et al., "Genome Engineering of *Drosophila* with the CRISPR RNA-Guided Cas9 Nuclease," *Genetics*, Aug. 2013, vol. 194, pp. 1029-1035.
Green L.L., et al., "Antigen-Specific Human Monoclonal Antibodies from Mice Engineered with Human Ig Heavy and Light Chain YACs," *Nature Genetics*, 1994, vol. 7 (1), pp. 13-21.
Green L.L., et al., "Regulation of B Cell Development by Variable Gene Complexity in Mice Reconstituted with Human Immunoglobulin Yeast Artificial Chromosomes," *The Journal of Experimental Medicine*, 1998, vol. 188 (3), pp. 483-495.
Grund M., European Patent Attorney, Grund Intellectual Property Group, Third-Party Observations according to Article 115 EPC regarding 11705964.2, dated Apr. 30, 2014, 4 pages.
Grund M., European Patent Attorney, Grund Intellectual Property Group, Third-Party Observations according to Article 115 EPC regarding 11705964.2, dated Aug. 5, 2016, 11 pages.
Grund M., European Patent Attorney, Grund Intellectual Property Group, Third-Party Observations according to Article 115 EPC regarding 11705964.2, dated Oct. 9, 2013, 8 pages.
Grund M., European Patent Attorney, Grund Intellectual Property Group, Third-Party Observations according to Article 115 EPC regarding 12171791.2, dated Aug. 4, 2014, 6 pages.
Grund M., European Patent Attorney, Grund Intellectual Property Group, Third-Party Observations according to Article 115 EPC regarding 12171791.2, dated Dec. 19, 2014, 7 pages.
Grund M., European Patent Attorney, Grund Intellectual Property Group, Third-Party Observations according to Article 115 EPC regarding 12171791.2, dated Feb. 26, 2014, 9 pages.
Grund M., European Patent Attorney, Grund Intellectual Property Group, Third-Party Observations according to Article 115 EPC regarding 12171793.8, dated Jun. 25, 2014, 7 pages.

(56) References Cited

OTHER PUBLICATIONS

Grund M., European Patent Attorney, Grund Intellectual Property Group, Third-Party Observations according to Article 115 EPC regarding 12194970.5, dated Apr. 25, 2014, 6 pages.
Grund M., European Patent Attorney, Grund Intellectual Property Group, Third-Party Observations according to Article 115 EPC regarding 12194970.5, dated Aug. 12, 2014, 5 pages.
Grund M., European Patent Attorney, Grund Intellectual Property Group, Third-Party Observations according to Article 115 EPC regarding 12194970.5, dated Mar. 5, 2014, 9 pages.
Grund M., European Patent Attorney, Grund Intellectual Property Group, Third-Party Observations according to Article 115 EPC regarding 12194970.5, dated Nov. 15, 2013, 6 pages.
Grund M., European Patent Attorney, Grund Intellectual Property Group, Third-Party Observations according to Article 115 EPC regarding 12194970.5, dated Sep. 9, 2013, 11 pages.
Grund M., European Patent Attorney, Grund Intellectual Property Group, Third-Party Observations according to Article 115 EPC regarding 12194977.0, dated May 12, 2015, 5 pages.
Grund M., European Patent Attorney, Grund Intellectual Property Group, Third-Party Observations according to Article 115 EPC regarding 12762377.5, dated Feb. 12, 2016, 8 pages.
Grund M., European Patent Attorney, Grund Intellectual Property Group, Third-Party Observations according to Article 115 EPC regarding 12762377.5, dated May 22, 2015, 7 pages.
Grund M., European Patent Attorney, Grund Intellectual Property Group, Third-Party Observations according to Article 115 EPC regarding 12772122.3, dated Mar. 12, 2015, 5 pages.
Grund M., European Patent Attorney, Grund Intellectual Property Group, Third-Party Observations according to Article 115 EPC regarding 12772122.3, dated May 17, 2016, 7 pages.
Grund M., European Patent Attorney, Grund Intellectual Property Group, Third-Party Observations according to Article 115 EPC regarding 12795606.8, dated Aug. 22, 2014, 8 pages.
Grund M., European Patent Attorney, Grund Intellectual Property Group, Third-Party Observations according to Article 115 EPC regarding 12795606.8, dated Feb. 26, 2014, 6 pages.
Grund M., European Patent Attorney, Grund Intellectual Property Group, Third-Party Observations according to Article 115 EPC regarding 12795606.8, dated Mar. 26, 2015, 4 pages.
Grund M., European Patent Attorney, Grund Intellectual Property Group, Third-Party Observations according to Article 115 EPC regarding 13711119.1, dated Dec. 9, 2015, 7 pages.
Grund M., European Patent Attorney, Grund Intellectual Property Group, Third-Party Observations according to Article 115 EPC regarding 13711119.1, dated Jul. 5, 2016, 7 pages.
Grund M., European Patent Attorney, Grund Intellectual Property Group, Third-Party Observations according to Article 115 EPC regarding 13711120.9, dated May 17, 2016, 11 pages.
Grund M., European Patent Attorney, Grund Intellectual Property Group, Third-Party Observations according to Article 115 EPC regarding 14176740.0, dated Aug. 10, 2015, 13 pages.
Grund M., European Patent Attorney, Grund Intellectual Property Group, Third-Party Observations according to Article 115 EPC regarding 14176740.0, dated Nov. 2, 2016, 4 pages.
Grund M., European Patent Attorney, Grund Intellectual Property Group, Third-Party Observations according to Article 115 EPC regarding EP12194977.0, dated Mar. 26, 2014, 4 pages.
Grund M., European Patent Attorney, Grund Intellectual Property Group, Third-Party Observations regarding Application No. PCT/GB2012/052297, dated Jan. 17, 2014, 3 pages.
Grund M., European Patent Attorney, Grund Intellectual Property Group, Third-Party Observations regarding Application No. PCT/GB2012/052298, dated Jan. 17, 2014, 4 pages.
Grund M., European Patent Attorney, Grund Intellectual Property Group, Third-Party Observations regarding Application No. PCT/GB2012/052380, dated Jan. 24, 2014, 4 pages.
Grund M., European Patent Attorney, Grund Intellectual Property Group, Third-Party Observations regarding Application No. PCT/GB2012/052956, dated Mar. 26, 2014, 2 pages.
Grund M., European Patent Attorney, Grund Intellectual Property Group, Third-Party Observations regarding Application No. PCT/GB2012/052960, dated Apr. 2, 2014, 3 pages.
Grund M., European Patent Attorney, Grund Intellectual Property Group, Third-Party Observations regarding Application No. PCT/GB2013/050682, dated Jul. 28, 2014, 3 pages.
Grund M., European Patent Attorney, Grund Intellectual Property Group, Third-Party Observations regarding Application No. PCT/US2012/026416, dated Jun. 6, 2013, 2 pages.
Grund M., European Patent Attorney, Grund Intellectual Property Group, Third-Party Observations regarding PCT/GB2013/050683, dated Jul. 28, 2014, 2 pages.
Grund M., European Patent Attorney, Grund Intellectual Property Group, Third-Party Observations according to Article 115 EPC regarding 11705964.2, dated Feb. 26, 2015, 5 pages.
Guan C. et al., "A Review of Current Large-Scale Mouse Knockout Efforts," *Genesis*, vol. 48, 2010, pp. 73-85.
Guirouilh-Barbat J. et al., "Is homologous recombination really an error-free process?", *Frontiers in Genetics*, Jun. 2014, vol. 5 (175), 15 pages.
Guo, Y., et al., "A Preliminary Analysis of the Immunoglobulin Genes in the African Elephant (*Loxodonta Africana*)," *PLOS ONE*, Feb. 2011, vol. 6 (2), pp. e16889-1-e16889-14.
Hamers-Caterman C. et al., "Naturally occurring antibodies devoid of light chains," *Nature*, Jun. 1993, vol. 363, pp. 446-448.
Harding F.A., et al., "Class Switching in Human Immunoglobulin Transgenic Mice," *Annals of the New York Academy of Sciences*, 1995, vol. 764, pp. 536-546.
Hendricks J., et al., "Organization of the Variable Region of the Immunoglobulin Heavy-Chain Gene Locus of the Rat," *Immunogenetics*, 2010, vol. 62 (7), pp. 479-486.
Herschbach Jarrell B., Third-Party Pre-Issuance Submission Under 37 CFR Section 1.290 in U.S. Appl. No. 14/052,259, dated Aug. 6, 2014, 7 pages.
Hewitt S.L., et al., "Association between the lgk and lgh immunoglobulin loci mediated by the 3' lgk Enhancer Induces 'decontraction' of the lgh locus in pre-B cells," *Nature Immunology*, 2008, vol. 9 (4), pp. 396-404.
Houdebine L.M., "The Methods to Generate Transgenic Animals and to Control Transgene Expression," *Journal of Biotechnology*, 2002, vol. 98 (2-3), pp. 145-160.
Houdebine L.M., "Transgenic Animal Models in Biomedical Research," *Methods in Molecular Biology*, Chapter 10, 2007, vol. 360, pp. 163-202.
Houldsworth J., et al., "Comparative Genomic Hybridization: An Overview," *The American Journal of Pathology*, 1994, vol. 145 (6), pp. 1253-1260.
Hsu E., et al., "The plasticity of immunoglobulin gene systems in evolution," *Immunology Reviews*, vol. 210, Apr. 2006, pp. 8-26.
Huang, D., et al., "Sequence Analyses of Three Immunoglobulin G Anti-virus Antibodies Reveal Their Utilization of Autoantibody-related Immunoglobulin Vh Genes, but Not Vλ Genes," *Journal of Clinical Investigations*, Dec. 1992, vol. 90, pp. 2197-2208.
Huber V.C. et al., "Distinct Contributions of Vaccine-Induced Immunoglobulin G1 (IgG1) and IgG2a Antibodies to Protective Immunity Against Influenza," *Clinical and Vaccine Immunology*, 2006, vol. 13 (9), pp. 981-990.
Jakobovits A., "Production of Fully Human Antibodies by Transgenic Mice," *Current Opinion in Biotechnology*, 1995, vol. 6 (5), pp. 561-566.
Jakobovits A., "The Long-Awaited Magic Bullets: Therapeutic Human Monoclonal Antibodies from Transgenic Mice," *Expert Opinion Investigational Drugs*, 1998, vol. 7 (4), pp. 607-614.
Janeway C.A. et al., "The rearrangement of antigen-receptor gene segments controls lymphocyte development," *Immunobiology: The Immune System in Health and Disease*, 5th Edition, Aug. 2015, 13 pages. [Retrieved from the Internet: http://www.ncbi.nlm.nih.gov/books/NBK27113/].
Janeway et al., "Structural Variation in Immunoglobulin Constant Regions," *Immunobiology: The Immune System in Health and Disease*, 5th Edition, 2001, 5 pages.

(56) References Cited

OTHER PUBLICATIONS

Jasper, P.J., et al., "B lymphocyte deficiency in IgH-transgenic rabbits," *European Journal of Immunology*, 2007, vol. 37, pp. 2290-2299.

Jessen K.A., et al., "Molecular Analysis of Metastasis in a Polyomavirus Middle T Mouse Model: the Role of Osteopontin," *Breast Cancer Research*, 2004, vol. 6 (3), pp. R157-R169.

Johnston C.M., et al., "Complete Sequence Assembly and Characterization of the C57BL/6 Mouse Ig Heavy Chain V Region," *The Journal of Immunology*, 2006, vol. 176 (7), pp. 4221-4234.

Jones, Brendan T., Attorney for Applicant, Third-Party Pre-Issuance Submission Under 37 CFR Sec. 1.290 in U.S. Appl. No. 15/016,211, 59 pages, dated Oct. 4, 2016.

Jones, Brendan T., Attorney for Applicant, Third-Party Pre-Issuance Submission Under 37 CFR Sec. 1.290 in U.S. Appl. No. 15/018,670, 26 pages, dated Aug. 12, 2016.

Jones, Brendan T., Attorney for Applicant, Third-Party Pre-Issuance Submission Under 37 CFR Sec. 1.290 in U.S. Appl. No. 15/095,315, 26 pages, dated Sep. 16, 2016.

Karu A.E., et al., "Recombinant Antibody Technolgy," *ILAR Journal / National Research Council, Institute of Laboratory Animal Resources*, 1995, vol. 37 (3), pp. 132-141.

Kaushik A., et al., "Novel Insight into Antibody Diversification from Cattle," *Veterinary Immunology and Immunopathology*, 2002, vol. 87 (3-4), pp. 347-350.

Kenter A.L., et al., "Three-Dimensional Architecture of the IgH Locus Facilitates Class Switch Recombination," *Annals of the New York Academy of Sciences*, 2012, vol. 1267, pp. 86-94.

Kim T., et al., "Expression and Relationship of Male Reproductive ADAMs in Mouse," *Biology of Reproduction*, 2006, vol. 74 (4), pp. 744-750.

Kindt T.J. et al., "Organization and Expression of Immunoglobulin Genes," Chapter 5, *Immunology*, Sixth edition, 2007 (36 pages, including cover sheet and copyright page), pp. 111-144.

Kondo S., "Highly improved Gene Targeting by Germline-Specific Cas9 Expression in *Drosophila*," *Genetics*, vol. 195, Nov. 2013, pp. 715-721.

Kondo S., "Highly improved Gene Targeting by Germline-Specific Cas9 Expression in *Drosophila*," *Genetics*, vol. 195, Nov. 2013, pp. 715-721 (Abstract).

Kouskoff V., et al., "Cassette Vectors Directing Expression of T Cell Receptor Genes in Transgenic Mice," *Journal of Immunological Methods*, 1995, vol. 180 (2), pp. 273-280.

Kuraoka M., et al., "AID Expression During B-Cell Development: Searching for Answers," *Immunologic Research*, 2011, vol. 49 (1-3), pp. 3-13.

Kuzin I.I. et al, "Requirement for enhancer specificity in immunoglobulin heavy chain locus regulation," *Journal of Immunology*, Jun. 2008, vol. 180 (11), pp. 7443-7450.

Laffleur B., et al., "Production of Human or Humanized Antibodies in Mice," Chapter 9, *Methods in Molecular Biology*, 2012, vol. 901, pp. 149-159.

Largaespada D.A., "Transposon Mutagenesis in Mice," *Methods in Molecular Biology*, vol. 530, 2009, pp. 379-390.

Lee E.C., et al., "Complete Humanization of the Mouse Immunoglobulin Loci Enables Efficient Therapeutic Antibody Discovery," *Nature Biotechnology*, 2014, vol. 32 (4), pp. 356-363.

Lee E.C., et al., "The Application of Transgenic Mice for Therapeutic Antibody Discovery," *Methods in Molecular Biology*, Chapter 8, 2012, vol. 901, pp. 137-148.

Lefranc M., Appendix 1P, Abbreviations and Useful Data, "Nomenclature of the Human Immunoglobulin Genes," *Current Protocols in Immunology*, 2000, Supp. 40, pp. A.1P.1-A.1P.37.

Lefranc M.P. et al., "Immunoglobulin Lambda (IGL) Genes of Human and Mouse," *Molecular Biology of B Cells*, Chapter 4, p. 47, 2004 (Edtrs. Honjo et al.).

Lefranc M.P., et al., "IGHJ group," *The Immunoglobulin FactsBook*, IMGT, the international ImMunoGeneTics database, May 2001, 4 pages (including cover sheet and copyright pages).

Lefranc M.P., et al., Excerpts from "The Immunoglobulin FactsBook," IMGT, the international ImMunoGeneTics database, May 2001, 455 pages.

Lefranc M.P., "Nomenclature of the Human Immunoglobulin Heavy (IGH) Genes," *Experimental and Clinical Immunogenetics*, 2001, vol. 18 (2), pp. 100-116.

Lefranc M.P., "Nomenclature of the Human Immunoglobulin Kappa (IGK) Genes," *Experimental and Clinical Immunogenetics*, 2001, vol. 18 (3), pp. 161-174.

Lefranc M.P., "Nomenclature of the Human Immunoglobulin Lambda (IGL) Genes," *Experimental and Clinical Immunogenetics*, 2001, vol. 18 (4), pp. 242-254.

Levin A.M. et al., "Optimizing the affinity and specificity of proteins with molecular display," *Molecular Biosystems*, 2006, vol. 2, pp. 49-57.

Li H., et al., "Genetic Diversity of the Human Immunoglobulin Heavy Chain $V_H$ Region," Immunological Reviews, Dec. 2002, vol. 190, pp. 53-68.

Li M., Second Declaration of Dr. Meng (Amy) Li, dated Sep. 5, 2016, 2 pages.

Liang Q. et al., "Extensive genomic copy number variation in embryonic stem cells," *Proceedings of the National Academy of Sciences of the U.S.A.*, Nov. 2008, vol. 105 (45), pp. 17453-17456.

Little M., et al., "Generation of a Large Complex Antibody Library from Multiple Donors," *Journal of Immunological Methods*, 1999, vol. 231 (1-2), pp. 3-9.

Lonberg N., "Fully Human Antibodies from Transgenic Mouse and Phage Display Platforms," *Current Opinion in Immunology*, 2008, vol. 20 (4), pp. 450-459.

Lyon C., Attorney for Applicant, Third-Party Pre-Issuance Submission Under 37 CFR Sec. 1.290 in U.S. Appl. No. 14/056,700, dated Nov. 28, 2014, 6 pages.

Lyon C., Attorney for Applicant, Third-Party Pre-Issuance Submission Under 37 CFR Sec. 1.290 in U.S. Appl. No. 14/056,707, dated Nov. 28, 2014, 10 pages.

Lyon C., Attorney for Applicant, Third-Party Pre-Issuance Submission Under 37 CFR Sec. 1.290 in U.S. Appl. No. 13/846,672, dated Mar. 17, 2015, 32 pages.

Lyon C., Attorney for Applicant, Third-Party Pre-Issuance Submission Under 37 CFR Sec. 1.290 in U.S. Appl. No. 13/875,892, dated May 5, 2015, 49 pages.

Lyon C., Attorney for Applicant, Third-Party Pre-Issuance Submission Under 37 CFR Sec. 1.290 in U.S. Appl. No. 13/886,511, dated May 5, 2015, 18 pages.

Lyon C., Attorney for Applicant, Third-Party Pre-Issuance Submission Under 37 CFR Sec. 1.290 in U.S. Appl. No. 14/040,405, dated Jan. 16, 2015, 18 pages.

Lyon C., Attorney for Applicant, Third-Party Pre-Issuance Submission Under 37 CFR Sec. 1.290 in U.S. Appl. No. 14/040,427, dated Jan. 16, 2015, 20 pages.

Lyon C., Attorney for Applicant, Third-Party Pre-Issuance Submission Under 37 CFR Sec. 1.290 in U.S. Appl. No. 14/056,434, dated Dec. 15, 2014, 6 pages.

Lyon C., Attorney for Applicant, Third-Party Pre-Issuance Submission Under 37 CFR Sec. 1.290 in U.S. Appl. No. 14/080,630, dated Oct. 31, 2014, 8 pages.

Lyon C., Attorney for Applicant, Third-Party Pre-Issuance Submission Under 37 CFR Sec. 1.290 in U.S. Appl. No. 14/137,902, dated Nov. 13, 2014, 9 pages.

Lyon C., Attorney for Applicant, Third-Party Pre-Issuance Submission Under 37 CFR Sec. 1.290 in U.S. Appl. No. 14/220,080, dated Jul. 28, 2015, 28 pages.

Lyon C., Attorney for Applicant, Third-Party Pre-Issuance Submission Under 37 CFR Sec. 1.290 in U.S. Appl. No. 14/220,095, dated Aug. 4, 2015, 19 pages.

Lyon C., Attorney for Applicant, Third-Party Pre-Issuance Submission Under 37 CFR Sec. 1.290 in U.S. Appl. No. 14/220,099, dated Apr. 29, 2015, 43 pages.

Lyon C., Attorney for Applicant, Third-Party Pre-Issuance Submission Under 37 CFR Sec. 1.290 in U.S. Appl. No. 14/226,706, dated Jul. 28, 2015, 53 pages.

(56) References Cited

OTHER PUBLICATIONS

Lyon C., Attorney for Applicant, Third-Party Pre-Issuance Submission Under 37 CFR Sec. 1.290 in U.S. Appl. No. 14/263,158, dated Apr. 29, 2015, 16 pages.
Lyon C., Attorney for Applicant, Third-Party Pre-Issuance Submission Under 37 CFR Sec. 1.290 in U.S. Appl. No. 14/263,176, dated Apr. 29, 2015, 16 pages.
Lyon C., Attorney for Applicant, Third-Party Pre-Issuance Submission Under 37 CFR Sec. 1.290 in U.S. Appl. No. 14/497,054, dated Oct. 21, 2015, 81 pages.
Lyon C., Attorney for Applicant, Third-Party Pre-Issuance Submission Under 37 CFR Sec. 1.290 in U.S. Appl. No. 14/498,685, dated Sep. 18, 2015, 37 pages.
Lyon C., Attorney for Applicant, Third-Party Pre-Issuance Submission Under 37 CFR Sec. 1.290 in U.S. Appl. No. 14/516,461, dated Aug. 4, 2015, 27 pages.
Lyon C., Attorney for Applicant, Third-Party Pre-Issuance Submission Under 37 CFR Sec. 1.290 in U.S. Appl. No. 14/543,359, dated Nov. 13, 2015, 36 pages.
Ma B., et al., "Human Antibody Expression in Transgenic Rats: Comparison of Chimeric IgH Loci with Human $V_H$, D and $J_H$ but Bearing Different Rat C-Gene Regions," Journal of Immunological Methods, 2013, vol. 400-401, pp. 78-86.
MacDonald L., Curriculum Vitae of Lynn E. MacDonald, Ph.D., 3 pages.
MacDonald L., Declaration of Lynn E. MacDonald with Exhibits, dated Feb. 3, 2015, 13 pages, relating to International Application No. PCT/US02/04500 (Published as WO02/066630 A1).
MacDonald L., Declaration of Lynne E. Macdonald, dated Jun. 29, 2016, 4 pages.
MacDonald L., et al., Expanded Poster: "Velocigene® Technology Extended to Humanization of Several Megabases of Complex," Sep. 2006, 6 pages.
MacDonald L., et al., Poster: "Velocigene® Technology Extended to Humanization of Several Megabases of Complex" and evidence of unavailability, Sep. 2006, 42 pages.
MacDonald L., et al., "Velocigene Technology Extended to Humanization of Several Megabases of Complex Gene Loci," (Abstract—21) 1st International MUGEN Conference on Animal Models for Human Immunological Disease, Athens Greece, Sep. 10-13, 2006, 1 page.
Magadán S., et al., "Production of Antigen-Specific Human Monoclonal Antibodies: Comparison of Mice Carrying IgH/$_\kappa$ or IgH/$_{\kappa/\lambda}$ Transloci," Biotechniques, Sep. 2002, vol. 33 (3), pp. 680, 682, 684 passim.
Marchalonis J.J. et al., "Emergence of the immunoglobulin family: conservation in protein sequence and plasticity in gene organization," Glycobiology, vol. 6, 1996, pp. 657-663.
Martinez-Jean C., et al., "Nomenclature and Overview of the Mouse (Mus musculus and Mus sp.) Immunoglobulin Kappa (IGK) Genes," Experimental and Clinical Immunogenetics, 2001, vol. 18 (4), pp. 255-279.
Matthews V.B., et al., "A Locus Affecting Immunoglobulin Isotype Selection (Igisl) Maps to the MHC Region in C57BL, BALB/c and NOD Mice," Immunology & Cell Biology, 2001, vol. 79 (6), pp. 576-582.
Mattila P.S., et al., "Extensive Allelic Sequence Variation in the J Region of the Human Immunoglobulin Heavy Chain Gene Locus," European Journal of Immunology, 1995, vol. 25 (9), pp. 2578-2582.
McMurry M.T., et al., "Enhancer Control of Local Accessibility to V(D)J Recombinase," Molecular and Cellular Biology, Aug. 1997, vol. 17 (8), pp. 4553-4561.
Mester G., European Patent Attorney, Grund Intellectual Property Group, Third-Party Observations according to Article 115 EPC regarding EP 12778780.2, dated Sep. 30, 2016, 5 pages.
Mills F., et al., "Enhancer Complexes Located Downstream of Both Human Immunoglobulin $C_\alpha$ Genes," The Journal of Experimental Medicine, Sep. 1997, vol. 186 (6), pp. 845-858.

Minaee S., et al., "Mapping and Functional Analysis of Regulatory Sequences in the Mouse λ5-VpreB1 Domain," Molecular Immunology, 2005, vol. 42 (11), pp. 1283-1292.
Müller U., "Ten Years of Gene Targeting: Targeted Mouse Mutants, from Vector Design to Phenotype Analysis," Mechanisms of Development, 1999, vol. 82 (1-2), pp. 3-21.
Moffatt S. et al., "PEGylated J591 mAb loaded in PLGA-PEG-PLGA tri-block copolymer for targeted delivery: In vitro evaluation in human prostate cancer cells," International Journal of Pharmaceutics, 2006, vol. 317, pp. 10-13.
Monaco A.P., et al., "YACs, BACs, PACs and MACs: Artificial Chromosomes as Research Tools," Trends in Biotechnology, Jul. 1994, vol. 12 (7), pp. 280-286.
Moran N., et al., "Mouse Platforms Jostle for Slice of Humanized Antibody Market," Nature Biotechnology, Apr. 2013, vol. 31 (4), pp. 267-268.
Munoz M. et al., "Constraints to Progress in Embryonic Stem Cells from Domestic Species," Stem Cell Review and Reports, 2009, vol. 5, pp. 6-9.
Murphy A., "Declaration of Andrew J. Murphy," including Slide Presentation dated Nov. 3, 2009, at Wellcome Trust Advanced Course: Genetic Manipulation of ES Cells, in Hirixton, UK, entitled "BAC-based Modifications of the Mouse Genome: The Big and the Backward," cited in an IDS in U.S. Appl. No. 14/192,051 of MacDonald et al., 62 pages, dated Oct. 6, 2014.
Murphy D., "BAC-based Modifications of the Mouse Genome: The Big and the Backward," The Advanced Course: Genetic Manipulation of ES Cells, dated Nov. 3, 2009, VP Target Discovery, Regeneron Pharmaceuticals, 58 pages.
Murphy et al., The Generation of Lymphocyte Antigen Receptors, Ch. 4, excerpt from Janeway's Immunobiology (including cover and copyright pages), Seventh edition, 2008, p. 158.
Muyrers J.P., et al., "Rapid Modification of Bacterial Artificial Chromosomes by ET-Recombination," Nucleic Acids Research, 1999, vol. 27 (6), pp. 1555-1557.
Narayanan K., et al., "Efficient and Precise Engineering of a 200 kb β-globin Human/Bacterial Artificial Chromosome in E. Coli DH10B using an Inducible Homologous Recombination System," Gene Therapy, 1999, vol. 6 (3), pp. 442-447.
Neuberger M.S., et al., "Isotype Exclusion and Transgene Down-Regulation in Immunoglobulin-λ Transgenic Mice," Nature, Mar. 1989, vol. 338 (6213), pp. 350-352.
Neuberger M.S., "Expression and regulation of immunoglobulin heavy chain gene transfected into lymphoid cells," The EMBO Journal, 1983, vol. 2 (8), pp. 1373-1378.
New Zealand Patent Office, Simon Maguire, Authorized Officer, Further Examination Report for Patent No. 623756, dated Sep. 9, 2015, 3 pages.
Ohm-Laursen L., et al., "Identification of Two New Alleles, IGHV3-23*04 and IGHJ6*04, and the Complete Sequence of the IGHV3-h Pseudogene in the Human Immunoglobulin Locus and their Prevalences in Danish Caucasians," Immunogenetics, 2005, vol. 57 (9), pp. 621-627.
Oumard A. et al., "Recommended method for chomosome exploitation: RMCE-based cassette-exchange systems in animal cell biotechnology," Cytotechnology, 2006, vol. 50, pp. 93-108.
Parng C.L., et al., "Gene Conversion Contributes to Ig Light Chain Diversity in Cattle," Journal of Immunology, 1996, vol. 157 (12), pp. 5478-5486.
Pear W.S., et al., "Localization of the Rat Immunoglobulin Heavy Chain Locus to Chromosome 6," Immunogenetics, 1986, vol. 23 (6), pp. 393-395.
Perez-Luz S. et al., "Factor VIII mRNA expression from a BAC carrying the intact locus made by homologous recombination," Genomics, 2007, vol. 90, pp. 610-619.
Pettersson S., et al., "A second B cell-specific enhancer 3' of the immunoglobulin heavy-chain locus," Nature, Mar. 1990, vol. 344, pp. 165-168.
Pobursky K., Third-Party Pre-Issuance Submission Under 37 CFR 1.290 in U.S. Appl. No. 13/843,528, dated Mar. 18, 2014, 14 pages.
Pobursky K., Third-Party Pre-Issuance Submission Under 37 CFR 1.290 in U.S. Appl. No. 13/433,084, dated Apr. 1, 2014, 15 pages.

(56) References Cited

OTHER PUBLICATIONS

Pobursky K., Third-Party Pre-Issuance Submission Under 37 CFR 1.290 in U.S. Appl. No. 13/434,361, dated Apr. 1, 2014, 15 pages.
Pobursky K., Third-Party Pre-Issuance Submission Under 37 CFR 1.290 in U.S. Appl. No. 13/740,727, dated May 27, 2014, 25 pages.
Presta L., "Molecular engineering and design of therapeutic antibodies," Current Opinion in Immunology, 2008, vol. 20, pp. 460-470.
Pruzina S., et al., "Human Monoclonal Antibodies to HIV-1 gp140 from Mice Bearing YAC-Based Human Immunoglobulin Transloci," Protein Engineering, Design & Selection, 2011, vol. 24 (10), pp. 791-799.
Qi N.R., et al., "A New Transgenic Rat Model of Hepatic Steatosis and the Metabolic Syndrome," Hypertension, 2005, vol. 45 (5), pp. 1004-1011.
Ramírez-Solis R., et al., "Chromosome Engineering in Mice," Nature, 1995, vol. 378 (6558), pp. 720-724.
Ramsden D.A., et al., "Conservation of Sequence in Recombination Signal Sequence Spacers," Nucleic Acids Research, 1994, vol. 22 (10), pp. 1785-1796.
Ray P., et al., "Ectopic Expression of a c-kit$^{W42}$ Minigene in Transgenic Mice: Recapitulation of W Phenotypes and Evidence for c-kit Function in Melanoblast Progenitors," Genes & Development, 1991, vol. 5 (12A), pp. 2265-2273.
Regeneron Pharmaceuticals, Inc., Press Release—"Astellas Licenses Regeneron's Velocimmune Technology for Discovering Human Monoclonal Antibodies," dated Mar. 30, 2007, 2 pages.
Regeneron Pharmaceuticals, Inc., Press Release—"AstraZeneca Licenses Regeneron's VelocImmune Technology for Discovering Human Monoclonal Antibodies—AstraZeneca Is First Licensee of Novel Velocimmune Technology License Fees Total up to $120 Million Over Six Years," Feb. 5, 2007, 2 pages.
Regeneron Pharmaceuticals, Inc., Press Release—"Regeneron Initiates Major Global Collaboration with Sanofi-aventis of Develop and Commercialize Fully-Human Therapeutic Antibodies," Nov. 29, 2007, 2 pages.
Ren S.Y., et al., "Targeted Insertion Results in a Rhombomere 2-Specific Hoxa2 Knockdown and Ectopic Activation of Hoxa1 Expression," Developmental Dynamics, 2002, vol. 225 (3), pp. 305-315.
Renaut L. et al., "Affinity Maturation of Antibodies: Optimized Methods to Generate High-Quality ScFv Libraries and Isolate IgG Candidates by High-Throughput Screening," Antibody Engineering: Methods and Protocols, Chapter 26, Second Edition, 2012, vol. 907, pp. 451-461.
Ricker M., European Patent Attorney, Opposition against EP2421357B1 in the name of Kymab Limited Statement of Facts and Arguments pertaining to Application No. 10734546.4, dated Oct. 23, 2013, 29 pages.
Ristevski S., "Making Better Transgenic Models: Conditional, Temporal, and Spatial Approaches," Molecular Biotechnology, 2005, vol. 29 (2), pp. 153-163.
Rosner K., et al., "Third Complementarity-Determining Region of Mutated $V_H$ Immunoglobulin Genes Contains Shorter V, D, J, P, and N Components than Non-Mutated Genes," Immunology, 2001, vol. 103 (2), pp. 179-187.
Rourke J., Declaration of Jeffrey Rourke, Registered Patent Attorney for Regeneron Pharmaceuticals, Inc.—In the matter of Patent Acceptance 2011266843 in the Name of Kymab Limited and in the Matter of Opposition thereto by Regeneron Pharmaceuticals, Inc., dated Jan. 29, 2016, 5 pages.
Rusk N., "Making Mice at High Speed," Nature Methods, Mar. 2007, vol. 4 (3), pp. 196-197.
Scapini P., et al., "Myeloid Cells, BAFF, and IFN-γ Establish an Inflammatory Loop that Exacerbates Autoimmunity in Lyn-Deficient Mice," The Journal of Experimental Medicine, Jul. 2010, vol. 207 (8), pp. 1757-1773.
Schonewald, S.L., Attorney for Applicant, Third-Party Pre-Issuance Submission Under 37 CFR Sec. 1.290 in U.S. Appl. No. 14/220,074, dated Jul. 12, 2016, 46 pages.
Schonewald, S.L., Attorney for Applicant, Third-Party Pre-Issuance Submission Under 37 CFR Sec. 1.290 in U.S. Appl. No. 14/750,870, dated Aug. 10, 2016, 34 pages.
Schonewald, S.L., Attorney for Applicant, Third-Party Pre-Issuance Submission Under 37 CFR Sec. 1.290 in U.S. Appl. No. 14/818,162, dated May 24, 2016, 47 pages.
Schroeder, Jr. H.W., "Similarity and divergence in the development and expression of the mouse and human antibody repertoires," Developmental and Comparative Immunology, vol. 30, 2006, pp. 119-135.
Seals D.F., et al., "The ADAMs Family of Metalloproteases: Multidomain Proteins with Multiple Functions," Genes & Development, 2003, vol. 17 (1), pp. 7-30.
Seidl K.J., et al., "An Expressed Neo$^r$ Cassette Provides Required Functions of the 1γ2b Exon for Class Switching," International Immunology, 1998, vol. 10 (11), pp. 1683-1692.
Seidl K.J., et al., "Position-Dependent Inhibition of Class-Switch Recombination by PGK-neo$^r$ Cassettes Inserted into the Immunoglobulin Heavy Chain Constant Region Locus," Proceedings of the National Academy of Sciences of the U.S.A., Mar. 1999, vol. 96 (6), pp. 3000-3005.
Sekiguchi J., et al., "The Mechanism of V(D)J Recombination," Molecular Biology of B Cells, Chapter 5, 2004, pp. 61-82.
Shi B., et al., "Comparative Analysis of Human and Mouse Immunoglobulin Variable Heavy Regions from IMGT/LIGM-DB with IMGT/HighV-QUEST," Theoretical Biology and Medical Modelling, 2014, vol. 11, pp. 1-11.
Shi Y.P., et al., "The Mapping of Transgenes by Fluorescence in Situ Hybridization on G-Banded Mouse Chromosomes," Mammalian Genome, 1994, vol. 5 (6), pp. 337-341.
Shin H., "Discovery Process for Antibody-Based Therapeutics," Development of Antibody-Based Therapeutics, Chapter 2, 2012, pp. 9-32.
Sigmund C.D., "Viewpoint: Are Studies in Genetically Altered Mice Out of Control?," Arteriosclerosis, Thrombosis, and Vascular Biology, Jun. 2000, vol. 20 (6), pp. 1425-1429.
Smith K.R., "Gene Transfer in Higher Animals: Theoretical Considerations and Key Concepts," Journal of Biotechnology, 2002, vol. 99 (1), pp. 1-22.
Sopher B. et al., "Efficient recombination-based methods for bacterial artificial chromosome fusion and mutagenesis," Gene, 2006, vol. 371, pp. 136-143.
Sorrell D.A. et al., "Targeted modification of mammalian genomes," Biotechnology Advances, vol. 23, 2005, pp. 431-469.
Soukharev S., et al., "Segmental Genomic Replacement in Embryonic Stem Cells by Double Lox Targeting," Nucleic Acids Research, 1999, vol. 27 (18), pp. e21.
Spanopoulou E., et al., "Functional Immunoglobulin Transgenes Guide Ordered B-Cell Differentiation in Rag-1-Deficient Mice," Genes & Development, 1994, vol. 8 (9), pp. 1030-1042.
Stavnezer J., et al., "Mechanism and Regulation of Class Switch Recombination," Annual Review of Immunology, 2008, vol. 26, pp. 261-292.
Stephen R., Kymab Limited Statement of Facts and Evidence in opposition to EP2550363, Olswang LLP, dated Sep. 10, 2015, 22 pages.
Stephen R., Olswang, Response to Examination Report dated Jun. 6, 2016 for EP Application No. 14176740.0 as filed with the European Patent Office on Oct. 10, 2016, 4 pages.
Stephen R., Olswang, Response to Search Report dated Oct. 15, 2014 for Application No. 14176740.0, as filed with the European Patent Office on May 12, 2015, 4 pages.
Stephen R., Olswang, Response to Third-Party Observations dated Aug. 10, 2015 and Examination Report dated Oct. 23, 2015 for Application No. 14176740.0, as filed with the European Patent Office on Apr. 23, 2016, 6 pages.
Stevens S., et al., Expanded Poster: "VelocImmune™: Humanization of immunoglobulin loci using VelociGene technology," Sep. 2006, 6 pages.
Stevens S., et al., Poster: "VelocImmuneTM: Humanization of immunoglobulin loci using VelociGene technology" and evidence of unavailability, Sep. 2006, 42 pages.

(56) References Cited

OTHER PUBLICATIONS

Stevens S. et al., "VelocImmune: Humanization of Immunoglobulin Loci Using Velocigene Technology," (Abstract—4) Presented at 1st International MUGEN Conference on Animal Models for Human Immunological Disease, Athens, Greece, Sep. 10-13, 2006, 1 page.
Suárez E., et al., "Rearrangement of Only One Human IGHV Gene is Sufficient to Generate a Wide Repertoire of Antigen Specific Antibody Responses in Transgenic Mice," *Molecular Immunology*, 2006, vol. 43 (11), pp. 1827-1835.
Takeda S., et al., "Construction of Chimaeric Processed Immunoglobulin Genes Containing Mouse Variable and Human Constant Region Sequences," *Nature*, Apr. 1985, vol. 314 (6010), pp. 452-454.
Tan L.K., et al., "A Human-Mouse Chimeric Immunoglobulin Gene with a Human Variable Region is Expressed in Mouse Myeloma Cells," *Journal of Immunology*, Nov. 1985, vol. 135 (5), pp. 3564-3567.
Tanimoto Y., et al., "Embryonic Stem Cells Derived from C57BL/6J and C57BL/6N Mice," *Comparative Medicine*, Aug. 2008, vol. 58 (4), pp. 347-352.
Taylor L.D., et al., "Human Immunoglobulin Transgenes Undergo Rearrangement, Somatic Mutation and Class Switching in Mice that Lack Endogenous IgM," *International Immunology*, 1994, vol. 6 (4), pp. 579-591.
The Jackson Laboratory, "Breeding Strategies for Maintaining Colonies of Laboratory Mice," *A Jackson Laboratory Resource Manual*, 2007, pp. 1-29.
Thykjaer T., et al., "Gene Targeting Approaches Using Positive-Negative Selection and Large Flanking Regions," *Plant Molecular Biology*, 1997, vol. 35 (4), pp. 523-530.
Tonegawa S., "Somatic Generation of Antibody Diversity," *Nature*, Apr. 1983, vol. 302 (5909), pp. 575-581.
Tuaillon N., et al., "Human immunoglobulin heavy-chain minilocus recombination in transgenic mice: Gene-segment use in μ and γ transcripts," *Proceedings of the National Academy of Sciences of the U.S.A.*, Apr. 1993, vol. 90, pp. 3720-3724.
Tucker P.W., et al., "Mouse IgA Heavy Chain Gene Sequence: Implications for Evolution of Immunoglobulin Hinge Axons," *Proceedings of the National Academy of Sciences*, Dec. 1981, vol. 78 (12), pp. 7684-7688.
United Kingdom Intellectual Property Office, Combined Search and Examination Report under Sections 17 and 18(3) for Application No. GB1317410.7, dated Nov. 21, 2013, 8 pages.
United Kingdom Intellectual Property Office, Combined Search and Examination Report under Sections 17 and 18(3) for Application No. GB1317447.9, dated Jan. 14, 2014, 7 pages.
United Kingdom Intellectual Property Office, Corrected Search Report Under Section 17 for Application No. GB1122047.2, dated Apr. 20, 2012, 5 pages.
United Kingdom Intellectual Property Office, Search Report under Section 17 for Application No. GB1116122.1, dated Feb. 2, 2012, 1 page.
Urquhart-Dykes & Lord LLP, Third-Party Observation for Application No. EP20140772198, dated Dec. 14, 2015, 8 pages.
USPTO, Excerpts from U.S. Appl. No. 14/682,859, filed Apr. 9, 2015, including Applicant-initiated Interview Summary; Amendments to the Claims and Information Disclosure Statement, 14 pages.
Van Der Weyden L. et al., "Mouse Chromosome Engineering for Modeling Human Disease," *Europe PMC Funders Group*, Author Manuscript, Dec. 2008, 32 pages.
Van Dijk M., Declaration of Marcus Van Dijk with exhibits, Apr. 30, 2016, 139 pages.
Van Loo, P.F., et al., "Surrogate-Light-Chain Silencing Is Not Critical for the Limitation of Pre-B Cell Expansion but Is for the Termination of Constitutive Signaling," *Immunity*, Sep. 2007, vol. 27, pp. 468-480.
Van Snick J.L., et al., "Genetic Control of Rheumatoid Factor Production in the Mouse. Role of Genes Linked to the Immunoglobulin Heavy Chain Locus and to the Major Histocompatibility Complex," *Arthritis and Rheumatism*, Sep. 1983, vol. 26 (9), pp. 1085-1090.
Vieira P. et al., "The half-lives of serum immunoglobulins in adult mice," *European Journal of Immunology*, 1988, vol. 18, pp. 313-316.
Vollmer J., et al., "Antigen Contacts by Ni-Reactive TCR: Typical αβ Chain Cooperation Versus Alpha Chain-Dominated Specificity," *International Immunology*, 2000, vol. 12 (12), pp. 1723-1731.
Wagner S.D., et al., "Antibodies Generated from Human Immunoglobulin Miniloci in Transgenic Mice," *Nucleic Acids Research*, 1994, vol. 22 (8), pp. 1389-1393.
Wasserman R., et al., "The Pattern of Joining ($J_H$) Gene Usage in the Human IgH Chain Is Established Predominantly at the B PreCursor Cell Stage," *The Journal of Immunology*, Jul. 1992, vol. 149 (2), pp. 511-516.
Waterhouse P., et al., "Combinatorial Infection and in vivo Recombination: a Strategy for Making Large Phage Antibody Repertoires," *Nucleic Acids Research*, 1993, vol. 21 (9), pp. 2265-2266.
Waterston R.H., et al., "Initial Sequencing and Comparative Analysis of the Mouse Genome," *Nature*, Dec. 2002, vol. 420 (6915), pp. 520-562.
Webpage corroborating non-confidential nature of 2006 MUGEN Conference, Athens (www.mugen.noe.org), accessed Aug. 9, 2016, 4 pages.
Weichhold G.M., et al., "Megabase Inversions in the Human Genome as Physiological Events," *Nature*, Sep. 1990, vol. 347 (6288), pp. 90-92.
Weichhold G.M., et al., "The Human Immunoglobulin κ Locus Consists of Two Copies that are Organized in Opposite Polarity," *Genomics*, 1993, vol. 16 (2), pp. 503-511.
Weiner L.M., "Fully Human Therapeutic Monoclonal Antibodies," *Journal of Immunology*, Jan./Feb. 2006, vol. 29 (1), pp. 1-9.
Wikipedia, "Monoclonal antibody," 2008, 8 pages.
Wikipedia, "Polyclonal antibodies," 2008, 5 pages.
Wilke K., et al., "Diagnosis of Haploidy and Triploidy Based on Measurement of Gene Copy Number by Real-Time PCR," *Human Mutation*, 2000, vol. 16 (5), pp. 431-436.
Williams K., Attorney for Applicant, Third-Party Pre-Issuance Submission Under 37 CFR 1.290 in U.S. Appl. No. 14/600,829, dated Apr. 1, 2016, 18 pages.
Williams K., Attorney for Applicant, Third-Party Pre-Issuance Submission Under 37 CFR 1.290 in U.S. Appl. No. 14/679,949, dated Apr. 1, 2016, 18 pages.
Wuerffel R., et al., "S—S Synapsis During Class Switch Recombination is Promoted by Distantly Located Transcriptional Elements and Activation-Induced Deaminase," *Immunity*, Nov. 2007, vol. 27 (5), pp. 711-722.
Xu Y., et al., "Deletion of the Igκ Light Chain Intronic Enhancer/Matrix Attachment Region Impairs but does not Abolish VκJκ a Rearrangement," *Immunity*, Apr. 1996, vol. 4 (4), pp. 377-385.
Yamada M., et al., "Preferential Utilization of Specific Immunoglobulin Heavy Chain Diversity and Joining Segments in Adult Human Peripheral Blood B Lymphocytes," *Journal of Experimental Medicine*, Feb. 1991, vol. 173, pp. 395-407.
Yang X.W., et al., "Homologous Recombination Based Modification in *Escherichia coli* and Germline Transmission in Transgenic Mice of a Bacterial Artificial Chromosome," *Nature Biotechnology*, Sep. 1997, vol. 15 (9), pp. 859-865.
Yu Y., et al., "Engineering Chromosomal Rearrangements in Mice," *Nature Reviews Genetics*, 2001, vol. 2 (10), pp. 780-790.
Zemlin M., et al., "Expressed Murine and Human CDR-H3 Intervals of Equal Length Exhibit Distinct Repertoires that Differ in their Amino Acid Composition and Predicted Range of Structures," *Journal of Molecular Biology*, 2003, vol. 334 (4), pp. 733-749.
Zhang X. et al., "Combination of overlapping bacterial artificial chromosones by a two-step recombinogenic engineering method," *Nucleic Acids Research*, 2003, vol. 31 (15), pp. e81-1-e81-6.
Zhang Y., et al., "A New Logic for DNA Engineering Using Recombination in *Escherichia coli*," *Nature Genetics*, 1998, vol. 20 (2), pp. 123-128.
Zhao S., "A Comprehensive BAC Resource," *Nucleic Acids Research*, 2001, vol. 29 (1), pp. 141-143.

(56) References Cited

OTHER PUBLICATIONS

Zhao Y. et al., "Physical Mapping of the Bovine Immunoglobulin Heavy Chain Constant Region Gene Locus," *Journal of Biological Chemistry*, Sep. 2003, vol. 278 (37), pp. 35024-35032.

Zheng J., et al., "Immunoglobulin Gene Transcripts Have distinctive $V_H DJ_H$ Recombination Characteristics in Human Epithelial Cancer Cells", *Journal of Biological Chemistry*, Mar. 2009, vol. 284 (20), pp. 13610-13619.

Zou X., et al., "Removal of the BiP-Retention Domain in Cμ Permits Surface Deposition and Developmental Progression Without L-Chain," *Molecular Immunology*, 2008, vol. 45 (13), pp. 3573-3579.

French Patent Office, INPI, Laurent Deleu, Authorized officer, International Search Report for Patent Application No. 1359518, dated Aug. 20, 2014, 3 pages.

Grund M., European Patent Attorney, Grund Intellectual Property Group, Third-Party Observations according to Article 115 EPC regarding 12195041.4, dated Jul. 30, 2014, 5 pages.

U.S. Appl. No. 09/552,219, filed Apr. 19, 2000, issued May 28, 2002 as U.S. Pat. No. 6,395,487.

U.S. Appl. No. 09/552,626, filed Apr. 19, 2000, issued Oct. 8, 2002 as U.S. Pat. No. 6,461,818.

U.S. Appl. No. 13/310,431, filed Dec. 2, 2011.

U.S. Appl. No. 13/416,684, filed Mar. 9, 2012, issued Sep. 20, 2016 as U.S. Pat. No. 9,447,177.

U.S. Appl. No. 13/433,084, filed Mar. 28, 2012, issued Sep. 20, 2016 as U.S. Pat. No. 9,445,581.

U.S. Appl. No. 13/434,361, filed Mar. 29, 2012, issued Feb. 9, 2016 as U.S. Pat. No. 9,253,965.

U.S. Appl. No. 13/740,727, filed Jan. 14, 2013, issued Nov. 29, 2016 as U.S. Pat. No. 9,505,827.

U.S. Appl. No. 13/846,672, filed Mar. 18, 2013.

U.S. Appl. No. 13/875,892, filed May 2, 2013.

U.S. Appl. No. 13/886,511, filed May 3, 2013.

U.S. Appl. No. 14/040,405, filed Sep. 27, 2013.

U.S. Appl. No. 14/040,427, filed Sep. 27, 2013.

U.S. Appl. No. 14/052,259, filed Oct. 11, 2013.

U.S. Appl. No. 14/056,434, filed Oct. 17, 2013.

U.S. Appl. No. 14/056,700, filed Oct. 17, 2013.

U.S. Appl. No. 14/056,707, filed Oct. 17, 2013.

U.S. Appl. No. 14/080,630, filed Nov. 14, 2013.

U.S. Appl. No. 14/137,902, filed Dec. 20, 2013, issued Sep. 6, 2016 as U.S. Pat. No. 9,434,782.

U.S. Appl. No. 14/220,074, filed Mar. 19, 2014.

U.S. Appl. No. 14/220,080, filed Mar. 19, 2014.

U.S. Appl. No. 14/220,095, filed Mar. 19, 2014.

U.S. Appl. No. 14/220,099, filed Mar. 19, 2014.

U.S. Appl. No. 14/226,706, filed Mar. 26, 2014.

U.S. Appl. No. 14/263,158, filed Apr. 28, 2014.

U.S. Appl. No. 14/263,176, filed Apr. 28, 2014.

U.S. Appl. No. 14/498,685, filed Sep. 26, 2014.

U.S. Appl. No. 14/497,054, filed Sep. 25, 2014.

U.S. Appl. No. 14/516,461, filed Oct. 16, 2014.

U.S. Appl. No. 14/543,359, filed Nov. 17, 2014.

U.S. Appl. No. 14/750,870, filed Jun. 25, 2015.

U.S. Appl. No. 14/818,162, filed Aug. 4, 2015.

U.S. Appl. No. 14/935,010, filed Nov. 6, 2015, issued Nov. 29, 2016 as U.S. Pat. No. 9,504,236.

U.S. Appl. No. 15/016,211, filed Feb. 4, 2016.

U.S. Appl. No. 15/018,670, filed Feb. 8, 2016.

U.S. Appl. No. 15/088,805, filed Apr. 1, 2016.

U.S. Appl. No. 15/095,315, filed Apr. 11, 2016.

U.S. Appl. No. 15/199,575, filed Jun. 30, 2016.

U.S. Appl. No. 15/214,963, filed Jul. 20, 2016.

U.S. Appl. No. 15/232,122, filed Aug. 9, 2016.

U.S. Appl. No. 15/251,969, filed Aug. 30, 2016.

U.S. Appl. No. 15/360,502, filed Nov. 23, 2016.

U.S. Appl. No. 15/369,595, filed Dec. 5, 2016.

U.S. Appl. No. 15/383,101, filed Dec. 19, 2016.

U.S. Appl. No. 15/383,188, filed Dec. 19, 2016.

U.S. Appl. No. 15/383,196, filed Dec. 19, 2016.

U.S. Appl. No. 15/383,202, filed Dec. 19, 2016.

U.S. Appl. No. 15/383,342, filed Dec. 19, 2016.

U.S. Appl. No. 15/385,348, filed Dec. 20, 2016.

U.S. Appl. No. 15/383,353, filed Dec. 19, 2016.

U.S. Appl. No. 15/385,372, filed Dec. 20, 2016.

U.S. Appl. No. 15/656,897, filed Jul. 21, 2017.

U.S. Appl. No. 15/690,183, filed Aug. 29, 2017.

Baxendale H.E., et al., "Natural human antibodies to pneumococcus have distinctive molecular characteristics and protect against pneumococcal disease," *Clinical and Experimental Immunology*, 2007, vol. 151, pp. 51-60.

Beck J.A., et al., "Genealogies of mouse inbred strains," *Nature Genetics*, 2000, vol. 24, pp. 23-25 (with supporting table and chart).

Bentham, A., Attorneys for Regeneron Pharmaceuticals, Inc., Opposition against EP2421357B1 in the name of Kymab Ltd. pertaining to Application No. 10734546.4, dated Jan. 9, 2017, 13 pages.

Bornstein, G.G. et al., "Development of a new fully human anti-CD20 monoclonal antibody for the treatment of B-cell malignancies", *Investigational New Drugs*, 2010, vol. 28, pp. 561-574.

Brault V., et al., "Modeling Chromosomes in Mouse to Explore the Function of Genes, Genomic Disorders, and Chromosonal Organization," *PLoS Genetics*, Jul. 2006, vol. 2 (7), pp. e86-1-e86-9.

Call L.M., et al., "A Cre-lox recombination system for the targeted integration of circular yeast artificial chromosomes into embryonic stem cells," *Human Molecular Genetics*, 2000, vol. 9 (12), pp. 1745-1751.

Carter T.C., et al., "Standardized Nomenclature for Inbred Strains of Mice," *Cancer Research*, 1952, vol. 12 (8), pp. 602-613.

Chia R., et al., "The origins and uses of mouse outbred stocks," *Nature Genetics*, 2005, vol. 37 (11), pp. 1181-1186.

Collins A.M., et al., "The reported germline repertoire of human immunoglobulin kappa chain genes is relatively complete and accurate," *Immunogenetics*, 2008, vol. 60, pp. 669-676.

D'Eustachio P., et al., "Mouse Chromosome 12," *Mammalian Genome*, 1998, vol. 8, pp. S241-S257.

Engel H., et al., "Expression level of a transgenic λ2 chain results in isotype exclusion and commitment to B1 cells," *European Journal of Immunology*, 1998, vol. 28, pp. 2289-2299.

European Patent Office, Extended European Search Report for Application No. 16151215.7, dated Mar. 16, 2016, 11 pages.

European Patent Office, Opposition against EP2517557 Animal Models and Therapeutic Molecules in the name of Kymab Limited pertaining to Application No. 12171793.8, dated Jan. 17, 2017, 39 pages.

Festing, M.F.W., et al., "Revised nomenclature for strain 129 mice," *Mammalian Genome*, 1999, vol. 10, p. 836.

Forsman A., et al., "Llama Antibody Fragments with Cross-Subtype Human Immunodeficiency Virus Type I (HIV-1)-Neutralizing Properties and High Affinity for HIV-1 gp120," *Journal of Virology*, Dec. 2008, vol. 82 (24), pp. 12069-12081.

Grandea A.G., III., et al., "Human antibodies reveal a protective epitope that is highly conserved among human and nonhuman influenza A viruses," *Proceedings of the National Academy of Sciences of the U.S.A.*, Jul. 2010, vol. 107 (28), pp. 12658-12663.

Grippo V., et al., "The Heavy Chain Variable Segment Gene Repertoire in Chronic Chagas' Heart Disease," *The Journal of Immunology*, Dec. 2009, vol. 182 (12), pp. 8015-8025.

Grund M., European Patent Attorney, Grund Intellectual Property Group, Third-Party Observations according to Article 115 EPC regarding 12762377.5, dated Jun. 20, 2017, 4 pages.

Grund M., European Patent Attorney, Grund Intellectual Property Group, Third-Party Observations according to Article 115 EPC regarding 12762378.3, dated Feb. 15, 2017, 6 pages.

Grund M., European Patent Attorney, Grund Intellectual Property Group, Third-Party Observations according to Article 115 EPC regarding 16189625.3, dated Mar. 23, 2017, 5 pages.

Grund M., European Patent Attorney, Grund Intellectual Property Group, Third-Party Observations according to Article 115 EPC regarding 16151215.7, dated Mar. 1, 2017, 4 pages.

(56) References Cited

OTHER PUBLICATIONS

Hong J., et al., "Derivation and Characterization of Embryonic Stem Cells Lines Derived from Transgenic Fischer 344 and Dark Agouti Rats," *Stem Cells and Development*, 2012, vol. 21 (6), pp. 1571-1586.
Jones, B.T., Attorney for Applicant, Third-Party Pre-Issuance Submission Under 37 CFR Sec. 1.290 in U.S. Appl. No. 15/232,122, filed Mar. 13, 2017, 32 pages.
Jones B.T., Attorney for Applicant, Third-Party Pre-Issuance Submission Under 37 CFR Sec. 1.290 in U.S. Appl. No. 15/251,969, filed May 4, 2017, 22 pages.
Jones, B.T., Attorney for Applicant, Third-Party Pre-Issuance Submission Under 37 CFR Sec. 1.290 in U.S. Appl. No. 15/360,502, filed May 8, 2017, 40 pages.
Jones B.T., Attorney for Applicant, Third-Party Pre-Issuance Submission Under 37 CFR Sec. 1.290 in U.S. Appl. No. 15/383,101, filed May 30, 2017, 32 pages.
Jones B.T., Attorney for Applicant, Third-Party Pre-Issuance Submission Under 37 CFR Sec. 1.290 in U.S. Appl. No. 15/383,196, filed May 8, 2017, 25 pages.
Jones B.T., Attorney for Applicant, Third-Party Pre-Issuance Submission Under 37 CFR Sec. 1.290 in U.S. Appl. No. 15/214,963, filed Mar. 2, 2017, 42 pages.
Jones B.T., Attorney for Applicant, Third-Party Pre-Issuance Submission Under 37 CFR Sec. 1.290 in U.S. Appl. No. 15/383,188, filed May 30, 2017, 33 pages.
Jones B.T., Attorney for Applicant, Third-Party Pre-Issuance Submission Under 37 CFR Sec. 1.290 in U.S. Appl. No. 15/383,202, filed May 3, 2017, 23 pages.
Magdelaine-Beuzelin C., et al., "Structure-function relationships of the variable domains of monoclonal antibodies approved for cancer treatment," *Critical Reviews in Oncology/Hematology*, 2007, vol. 64, pp. 210-225.
Martinez C., et al., "The Mouse (*Mus musculus*) Immunoglobulin Kappa Variable (IGKV) Genes and Joining (IGKJ) Segments," *Experimental and Clinical Immunogenetics*, Jul. 1998, vol. 15, pp. 184-193.
Martinez P., et al., "Antibody Synthesis in Vitro," Encyclopedia of Life Sciences, 2005, pp. 1-8.
Mgi, "Guidelines for Nomenclature of Mouse and Rat Strains," International Committee on Standardized Genetic Nomenclature for Mice / Rat Genome and Nomenclature Committee; Chairpersons: J.T. Eppig and G. Levan, Oct. 2011, 11 pages. [printed: Mar. 6, 2012—http://www.informatics.jax.org/mgihome/nomen/strains.shtml].
O'Dea, T.P., Attorney for Applicant, Third-Party Pre-Issuance Submission Under 37 CFR Sec. 1.290 in U.S. Appl. No. 15/385,348, filed Jul. 28, 2017, 48 pages.
O'Dea, T.P., Attorney for Applicant, Third-Party Pre-Issuance Submission Under 37 CFR Sec. 1.290 in U.S. Appl. No. 15/385,372, filed Jul. 28, 2017, 48 pages.
Printout of PDF file available from the University of California website presented in support of European opposition in the name of Kymab Ltd. pertaining to Application No. EP12171793.8 as filed on Jan. 19, 2017, 4 pages. [http://www.research.uci.edu/facilities-services/tmf/presentations/Mouse_ES_CellLine].
Rock E.P., et al., "CDR3 Length in Antigen-specific Immune Receptors", *Journal of Experimental Medicine*, Jan. 1994, vol. 179, pp. 323-328.
Schonewald, S.L., Attorney for Applicant, Third-Party Pre-Issuance Submission Under 37 CFR Sec. 1.290 in U.S. Appl. No. 14/935,010, dated Aug. 19, 2016, 27 pages.
Sequence Listing to WO2008054606A2, 163 pages.
Shore, D.E., Attorney for Applicant, Third-Party Pre-Issuance Submission Under 37 CFR Sec. 1.290 in U.S. Appl. No. 14/543,359, filed Mar. 3, 2017, 16 pages.
Shore, D.E., Attorney for Applicant, Third-Party Pre-Issuance Submission Under 37 CFR Sec. 1.290 in U.S. Appl. No. 15/199,575, filed May 31, 2017, 37 pages.
Stein R., et al., "Characterization of a humanized IgG4 anti-HLA-DR monoclonal antibody that lacks effector cell functions but retains direct antilymphoma activity and increases the potency of rituximab," *Blood*, Oct. 2006, vol. 108 (8), pp. 2736-2744.
Suárez E. et al., "Human monoclonal antibodies produced in transgenic BABκ,λ mice recognising idiotypic immunoglobulins of human lymphoma cells," *Molecular Immunology*, 2004, vol. 41, pp. 519-526.
Sun Y., et al., "Repertoire of Human Antibodies against the Polysaccharide Capsule of *Streptococcus pneumoniae* Serotype 6B," *Infection and Immunity*, Mar. 1999, vol. 67 (3), pp. 1172-1179.
Wang X., et al., "Recombination, transcription, and diversity of a partially germline-joined VH in a mammal," *Immunogenetics*, 2012, vol. 64, pp. 713-717.
Xiao X., et al., "Germline-like predecessors of broadly neutralizing antibodies lack measurable binding to HIV-1 envelope glycoproteins: Implications for evasion of immune responses and design of vaccine immunogens," *Biochemical and Biophysical Communications*, 2009, vol. 390, pp. 404-409.
Zhu Z., et al., "Cross-Reactive HIV-1-Neutralizing Human Monoclonal Antibodies Identified from a Patient with 2F5-Like Antibodies," *Journal of Virology*, Nov. 2011, vol. 85 (21), pp. 11401-11408.
Zou X., et al., "Subtle differences in antibody responses and hypermutation of lambda λ chains in mice with a disrupted x contant region," *European Journal of Immunology*, 1995, vol. 25, pp. 2154-2162.
Hagiwara et al., Transgenic expression of VpreB-3 under the control of the immunoglobulin heavy chain enhancer and SV40 promoter, Kobe J. Med. Sci. 42(1): 43-59, 1996; abstract only.†
Atlas of Genetics and Cytogenetics in Oncology and Haematology: VPREB1. Accessed Online: <http://atlasgeneticsoncology.org/Genes/GC_VPREB1.html> on May 25, 2015.†
Lefranc, M.-P., Nomenclature of the Human Immunoglobulin Genes, Current Protocols Immunol. A.1P.1-A.1P.37, 2000.†
Janeway et al., The rearrangement of antigen-receptor gene segments controls lymphocyte development. In Immunobiology, 5th edition (retrieved online at <http://www.ncbi.nlm.nih.gov/books/NBK27113/>). New York: Garland Biosciences. 2001.†
Murphy, A. 2009. VelocImmune: Immunoglobulin Variable Region Humanized Mice. In M. Little (ed.), Recombinant Antibodies for Immunotherapy (pp. 100-107). New York, NY: Cambridge University Press.†

\* cited by examiner
† cited by third party

CHIMAERIC SURROGATE LIGHT CHAINS (SLC) COMPRISING HUMAN VPREB

This application is a continuation of PCT/GB2012/052380, filed Sep. 26, 2012, which claims the benefit of GB 1116495.1, filed Sep. 26, 2011, and GB 1120423.7, filed Nov. 28, 2011, the contents of each application being incorporated by reference herein in their entirety. The attached sequence listing is hereby incorporated by reference.

The present invention relates inter alia to improvements in the production of chimaeric antibodies in non-human transgenic vertebrates such as mice and rats bearing one or more chimaeric antibody transgenes. In particular, the invention provides for improved non-human vertebrates and cells in which VpreB has been species-matched with the variable region of the chimaeric antibodies. Also, embodiments provide for species-matching of the entire surrogate light chain for efficient pairing with chimaeric heavy chains during B-cell development in vivo in a non-human transgenic vertebrate setting.

Furthermore, the invention relates to a method of using the vertebrates to isolate antibodies or nucleotide sequences encoding antibodies. Antibodies, nucleotide sequences, pharmaceutical compositions and uses are also provided by the invention.

BACKGROUND

Advancements in the construction of transgenic mice bearing human antibody gene loci have led researchers to move away from the provision of entirely human transgenic antibody loci (bearing human variable and constant region gene segments) to chimaeric transgenic antibody loci. The transgenic loci comprise human V(D)J segments operably connected upstream of non-human constant regions. The use of constant regions that are endogenous to the transgenic non-human vertebrate (eg, endogenous mouse or rat constant regions) are desirable to harness the endogenous control of antibody generation and maturation following immunisation of the vertebrate with antigen.

B-cell development is characterized by the ordered rearrangement of immunoglobulin variable region genes. After the VDJ rearrangement of the H chain gene segments, a precursor (pre)-B-cell is generated. After the functional rearrangement of a light chain gene, the cells develop into surface IgM-bearing mature B-cells. Fully assembled IgH and L chains are transported onto the surface of B-cells, while free H chains are retained in the endoplasmic reticulum (ER) in association with BiP.

A critical step in B-cell differentiation is the selective expansion of cells with a functional μ heavy chain resulting from productive IgH rearrangement. This is achieved by the association of the μ heavy chain with the surrogate light chain (SLC) proteins λ5 and VpreB and the signal transducing heterodimer Igα and β to form the pre-B-cell receptor (pre-BCR). The expression and formation of a pre-BCR dramatically improves the efficiency of pre-B and B-cell production, by signalling proliferative expansion of pre-B-cells. The major function of the pre-BCR is the selection and expansion of cells that have undergone a productive VDJ rearrangement. The expression of membrane-bound μ chains is essential for the clonal expansion, and initiation of L chain gene rearrangement.

The association of SLC with μ chain works as a checkpoint to determine whether the cell has successfully completed VDJ combination and expresses a functional μH chain. More than half of all μ chains cannot assemble with the SLC, accounting for most of the changes in the V heavy repertoire during B-cell development.

VpreB is homologous to variable regions, λ 5 is homologous to light chain constant region. The protein encoded by the two genes can form a tightly, but noncovalently bound heterodimer with the general structure of an L chain. λ 5 protein can be covalently disulphide-bonded to μ H chains in pre-B-cells. Whereas VpreB alone can associate with Igμ, λ 5 alone cannot. Only when it is non-covalently associated with VpreB does λ 5 form a disulphide bridge with the first constant region (CH1) of an Igμ chain to form the pre-BCR.

The λ5 and VpreB, which together form the SLC, are early markers of B-cell commitment. They are expressed at the pro- and pre-B-cell stages and silenced in immature and mature B-cells. In pre-B-cells, following rearrangement of the heavy chain locus, the surrogate light chain (SLC) acts as a chaperone, mediating transport of the newly synthesised heavy chain mu to the cell surface and together with C mu forms part of the pre-BCR (Immuno) Today. 1993 February; 14(2):60-8; The surrogate light chain in B-cell development; Melchers F, Karasuyama H, Haasner D, Bauer S, Kudo A, Sakaguchi N, Jameson B, Rolink A). The pre-BCR mediates signalling, leading to proliferation of pre-B-cells that have a productive heavy chain rearrangement. Mice that lack a functional λ5 show a drastic reduction in the number of B-cells. Using VpreB knock-out mice, it has been shown that VpreB is also required for efficient B-cell development, particularly for the transition to pre-BCR bearing cells (pre-BII stage) (see, Int Immunol. 1999 March; 11(3):453-60; Partial block in B lymphocyte development at the transition into the pre-B cell receptor stage in Vpre-B1-deficient mice; Mårtensson A, Argon Y, Melchers F, Dul J L, Mårtensson I L; and Sabbattini & Dillon 2005 infra). As the degree of proliferation has been proposed to be dependent upon the stability of the association of the mu heavy chain with the components of the SLC, the pre-BCR is thought to influence the choice, and thus the extent and diversity of, the heavy chain variable region repertoire.

Besides its role in signalling proliferation, the pre-BCR is also thought to mediate down regulation of the RAG genes, thereby preventing the rearrangement of other IgH loci (allelic exclusion) and the occurrence of double-strand breaks in dividing pre-B-cells. The pre-BCR has also been proposed to exert a negative feedback on λ5 and VpreB expression so that, after a phase of clonal expansion, the large pre-BII cells become depleted of pre-BCR, exit the cell cycle and differentiate into resting small pre-BII cells. At this stage, the SLC is repressed while the IgL loci start to be rearranged. The product of a successfully rearranged IgL gene will then pair with the mu heavy chain to form a BCR with antigen-binding capability on the surface of immature B-cells. These cells migrate to the peripheral blood and secondary lymphoid organs, and develop into mature B-cells ready for subsequent encounter with antigen (Sabbattini & Dillon 2005 infra).

SUMMARY OF THE INVENTION

The inventors were aware of the desirability to use endogenous non-human (eg, mouse or rat) constant regions to harness the endogenous control of antibody generation and maturation following immunisation. They have realised, however, that these considerations do not address earlier B-cell stages in vivo (prior to antigen stimulation) when the animal's B-cell repertoire is maturing. Such maturation includes transition from immature pro-B-cells to pre-B- cells, including the pre-BII stage when B-cells bear surface B-cell receptors (BCR) in which the heavy chain variable region is paired with the VpreB. CH1 regions of heavy chains are paired with λ5 in the pre-BCRs. The inventors realised that the provision of genes encoding chimaeric antibodies is not tailored to the pre-BII stage, and they realised that it is important to address this since this stage features huge clonal expansion required to provide a pool of B-cells for functional heavy chain selection during subsequent B-cell development.

To this end, the present invention provides for species-matching of human V regions in chimaeric heavy chains with human VpreB. In embodiments, the invention also provides for species-matching of the mu constant region with λ5, so that heavy chains in pre-BCRs are completely species-matched with chimaeric surrogate light chain (SLC). Thus, a First Configuration of the Present Invention Provides, A non-human vertebrate (eg, a mouse or rat) or cell (eg, a mouse cell or rat cell) whose genome comprises an antibody heavy chain transgene,
the transgene comprising
(a) one or more human VH gene segments, one or more human D gene segments and one or more human JH gene segments operably connected upstream of a constant region gene so that the transgene is capable of undergoing VDJ recombination in vivo to produce an antibody gene comprising a rearranged VDJC encoding an antibody heavy chain having a human variable region and a constant region; or
(b) a rearranged VDJ encoding a human variable region operably connected upstream of a constant region gene so that the transgene encodes (optionally following VDJ combination with the constant region) a chimaeric antibody heavy chain having a human variable region and a constant region;
the genome further comprising a human VpreB gene capable of expressing a human VpreB.

The present invention is applicable to the production of 4-chain antibodies in transgenic animals, where the antibodies each contain 2 heavy chains and 2 light chains. Alternatively, the invention can be applied to the production of H2 antibodies (heavy chain antibodies) which are devoid of CH1 and light chains.

In a Second Embodiment, the Invention Provides

A method of constructing a transgenic non-human vertebrate cell (eg, an ES cell, eg, a mouse or rat ES cell), the method comprising
(i) introducing into the genome of a non-human vertebrate cell (or an ancestor thereof) one or more human VH gene segments, one or more human D gene segments and one or more human JH gene segments so that said gene segments are operably connected upstream of a constant region gene (optionally an endogenous non-human vertebrate constant region gene) to form a heavy chain transgene, wherein in said cell or a progeny thereof the transgene is capable of undergoing VDJ recombination in vivo to produce an antibody gene comprising a rearranged VDJC encoding an antibody heavy chain having a human variable region and a constant region; or
(ii) introducing into the genome of a non-human vertebrate cell (or an ancestor thereof) a rearranged VDJ encoding a human variable region so that said VDJ is operably connected upstream of a constant region gene (optionally an endogenous non-human vertebrate constant region gene) to form a heavy chain transgene, wherein in said cell or a progeny thereof the transgene encodes (optionally following VDJ combination with the constant region) an antibody heavy chain having a human variable region and a constant region; and wherein the method further comprises introducing into the cell a human VpreB gene capable of expressing a human VpreB.

In a Third Embodiment, the Invention Provides

A method of promoting B-cell development in a non-human vertebrate (eg, a mouse or rat), the method comprising
(a) providing in a non-human vertebrate embryonic stem (ES) cell genome an immunoglobulin transgene capable of expressing an antibody mu heavy chain, wherein the antibody heavy chain comprises a human variable region and a mu constant region (optionally an endogenous non-human vertebrate mu constant region); and creating a first non-human vertebrate from said ES cell or a progeny thereof;
(b) providing in a second ES cell genome a second transgene comprising a human VpreB gene capable of expressing a human VpreB; and creating a second non-human vertebrate from said ES cell or a progeny thereof; and
(c) creating by breeding a third non-human vertebrate capable of co-expressing the mu antibody heavy chain and human vpreB wherein a pre-B-cell receptor can form to promote B-cell development of cells bearing a mu heavy chain in said third vertebrate; the third vertebrate being made by crossing said first and second vertebrates or progeny thereof by breeding to create said third vertebrate, the third vertebrate comprising the first and second transgenes, and wherein endogenous heavy chain expression has been inactivated in said third vertebrate.

In a Fourth Embodiment, the Invention Provides

A method of promoting B-cell development in a non-human vertebrate (eg, a mouse or rat), the method comprising
(i) inactivating endogenous heavy chain expression in said vertebrate;
(ii) providing in the genome of said vertebrate an immunoglobulin transgene capable of expressing an antibody mu heavy chain, wherein the antibody heavy chain comprises a human variable region and a non-human vertebrate mu constant region (optionally an endogenous non-human vertebrate mu constant region); and
(ii) providing in the genome of said vertebrate a second transgene capable of expressing a human VpreB wherein a pre-B-cell receptor can form to promote B-cell development of cells bearing a mu heavy chain in said vertebrate;
Optionally wherein the genome is homozygous for said first transgene.

An aspect of the invention further provides for the possibility of species-matching in vivo the variable and constant regions of the antibody heavy chain with a chimaeric SLC. This is useful for promoting B-cell development in the transgenic non-human vertebrate (eg, a mouse or rat). To this End, the Invention Provides a Fifth Embodiment:

A non-human vertebrate (eg, a mouse or rat) or cell (eg, a mouse cell or rat cell) whose genome comprises an antibody heavy chain transgene,
the transgene comprising
(a) one or more human VH gene segments, one or more human D gene segments and one or more human JH gene segments operably connected upstream of a constant region gene of a non-human vertebrate (eg, mouse or rat) species so that the transgene is capable of undergoing VDJ recombination in vivo to produce an antibody gene comprising a rearranged VDJC encoding a chimaeric antibody heavy chain having a human variable region and a non-human vertebrate constant region; or (b) a rearranged VDJ encoding a human variable region operably connected upstream of a constant region gene of a non-human vertebrate (eg, mouse or rat) species so that the transgene encodes (optionally following VDJ combination with the constant region) a chimaeric antibody heavy chain having a human variable region and a non-human vertebrate constant region;

the genome further comprising one or more genes together encoding a chimaeric surrogate light chain, the surrogate light chain comprising a human VpreB and λ5 of said non-human vertebrate (eg, mouse or rat) species.

A Sixth Embodiment of the Invention Provides

A method of constructing a transgenic non-human vertebrate cell (eg, an ES cell, eg, a mouse or rat ES cell), the method comprising (i) introducing into a non-human vertebrate cell (or an ancestor thereof) one or more human VH gene segments, one or more human D gene segments and one or more human JH gene segments so that said gene segments are operably connected upstream of an endogenous non-human vertebrate constant region gene, wherein in said cell or a progeny thereof the transgene is capable of undergoing VDJ recombination in vivo to produce an antibody gene comprising a rearranged VDJC encoding a chimaeric antibody heavy chain having a human variable region and a non-human vertebrate constant region; or (ii) introducing into a non-human vertebrate cell (or an ancestor thereof) a rearranged VDJ encoding a human variable region so that said VDJ is operably connected upstream of an endogenous non-human vertebrate constant region gene, wherein in said cell or a progeny thereof the transgene encodes (optionally following VDJ combination with the constant region) a chimaeric antibody heavy chain having a human variable region and a non-human vertebrate constant region;

and wherein the method further comprises introducing into the cell a human VpreB gene such that the cell or a progeny thereof is capable of expressing a chimaeric surrogate light chain as well as said chimaeric antibody heavy chain, wherein the surrogate light chain comprises a human VpreB and an endogenous non-human vertebrate λ5.

A Seventh Embodiment of the Invention Further Provides

A method of promoting B-cell development in a non-human vertebrate (eg, a mouse or rat), the method comprising (a) providing in a non-human vertebrate embryonic stem (ES) cell an immunoglobulin transgene capable of expressing a chimaeric antibody mu heavy chain, wherein the chimaeric antibody heavy chain comprises a human variable region and an endogenous non-human vertebrate mu constant region; and creating a first non-human vertebrate from said ES cell or a progeny thereof;

(b) providing in a second ES cell a second transgene capable of expressing a human VpreB so that the human VpreB and an endogenous λ5 form a chimaeric surrogate light chain; and creating a second non-human vertebrate from said ES cell or a progeny thereof; and (c) creating by breeding a third non-human vertebrate capable of co-expressing the chimaeric mu antibody heavy chain and chimaeric surrogate light chain wherein a pre-BCR can form to promote B-cell development in said third vertebrate; the third vertebrate being made by crossing said first and second vertebrates or progeny thereof by breeding to create said third vertebrate, the third vertebrate comprising the first and second transgenes, and wherein endogenous heavy chain expression has been inactivated in said third vertebrate.

A transgenic mouse according to the vertebrate of this method, or a progeny thereof, is provided.

An Eighth Embodiment of the Invention Provides

A method of promoting B-cell development in a non-human vertebrate (eg, a mouse or rat), the method comprising (i) inactivating endogenous heavy chain expression in said vertebrate;

(ii) providing in the genome of said vertebrate an immunoglobulin transgene capable of expressing a chimaeric antibody mu heavy chain, wherein the chimaeric antibody heavy chain comprises a human variable region and an endogenous non-human vertebrate mu constant region; and (ii) providing in the genome of said vertebrate a second transgene capable of expressing a human VpreB so that the human VpreB and an endogenous λ5 form a chimaeric surrogate light chain; so that the vertebrate is capable of co-expressing the chimaeric mu antibody heavy chain and chimaeric surrogate light chain wherein a pre-BCR can form to promote B-cell development in said vertebrate;

Optionally wherein the genome is homozygous for said first transgene.

A transgenic mouse according to the vertebrate of this method, or a progeny thereof, is provided.

DETAILED DESCRIPTION OF THE INVENTION

Figure 1A:
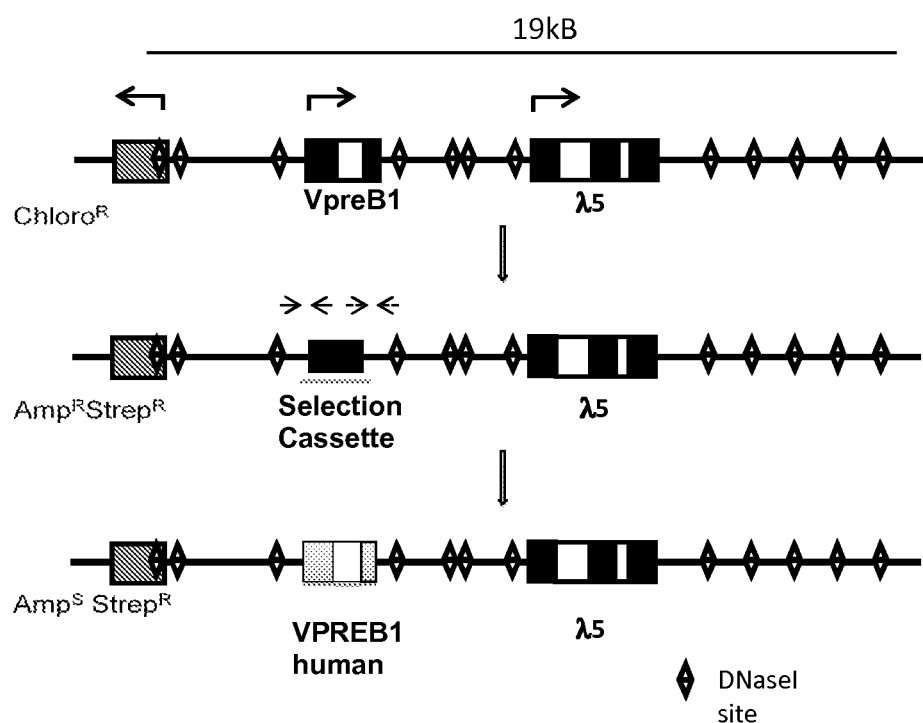
FIGS. 1A & B: Schematic representation of the steps involved in replacement of the mouse VpreB1 with human VpreB1. The most 5' gene is Topo3β.

The invention is useful for promoting the appropriate human IGH repertoire on mature B-cells in the vertebrate (or progeny thereof) or in transgenic vertebrates derived from non-human vertebrate cells. At the transition of pre-BI to pre-BII cells, VH to DH-JH rearrangements are initiated (see, eg, Mårtensson & Ceredig, Immunology 2000, 101, 435-441; Role of the surrogate light chain and the pre-B-cell receptor in mouse B-cell development). Whenever they occur in-frame, a mu chain can be produced and presented on the cell surface only if it associates with the surrogate light chain to form the pre-B-cell receptor (pre-BCR). The pre-BCR on the cell surface is required for clonal expansion of pre-BII cells before light chain rearrangement. Compromised presentation of pre-BCR on the cell surface due to the impairment of association of a mu chain carrying a certain variable region with a surrogate light chain will result in no clonal expansion of such a clone and reduce the representation of this variable region in the mature B cells. Human VpreB1 only shares a low identity with rodent VpreB1/2, suggesting that species specificity for the pre-BCR assembly exists. To this end, the inventors realised the importance for appropriate VpreB/variable region pairing on generation of effective antibody diversity in the context of an antibody heavy chain transgene encoding human variable regions, when this transgene is harboured in a non-human environment such as a transgenic mouse or rat.

The CH1 constant region pairs with the λ5 protein. Together, the VpreB and λ5 make up the surrogate light chain (SLC) that pairs with mu heavy chains to form the pre-BCR. For H2 antibodies pairing with the CH1 is not possible (since no CH1 is present), but the desirability to pair human VH regions with human VpreB according to the invention still applies.

Pairing Human Variable Regions of Pre-BCRs with Human VpreB

The extent of homology between human VpreB with mouse and rat VpreB is relatively low (about 73% amino acid identity). As discussed above, the inventors have realised the advantage of matching human antibody heavy chain variable regions with human VpreB in receptors of pre-B cells for promoting B-cell development in transgenic non-human vertebrates bearing human antibody variable region genes.

In a First Configuration, the Invention Thus Provides:

A non-human vertebrate (eg, a mouse or rat) or cell (eg, a mouse cell or rat cell) whose genome comprises an antibody heavy chain transgene, the transgene comprising (a) one or more human VH gene segments, one or more human D gene segments and one or more human JH gene segments operably connected upstream of a constant region gene so that the transgene is capable of undergoing VDJ recombination in vivo to produce an antibody gene comprising a rearranged VDJC encoding an antibody heavy chain having a human variable region and a constant region; or (b) a rearranged VDJ encoding a human variable region operably connected upstream of a constant region gene so that the transgene encodes (optionally following VDJ combination with the constant region) a chimaeric antibody heavy chain having a human variable region and a constant region;
the genome further comprising a human VpreB gene capable of expressing a human VpreB.

The sequences of VpreB's and λ5's are given below:—
SEQ ID NO: 1
    Human VpreB1 nucleotide sequence (GenBank Accession No=NG_029387.1)
SEQ ID NO: 2
    Human VpreB1 amino acid sequence (GenBank Accession No=NP_009059.1)
SEQ ID NO: 3
    Human VpreB3 nucleotide sequence (GenBank Accession No=NC_000022.10)
SEQ ID NO: 4
    Human VpreB3 amino acid sequence (GenBank Accession No=NP_037510)
SEQ ID NO: 5
    Mouse VpreB1 nucleotide sequence (GenBank Accession No=NC_000082.5)
SEQ ID NO: 6
    Mouse VpreB1 amino acid sequence (GenBank Accession No=NP_058678)
SEQ ID NO: 7
    Mouse VpreB2 nucleotide sequence (GenBank Accession No=NC_000082)
SEQ ID NO: 8
    Mouse VpreB2 amino acid sequence (GenBank Accession No=NP_058679.1)
SEQ ID NO: 9
    Rat VpreB1 nucleotide sequence (GenBank Accession No=NM_001108845.1)
SEQ ID NO: 10
    Rat VpreB1 amino acid sequence (GenBank Accession No=NP_001102315.1)
SEQ ID NO: 11
    Rat VpreB2 nucleotide sequence (GenBank Accession No=NC_005110)
SEQ ID NO: 12
    Rat VpreB2 amino acid sequence (GenBank Accession No=NP_001128260)
SEQ ID NO: 13
    Human λ5 nucleotide sequence (GenBank Accession No=NG_009791)
SEQ ID NO: 14
    Human λ5 amino acid sequence (GenBank Accession No=NP_064455)
SEQ ID NO: 15
    Mouse λ5 nucleotide sequence (GenBank Accession No=AC_000038)
SEQ ID NO: 16
    Mouse λ5 amino acid sequence (GenBank Accession No=NP_001177254)
SEQ ID NO: 17
    Rat λ5 nucleotide sequence (GenBank Accession No=NC_005110)
SEQ ID NO: 18
    Rat λ5 amino acid sequence (GenBank Accession No=NP_001177270)

In one embodiment of any configuration of the invention, the human VpreB is human VpreB1. In another embodiment, the human VpreB is human VpreB3.

TABLE 1

Sequence Identity:
VpreB: Human vs. Mouse vs. Rat

|  | Human VpreB1 | Mouse VpreB1 | Mouse VpreB2 | Rat VpreB1 | Rat VpreB2 |
|---|---|---|---|---|---|
| Human VpreB1 |  | 72.5 | 72.5 | 72.6 | 72.6 |
| Mouse VpreB1 |  |  | 97.2 | 84.4 | 83.7 |
| Mouse VpreB2 |  |  |  | 86.7 | 85.9 |
| Rat VpreB1 |  |  |  |  | 99.3 |
| Rat VpreB2 |  |  |  |  |  |

TABLE 2

Sequence Identity:
Lambda 5: Human vs. Mouse vs. Rat

| | Human λ5 | Mouse λ5 | Rat λ5 |
|---|---|---|---|
| Human λ5 | | 55.8 | 57.2 |
| Mouse λ5 | | | 90.4 |
| Rat λ5 | | | |

All nucleotide co-ordinates for the mouse are those corresponding to NCBI m37 for the mouse C57BL/6J strain, e.g. April 2007 ENSEMBL Release 55.37 h, e.g. NCBI37 July 2007 (NCBI build 37) (e.g. UCSC version mm9 see www.genome.ucsc.edu and http://genome.ucsc.edu/FAQ/FAQreleases.html) unless otherwise specified. Human nucleotides coordinates are those corresponding to GRCh37 (e.g. UCSC version hg 19, http://genome.ucsc.edu/FAQ/FAQreleases.html), February 2009 ENSEMBL Release 55 or are those corresponding to NCBI36, Ensemble release 54 unless otherwise specified. Rat nucleotides are those corresponding to RGSC 3.4 Dec. 2004 ENSEMBL release 55.34 w, or Baylor College of Medicine HGSC v3.4 Nov. 2004 (e.g., UCSC rn4, see www.genome.ucsc.edu and http://genome.ucsc.edu/FAQ/FAQreleases.html) unless otherwise specified.

In one example of the vertebrate or cell, the genome is homozygous for said transgene and endogenous non-human vertebrate antibody heavy chain expression has been inactivated. Alternatively or additionally, endogenous non-human vertebrate antibody light chain expression has been inactivated. Details on possible methods of inactivation are explained in more detail below.

The present invention is applicable to the production of 4-chain antibodies in transgenic animals, where the antibodies each contain 2 heavy chains and 2 light chains. Alternatively, the invention can be applied to the production of H2 antibodies (heavy chain antibodies) which are devoid of CH1 and light chains (see, eg, Nature. 1993 Jun. 3; 363 (6428): 446-8; Naturally occurring antibodies devoid of light chains; Hamers-Casterman C, Atarhouch T, Muyldermans S, Robinson G, Hamers C, Songa E B, Bendahman N, Hamers R). These antibodies function to specifically bind antigen, such antibodies being found in the blood of *Camelidae* (eg, llamas, camels, alpacas). Such antibodies with VH pairs can also be synthetically produced to provide therapeutic and prophylactic medicaments (eg, see WO1994004678, WO2004041862, WO2004041863). Transgenic mice also can produce such heavy chain antibodies and the in vivo production of the antibodies allows the mouse's immune system to select for human VH-VH pairings, sometimes selecting for such pairings in which mutations have been introduced in vivo by the mouse to accommodate the pairing (WO2010109165A2). Thus, in an embodiment of the present invention, the heavy chain transgene is devoid of a CH1 gene segment and the genome comprises no functional antibody light chain locus.

Throughout this text, and with application to any configuration, aspect, embodiment or example of the invention, the term "endogenous" (eg, endogenous constant region gene or endogenous λ5) in relation to a non-human vertebrate or cell indicates that the constant region, λ5 etc is a type of constant region or λ5 that is normally found in the vertebrate or cell (as opposed to an exogenous constant region or λ5 whose sequence is not normally found in such a vertebrate or cell). For example, the endogenous constant region and λ5 can be those encoded by the wild-type genome of the non-human vertebrate/cell. So, in an example wherein the vertebrate cell is a mouse ES cell, the endogenous constant region and λ5 would be mouse constant region and λ5. Going further, the endogenous regions are, in an example, strain-matched to the vertebrate/cell. So, in one embodiment, the vertebrate cell is a mouse 129 ES cell, the endogenous constant region and λ5 would be mouse 129 constant region and λ5. In another embodiment, the vertebrate cell is a mouse JM8 ES cell, the endogenous constant region and λ5 would be mouse JM8 constant region and λ5. In another embodiment, the vertebrate is a Black 6 mouse, the endogenous constant region and λ5 would be mouse Black 6 constant region and λ5.

In any configuration, aspect, embodiment or example of the invention, the constant region of the heavy chain transgene is a non-human vertebrate constant region (eg, mouse or rat constant region). Optionally, the constant region is endogenous to said non-human vertebrate or cell. Alternatively, the constant region of the heavy chain transgene is human constant region. For example, the constant region is human and devoid of a CH1. This is useful for producing human H2 antibodies (especially when the vertebrate or cell is not capable of expressing light chains).

In one example of the vertebrate or cell of the invention, the constant region is a Cmu, eg, a mouse or rat Cmu. For example, where the vertebrate is a mouse (or cell is a mouse cell), the Cmu is an endogenous mouse Cmu. The transgene, in an example, comprises a Smu switch 5' of the Cmu and a Cgamma 3' of the Cmu, with a S gamma switch between the Cmu and Cgamma. In an embodiment, the Cmu, Cgamma and switches are endogenous mouse C regions and switches. For example, the C regions and switches are mouse 129 C regions and switches; or the C regions and switches are mouse Black 6 C regions and switches. In another embodiment, the S gamma and C regions are mouse S gamma and C regions, and the Smu is a rat Smu.

In an example of any configuration, aspect, embodiment or example of the invention, the human VpreB gene has a nucleotide sequence that is at least 80, 85, 90, 91, 92, 93, 94, 95, 96, 97, 98 or 99% identical to SEQ ID NO: 1. The VpreB gene encodes a human VpreB that pairs with the heavy chain human variable region. In an example, the human VpreB gene has a nucleotide sequence that is identical to SEQ ID NO:1.

In an example of any configuration, aspect, embodiment or example of the invention, the human VpreB gene encodes a human VpreB comprising an amino acid sequence that is at least 80, 85, 90, 91, 92, 93, 94, 95, 96, 97, 98 or 99% identical to SEQ ID NO: 2. The VpreB gene encodes a human VpreB that pairs with the heavy chain human variable region. In an example, the human VpreB gene encodes a human VpreB comprising an amino acid sequence that is identical to SEQ ID NO:2; or optionally with from one to 15 amino acid changes (eg, 1, 2, 3, 4, 5, 6, 7, 8, 9, 10, 11, 12, 13, 14 or 15 changes) compared with SEQ ID NO: 2.

In any configuration, aspect, embodiment or example of the invention, the human VpreB gene encodes a human VpreB that pairs with the heavy chain human variable region, the human VpreB gene having from one to 25 nucleotide changes (eg, 1, 2, 3, 4, 5, 6, 7, 8, 9, 10, 11, 12, 13, 14, 15, 16, 17, 18, 19, 20, 21, 22, 23, 24 or 25 changes) compared to human VpreB (SEQ ID NO: 1). The VpreB gene can be manipulated in vitro by creation of a targeting vector comprising the gene sequence and homology arms flanking the sequence. This can be introduced into the genome of, for example an ES cell, using the standard technique of homologous recombination as will be apparent to the skilled person. Alternatively, recombinase mediated cassette exchange (RMCE)—another standard technique—can be used to effect precise insertion of the VpreB gene into the genome.

Homologous recombination or RMCE are generally-useful techniques for the specific, targeted, introduction of sequences into a genome. One or both of these techniques are readily applicable for introducing into a vertebrate or cell genome a human VpreB sequence (wild-type or mutant); V, D, J and C regions; switches; enhancers and other immunoglobulin control elements; and λ5 genes. These and other techniques for target insertion are known to the skilled addressee.

In an example of any configuration, aspect, embodiment or example of the invention, the genome does not comprise a non-human vertebrate (eg, mouse or rat) species VpreB1 and/or VpreB2 gene. In this embodiment, the possibility of non-human VpreB competing with the human VpreB for binding to the human variable regions is eliminated. Thus, pairing of human V regions with human VpreB on pre-B cells is not hampered by such competition, which is advantageous for promoting B-cell development.

In an example of any configuration, aspect, embodiment or example of the invention, the genome further comprises a λ5 gene (eg, a human, mouse or rat λ5); optionally wherein the λ5 gene is a λ5 of a non-human vertebrate (eg, mouse or rat) species and said constant region gene is a constant region gene of the same non-human vertebrate (eg, mouse or rat) species as the λ5 gene. For example, the constant region and λ5 genes are mouse constant region and λ5 genes, eg, mouse 129 constant region and λ5 genes; or mouse JM8 constant region and λ5 genes). For example, the constant region and λ5 genes are rat constant region and λ5 genes. In an example, constant region gene and λ5 gene are endogenous genes of said vertebrate or cell. Thus, the invention contemplates close matching of not only the V-region/VpreB part of pre-BCRs but also close matching of the Cmu/λ5 part. While not wishing to be bound to any theory, the inventors believe that this is useful for stabilising the pre-BCRs to promote B-cell development in vivo, thus improving the B-cell pool (and potentially diversity) from which to select antigen-specific antibodies following immunisation of vertebrates according to the inventions.

In another embodiment of any configuration, aspect, embodiment or example of the invention, the λ5 is a chimaeric λ5 comprising a non-human vertebrate λ5 (eg, endogenous mouse or rat λ5) in which amino acid sequences have been replaced by corresponding amino acids from a human λ5. For example, the region of λ5 that interfaces with VpreB to form the SLC is replaced with the corresponding part from a human λ5 to form a chimaeric λ5 with a human part (ie, species-matched with the human VpreB) and a non-human vertebrate (eg, mouse or rat) part that is species matched with the CH1 of the non-human vertebrate Cmu of the heavy chain transgene. In the alternative embodiment where the λ5 is a human λ5, the λ5 is advantageously species-matched to interface with the human λ5.

In one aspect the non-human vertebrate is able to generate a diversity of at least $1 \times 10^6$ different functional chimaeric antibody sequence combinations.

In a second configuration, the method provides

A method of constructing a transgenic non-human vertebrate cell (eg, an ES cell, eg, a mouse or rat ES cell), the method comprising (i) introducing into the genome of a non-human vertebrate cell (or an ancestor thereof) one or more human VH gene segments, one or more human D gene segments and one or more human JH gene segments so that said gene segments are operably connected upstream of a constant region gene (optionally an endogenous non-human vertebrate constant region gene) to form a heavy chain transgene, wherein in said cell or a progeny thereof the transgene is capable of undergoing VDJ recombination in vivo to produce an antibody gene comprising a rearranged VDJC encoding an antibody heavy chain having a human variable region and a constant region; or (ii) introducing into the genome of a non-human vertebrate cell (or an ancestor thereof) a rearranged VDJ encoding a human variable region so that said VDJ is operably connected upstream of a constant region gene (optionally an endogenous non-human vertebrate constant region gene) to form a heavy chain transgene, wherein in said cell or a progeny thereof the transgene encodes (optionally following VDJ combination with the constant region) an antibody heavy chain having a human variable region and a constant region;

and wherein the method further comprises introducing into the cell (before, after or concomitantly with step (i) or (ii)) a human VpreB gene capable of expressing a human VpreB.

Targeting of the genome of an ES cell to produce a transgenic cell and subsequently a transgenic vertebrate (eg, a mouse) may be carried out using a protocol as explained by reference to the FIGS. 1-18 and description in WO2011004129, the disclosure of which is incorporated herein by reference. A suitable mouse ES cell is selected from AB2.1 cells (available from Baylor College of Medicine, Texas, USA), AB2.2 cells and JM8 cells.

In any configuration, aspect, embodiment or example of the invention, the cell is an ES cell is capable of developing into a non-human mammal able to produce a repertoire of antibodies which are chimaeric, said chimaeric antibodies having a non-human mammal constant region and a human variable region. Optionally the genome of the cell is modified to prevent expression of fully host-species specific antibodies.

In one aspect the cell is an induced pluripotent stem cell (iPS cell).

In one aspect cells are isolated non-human mammalian cells.

In one aspect a cell as disclosed herein is preferably a non-human mammalian cell.

In one aspect the cell is a cell from a mouse strain selected from C57BL/6, M129 such as 129/SV, BALB/c, and any hybrid of C57BL/6, M129 such as 129/SV, or BALB/c. In an example, the mouse is a C57BL/6-129/Sv hybrid.

Maintaining the performance of the ES cell clones through multiple rounds of manipulation without the need to test the germ line potential of the ES cell line at every step may be important in the method of constructing a transgenic locus. The cell lines currently in use for the KOMP and EUCOMM global knockout projects have been modified twice prior to their use for this project and their germ line transmission rates are unchanged from the parental cells (these lines are publicly available, see www.komp.org and www.eucomm.org). This cell line, called JM8, can generate 100% ES cell-derived mice under published culture conditions (Pettitt, S. J., Liang, Q., Rairdan, X. Y., Moran, J. L., Prosser, N. M., Beier, D. R., Lloyd, K. C., Bradley, A., and Skarnes, W. C. (2009). Agouti C57BL/6N embryonic stem cells for mouse genetic resources. Nature Methods.). These cells have demonstrated ability to reproducibly contribute to somatic and germ line tissue of chimaeric animals using standard mouse ES cell culture conditions. This capability can be found with cells cultured on a standard feeder cell line (SNL) and even feeder-free, grown only on gelatine-coated tissue culture plates. One particular sub-line, JM8A3, maintained the ability to populate the germ line of chimeras after several serial rounds of sub-cloning. Extensive genetic manipulation via, for example, homologous recombination—as could be the case in the present method—cannot compromise the pluripotency of the cells. The ability to generate chimeras with such high percentage of ES cell-derived tissue has other advantages. First, high levels of chimaerism correlates with germ line transmission potential and provide a surrogate assay for germ line transmission while only taking 5 to 6 weeks. Second, since these mice are 100% ES cell derived the engineered loci can be directly tested, removing the delay caused by breeding. Testing the integrity of the new Ig loci is possible in the chimera since the host embryo will be derived from animals that are mutant for the RAG-1 gene as described in the next section.

Another cell line that may be used is an HPRT-negative cell line, such as AB2.1, as disclosed in "Chromosome engineering in mice, Ramirez-Solis R, Liu P and Bradley A, Nature 1995; 378; 6558; 720-4.

RAG-1 Complementation

While many clones will generate 100% ES derived mice some will not. Thus, at every step mice can be generated in a RAG-1-deficient background. This provides mice with 100% ES-derived B- and T-cells which can be used directly for immunization and antibody production. Cells having a RAG-2 deficient background, or a combined RAG-1/RAG-2 deficient background may be used, or equivalent mutations in which mice produce only ES cell-derived B cells and/or T cells.

In order that only the human-mouse IgH (and optionally also light chain) loci are active in these mice, the human-mouse IgH (and optionally light chain loci) can be engineered in a cell line in which one allele of the IgH (and optionally light chain) locus has already been inactivated. Alternatively the inactivation of the host Ig locus/loci can be carried out after insertion.

Mouse strains that have the RAG-1 gene mutated are immunodeficient as they have no mature B- or T-lymphocytes (U.S. Pat. No. 5,859,307). T- and B-lymphocytes only differentiate if proper V(D)J recombination occurs. Since RAG-1 is an enzyme that is crucial for this recombination, mice lacking RAG-1 are immunodeficient. If host embryos are genetically RAG-1 homozygous mutant, a chimera produced by injecting such an embryo will not be able to produce antibodies if the animal's lymphoid tissues are derived from the host embryo. However, JM8 cells and AB2.1 cells, for example, generally contribute in excess of 80% of the somatic tissues of the chimaeric animal and would therefore usually populate the lymphoid tissue. JM8 cells have wild-type RAG-1 activity and therefore antibodies produced in the chimaeric animal would be encoded by the engineered JM8 ES cell genome only. Therefore, the chimaeric animal can be challenged with an antigen by immunization and subsequently produce antibodies to that antigen. This allows one skilled in the art to test the performance of the engineered human/mouse Ig loci as described in the present invention.

One skilled in the art could use the chimaeric animal as described to determine the extent of antibody diversity (see e.g. Harlow, E. & Lane, D. 1998, 5$^{th}$ edition, Antibodies: A Laboratory Manual, Cold Spring Harbor Lab. Press, Plainview, N.Y.). For example, the existence in the chimaeric animal's serum of certain antibody epitopes could be ascertained by binding to specific anti-idiotype antiserum, for example, in an ELISA assay. One skilled in the art could also sequence the genomes or heavy chain RNA or DNA sequences of B-cell clones derived from the chimaeric animal (naïve or immunised) and compare said sequence to wild-type sequence (ie, minus human VpreB) to assess the B-cell repertoire and ascertain the level of hypermutation, such hypermutation being indicative of normal antibody maturation.

One skilled in the art would also use said chimaeric animal to examine antibody function wherein said antibodies are encoded from the engineered Ig loci (see e.g. Harlow, E. & Lane, D. 1998, 5$^{th}$ edition, Antibodies: A Laboratory Manual, Cold Spring Harbor Lab. Press, Plainview, N.Y.). For example, antisera could be tested for binding an antigen, said antigen used to immunize the chimaeric animal. Such a measurement could be made by an ELISA assay. Alternatively, one skilled in the art could test for neutralization of the antigen by addition of the antisera collected from the appropriately immunized chimaeric animal.

It is well known to those skilled in the art that positive outcomes for any of these tests demonstrate the ability of the engineered Ig loci in the presence of VpreB during B-cell development according to the instant invention, to encode antibodies with human variable regions and non-human vertebrate constant regions, said antibodies capable of functioning in the manner of wild-type antibodies.

The introduction of human gene segment DNA into the genome can be carried out using vectors carrying the DNA, as more fully explained below. In one aspect such vectors are BACs (bacterial artificial chromosomes). It will be appreciated that other cloning vectors may be used in the invention, and therefore reference to BACs herein may be taken to refer generally to any suitable vector. As described in WO2011004129, in one aspect the inserted DNA is built up in the genome of a cell, such as an ES cell, in a stepwise manner using 2, 3, 4, 5, 6, 7, 8, 9, 10, 11, 12, 13, 14, 15, 20 or more separate insertions for the heavy chain gene segments. Fragments are suitably inserted at the same or substantially the same cell locus, e.g. ES cell locus, one after another, to form the complete VDJ region.

In a further aspect the method comprises the insertion of human heavy chain gene segments upstream of the non-human vertebrate constant region by step-wise insertion of multiple fragments by homologous recombination, preferably using an iterative process. Suitably fragments of approximately 100 KB from the human VDJ locus are inserted, suitably to form a VDJ region after the final iteration of the insertion process, as described in WO2011004129.

In one aspect the insertion process commences at a site where an initiation cassette has been inserted into the genome of a cell, such as an ES cell, providing a unique targeting region. In one aspect the initiation cassette is inserted in the non-human vertebrate heavy chain locus, for use in insertion of human heavy chain DNA. The initiation cassette suitably comprises a vector backbone sequence with which a vector having a human DNA fragment in the same backbone sequence can recombine to insert the human DNA into the cell (e.g. ES) cell genome, and suitably a selection marker, such as a negative selection marker. Suitably the vector backbone sequence is that of a BAC library, to allow BACs to be used in the construction of the ES cells and mammals. The vector backbone sequence may however be any sequence which serves as a target site into which a homologous sequence can insert, for example by homologous recombination and, for example RMCE, and is optionally not DNA encoding any of the VDJ or constant region.

Suitable BACs are available from the Sanger centre, see "A genome-wide, end-sequenced 129Sv BAC library resource for targeting vector construction". Adams D J, Quail M A, Cox T, van der Weyden L, Gorick B D, Su Q, Chan W I, Davies R, Bonfield J K, Law F, Humphray S, Plumb B, Liu P, Rogers J, Bradley A. Genomics. 2005 December; 86(6):753-8. Epub 2005 Oct. 27. The Welcome Trust Sanger Institute, Hinxton, Cambridgeshire CB10 1SA, UK. BACs containing human DNA are also available from, for example, Invitrogen. A suitable library (source of human heavy chain gene segments) is described in Osoegawa K et al, Genome Research 2001. 11: 483-496 and obtainable from the Roswell Park Cancer Institute (USA)/Invitrogen.

In any configuration, aspect, embodiment or example of the invention, non-human vertebrates, such as mice, are generated in a RAG-1 or RAG-2-deficient background, or other suitable genetic background which prevents the production of mature host B and T lymphocytes.

In any configuration, aspect, embodiment or example of the invention, the non-human vertebrate is a rodent, suitably a mouse, and cells of the invention, are rodent cells or ES cells, suitably mouse ES cells.

The ES cells of the present invention can be used to generate animals using techniques well known in the art, which comprise injection of the ES cell into a blastocyst followed by implantation of chimaeric blastocystys into females to produce offspring which can be bred and selected for homozygous recombinants having the required insertion. In one aspect the invention relates to a chimeric non-human vertebrate comprised of ES cell-derived tissue and host embryo derived tissue, wherein the ES cell is according to the invention. In one aspect the invention relates to genetically-altered subsequent generation non-human vertebrates, which include vertebrates homozygous for the human VDJ region.

In one any configuration, aspect, example or embodiment, the genome of the cell or vertebrate comprises: one or more human Ig light chain kappa V regions and one or more human Ig light chain kappa J regions upstream of all or part of a kappa constant region.

In one any configuration, aspect, example or embodiment, the genome of the cell or vertebrate comprises: one or more human Ig light chain lambda V regions and one or more human Ig light chain lambda J regions upstream of all or part of a lambda constant region.

Suitably the light chain VJ and C regions are able to form antibody light chains in vivo capable of forming an antibody with one or more of the chimaeric heavy chains to form an antibody that binds a predetermined antigen.

In such aspects a human kappa and/or lambda region is inserted into the genome, in combination with insertion of the heavy chain VDJ region or part thereof, upstream of the host heavy chain constant region as disclosed herein.

Suitably the insertion of the human VJC light chain DNA, or part thereof as disclosed above, is made at the equivalent mouse locus. In one aspect the human light chain kappa VJC DNA, or part thereof, is inserted immediately upstream or downstream of the mouse kappa VJC region. In one aspect, the human light chain lambda VJC region or part thereof is inserted immediately upstream or downstream of the mouse lambda VJC region. In one aspect only the human kappa VJC locus is inserted and not the human lambda VJC locus. In one aspect only the human lambda VJC locus is inserted and not the human kappa VJC locus. Insertions may be made using the techniques disclosed herein, and suitably do not remove the host sequences from the genome. In one aspect the non-human mammal host VJC sequences may be inactivated in some way, by mutation, or inversion, or by insertion of the human variable region DNA, or by any other means. In one aspect the cell or non-human mammal of the invention may comprise an insertion of the complete VJC human region.

The human kappa variable region DNA might be inserted into the genome in functional arrangement with a lambda constant region, for example inserted upstream of a lambda constant region. Alternatively human lambda region variable DNA might be inserted in functional arrangement with a kappa constant region, for example inserted upstream of a kappa constant region.

In one any configuration, aspect, example or embodiment, the genome of the cell or vertebrate comprises: one or more non-human vertebrate control sequences such as the enhancer sequence(s) is maintained upstream of the nonhuman vertebrate Mu constant region, suitably in its native position with respect to the distance from the constant region.

In one any configuration, aspect, example or embodiment, one or more non-human mammal control sequences such as an enhancer sequence(s) are maintained downstream of the nonhuman vertebrate Mu constant region, suitably in its native position with respect to the distance from the constant region.

In one any configuration, aspect, example or embodiment, a non-human mammal switch sequence, suitably the endogenous switch sequence, is maintained upstream of the non-human vertebrate Mu constant region, suitably in its native position with respect to distance from the constant region.

In such location the host enhancer or switch sequences are operative in vivo with the host constant region sequence(s).

In one aspect a switch sequence is neither human, nor native in the non-human mammal, for example in one aspect a non-human mammal switch sequence is not a mouse or human switch sequence. The switch sequence may be, for example, a rodent or primate sequence, or a synthetic sequence. In particular the switch sequence may be a rat sequence where the non-human mammal is a mouse. By way of example, a mouse or human constant mu sequence may be placed under the control of a switch sequence from a rat, or chimp, or other switch sequence, suitably capable of allowing isotype switching to occur in vivo.

One combination envisaged is a rat switch with mouse enhancer sequences and mouse constant regions in a mouse cell.

In one aspect the human promoter and/or other control elements that are associated with the different human V, D or J regions are maintained in after insertion of the human VDJ into the mouse genome.

The functional replacement of human promoter or other control regions by non-human mammal promoter or control regions may be carried out by use of recombineering, or other recombinant DNA technologies, to insert a part of the human Ig region (such as a human V region) into a vector (such as a BAC) containing a non-human Ig region. The recombineering/recombinant technique suitably replaces a portion of the non-human (e.g. mouse) DNA with the human Ig region, and thus places the human Ig region under control of the non-human mammal promoter or other control region. Suitably the human coding region for a human V region replaces a mouse V region coding sequence. Suitably the human coding region for a human D region replaces a mouse D region coding sequence. Suitably the human coding region for a human J region replaces a mouse J region coding sequence. In this way human V, D or J regions may be placed under the control of a non-human mammal promoter, such as a mouse promoter.

In one any configuration, aspect, example or embodiment, the human DNA inserted into the genome of the non-human vertebrate or cell are placed under control of the host regulatory sequences or other (non-human, non-host) sequences, In one aspect reference to human coding regions includes both human introns and exons, or in another aspect simply exons and no introns, which may be in the form of cDNA.

It is also possible to use recombineering, or other recombinant DNA technologies, to insert a non-human-mammal (e.g. mouse) promoter or other control region, such as a promoter for a V region or VpreB, into a BAC containing a human Ig region. The A recombineering step then places a portion of human DNA under control of the mouse promoter or other control region.

Generally, insertion of human variable region DNA at or close to the equivalent endogenous locus in the recipient genome is preferred, for example within 1, 2, 3, 4, 5, 6, 7, 8, 9, or 10 kb of the boundary (upstream or downstream) of a host immunoglobulin locus.

In one embodiment of the method of the second configuration of the invention, said genome is homozygous for said transgene and endogenous non-human vertebrate antibody heavy chain expression is inactivated.

In one embodiment of the method of the second configuration of the invention, endogenous non-human vertebrate antibody light chain expression is inactivated.

In one embodiment of the method of the second configuration of the invention, the heavy chain transgene is devoid of a CH1 gene segment and the genome comprises no functional antibody light chain locus.

In one embodiment of the method of the second configuration of the invention, said constant region is a Cmu. For example, the Cmu is a non-human vertebrate Cmu or an endogenous Cmu of said vertebrate or cell.

In one embodiment of the method of the second configuration of the invention, said genome does not comprise a non-human vertebrate (eg, mouse or rat) species VpreB1 and/or VpreB2 gene.

In one embodiment of the method of the second configuration of the invention, the genome further comprises a λ5 gene; optionally wherein the λ5 gene is a λ5 of a non-human vertebrate (eg, mouse or rat) species and said constant region gene is a constant region gene of the same non-human vertebrate (eg, mouse or rat) species as the λ5 gene.

In one embodiment of the method of the second configuration of the invention, said constant region gene and λ5 gene are endogenous genes of said vertebrate or cell.

In one embodiment of the method of the second configuration of the invention, the method comprises making a progeny of the cell made according to the method, wherein the progeny is homozygous for said heavy chain transgene and endogenous non-human vertebrate antibody expression has been inactivated.

A third configuration of the invention provides

A method of promoting B-cell development in a non-human vertebrate (eg, a mouse or rat), the method comprising
(a) providing in a non-human vertebrate embryonic stem (ES) cell genome an immunoglobulin transgene capable of expressing an antibody mu heavy chain, wherein the antibody heavy chain comprises a human variable region and a mu constant region (optionally an endogenous non-human vertebrate mu constant region); and creating a first non-human vertebrate from said ES cell or a progeny thereof;
(b) providing in a second ES cell genome a second transgene comprising a human VpreB gene capable of expressing a human VpreB; and creating a second non-human vertebrate from said ES cell or a progeny thereof; and
(c) creating by breeding a third non-human vertebrate capable of co-expressing the mu antibody heavy chain and human vpreB wherein a pre-B-cell receptor can form to promote B-cell development of cells bearing a mu heavy chain in said third vertebrate; the third vertebrate being made by crossing said first and second vertebrates or progeny thereof by breeding to create said third vertebrate, the third vertebrate comprising the first and second transgenes, and wherein endogenous heavy chain expression has been inactivated in said third vertebrate.

In one embodiment of the method of the third configuration of the invention, in (a) the heavy chain transgene is constructed to be devoid of a CH1 gene segment and the genome of the third non-human vertebrate comprises no functional antibody light chain locus.

In one embodiment of the method of the third configuration of the invention, the genome of the third vertebrate does not comprise a non-human vertebrate (eg, mouse or rat) species VpreB1 and/or VpreB2 gene.

In one embodiment of the method of the third configuration of the invention, the third non-human vertebrate expresses a λ5 of a non-human vertebrate (eg, mouse or rat) species and said constant region is a constant region of the same non-human vertebrate (eg, mouse or rat) species as the λ5 gene; optionally wherein the λ5 and constant region are an endogenous λ5 and constant region of mouse or rat.

The invention further provides a transgenic mouse according to the third vertebrate, or a progeny thereof.

In a fourth aspect, the invention provides

A method of promoting B-cell development in a non-human vertebrate (eg, a mouse or rat), the method comprising
(i) inactivating endogenous heavy chain expression in said vertebrate;
(ii) providing in the genome of said vertebrate an immunoglobulin transgene capable of expressing an antibody mu heavy chain, wherein the antibody heavy chain comprises a human variable region and a non-human vertebrate mu constant region (optionally an endogenous non-human vertebrate mu constant region); and
(ii) providing in the genome of said vertebrate a second transgene capable of expressing a human VpreB wherein a pre-B-cell receptor can form to promote B-cell development of cells bearing a mu heavy chain in said vertebrate;
Optionally wherein the genome is homozygous for said first transgene.

In one embodiment of the method of the fourth configuration of the invention, the heavy chain transgene is devoid of a CH1 gene segment and the genome of the vertebrate comprises no functional antibody light chain locus.

In one embodiment of the method of the fourth configuration of the invention, the genome of the vertebrate does not comprise a non-human vertebrate (eg, mouse or rat) species VpreB1 and/or VpreB2 gene.

In one embodiment of the method of the fourth configuration of the invention, the non-human vertebrate expresses a λ5 of a non-human vertebrate (eg, mouse or rat) species and said constant region is a constant region of the same non-human vertebrate (eg, mouse or rat) species as the λ5 gene; optionally wherein the λ5 and constant region are an endogenous λ5 and constant region of mouse or rat.

The invention also provides a transgenic mouse according to the fourth configuration, or a progeny thereof.

Chimaeric Surrogate Light Chains

The extent of homology between human λ5 with mouse and rat λ5 is relatively low (about 56% amino acid identity). The inventors realised the advantage of species-matching the λ5 in the SLC in a transgenic non-human vertebrate with the species of mu constant region in the pre-BCRs in such transgenic animals. Thus, the invention further provides aspects that provide for the possibility of species-matching in vivo the variable and constant regions of the antibody heavy chain with both components (VpreB and λ5) of a chimaeric SLC. This is useful for promoting B-cell development in the transgenic non-human vertebrate (eg, a mouse or rat).

Thus, in an embodiment of the vertebrates, cells and methods of the invention, the genome further comprises a λ5 gene; optionally wherein the λ5 gene is a λ5 of a non-human vertebrate (eg, mouse or rat) species and said constant region gene is a constant region gene of the same non-human vertebrate (eg, mouse or rat) species as the λ5 gene. For example, the vertebrate is a mouse or rat (or cell is a mouse or rat cell) and the λ5 is a λ5 that is endogenous to the mouse or rat (or mouse or rat cell). In this example, the constant region of the heavy chain transgene is an constant region (eg, Cmu) endogenous to the mouse or rat. In this way, the λ5 is matched for pairing to the constant region at the cell surface in the pre-BII stage, and the human VpreB is matched for pairing with the human variable region encoded by the transgene.

To this end, the invention provides in a fifth configuration

A non-human vertebrate (eg, a mouse or rat) or cell (eg, a mouse cell or rat cell) whose genome comprises an antibody heavy chain transgene, the transgene comprising
(a) one or more human VH gene segments, one or more human D gene segments and one or more human JH gene segments operably connected upstream of a constant region gene of a non-human vertebrate (eg, mouse or rat) species so that the transgene is capable of undergoing VDJ recombination in vivo to produce an antibody gene comprising a rearranged VDJC encoding a chimaeric antibody heavy chain having a human variable region and a non-human vertebrate constant region; or
(b) a rearranged VDJ encoding a human variable region operably connected upstream of a constant region gene of a non-human vertebrate (eg, mouse or rat) species so that the transgene encodes (optionally following VDJ combination with the constant region) a chimaeric antibody heavy chain having a human variable region and a non-human vertebrate constant region;
the genome further comprising one or more genes together encoding a chimaeric surrogate light chain, the surrogate light chain comprising a human VpreB and λ5 of said non-human vertebrate (eg, mouse or rat) species.

In one embodiment of the method of the fifth configuration of the invention, said genome is homozygous for said transgene and endogenous non-human vertebrate antibody heavy chain expression has been inactivated.

In one embodiment of the method of the fifth configuration of the invention, said constant region gene is a Cmu gene.

In one embodiment of the method of the fifth configuration of the invention, said constant region gene and λ5 gene are endogenous genes of said vertebrate or cell.

In one embodiment of the method of the fifth configuration of the invention, said genome does not comprise a non-human vertebrate (eg, mouse or rat) species VpreB1 and/or VpreB2 gene.

In a sixth configuration, the invention further provides

A method of constructing a transgenic non-human vertebrate cell (eg, an ES cell, eg, a mouse or rat ES cell), the method comprising
(i) introducing into a non-human vertebrate cell (or an ancestor thereof) one or more human VH gene segments, one or more human D gene segments and one or more human JH gene segments so that said gene segments are operably connected upstream of an endogenous non-human vertebrate constant region gene, wherein in said cell or a progeny thereof the transgene is capable of undergoing VDJ recombination in vivo to produce an antibody gene comprising a rearranged VDJC encoding a chimaeric antibody heavy chain having a human variable region and a non-human vertebrate constant region; or
(ii) introducing into a non-human vertebrate cell (or an ancestor thereof) a rearranged VDJ encoding a human variable region so that said VDJ is operably connected upstream of an endogenous non-human vertebrate constant region gene, wherein in said cell or a progeny thereof the transgene encodes (optionally following VDJ combination with the constant region) a chimaeric antibody heavy chain having a human variable region and a non-human vertebrate constant region;
and wherein the method further comprises introducing into the cell a human VpreB gene such that the cell or a progeny thereof is capable of expressing a chimaeric surrogate light chain as well as said chimaeric antibody heavy chain, wherein the surrogate light chain comprises a human VpreB and an endogenous non-human vertebrate λ5.

In one embodiment of the method of the sixth configuration of the invention, said constant region gene is a Cmu gene.

In one embodiment of the method of the sixth configuration of the invention, each endogenous non-human vertebrate VpreB gene is inactivated or deleted from said genome.

In one embodiment, the method of the sixth configuration of the invention comprises making a progeny of the cell made according to the method, wherein the progeny is homozygous for said heavy chain transgene and endogenous non-human vertebrate antibody heavy chain expression has been inactivated.

In a seventh configuration, the invention provides

A method of promoting B-cell development in a non-human vertebrate (eg, a mouse or rat), the method comprising
(a) providing in a non-human vertebrate embryonic stem (ES) cell an immunoglobulin transgene capable of expressing a chimaeric antibody mu heavy chain, wherein the chimaeric antibody heavy chain comprises a human variable region and an endogenous non-human vertebrate mu constant region; and creating a first non-human vertebrate from said ES cell or a progeny thereof;
(b) providing in a second ES cell a second transgene capable of expressing a human VpreB so that the human VpreB and an endogenous λ5 form a chimaeric surrogate light chain; and creating a second non-human vertebrate from said ES cell or a progeny thereof; and
(c) creating by breeding a third non-human vertebrate capable of co-expressing the chimaeric mu antibody heavy chain and chimaeric surrogate light chain wherein a pre-BCR can form to promote B-cell development in said third vertebrate; the third vertebrate being made by crossing said first and second vertebrates or progeny thereof by breeding to create said third vertebrate, the third vertebrate comprising the first and second transgenes, and wherein endogenous heavy chain expression has been inactivated in said third vertebrate.

The invention provides a transgenic mouse according to the vertebrate of this method, or a progeny thereof.

In an eighth configuration, the invention provides

A method of promoting B-cell development in a non-human vertebrate (eg, a mouse or rat), the method comprising (i) inactivating endogenous heavy chain expression in said vertebrate;
(ii) providing in the genome of said vertebrate an immunoglobulin transgene capable of expressing a chimaeric antibody mu heavy chain, wherein the chimaeric antibody heavy chain comprises a human variable region and an endogenous non-human vertebrate mu constant region; and
(ii) providing in the genome of said vertebrate a second transgene capable of expressing a human VpreB so that the human VpreB and an endogenous λ5 form a chimaeric surrogate light chain; so that the vertebrate is capable of co-expressing the chimaeric mu antibody heavy chain and chimaeric surrogate light chain wherein a pre-BCR can form to promote B-cell development in said vertebrate;

Optionally wherein the genome is homozygous for said first transgene.

A transgenic mouse according to the vertebrate of this method, or a progeny thereof, is provided.

In any configuration, aspect, embodiment or example of the invention, the inserted human genes may be derived from the same individual or different individuals, or be synthetic or represent human consensus sequences.

Techniques for constructing non-human vertebrates and vertebrate cells whose genomes comprise a transgene containing human V, J and D regions are well known in the art. For example, reference is made to WO2011004192, U.S. Pat. No. 7,501,552, U.S. Pat. No. 6,673,986, U.S. Pat. No. 6,130,364, WO2009/076464 and U.S. Pat. No. 6,586,251, the disclosures of which are incorporated herein by reference in their entirety.

In one embodiment in any configuration of the invention, the vertebrate is a non-human mammal and the vertebrate cell is a non-human mammalian cell. In one embodiment in any configuration of the invention, the vertebrate is a mouse, rat, rabbit, Camelid (eg, a llama, alpaca or camel) or shark; or the vertebrate cell is a mouse, rat, rabbit, Camelid (eg, a llama, alpaca or camel) or shark cell.

In one aspect the human heavy chain gene segments are inserted into the genome so that they are placed under control of the host regulatory sequences (eg, enhancers, promoters and/or switches) or other (non-human, non-host) sequences. In one aspect reference to human coding regions includes both human introns and exons, or in another aspect simply exons and no introns, which may be in the form of cDNA.

Alternatively it is possible to use recombineering, or other recombinant DNA technologies, to insert a non human-vertebrate (e.g. mouse) promoter or other control region, such as a promoter for a V region, into a BAC containing a human Ig region. The recombineering step then places a portion of human DNA under control of the mouse promoter or other control region.

The invention also relates to a cell line which is grown from or otherwise derived from cells as described herein, including an immortalised cell line. The cell line may comprise inserted human V, D or J genes as described herein, either in germline configuration or after rearrangement following in vivo maturation. The cell may be immortalised by fusion to a tumour cell to provide an antibody producing cell and cell line, or be made by direct cellular immortalisation.

In one aspect the non-human vertebrate of any configuration of the invention is able to generate a diversity of at least $1 \times 10^6$ different functional chimaeric immunoglobulin sequence combinations.

Optionally in any configuration of the invention the constant region is endogenous to the vertebrate and optionally comprises an endogenous switch. In one embodiment, the constant region comprises a Cgamma (Cγ) region and/or a Smu (Sμ) switch. Switch sequences are known in the art, for example, see Nikaido et al, Nature 292: 845-848 (1981) and also WO2011004192, U.S. Pat. No. 7,501,552, U.S. Pat. No. 6,673,986, U.S. Pat. No. 6,130,364, WO2009/076464 and U.S. Pat. No. 6,586,251, eg, SEQ ID NOs: 9-24 disclosed in U.S. Pat. No. 7,501,552. Optionally the constant region comprises an endogenous S gamma switch and/or an endogenous Smu switch. One or more endogenous switch regions can be provided, in one embodiment, by constructing a transgenic immunoglobulin locus in the vertebrate or cell genome in which at least one human V region, at least one human J region, and optionally at least one human D region, or a rearranged VDJ or VJ region, are inserted into the genome in operable connection with a constant region that is endogenous to the vertebrate or cell. For example, the human V(D)J regions or rearranged VDJ or VJ can be inserted in a cis orientation onto the same chromosome as the endogenous constant region. A trans orientation is also possible, in which the human V(D)J regions or rearranged VDJ or VJ are inserted into one chromosome of a pair (eg, the chromosome 6 pair in a mouse or the chromosome 4 in a rat) and the endogenous constant region is on the other chromosome of the pair, such that trans-switching takes place in which the human V(D)J regions or rearranged VDJ or VJ are spliced inoperable linkage to the endogenous constant region. In this way, the vertebrate can express antibodies having a chain that comprises a variable region encoded all or in part by human V(D)J or a rearranged VDJ or VJ, together with a constant region (eg, a Cgamma or Cmu) that is endogenous to the vertebrate.

Human variable regions are suitably inserted upstream of non-human vertebrate constant region, the latter comprising all of the DNA required to encode the full constant region or a sufficient portion of the constant region to allow the formation of an effective chimaeric antibody capable of specifically recognising an antigen.

In one aspect the chimaeric antibodies or antibody chains have a part of a host constant region sufficient to provide one or more effector functions seen in antibodies occurring naturally in a host vertebrate, for example that they are able interact with Fc receptors, and/or bind to complement.

Reference to a chimaeric antibody or antibody chain having a non-human vertebrate constant region herein therefore is not limited to the complete constant region but also includes chimaeric antibodies or chains which have all of the host constant region, or a part thereof sufficient to provide one or more effector functions. This also applies to non-human vertebrate mammals and cells and methods of the invention in which human variable region DNA may be inserted into the host genome such that it forms a chimaeric antibody chain with all or part of a host constant region. In one aspect the whole of a host non-human vertebrate constant region is operably linked to human variable region DNA.

The host non-human vertebrate constant region herein is optionally the endogenous host wild-type constant region located at the wild type locus, as appropriate for the heavy or light chain. For example, the human heavy chain DNA is suitably inserted on mouse chromosome 12, suitably adjacent the mouse heavy chain constant region, where the vertebrate is a mouse.

In one optional aspect where the vertebrate is a mouse, the insertion of the human DNA, such as the human VDJ region is targeted to the region between the J4 exon and the Cµ locus in the mouse genome IgH locus, and in one aspect is inserted between coordinates 114,667,090 and 114,665,190, suitably at coordinate 114,667,091, after 114,667,090. In one aspect the insertion of the human DNA, such as the human light chain kappa VJ is targeted into mouse chromosome 6 between coordinates 70,673,899 and 70,675,515, suitably at position 70,674,734, or an equivalent position in the lambda mouse locus on chromosome 16.

In one aspect the host non-human vertebrate constant region for forming the chimaeric antibody may be at a different (non endogenous) chromosomal locus. In this case the inserted human DNA, such as the human variable VDJ or VJ region(s) may then be inserted into the non-human genome at a site which is distinct from that of the naturally occurring heavy or light constant region. The native constant region may be inserted into the genome, or duplicated within the genome, at a different chromosomal locus to the native position, such that it is in a functional arrangement with the human variable region such that chimaeric antibodies of the invention can still be produced.

In one aspect the human DNA is inserted at the endogenous host wild-type constant region located at the wild type locus between the host constant region and the host VDJ region.

Reference to location of the variable region upstream of the non-human vertebrate constant region means that there is a suitable relative location of the two antibody portions, variable and constant, to allow the variable and constant regions to form a chimaeric antibody or antibody chain in vivo in the vertebrate. Thus, the inserted human DNA and host constant region are in operable connection with one another for antibody or antibody chain production.

In one aspect the inserted human DNA is capable of being expressed with different host constant regions through isotype switching. In one aspect isotype switching does not require or involve trans switching. Insertion of the human variable region DNA on the same chromosome as the relevant host constant region means that there is no need for trans-switching to produce isotype switching.

In the present invention, optionally host non-human vertebrate constant regions are maintained and it is preferred that at least one non-human vertebrate enhancer or other control sequence, such as a switch region, is maintained in functional arrangement with the non-human vertebrate constant region, such that the effect of the enhancer or other control sequence, as seen in the host vertebrate, is exerted in whole or in part in the transgenic animal. This approach is designed to allow the full diversity of the human locus to be sampled, to allow the same high expression levels that would be achieved by non-human vertebrate control sequences such as enhancers, and is such that signalling in the B-cell, for example isotype switching using switch recombination sites, would still use non-human vertebrate sequences.

A non-human vertebrate having such a genome would produce chimaeric antibodies with human variable and non-human vertebrate constant regions, but these are readily humanized, for example in a cloning step. Moreover the in vivo efficacy of these chimaeric antibodies could be assessed in these same animals.

In one aspect the inserted human IgH VDJ region comprises, in germline configuration, all of the V, D and J regions and intervening sequences from a human. Optionally, non-functional V and/or D and/or J gene segments are omitted. For example, VH which are inverted or are pseudogenes may be omitted.

In one aspect 800-1000 kb of the human IgH VDJ region is inserted into the non-human vertebrate IgH locus, and in one aspect a 940, 950 or 960 kb fragment is inserted. Suitably this includes bases 105,400,051 to 106,368,585 from human chromosome 14.

In one aspect the inserted IgH human fragment consists of bases 105,400,051 to 106,368,585 from chromosome 14. In one aspect the inserted human heavy chain DNA, such as DNA consisting of bases 105,400,051 to 106,368,585 from chromosome 14, is inserted into mouse chromosome 12 between the end of the mouse J4 region and the Eµ region, suitably between co-ordinates 114,667,090 and 114,665, 190, or at co-ordinate 114,667,091, after 114,667,090. In one aspect the insertion is between co-ordinates 114,667,089 and 114,667,090 (co-ordinates refer to NCBI m37, for the mouse C57BL/6J strain), or at equivalent position in another non-human vertebrate genome.

A cell or non-human vertebrate of the invention, in one embodiment, comprises an insertion of human heavy chain variable region DNA between co-ordinates 114, 666, 183 and 114, 666, 725, such as between 114 666 283 and 114 666 625, optionally between co-ordinates 114,666,335 and 114, 666,536, optionally between 114,666,385 and 114,666,486, or between 114,666,425 and 114,666,446, or between 114, 666,435 and 114,666,436 of mouse chromosome 12 with reference to NCBIM37 for the mouse genome, relating to mouse strain C57BL/6J or an equivalent position of mouse chromosome 12 from a different mouse strain or an equivalent position in the genome of another non-human vertebrate, e.g., a rat. The insertion between co-ordinates 114, 666,435 and 114,666,436 relating to mouse strain C57BL/6J is equivalent to an insertion between co-ordinates 1207826 and 1207827 on chromosome 12 with reference to the 129/SvJ genomic sequence of the geneBank access number NT114985.2. An insertion may be made at equivalent position in another genome, such as another mouse genome. In an example of this embodiment, the cell or mammal of the invention comprises a human IgH VDJ region which comprises or consists of nucleotides 106,328,851-107,268,544, such as nucleotides 106,328,901-107,268,494, such as nucleotides 106,328,941-107,268,454, such as nucleotides 106,328,951-107,268,444 of human Chromosome 14, with reference to the GRCH37/hg19 sequence database, or insertion of equivalent nucleotides relating to chromosome 14 from a different human sequence or database. The human insertion may be made between the regions indicated above.

In one aspect there is inserted into the genome the human kappa VJ region which comprises, in germline configuration, all of the V and J regions and intervening sequences from a human. Optionally, non-functional V and/or J gene segments are omitted.

Suitably this includes bases 88,940,356 to 89,857,000 from human chromosome 2, suitably approximately 917 kb. In a further aspect the light chain VJ insert may comprise only the proximal clusters of V segments and J segments. Such an insert would be of approximately 473 kb.

In one aspect the human light chain kappa DNA, such as the human Igκ fragment of bases 88,940,356 to 89,857,000 from human chromosome 2, is suitably inserted into mouse chromosome 6 between coordinates 70,673,899 and 70,675,515, suitably at position 70,674,734.

In one aspect the human lambda V (or VJ) region is inserted into the genome, which comprises, in germline configuration, all of the V (and optionally J) regions and intervening sequences from a human (which will thus include the human VpreB gene and a promoter). Suitably this includes analogous bases to those selected for the kappa fragment, from human chromosome 2. Optionally, non-functional V and/or J gene segments are omitted.

All specific human fragments described above may vary in length, and may for example be longer or shorter than defined as above, such as 500 bases, 1 KB, 2K, 3K, 4K, 5 KB, 10 KB, 20 KB, 30 KB, 40 KB or 50 KB or more, which suitably comprise all or part of the human V(D)J region, whilst preferably retaining the requirement for the final insert to comprise human genetic material encoding the complete heavy chain region and light chain region, as appropriate, as described above.

In one aspect the 3' end of the last inserted human sequence, generally the last human J sequence, is inserted less than 2 kb, preferably less than 1 KB from the human/non-human vertebrate (eg, human/mouse or human/rat) join region.

Optionally, the genome is homozygous at at least the IgH, or a second, or all three immunoglobulin loci (IgH, Igλ and Igκ).

In another aspect the genome may be heterozygous at one or more of the loci, such as heterozygous for DNA encoding a chimaeric antibody chain and native (host cell) antibody chain. In one aspect the genome may be heterozygous for DNA capable of encoding 2 different antibody heavy chains encoded by immunoglobulin transgenes of the invention, for example, comprising 2 different chimaeric heavy chains and a human lambda light chain.

In one aspect the invention relates to a non-human vertebrate or cell, and methods for producing said vertebrate or cell, as described herein, wherein the inserted human DNA, such as the human IgH VDJ region and/or light chain V, J regions are found on only one allele and not both alleles in the mammal or cell. In this aspect a mammal or cell has the potential to express both an endogenous host antibody heavy or light chain and a chimaeric heavy or light chain.

In one embodiment in any configuration of the invention, the genome has been modified to prevent or reduce the expression of fully-endogenous antibody. Examples of suitable techniques for doing this can be found in WO2011004192, U.S. Pat. No. 7,501,552, U.S. Pat. No. 6,673,986, U.S. Pat. No. 6,130,364, WO2009/076464, EP1399559 and U.S. Pat. No. 6,586,251, the disclosures of which are incorporated herein by reference. In one embodiment, the non-human vertebrate VDJ region of the endogenous heavy chain immunoglobulin locus, and optionally VJ region of the endogenous light chain immunoglobulin loci (lambda and/or kappa loci), have been inactivated. For example, all or part of the non-human vertebrate VDJ region is inactivated by inversion in the endogenous heavy chain immunoglobulin locus of the mammal, optionally with the inverted region being moved upstream or downstream of the endogenous Ig locus. For example, all or part of the non-human vertebrate VJ region is inactivated by inversion in the endogenous kappa chain immunoglobulin locus of the mammal, optionally with the inverted region being moved upstream or downstream of the endogenous Ig locus. For example, all or part of the non-human vertebrate VJ region is inactivated by inversion in the endogenous lambda chain immunoglobulin locus of the mammal, optionally with the inverted region being moved upstream or downstream of the endogenous Ig locus. In one embodiment the endogenous heavy chain locus is inactivated in this way as is one or both of the endogenous kappa and lambda loci.

Additionally or alternatively, the vertebrate has been generated in a genetic background which prevents the production of mature host B and T lymphocytes, optionally a RAG-1-deficient and/or RAG-2 deficient background. See U.S. Pat. No. 5,859,301 for techniques of generating RAG-1 deficient animals.

In one embodiment in any configuration of the invention, the human V, J and optional D regions are provided by all or part of the human IgH locus; optionally wherein said all or part of the IgH locus includes substantially the full human repertoire of IgH V, D and J regions and intervening sequences. A suitable part of the human IgH locus is disclosed in WO2011004192. In one embodiment, the human IgH part includes (or optionally consists of) bases 105,400,051 to 106,368,585 from human chromosome 14 (coordinates from NCBI36). Additionally or alternatively, optionally wherein the vertebrate is a mouse or the cell is a mouse cell, the human V, J and optional D regions are inserted into mouse chromosome 12 at a position corresponding to a position between coordinates 114,667,091 and 114,665,190, optionally at coordinate 114,667,091 (coordinates from NCBIM37, relating to mouse strain C57BL/6J).

In one embodiment of any configuration of the vertebrate or vertebrate cell of the invention when the vertebrate is a mouse, (i) the constant region comprises a mouse or rat Sμ switch and optionally a mouse Cμ region. For example the constant region is provided by the constant region endogenous to the mouse, eg, by inserting human V(D)J region sequences into operable linkage with the endogenous constant region of a mouse genome or mouse cell genome.

In one embodiment of any configuration of the vertebrate or vertebrate cell of the invention when the vertebrate is a rat, (i) the constant region comprises a mouse or rat Sμ switch and optionally a rat Cμ region. For example the constant region is provided by the constant region endogenous to the rat, eg, by inserting human V(D)J region sequences into operable linkage with the endogenous constant region of a rat genome or rat cell genome.

In one embodiment of any configuration of the vertebrate or vertebrate cell of the invention the genome comprises an antibody light chain transgene which comprises all or part of the human Igλ locus including at least one human Jλ region and at least one human Cλ region, optionally $C_\lambda 6$ and/or $C_\lambda 7$. Optionally, the transgene comprises a plurality of human Jλ regions, optionally two or more of $J_\lambda 1$, $J_\lambda 2$, $J_\lambda 6$ and $J_\lambda 7$, optionally all of $J_\lambda 1$, $J_\lambda 2$, $J_\lambda 6$ and $J_\lambda 7$. The human lambda immunoglobulin locus comprises a unique gene architecture composed of serial J-C clusters. In order to take advantage of this feature, the invention in optional aspects employs one or more such human J-C clusters inoperable linkage with the constant region in the transgene, eg, where the constant region is endogenous to the non-human vertebrate or non-human vertebrate cell. Thus, optionally the transgene comprises at least one human $J_\lambda$-$C_\lambda$ cluster, optionally at least $J_\lambda 7$-$C_\lambda 7$. The construction of such transgenes is facilitated by being able to use all or part of the human lambda locus such that the transgene comprises one or more J-C clusters in germline configuration, advantageously also including intervening sequences between clusters and/or between adjacent J and C regions in the human locus. This preserves any regulatory elements within the intervening sequences which may be involved in VJ and/or JC recombination and which may be recognised by AID (activation-induced deaminase) or AID homologues.

Where endogenous regulatory elements are involved in CSR (class-switch recombination) in the non-human vertebrate, these can be preserved by including in the transgene a constant region that is endogenous to the non-human vertebrate. In the invention, one can match this by using an AID or AID homologue that is endogenous to the vertebrate or a functional mutant thereof. Such design elements are advantageous for maximising the enzymatic spectrum for SHM (somatic hypermutation) and/or CSR and thus for maximising the potential for antibody diversity.

Optionally, the lambda transgene comprises a human Eλ enhancer. Optionally, the kappa transgene comprises a human Eκ enhancer. Optionally, the heavy chain transgene comprises a heavy chain human enhancer.

In one embodiment of any configuration of the invention the constant region is endogenous to the non-human vertebrate or derived from such a constant region. For example, the vertebrate is a mouse or the cell is a mouse cell and the constant region is endogenous to the mouse. For example, the vertebrate is a rat or the cell is a rat cell and the constant region is endogenous to the rat.

In one embodiment of any configuration of the invention the heavy chain transgene comprises a plurality human IgH V regions, a plurality of human D regions and a plurality of human J regions, optionally substantially the full human repertoire of IgH V, D and J regions.

In one embodiment of any configuration of the invention, the vertebrate or cell comprises a heavy chain further transgene, the further transgene comprising at least one human IgH V region, at least one human D region and at least one human J region, optionally substantially the full human repertoire of IgH V, D and J regions.

In one embodiment of any configuration of the invention, (i) the heavy chain transgene comprises at least one human IgH V region, at least one human J region, and optionally at least one human D region; and
(ii) the vertebrate or cell comprises a kappa transgene, the kappa transgene comprising at least one human Igκ V region and at least one human J region.

In one embodiment of any configuration of the invention, (i) the heavy chain transgene comprises at least one human IgH V region, at least one human J region, and optionally at least one human D region; and
(ii) the vertebrate or cell comprises a lambda transgene, the lambda transgene comprising at least one human Igλ V region and at least one human J region.

In one embodiment of any configuration of the invention, (i) the heavy chain transgene comprises substantially the full human repertoire of IgH V, D and J regions; and
(ii) the vertebrate or cell comprises substantially the full human repertoire of Igκ V and J regions and/or substantially the full human repertoire of Igλ V and J regions.

An aspect provides a B-cell, hybridoma or a stem cell, optionally an embryonic stem cell or haematopoietic stem cell, according to any configuration of the invention. In one embodiment, the cell is a BALB/c, JM8 or AB2.1 or AB2.2 embryonic stem cell (see discussion of suitable cells, and in particular JM8 and AB2.1 cells, in WO2011004192, which disclosure is incorporated herein by reference). In one aspect the ES cell is derived from the mouse BALB/c, C57BL/6N, C57BL/6J, 12955 or 129Sv strain.

An aspect provides a method of isolating an antibody or nucleotide sequence encoding said antibody, the method comprising (a) immunising (see e.g. Harlow, E. & Lane, D. 1998, 5$^{th}$ edition, Antibodies: A Laboratory
Manual, Cold Spring Harbor Lab. Press, Plainview, N.Y.; and Pasqualini and Arap, Proceedings of the National Academy of Sciences (2004) 101:257-259) a vertebrate according to any configuration or aspect of the invention with an antigen such that the vertebrate produces antibodies; and
(b) isolating from the vertebrate an antibody that specifically binds to said antigen and/or a nucleotide sequence encoding at least the heavy and/or the light chain variable regions of said antibody;
optionally wherein the variable regions of said antibody are subsequently joined to a human constant region. Such joining can be effected by techniques readily available in the art, such as using conventional recombinant DNA and RNA technology as will be apparent to the skilled person. See e.g. Sambrook, J and Russell, D. (2001, 3'd edition) Molecular Cloning: A Laboratory Manual (Cold Spring Harbor Lab. Press, Plainview, N.Y.).

Suitably an immunogenic amount of the antigen is delivered. The invention also relates to a method for detecting a target antigen comprising detecting an antibody produced as above with a secondary detection agent which recognises a portion of that antibody.

Isolation of the antibody in step (b) can be carried out using conventional antibody selection techniques, eg, panning for antibodies against antigen that has been immobilised on a solid support, optionally with iterative rounds at increasing stringency, as will be readily apparent to the skilled person.

As a further optional step, after step (b) the amino acid sequence of the heavy and/or the light chain variable regions of the antibody are mutated to improve affinity for binding to said antigen. Mutation can be generated by conventional techniques as will be readily apparent to the skilled person, eg, by error-prone PCR. Affinity can be determined by conventional techniques as will be readily apparent to the skilled person, eg, by surface plasmon resonance, eg, using Biacore™.

Additionally or alternatively, as a further optional step, after step (b) the amino acid sequence of the heavy and/or the light chain variable regions of the antibody are mutated to improve one or more biophysical characteristics of the antibody, eg, one or more of melting temperature, solution state (monomer or dimer), stability and expression (eg, in CHO or *E. coli*).

An aspect provides an antibody produced by the method of the invention, optionally for use in medicine, eg, for treating and/or preventing a medical condition or disease in a patient, eg, a human.

An aspect provides a nucleotide sequence encoding the antibody of the invention, optionally wherein the nucleotide sequence is part of a vector. Suitable vectors will be readily apparent to the skilled person, eg, a conventional antibody expression vector comprising the nucleotide sequence together in operable linkage with one or more expression control elements.

An aspect provides a pharmaceutical composition comprising the antibody of the invention and a diluent, excipient or carrier, optionally wherein the composition is contained in an IV container (eg, and IV bag) or a container connected to an IV syringe.

An aspect provides the use of the antibody of the invention in the manufacture of a medicament for the treatment and/or prophylaxis of a disease or condition in a patient, eg a human.

In a further aspect the invention relates to a method for producing an antibody specific to a desired antigen the method comprising immunizing a transgenic non-human vertebrate as above with a predetermined antigen and recovering a chimaeric antibody (see e.g. Harlow, E. & Lane, D. 1998, 5$^{th}$ edition, Antibodies: A Laboratory Manual, Cold Spring Harbor Lab. Press, Plainview, N.Y.; and Pasqualini and Arap, Proceedings of the National Academy of Sciences (2004) 101:257-259). Suitably an immunogenic amount of the antigen is delivered. The invention also relates to a method for detecting a target antigen comprising detecting an antibody produced as above with a secondary detection agent which recognises a portion of that antibody.

In a further aspect the invention relates to a method for producing a fully humanised antibody comprising immunizing a transgenic non-human vertebrate as above with a predetermined antigen, recovering a chimaeric antibody or cells expressing the antibody, and then replacing the non-human vertebrate constant region with a human constant region. This can be done by standard cloning techniques at the DNA level to replace the non-human vertebrate constant region with an appropriate human constant region DNA sequence—see e.g. Sambrook, J and Russell, D. (2001, 3'd edition) Molecular Cloning: A Laboratory Manual (Cold Spring Harbor Lab. Press, Plainview, N.Y.).

In a further aspect the invention relates to humanised antibodies and antibody chains produced according to the present invention, both in chimaeric and fully humanised form, and use of said antibodies in medicine. The invention also relates to a pharmaceutical composition comprising such an antibody and a pharmaceutically acceptable carrier or other excipient.

Antibody chains containing human sequences, such as chimaeric human-non-human antibody chains, are considered humanised herein by virtue of the presence of the human protein coding regions region. Fully humanised antibodies may be produced starting from DNA encoding a chimaeric antibody chain of the invention using standard techniques.

Methods for the generation of both monoclonal and polyclonal antibodies are well known in the art, and the present invention relates to both polyclonal and monoclonal antibodies of chimaeric or fully humanised antibodies produced in response to antigen challenge in non-human vertebrates of the present invention.

In a yet further aspect, chimaeric antibodies or antibody chains generated in the present invention may be manipulated, suitably at the DNA level, to generate molecules with antibody-like properties or structure, such as a human variable region from a heavy chain absent a constant region, for example a domain antibody; or a human variable region with any constant region from either heavy or light chain from the same or different species; or a human variable region with a non-naturally occurring constant region; or human variable region together with any other fusion partner. The invention relates to all such chimaeric antibody derivatives derived from chimaeric antibodies identified according to the present invention.

In an example, the genome of the cell or non-human vertebrate of the invention encodes an antibody comprising an antibody chain having a human heavy chain variable region upstream of a mouse light chain constant region in combination with one of:
a fully human antibody light chain;
a non-human vertebrate (e.g., mouse or rat) antibody light chain;
a chimaeric non-human vertebrate (e.g., mouse or rat)—human antibody chain; or
an antibody chain having a human heavy chain variable region upstream of a non-human vertebrate (e.g., mouse or rat) light chain constant region;

In a further aspect, the invention relates to use of non-human vertebrates of the present invention in the analysis of the likely effects of drugs and vaccines in the context of a quasi-human antibody repertoire.

The invention also relates to a method for identification or validation of a drug or vaccine, the method comprising delivering the vaccine or drug to a vertebrate of the invention and monitoring one or more of: the immune response, the safety profile; the effect on disease.

The invention also relates to a kit comprising an antibody or antibody derivative as disclosed herein and either instructions for use of such antibody or a suitable laboratory reagent, such as a buffer, antibody detection reagent.

The invention also relates to a method for making an antibody, or part thereof, the method comprising providing:
(i) a nucleic acid encoding an antibody, or a part thereof, obtained according to the present invention; or
(ii) sequence information from which a nucleic acid encoding an antibody obtained according to the present invention, or part thereof, can be expressed to allow an antibody to be produced.

In an embodiment, the invention provides
The non-human vertebrate, mouse, rat, cell or method of any preceding configuration, wherein the genome comprises
(a) said antibody heavy chain transgene; and
(b) an antibody kappa light chain transgene and/or an antibody lambda chain transgene;
wherein all of the V, D and J in said transgenes are human V, D and J;
wherein endogenous antibody heavy and light chain expression has been inactivated; and optionally wherein said genome is homozygous for said heavy and light chain transgenes.

In an embodiment, the kappa and lambda chain transgenes comprise constant regions of said non-human vertebrate species capable of pairing with the constant region of the heavy chain.

In an embodiment, the heavy chain transgene comprises a substantially complete human functional VH, D and JH repertoire.

In an embodiment, the kappa chain transgene comprises a substantially complete human functional Vκ and Jκ repertoire; and the lambda chain transgene comprises a substantially complete human functional Vλ and Jλ repertoire.

In a ninth embodiment, the invention provides
A transgenic mouse or rat, or a transgenic mouse or rat cell (eg, an ES cell), whose genome comprises
(a) an antibody heavy chain transgene, the transgene comprising a substantially complete human functional VH, D and JH repertoire operably connected upstream of an endogenous (mouse or rat) mu constant region gene so that the transgene is capable of undergoing VDJ recombination in vivo to produce an antibody gene comprising a rearranged VDJC encoding an antibody heavy chain having a human variable region and an endogenous mu constant region;
(b) an antibody kappa light chain transgene and/or an antibody lambda chain transgene;
    wherein all of the V, D and J in said transgenes are human V, D and J;
    wherein the kappa chain transgene comprises a substantially complete human functional Vκ and Jκ repertoire;

and the lambda chain transgene comprises a substantially complete human functional Vλ and Jλ repertoire;
wherein the kappa and/or lambda chain transgenes comprise endogenous constant regions capable of pairing with the constant region of the heavy chain;
(c) a human VpreB gene capable of expressing a human VpreB;
optionally wherein the human VpreB gene is operably linked to an endogenous VpreB promoter; and
(d) an endogenous λ5 gene capable of expressing an endogenous λ5;
wherein endogenous antibody heavy and light chain expression has been inactivated; and
optionally wherein said genome is homozygous for said heavy and light chain transgenes.

In a tenth embodiment, the invention provides
A transgenic mouse or rat, or a transgenic mouse or rat cell (eg, an ES cell), whose genome comprises
(a) an antibody heavy chain transgene, the transgene comprising a substantially complete human functional VH, D and JH repertoire operably connected upstream of an endogenous (mouse or rat) mu constant region gene so that the transgene is capable of undergoing VDJ recombination in vivo to produce an antibody gene comprising a rearranged VDJC encoding an antibody heavy chain having a human variable region and an endogenous mu constant region;
wherein all of the V, D and J in said transgene are human V, D and J;
wherein the heavy chain transgene is devoid of a CH1 gene segment and the genome of the vertebrate comprises no functional antibody light chain locus;
wherein endogenous antibody heavy chain expression has been inactivated; and
optionally wherein said genome is homozygous for said heavy chain transgene;
(c) a human VpreB gene capable of expressing a human VpreB;
optionally wherein the human VpreB gene is operably linked to an endogenous VpreB promoter; and
(d) an endogenous λ5 gene capable of expressing an endogenous λ5.

Insertion of Human VpreB Gene

As described above, precise insertion of exogenous DNA (such as human VpreB or antibody gene segment DNA) can be effected by homolgous recombination, RMCE or other techniques that will be apparent to the skilled person. Vector manipulation can be effected using recombineering as is well known.

The human VpreB gene is found in human cells within the human antibody Vλ gene segment cluster (in the nucleotide region between human Igλ V gene segments IV-53 and 5-52 (the nucleotide region being positions 22599200 to 22599926 on human chromosome 22)). Thus, in one embodiment, a nucleotide sequence found between human Igλ V gene segments IV-53 and 5-52, eg, positions 22599200 to 22599926 on human chromosome 22, is inserted into the genome of the cell or vertebrate, wherein the nucleotide sequence comprises a human VpreB gene and optionally the associated human promoter. For example, the nucleotide sequence is inserted in the endogenous lambda antibody locus upstream of the endogenous lambda constant region. In one embodiment, a region of the human Vλ gene segment cluster comprising at least one (or substantially all) human Vλ gene segments and the human VpreB and promoter is inserted upstream of the endogenous (eg, mouse or rat) Cλ. In one example, the insertion is between the most 3' endogenous Jλ and the endogenous Cλ. In another embodiment, the insertion is in the endogenous Vλ cluster, optionally replacing the Vλ in whole or in part. In one embodiment, all of the human lambda Vλ gene segment cluster (including introns) is inserted into the genome so that it replaces the enogenous Vλ gene segment cluster. In one embodiment, the cell or vertebrate is a mouse or rat, so "endogenous" refers to the regions found in the genome of a mouse or rat.

Expression of the λ5 and VpreB genes is B-cell lineage restricted and is also subject to stage-specific regulation during B-cell development. Binding sites for the transcription factors EBF, E47, Pax-5 and Ikaros are present in the λ5 and VpreB promoters. The mouse VpreB1 and λ5 genes are both located in the λ5-VpreB1 locus and 4 kb away from each other. A locus control region (LCR) located within the λ5-VpreB1 locus provides the regulatory elements for these genes are. Hence, the region around the two genes are important for the transcription of the VpreB1 and λ5 genes. Furthermore, these two genes are subject to tight stage-specific control during B-cell development. For activation at the pro-B cell stage, early B cell factor (EBF) initiates the activation of the λ5-VpreB1 locus. It has been observed that the EBF with some other factors (E2As) bind the promoters of the two genes. The transcription of these two genes has to be silenced during the transition from the pre-B to the immature B cell stage, in order for light chain rearrangement and binding with heavy chain. Ikaros gene acts as a repressor by competing with EBF for binding to the same sites in the promoters of the VpreB1 and λ5 genes. In summary, the λ5-VpreB1 locus seems to be important for the temporally-controlled activation and inactivation of the surrogate light chain during B-cell development. See:—

Mol Cell Biol. 1999 January; 19(1):671-9; Analysis of mice with single and multiple copies of transgenes reveals a novel arrangement for the lambda5-VpreB1 locus control region; Sabbattini P, Georgiou A, Sinclair C, Dillon N.

Seminars in Immunology, 2005 April; 17(2):121-7; The lambda5-VpreB1 locus-a model system for studying gene regulation during early B cell development; Sabbattini P, Dillon N.

Thus, in one embodiment the invention provides a non-human vertebrate, mouse, rat, cell or method according to any configuration, aspect, embodiment or example, wherein the expression of the human VpreB gene is under endogenous control. For example, the vertebrate is a mouse or rat or the cell is a mouse or rat cell (eg, an ES cell) and the human VpreB is under the control of the gene expression control elements of the mouse or rat (cell). This can be achieved, in one example, by replacing an endogenous VpreB (eg, VpreB1) gene with a human VpreB gene at the location where the former usually resides in the genome. Precise gene replacement in genomes can be carried out by homolgous recombination or RMCE as herein described.

Mouse VpreB1 and VpreB2 are found at the following position in a mouse genome:—

Mouse VpreB1: chromosome 16: 16868494 to 16869348
Mouse VpreB2: chromosome 16: 17980658 to 17981173

Thus, the invention provides a non-human vertebrate, mouse, rat, cell or method according to any configuration, aspect, embodiment or example, wherein the human VpreB gene is operably linked to an endogenous promoter, optionally an endogenous VpreB promoter (eg, a VpreB1 or VpreB2 promoter). Thus, where the vertebrate (or cell) is a mouse or rat (cell), the human VpreB is operably linked to a VpreB1 or VpreB2 promoter of said mouse or rat (cell). Operable linkage enables the promoter to control expression of the human gene. It is desirable to use endogenous gene expression control (eg, using an endogenous promoter) for human VpreB expression since this will harness the endogenous (eg, mouse or rat) temporal expression control for turning on and off the human VpreB gene (and coordinating this with λ5 expression) during the various stages of B-cell development, particularly up to the point where light chain pairing with heavy chains occurs in immature B-cells. Thereafter, the usual switching off of SLC-component gene expression can be controlled properly by the endogenous control mechanisms when the pre-BCR is no longer participating in B-cell maturation.

Thus, the invention provides a non-human vertebrate, mouse, rat, cell or method according to any configuration, aspect, embodiment or example, wherein the human VpreB gene is operably linked to an endogenous VpreB-λ5 locus control region (LCR). Thus, where the vertebrate (or cell) is a mouse or rat (cell), the human VpreB is operably linked to a VpreB-λ5 LCR of said mouse or rat (cell). LCRs are dominant activating sequences that are able to activate gene expression at any location in the genome. Optionally, the LCR is present at the wild-type position in the genome of the vertebrate or cell. In another example, the LCR is not at the wild-type position in the genome of the vertebrate or cell. In this case, therefore, the human VpreB is positioned away from the endogenous VpreB gene in the genome, which may be advantageous for controlling the human VpreB expression independently of the endogenous λ5.

In an embodiment, the invention provides a non-human vertebrate, mouse, rat, cell or method according to any configuration, aspect, embodiment or example, wherein the human VpreB gene is operably linked to an endogenous VpreB locus control region (LCR). Thus, where the vertebrate (or cell) is a mouse or rat (cell), the human VpreB is operably linked to a VpreB LCR of said mouse or rat (cell). Optionally, the LCR is present at the wild-type position in the genome of the vertebrate or cell. In another example, the LCR is not at the wild-type position in the genome of the vertebrate or cell. In this case, therefore, the human VpreB is positioned away from the endogenous VpreB gene in the genome, which may be advantageous for controlling the human VpreB expression independently of the endogenous λ5.

Optionally one or more DNase I hypersensitive sites (HS) is operably linked in the genome to the human VpreB gene. For example, the HS forms part of the LCR or is 3' of the LCR or 3' of the LCR-human VpreB (see, Sabbattini et al 1999, supra).

Optionally in any configuration, aspect, embodiment or example of the inventions, the human VpreB gene is present in multiple copies in the genome, eg, the genome comprises 2, 3, 4, 5, 6, 7, 8, 9 or 10 copies of the human VpreB gene. For example, 2, 3, 4 or 5 copies are operably linked to the control element (eg, promoter and/or LCR) mentioned above.

Assessing the Development of the B-Cell Repertoire

Some assays can be used to investigate if the invention leads to promotion of B-cell development and repertoire. Although described in the context of transgenic mice below, these comments apply equally to other transgenic non-human vertebrates of the invention.

1. In chimaeric mouse, after introducing the human DNA fragment covering several human Vs, all Ds and is between mouse is and mouse Cs, the usage of the inserted human Vs can be tested by sequencing the mRNA products of the IgH locus in chimaeric mouse. In this case, human Vs will compete with endogenous mouse Vs for formation of the heavy chain. The usage of human Vs vs mouse Vs will be compared in mice with and without introduction of human VpreB gene into the chimaeric mouse with/without the endogenous mouse VpreB gene. More detail is provided in the non-limiting example below.

2. The use of human VpreB or mouse VpreB protein for pre-BCR assembly can be analysed in pre-B cell populations from mice with or without the human VpreB. Surrogate light chain can only be detected in the transitional pre-BI and large pre-BII stages in bone marrow. To enrich the cell populations in bone marrow for investigating pre-BCR, the deregulation of surrogate light chain can be blocked by inactivation of SLP65 gene (Nature Immunol. 2003 4, 38-43; The adaptor protein SLP-65 acts as a tumor suppressor that limits pre-B cell expansion. Flemming, A., Brummer, T., Reth, M. & Jumaa, H.) or both IRF4 (interferon-regulatory factor 4) and IRF8 genes (Genes Dev. 2003 17, 1703-1708; IRF-4,8 orchestrate the pre-B-to-B transition in lymphocyte development. Lu, R., Medina, K. L., Lancki, D. W. & Singh, H). It has been reported that pre-BII cells from mice that are deficient in these factors continue to express surrogate-light-chain genes and therefore retain pre-BCR expression. The unlimited supply of surrogate light chains lead to a hyperplastic pre-BII-cell phenotype in vivo and provide large number of pre-B cells for us to analyze.

3. In instances (eg, as described in part 1 above), where mouse Vs are retained following insertion of human gene segments, the mouse endogenous heavy chain VDJ is inactivated, and this may be done while leaving mouse Vs intact. Thus, for the formation of chimaeric heavy chain genes, the heavy chain V regions should only be transcribed from human heavy VDJs. To assess the relative use of human v mouse Vs for heavy chain gene formation, the B-cell repertoire and diversity will be compared between mice having human VpreB gene v mice lacking the human VpreB (eg, mice with mouse VpreB only). Pairing of human Vs with human VpreB will be preferable to pairing of mouse Vs with human VpreB, and thus antibody heavy chains comprising human variable regions will be selected during B-cell development.

As cells transit from the pre-BI to pre-BII stage, the pre-BCR induces a signal for proliferative expansion. Pre-BCR controls the number of developing pre-B cells by controlling proliferation, which represents clonal expansion. Pre-BII cells enter two to seven rounds of cell division when Igµ chain assembles into pre-BCRs. This ultimately results in a more diverse antibody repertoire, as later in development, each cell will recombine and express a unique L chain. In this process, the association of surrogate light chain with µ chain monitors the cells to determine whether it has successfully completed VDJH recombination and expresses a functional µH chain which will form the pre-PCR for downstream signalling. In this case, the strength of the pairing between the µH and SL chains may determine the amplitude of the transmitted signal, and thereby, the extent of proliferation (J. Immunol. 2006, 177 pp. 2242-2249; Pre-B cell receptor assesses the quality of IgH chains and tunes the Pre-B cell repertoire by delivering differential signals. Y. Kawano, S. Yoshikawa, Y. Minegishi and H. Karasuyama). Therefore, in the mouse with chimaeric heavy chain (human VDJs and mouse Cs), by introducing the human VpreB gene to provide complete species-matching with the chimaeric heavy chain, It is expected that the repertoire and so the diversity of chimaeric antibodies will be improved by using human VpreB instead of mouse VpreB for association with the heavy chains. The improvement for B cell repertoire and diversity can be showed by increased usage of human heavy VDJs and/or a shift in VH gene family usage in mouse expressing human VpreB (see the examples below for possible techniques).

The invention provides the following aspects:—

1. A non-human vertebrate (eg, a mouse or rat) or cell (eg, a mouse cell or rat cell) whose genome comprises an antibody heavy chain transgene,
   the transgene comprising
   (a) one or more human VH gene segments, one or more human D gene segments and one or more human JH gene segments operably connected upstream of a constant region gene so that the transgene is capable of undergoing VDJ recombination in vivo to produce an antibody gene comprising a rearranged VDJC encoding an antibody heavy chain having a human variable region and a constant region; or
   (b) a rearranged VDJ encoding a human variable region operably connected upstream of a constant region gene so that the transgene encodes (optionally following VDJ combination with the constant region) an antibody heavy chain having a human variable region and a constant region;
   the genome further comprising
   (i) a human VpreB gene capable of expressing a human VpreB, and
   (ii) a non-human vertebrate (eg, mouse or rat) λ5 gene;
   wherein the vertebrate or cell is capable of expressing a chimaeric surrogate light chain comprising human VpreB and non-human vertebrate λ5 for pairing with the heavy chain.

2. The vertebrate or cell of aspect 1, wherein the constant region is a non-human vertebrate (eg, mouse or rat) constant region so that the chimaeric surrogate light chain is species- or strain-matched with the heavy chain.

3. A mouse or mouse cell according to aspect 1 or 2, wherein the constant region and the λ5 gene are mouse constant region and mouse λ5 gene, optionally of the same mouse strain.

4. The vertebrate or cell of aspect 2 or 3, wherein the strain is a 129-derived, mouse black 6-derived or JM8-derived strain (eg, a C57BL/6-129/Sv hybrid strain).

5. The vertebrate or cell of aspect 2 or 3, wherein the constant region is a mouse 129 or mouse Black 6 constant region and the λ5 gene is a mouse 129 or mouse Black 6 λ5 gene.

6. The vertebrate or cell of any preceding aspect, wherein said constant region gene and λ5 gene are endogenous genes of said vertebrate or cell.

7. The vertebrate or cell of any preceding aspect, wherein said genome is homozygous for said transgene, human VpreB gene and non-human vertebrate λ5 gene.

8. The vertebrate or cell of any preceding aspect, wherein endogenous non-human vertebrate antibody heavy chain expression has been inactivated.

9. The vertebrate or cell of any preceding aspect, wherein endogenous non-human vertebrate antibody light chain expression has been inactivated.

10. The vertebrate or cell of any preceding aspect, wherein the heavy chain transgene is devoid of a CH1 gene segment and the genome comprises no functional antibody light chain locus.

11. The vertebrate or cell of any preceding aspect, wherein the heavy chain transgene is devoid of a gamma CH1 gene segment and the genome comprises no functional antibody light chain locus.

12. The vertebrate or cell of any preceding aspect, wherein the heavy chain transgene is devoid of a mu CH1 gene segment and the genome comprises no functional antibody light chain locus.

13. The vertebrate or cell of any preceding aspect, wherein said constant region is a mu constant region, optionally endogenous mu constant region.

14. The vertebrate or cell of any preceding aspect, wherein the human VpreB gene has a nucleotide sequence that is at least 85% identical to SEQ ID NO: 1.

15. The vertebrate or cell of any preceding aspect, wherein said genome does not comprise a non-human vertebrate (eg, mouse or rat) species VpreB1 and/or VpreB2 gene.

16. The cell of any preceding aspect, wherein the cell is an ES cell, an iPS cell, a hybridoma, an immortalised cell or a B-cell (eg, an immortalised B-cell).

17. The cell of aspect 16, wherein the cell is derived from C57BL/6, M129 (eg, 129/SV), BALB/c or a hybrid of C57BL/6, M129 or BALB/c (eg, a C57BL/6-129/Sv hybrid).

18. The vertebrate or cell of any preceding aspect, wherein the genome comprises an insertion of a human lambda V (or Vi) region comprising all of the V (and optionally also J) regions and intervening sequences, wherein the lambda V (or Vi) region comprises a human VpreB gene.

19. The vertebrate or cell of aspect 18, wherein non-functional V and/or J gene segments are omitted.

20. The vertebrate or cell of aspect 18 or 19, wherein the lambda V (or Vi) region comprises a human VpreB gene and its associated human promoter.

21. The vertebrate or cell of any preceding aspect, wherein the genome comprises an insertion of DNA corresponding to positions 22599200 to 22599926 on human chromosome 22.

22. The vertebrate or cell of any one of aspects 18 to 21, wherein the insertion is an insertion into an antibody light chain locus; optionally an insertion into endogenous lambda locus upstream of the endogenous lambda constant region or an insertion into endogenous kappa locus upstream of the endogenous kappa constant region.

23. The vertebrate or cell of any one of aspects 18 to 22, wherein the insertion replaces the endogenous Vλ in whole or in part.

24. The vertebrate or cell of any preceding aspect, wherein the human VpreB gene is not within the endogenous (non-human vertebrate or cell) VpreB-λ5 locus.

25. The vertebrate or cell of any preceding aspect, wherein the expression of the human VpreB gene is under endogenous (non-human vertebrate or cell) control.

26. The vertebrate or cell of any preceding aspect, wherein the human VpreB gene is operably linked to one or more DNase I hypersensitive sites.

27. The vertebrate or cell of any preceding aspect, wherein the human VpreB gene is present in the genome in 2, 3, 4, 5, 6, 7, 8, 9 or 10 copies.

28. The vertebrate or cell of any preceding aspect, which is a rodent, mouse or rat; or a rodent, mouse or rat cell.

29. The vertebrate or cell of any preceding aspect, wherein all λ5 sequences in the genome are non-human vertebrate λ5 sequences.

30. The vertebrate or cell of any preceding aspect, wherein the genome is devoid of a human λ5 nucleotide sequence.

31. A non-human vertebrate (eg, a mouse or rat) or cell (eg, a mouse cell or rat cell) whose genome comprises an antibody heavy chain transgene for producing heavy chains that are devoid of a CH1, the transgene comprising
  (a) one or more human VH gene segments, one or more human D gene segments and one or more human JH gene segments operably connected upstream of a constant region gene so that the transgene is capable of undergoing VDJ recombination in vivo to produce an antibody gene comprising a rearranged VDJC encoding an antibody heavy chain having a human variable region and a constant region; or
  (b) a rearranged VDJ encoding a human variable region operably connected upstream of a constant region gene so that the transgene encodes (optionally following VDJ combination with the constant region) an antibody heavy chain having a human variable region and a constant region;
  the genome further comprising a human VpreB gene capable of expressing a human VpreB;
  wherein the constant region is devoid of a functional CH1 gene; and
  wherein the vertebrate or cell is capable of expressing a human VpreB for pairing with the heavy chains devoid of CH1.

32. The vertebrate or cell of aspect 31, wherein the human VpreB gene does not comprise a λ5 sequence or constant region sequence.

33. The vertebrate or cell of aspect 31 or 32, wherein the constant region is a human constant region.

34. The vertebrate or cell of aspect 31 or 32, wherein the constant region is a non-human vertebrate (eg, mouse or rat) constant region; optionally of a strain as recited in aspect 4.

35. The vertebrate or cell of any one of aspects 31 to 34, wherein said genome is homozygous for said transgene and human VpreB gene.

36. The vertebrate or cell of any one of aspects 31 to 35, wherein endogenous non-human vertebrate antibody heavy chain expression has been inactivated.

37. The vertebrate or cell of any one of aspects 31 to 36, wherein endogenous non-human vertebrate antibody light chain expression has been inactivated.

38. The vertebrate or cell of any one of aspects 31 to 37, wherein the genome comprises no functional antibody light chain locus.

39. The vertebrate or cell of any one of aspects 31 to 38, wherein the heavy chain transgene is devoid of a gamma CH1 gene segment and the genome comprises no functional antibody light chain locus.

40. The vertebrate or cell of any one of aspects 31 to 39, wherein the heavy chain transgene is devoid of a mu CH1 gene segment and the genome comprises no functional antibody light chain locus.

41. The vertebrate or cell of any aspects 31 to 40, wherein said constant region is a mu constant region (optionally endogenous mu constant region) or a gamma constant region (optionally endogenous gamma constant region).

42. The vertebrate or cell of any one of aspects 31 to 41, wherein the human VpreB gene has a nucleotide sequence that is at least 85% identical to SEQ ID NO: 1.

43. The vertebrate or cell of any one of aspects 31 to 42, wherein said genome does not comprise a non-human species VpreB gene.

44. The cell of any one of aspects 31 to 43, wherein the cell is an ES cell, an iPS cell, a hybridoma, an immortalised cell or a B-cell (eg, an immortalised B-cell).

45. The cell of aspect 44, wherein the cell is derived from C57BL/6, M129 (eg, 129/SV), BALB/c or a hybrid of C57BL/6, M129 or BALB/c (eg, a C57BL/6-129/Sv hybrid).

46. The vertebrate or cell of any one of aspects 31 to 45, wherein the genome comprises an insertion of a human lambda V (or Vi) region comprising all of the V (and optionally also J) regions and intervening sequences, wherein the lambda V (or Vi) region comprises a human VpreB gene.

47. The vertebrate or cell of aspect 46, wherein non-functional V and/or J gene segments are omitted.

48. The vertebrate or cell of aspect 46 or 47, wherein the lambda V (or Vi) region comprises a human VpreB gene and its associated human promoter.

49. The vertebrate or cell of any one of aspects 31 to 48, wherein the genome comprises an insertion of DNA corresponding to positions 22599200 to 22599926 on human chromosome 22.

50. The vertebrate or cell of any one of aspects 46 to 49, wherein the insertion is an insertion into an antibody light chain locus; optionally an endogenous lambda locus upstream of the endogenous lambda constant region.

51. The vertebrate or cell of any one of aspects 46 to 50, wherein the insertion replaces the endogenous Vλ in whole or in part.

52. The vertebrate or cell of any one of aspects 31 to 51, wherein the human VpreB gene is not within the endogenous (non-human vertebrate or cell) VpreB-λ5 locus.

53. The vertebrate or cell of any one of aspects 31 to 52, wherein the expression of the human VpreB gene is under endogenous (non-human vertebrate or cell) control.

54. The vertebrate or cell of any one of aspects 31 to 53, wherein the human VpreB gene is operably linked to one or more DNase I hypersensitive sites.

55. The vertebrate or cell of any one of aspects 31 to 54, wherein the human VpreB gene is present in the genome in 2, 3, 4, 5, 6, 7, 8, 9 or 10 copies.

56. The vertebrate or cell of any one of aspects 31 to 55, which is a rodent, mouse or rat; or a rodent, mouse or rat cell.

57. The vertebrate or cell of any one of aspects 31 to 56, wherein the genome is devoid of a human λ5 gene.

58. The vertebrate or cell of any one of aspects 31 to 57, wherein the genome is devoid of a λ5 gene.

59. A method of constructing a transgenic non-human vertebrate cell (eg, an ES cell, eg, a mouse or rat ES cell), the method comprising
  (i) introducing into the genome of a non-human vertebrate cell (or an ancestor thereof) one or more human VH gene segments, one or more human D gene segments and one or more human JH gene segments so that said gene segments are operably connected upstream of a constant region gene (optionally an endogenous non-human vertebrate constant region gene) to form a heavy chain transgene, wherein in said cell or a progeny thereof the transgene is capable of undergoing VDJ recombination in vivo to produce an antibody gene comprising a rearranged VDJC encoding an antibody heavy chain having a human variable region and a constant region; or
  (ii) introducing into the genome of a non-human vertebrate cell (or an ancestor thereof) a rearranged VDJ encoding a human variable region so that said VDJ is operably connected upstream of a constant region gene (optionally an endogenous non-human vertebrate constant region gene) to form a heavy chain transgene, wherein in said cell or a progeny thereof the transgene encodes (optionally following VDJ combination with the constant region) an antibody heavy chain having a human variable region and a constant region;
and wherein the method further comprises introducing into the cell a human VpreB gene in the absence of a λ5 sequence, wherein the cell (or a progeny cell or vertebrate) is capable of expressing human VpreB for pairing with the human variable region of the heavy chain.

60. The method of aspect 59, wherein the genome of the product cell of the method is as recited in any one of aspects 1 to 58.

61. The method of aspect 59 or 60, further comprising making a progeny (progeny cell or vertebrate) of the product cell made according to aspect 59 or 60, wherein the progeny is homozygous for said heavy chain transgene and endogenous non-human vertebrate antibody expression has been inactivated.

62. The method of aspect 61, wherein the progeny cell is an ES cell, an iPS cell, a hybridoma, an immortalised cell or a B-cell (eg, an immortalised B-cell); optionally a cell derived from a strain or hybrid as recited in aspect 17.

63. The method of aspect 61, wherein the progeny vertebrate is a rodent, mouse or rat.

64. A method of promoting B-cell development in a non-human vertebrate (eg, a mouse or rat), the method comprising
  (a) providing in a non-human vertebrate embryonic stem (ES) cell genome an immunoglobulin transgene capable of expressing an antibody mu heavy chain, wherein the antibody heavy chain comprises a human variable region and a mu constant region (optionally an endogenous non-human vertebrate mu constant region); and creating a first non-human vertebrate from said ES cell or a progeny thereof;
  (b) providing in a second ES cell genome a second transgene comprising a human VpreB gene capable of expressing a human VpreB; and creating a second non-human vertebrate from said ES cell or a progeny thereof; and
  (c) creating by breeding a third non-human vertebrate capable of co-expressing the mu antibody heavy chain and human VpreB wherein a pre-B-cell receptor can form to promote B-cell development of cells bearing a mu heavy chain in said third vertebrate; the third vertebrate being made by crossing said first and second vertebrates or progeny thereof by breeding to create said third vertebrate, the third vertebrate comprising the first and second transgenes, and wherein endogenous heavy chain expression has been inactivated in said third vertebrate.

65. The method of aspect 64, wherein in (a) the heavy chain transgene is constructed to be devoid of a CH1 gene segment and the genome of the third non-human vertebrate comprises no functional antibody light chain locus.

66. The method of aspect 64 or 65, wherein the genome of the third non-human vertebrate is as recited in any one of aspects 1 to 58.

67. The method of any one of aspects 64 to 65, wherein the genome of the third vertebrate does not comprise a non-human vertebrate (eg, mouse or rat) species VpreB1 and/or VpreB2 gene.

68. The method of any one of aspects 64 to 67, wherein the third non-human vertebrate expresses a λ5 of a non-human vertebrate (eg, mouse or rat) species and said constant region is a constant region of the same non-human vertebrate (eg, mouse or rat) species as the λ5 gene; optionally wherein the λ5 and constant region are an endogenous λ5 and constant region of mouse or rat.

69. A transgenic mouse or rat according to the third vertebrate of any one of aspects 64 to 68, or a progeny thereof.

70. A method of promoting B-cell development in a non-human vertebrate (eg, a mouse or rat), the method comprising
  (i) inactivating endogenous heavy chain expression in said vertebrate;
  (ii) providing in the genome of said vertebrate an immunoglobulin transgene capable of expressing an antibody mu heavy chain, wherein the antibody heavy chain comprises a human variable region and a non-human vertebrate mu constant region (optionally an endogenous non-human vertebrate mu constant region); and
  (ii) providing in the genome of said vertebrate a second transgene capable of expressing a human VpreB wherein a pre-B-cell receptor can form to promote B-cell development of cells bearing a mu heavy chain in said vertebrate;
  Optionally wherein the genome is homozygous for said first transgene.

71. The method of aspect 70, wherein in (a) the heavy chain transgene is constructed to be devoid of a CH1 gene segment and the genome of the third non-human vertebrate comprises no functional antibody light chain locus.

72. The method of aspect 70 or 71, wherein the genome of the vertebrate is as recited in any one of aspects 1 to 58.

73. The method of any one of aspects 70 to 72, wherein the genome of the vertebrate does not comprise a non-human vertebrate (eg, mouse or rat) species VpreB1 and/or VpreB2 gene.

74. The method of any one of aspects 70 to 73, wherein the third vertebrate expresses a λ5 of a non-human vertebrate (eg, mouse or rat) species and said constant region is a constant region of the same non-human vertebrate (eg, mouse or rat) species as the λ5 gene; optionally wherein the λ5 and constant region are an endogenous λ5 and constant region of mouse or rat.

75. A transgenic mouse or rat obtained or obtainable by the method of any one of aspects 70 to 74, or a progeny thereof.

76. A non-human vertebrate, mouse, rat, cell or method according to any preceding aspect, wherein the expression of the human VpreB gene is under edogenous control.

77. The non-human vertebrate, mouse, rat, cell or method according to aspect 76, wherein the human VpreB gene is operably linked to an endogenous promoter, optionally an endogenous VpreB promoter (eg, a VpreB1 promoter).

78. The non-human vertebrate, mouse, rat, cell or method of any preceding aspect, wherein the genome comprises
  (a) said antibody heavy chain transgene; and
  (b) an antibody kappa light chain transgene and/or an antibody lambda chain transgene;
  wherein all of the V, D and J in said transgenes are human V, D and J;
  wherein endogenous antibody heavy and light chain expression has been inactivated; and
  optionally wherein said genome is homozygous for said heavy and light chain transgenes.

79. The non-human vertebrate, mouse, rat, cell or method of aspect 78, wherein the kappa and lambda chain transgenes comprise constant regions of said non-human vertebrate species capable of pairing with the constant region of the heavy chain.

80. The non-human vertebrate, mouse, rat, cell or method of aspect 78 or 79, wherein the heavy chain transgene comprises a substantially complete human functional VH, D and JH repertoire.

81. The non-human vertebrate, mouse, rat, cell or method of aspect 78, 79 or 80, wherein the kappa chain transgene comprises a substantially complete human functional Vκ and Jκ repertoire; and the lambda chain transgene comprises a substantially complete human functional Vλ and Jλ repertoire.

82. A transgenic mouse or rat, or a transgenic mouse or rat cell (eg, an ES cell), whose genome comprises
(a) an antibody heavy chain transgene, the transgene comprising a substantially complete human functional VH, D and JH repertoire operably connected upstream of an endogenous (mouse or rat) mu constant region gene so that the transgene is capable of undergoing VDJ recombination in vivo to produce an antibody gene comprising a rearranged VDJC encoding an antibody heavy chain having a human variable region and an endogenous mu constant region;
(b) an antibody kappa light chain transgene and/or an antibody lambda chain transgene;
wherein all of the V, D and J in said transgenes are human V, D and J;
wherein the kappa chain transgene comprises a substantially complete human functional Vλ and Jκ repertoire; and the lambda chain transgene comprises a substantially complete human functional Vλ and Jλ repertoire;
wherein the kappa and/or lambda chain transgenes comprise endogenous constant regions capable of pairing with the constant region of the heavy chain;
(c) a human VpreB gene capable of expressing a human VpreB;
optionally wherein the human VpreB gene is operably linked to an endogenous VpreB promoter or its associated human promoter; and
(d) an endogenous λ5 gene capable of expressing an endogenous λ5;
wherein endogenous antibody heavy and light chain expression has been inactivated; and
optionally wherein said genome is homozygous for said heavy and light chain transgenes.

83. A transgenic mouse or rat, or a transgenic mouse or rat cell (eg, an ES cell), whose genome comprises
(a) an antibody heavy chain transgene, the transgene comprising a substantially complete human functional VH, D and JH repertoire operably connected upstream of an endogenous (mouse or rat) mu constant region gene so that the transgene is capable of undergoing VDJ recombination in vivo to produce an antibody gene comprising a rearranged VDJC encoding an antibody heavy chain having a human variable region and an endogenous mu constant region;
wherein all of the V, D and J in said transgene are human V, D and J;
wherein the heavy chain transgene is devoid of a CH1 gene segment (eg, a gamma CH1) and the genome of the vertebrate comprises no functional antibody light chain locus;
wherein endogenous antibody heavy chain expression has been inactivated; and
optionally wherein said genome is homozygous for said heavy chain transgene;
(c) a human VpreB gene capable of expressing a human VpreB;
optionally wherein the human VpreB gene is operably linked to an endogenous VpreB promoter or its associated human promoter; and
(d) optionally an endogenous λ5 gene capable of expressing an endogenous λ5.

As demonstrated in Example below, the present invention is useful for influencing the repertoire of human heavy chain variable domains and variable region DNA and RNA sequences that can be produced in a non-human vertebrate. Thus, the invention provides:—

84. A mouse according to any one of aspects 1 to 58 or 75 to 83, which expresses a repertoire of Ig heavy chain variable regions that significantly differs (eg, as indicated by a probability of less than 0.05 in a chi-squared test) from the heavy chain variable region repertoire of a control vertebrate in the proportion (eg, percentage) of use of heavy chain variable gene segments, wherein the control and said non-human vertebrate genomes are of the same background mouse strain and both comprise said antibody heavy chain transgene, the transgenes being identical in the control and said mouse, and wherein the control does not express a human VpreB.

In an example of any aspect, the mouse and control strains are 129 or 129-derived (eg, 129 crossed with C57BL/6).

In an example of any aspect, each repertoire is a repertoire of heavy chain variable region RNA. Optionally, the variable regions are provided as part of IgH heavy chains or corresponding RNA.

In an example of any aspect, each transgene comprises at least 11 human gene segments, all or substantially all human D gene segments and all or substantially all human JH gene segments. For example, each transgene comprises human D1-1, 2-2, 3-9, 3-10, 4-11, 5-12, 6-13, 1-14, 2-15, 3-16, 4-17, 5-18, 6-19, 1-20, 2-21, 3-22, 4-23, 5-24, 6-25, 1-26 and 7-27. For example, each transgene comprises human J1, J2, J3, J4, J5 and J6. For example, each transgene comprises (optionally in 5' to 3' order) VH3-13, 3-11, 3-9, 1-8, 3-7, 2-5, 7-4-1, 4-4, 1-3, 1-2 and 6-1.

85. A mouse according to any one of aspects 1 to 58 or 75 to 84, which expresses a repertoire of Ig heavy chain variable regions that significantly differs (eg, as indicated by a probability of less than 0.05 in a binomial distribution test) from the IgH heavy chain variable region repertoire of a control vertebrate in the proportion (eg, percentage) of use of heavy chain JH gene segments, wherein the control and said non-human vertebrate genomes are of the same background mouse strain and both comprise said antibody heavy chain transgene, the transgenes being identical in the control and said mouse, and wherein the control does not express a human VpreB.

86. A mouse according to any one of aspects 1 to 58 or 75 to 85, which expresses a repertoire of Ig heavy chain variable regions that significantly differs (eg, as indicated by a probability of less than 0.05 in a binomial distribution test) from the IgH heavy chain variable region repertoire of a control vertebrate in the proportion (eg, percentage) of use of one, more or all heavy chain variable gene segments selected from VH6-1, VH1-3, VH3-7, VH1-8, VH3-9, VH3-11, JH1 and JH6, wherein the control and said non-human vertebrate genomes are of the same background mouse strain and both comprise said antibody heavy chain transgene, the transgenes being identical in the control and said mouse, and wherein the control does not express a human VpreB.

87. The mouse of any one of aspects 84 to 86, wherein use of one, more or all of VH6-1, VH1-3, VH3-9 and JH1 is higher in the repertoire of said mouse than in the repertoire of the control.
88. The mouse of any one of aspects 84 to 87, wherein use of one, more or all of VH3-7, VH1-8, VH3-11 and JH6 is lower in the repertoire of said mouse than in the repertoire of the control.

In an example of any of aspects 84 onwards, the IgH heavy chain variable region repertoire is naïve, ie, has not been preselected against a predetermined target antigen.

In an example of any of aspects 84 onwards, the scope is not limited to a mouse, but the scope of the aspect relates to a non-human vertebrate (eg, a mouse or a rat). Aspects 84 onwards can in the alternative, therefore, be read with this scope and for possible inclusion in claims herein.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or an when used in conjunction with the term "comprising" in the claims and/or the specification may mean "one," but it is also consistent with the meaning of "one or more," "at least one," and "one or more than one." The use of the term or in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term or combinations thereof as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non limiting prophetic exemplification (Examples 1-5). An additional example, Example 6, not prophetic, but was actually performed and yielded data whose results demonstrate the present invention.

EXAMPLES

Example 1: Introduction of Human DNA Gene Segments into ES Cells

By way of illustration, the following example is provided on the introduction of human antibody gene segment DNA into Cell culture of C57BL/6N-derived cell lines, such as the JM8 male ES cells. This will follow standard techniques. The JM8 ES cells have been shown to be competent in extensively contributing to somatic tissues and to the germline, and are being used for large mouse mutagenesis programs at the Sanger Institute such as EUCOMM and KOMP (Pettitt, S. J., Liang, Q., Rairdan, X. Y., Moran, J. L., Prosser, H. M., Beier, D. R., Lloyd, K. C., Bradley, A., and Skarnes, W. C. (2009). Agouti C57BL/6N embryonic stem cells for mouse genetic resources. Nature Methods.). JM8 ES cells ($1.0 \times 10^7$) will be electroporated (500 g, 230V; BioRad) with 10 µg I-Scel linearized human BAC DNA. The transfectants will be selected with either Puromycin (3 µg/ml) or G418 (150 µg/ml). The selection will begin either 24 hours (with G418) or 48 hours (with Puromycin) post electroporation and proceed for 5 days. 10 µg linearized human BAC DNA can yield up to 500 Puromycin or G418 resistant ES cell colonies. The antibiotic resistant ES cell colonies will be picked into 96-well cell culture plates for genotyping to identify the targeted clones.

Once targeted mouse ES cell clones are identified, they will be analyzed by array Comparative Genomic Hybridization (CGH) for total genome integrity (Chung, Y. J., Jonkers, J., Kitson, H., Fiegler, H., Humphray, S., Scott, C., Hunt, S., Yu, Y., Nishijima, I., Velds, A., et al. (2004). A whole-genome mouse BAC microarray with 1-Mb resolution for analysis of DNA copy number changes by array comparative genomic hybridization. Genome research 14, 188-196 and Liang, Q., Conte, N., Skarnes, W. C., and Bradley, A. (2008). Extensive genomic copy number variation in embryonic stem cells. Proceedings of the National Academy of Sciences of the United States of America 105, 17453-17456.). ES cells that have abnormal genomes do not contribute to the germline of the chimaeric mice efficiently. BAC integrity will be examined by PCR-amplifying each known functional V gene in the BAC. For example, in one approach the first human BAC chosen for the IgH locus has 6 functional VH gene segments and all human D and JH gene segments. To confirm the integrity of this BAC for the presence of these IgH genes, pairs of PCR primers will be designed and used to PCR-amplify genomic DNA from the targeted ES cells. The human wild-type size and sequence of these fragments will ensure that the inserted BAC has not been rearranged. More detailed CGH will also confirm the integrity of the inserted BACs. For example, one skilled in the art could use an oligo aCGH platform, which is developed by Agilent Technologies, Inc. This platform not only enables one to study genome-wide DNA copy number variation at high resolution (Barrett, M. T., Scheffer, A., Ben-Dor, A., Sampas, N., Lipson, D., Kincaid, R., Tsang, P., Curry, B., Baird, K., Meltzer, P. S., et al. (2004). Comparative genomic hybridization using oligonucleotide microarrays and total genomic DNA. Proceedings of the National Academy of Sciences of the United States of America 101, 17765-17770), but permit examination of a specific genome region using custom designed arrays. Comparing the traditional aCGH techniques which rely on cDNA probes or whole BAC probes, the 60-mer oligonucleotides probes can ensure specific hybridization and high sensitivity and precision that is needed in order to detect the engineered chromosome alterations that we have made. For example, oligos designed to hybridize at regular intervals along the entire length of the inserted BAC would detect even quite short deletions, insertions or other rearrangements. Also, this platform provides the greatest flexibility for customized microarray designs. The targeted ES cell genomic DNA and normal human individual genomic DNA will be labelled separately with dyes and hybridized to the array. Arrays slides will be scanned using an Aglient Technologies DNA microarray scanner. Reciprocal fluorescence intensities of dye Cy5 and dye Cy3 on each array image and the log 2 ratio values will be extracted by using Bluefuse software (Bluegnome). Spots with inconsistent fluorescence patterns ("confidence"<0.29 or "quality"=0) will be excluded before normalizing all log 2 ratio values. Within an experiment, Log 2 ratio between −0.29 and +0.29 for the signal from any oligo probe are regarded as no copy number change. The log 2 ratio threshold for "Duplication" is usually >0.29999, and for deletion is <0.29999.

Example 2: Introducing the Human VpreB Gene into the Mouse Lambda Locus by Inserting the Human Lambda V Gene Segment Cluster The human VpreB gene is inserted into a mouse genome by introducing human lambda gene segment DNA, wherein the nucleotide sequence of the DNA comprises a human VpreB gene and optionally the associated human promoter. Human VpreB1 and VpreB3 genes are both located in chromosome 22. The human VpreB1 gene is between human Igλ V gene segments IV-53 and 5-52 (Chromosome 22: 22599200 to 22599926). Therefore, the human lambda gene segment which covers the human VpreB1 gene and contains multiple Vs flanking this gene is inserted in the endogenous lambda antibody locus upstream of the endogenous lambda constant region between the most 3' endogenous Jλ and the endogenous Cλ following the approach in Example 1 and as further explained in WO2011004129.

Example 3: Introducing the Human VpreB Gene within the Mouse VpreB-λ5 Locus and Targeting into the Mouse Heavy or Lambda Locus The following example illustrates the insertion of the human VpreB1 gene within the mouse VpreB-λ5 locus to bring the human gene under the endogenous LCR influence.

The mouse VpreB1 and λ5 genes are closely associated, both within a 19-kb fragment called the λ5-VpreB1 locus. Apart from these two genes, this locus contains a locus control region (LCR) required for correct levels of expression and tissue-specificity of λ5 and VpreB1. Locus control regions (LCRs) are sequences that mediate reorganisation of chromatin and activation of transcription by sequence-specific transcription factors. The characteristic of an LCR is the ability to drive gene expression in transgenic mice at any site of integration at levels that are substantially equivalent to those of the gene in its natural location. It has been shown that the LCR in the λ5-VpreB1 locus is able to promote efficient and stage-specific expression of both genes in transgenic mice at all sites of integration tested.

To make sure that the expression of the inserted human VpreB1 gene is properly controlled in mouse, the mouse λ5-VpreB1 locus is retrieved and cloned into a vector (pBlueScript II SK(+)). The mouse VpreB1 nucleotide sequence is replaced by the human VpreB1 sequence by cloning. The construct containing the fragment of mouse λ5-human VpreB1 locus is then cloned into a BAC containing a human heavy chain locus fragment. Then it is targeted into the genome of a mouse ES cell following the introduction of the human BAC into the mouse heavy chain locus upstream of the endogenous heavy chain mu constant region. In this case, the human VpreB function can be directly tested in the F1 mouse generated from the ES cells. Manipulation of constructs and BACs can be effected by standard recombineering.

Insertion of the mouse λ5-human VpreB1 can be carried out using homologous recombination or RMCE. Homologous combination can employ homology arms corresponding to the endogenous sequences flanking the mouse λ5-mouse VpreB1 in the mouse ES genome, so that insertion of the mouse λ5-human VpreB1 replaces (and thus deletes) the endogenous mouse λ5-mouse VpreB1 and places the inserted construct under the control of the endogenous LCR.

RMCE can be used to insert the mouse λ5-human VpreB1 construct (optionally with the endogenous mouse λ5-mouse VpreB1 LCR) anywhere in the genome. RMCE can also be used to precisely delete the endogenous mouse λ5-mouse VpreB1 so that the inserted mouse λ5-human VpreB1 construct is the only source of a VpreB1 gene.

In the alternative, the method can be modified to insert the mouse lambda 5-human VpreB1 construct into the endogenous lambda5-VpreB locus on the mouse lambda locus, for example to bring the human VpreB1 gene under endogenous control (eg, control of the lambda5-VpreB LCR). To do this, the cloned mouse lambda 5-human VpreB1 construct (produced by standard recombineering) is inserted into a homologous recombination vector using in vitro recombineering to add homology arms flanking the construct. Using homologous recombination in the presence of a marker carried by the vector, the construct is inserted precisely to replace the endogenous mouse lambda 5-mouse VpreB1 in the genome of a mouse ES cell. Alternatively, instead of homologous recombination, standard RMCE can be used to effect precise insertion into the genome.

A suitable protocol is provided in Example 5.

Example 4: Assessing the B-Cell Development and Repertoire in Chimaeric Mouse Containing Human VpreB Gene The following example is provided on assessing the advantage of having the human VpreB gene in the chimaeric mouse.

The mouse embryonic stem cells (eg, AB2.1 cells; Baylor College of Medicine) containing the targeted human VpreB1 gene are grown on a feeder layer of SNL7 fibroblasts (Baylor College of Medicine) in embryonic stem cell medium containing 15% serum. Then the cells are microinjected into blastocysts which are transferred to the uteri of pseudopregnant $F_1$ female mice. To test for germline transmission, male chimeras are bred to C57BL/6-Tyr$^{c\text{-}Brd}$ albino female mice (Baylor College of Medicine). After obtaining mice with both chimaeric heavy chain gene (human V region and mouse C region) and human VpreB1 gene, the following assays are performed to show the advantage of human VpreB v mouse VpreB.

1. Pre-B Cell Populations Containing Pre-BCR from Human VpreB v Mouse VpreB

In the pre-B cells, µ heavy chain associated with surrogate light chain will deposit on the cell surface to signal the cell survival and proliferation. The pre-B cell populations with the pre-BCR from human VpreB protein v mouse VpreB protein are analyzed by flow cytometry.

Cells from bone marrow are surface stained with fluorescence-labelled mAb and then analysied with MACSQuant (Miltenyi Biotech) on B220$^+$ cells. Pre-B cell population can be detected using pre-BCR-specific mAB and/or mouse λ5$^+$ cells. The cells with pre-BCR of human VpreB v mouse VpreB are distinguished by using monoclonal antibody specifically to human or mouse VpreB.

2. Usage of Human Vs in the Mouse with Chimaeric Antibody

In the mouse with the insertion of human $V_H D_H J_H$s between endogenous mouse $V_H D_H J_H$s and $C_H$s, the usage of human Vs v endogenous mouse Vs are compared by sequencing the heavy chain products in naive mice.
Approach:
  a. Total RNA extraction (use TRIzol® Reagent) from mouse spleen
  b. By a standard 5' RACE (Rapid amplification of 5' complementary DNA ends) method, using a mouse Cµ-specific primer, PCR fragments from mouse synthesized heavy chain mRNAs can be amplified.
  c. The PCR products are cloned into a vector and then sequenced.
  d. The sequences map to heavy V D J sequences which contain either mouse V or human V. Then we compare the usage of human Vs v mouse Vs.
  e. The usage of human Vs v mouse Vs is analysed in the mice with/without a human
VpreB1 gene. We expect by introducing human VpreB1 gene, the human V usage will increase in the mouse with chimaeric IgH gene.

3. Improvement of Repertoire and Diversity of Chimaeric Antibody

In this embodiment, in mice with the chimaeric heavy locus, endogenous mouse V genes are inactivated by deletion or inversion of the mouse V locus. Therefore, all the heavy chain products are transcribed from human Vs.

Using the same methods in Example 3, the heavy chain products from naïve and/or immunized mice are sequenced and map to human $V_H D_H J_H$s with different CDR sequences.

The repertoire of heavy V D J selected by surrogate light chain from human VpreB and mouse VpreB can be compared from several aspects. First is the improvement of usage of human heavy V D Js and hypervariabilities for mice having human VpreB. Second is the shift of usage in terms of human heavy V gene families caused by human VpreB v mouse VpreB.

Example 5: Surrogate Light Chain Targeting Protocol

Mouse λ5 and VpreB1 sequences will be substituted with human λ5 and VPREB1 sequences. The regulation and expression will be controlled by mouse endogenous regulatory elements (FIG. 1; references 1 & 2) that are used during B cell development. In a mouse genome this VpreB1 is found on chromosome 16 at coordinates 16,868,494-16,869,348. In a human genome VPREB1 is found on chromosome 22 at coordinates 22,599,087-22,599,927.

REFERENCES

1. Minaee S, Farmer D, Georgiou A, Sabbattini P, Webster Z, Chow C M, Dillon N, Mapping and functional analysis of regulatory sequences in the mouse lambda5-VpreB1 domain, Mol Immunol. 2005 July; 42(11):1283-92.
2. Sabbattini P, Georgiou A, Sinclair C, Dillon N., Analysis of mice with single and multiple copies of transgenes reveals a novel arrangement for the lambda5-VpreB1 locus control region, Mol Cell Biol. 1999 January; 19(1): 671-9.

Insertion of Human VpreB1 into Mouse BAC

A bacterial artificial chromosome (BAC) containing mouse λ5 and VpreB1 genes will be used for recombineering in bacteria (*E. coli*) to replace mouse genes with human genes. A suitable source of BACs is mouse BAC library collection, RP23-220N17 (BacPac Resource Center; http://bacpac.chori.org). The following steps will be followed to generate a targeting construct that will be used further for targeting of DNA into mouse AB2.1 ES cells and generation of a transgenic mouse harbouring the human sequences.

Figure 1B:
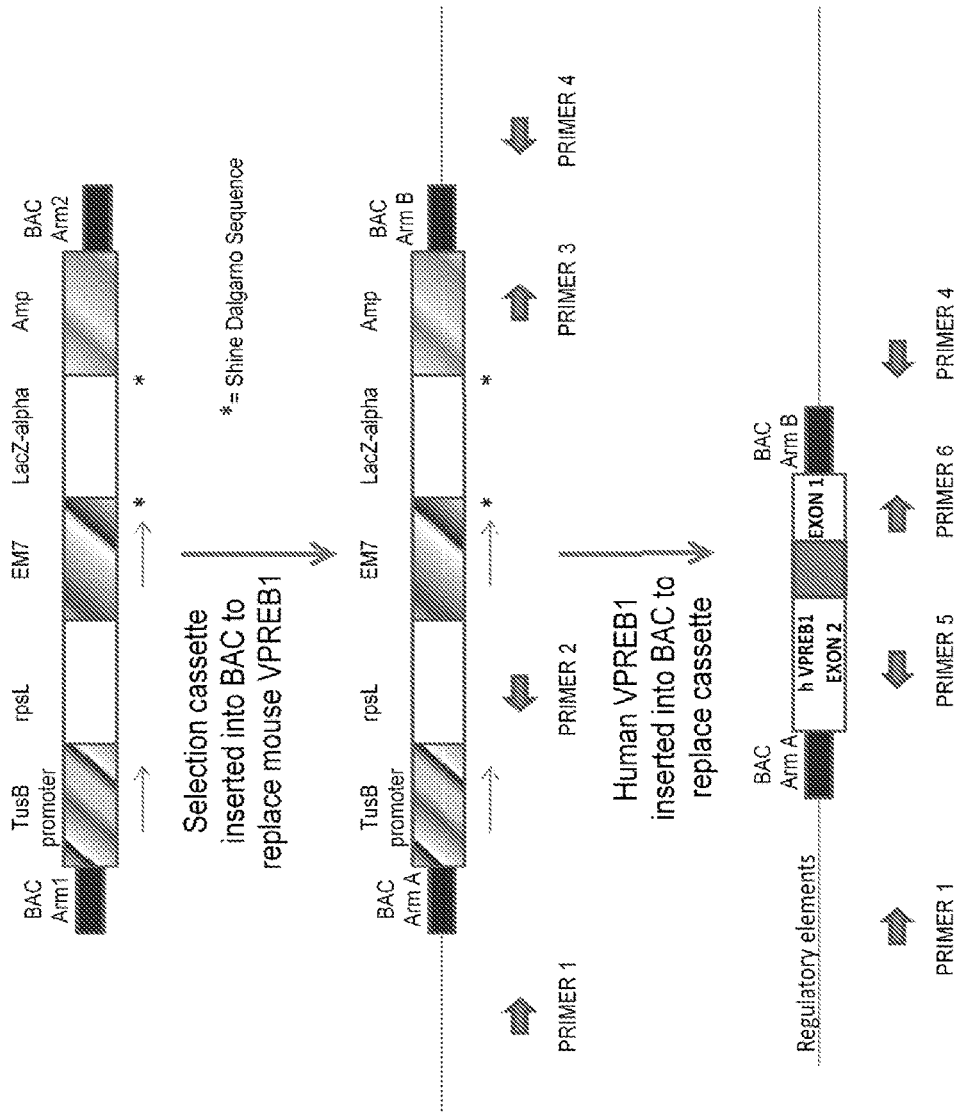

The first step is to delete the mouse VpreB1 gene on a BAC containing this mouse gene, by using a positive/negative selection cassette flanked by 5' and 3' 50 bp homology arms (ie, stretches of mouse genomic sequence that flank the endogenous VpreB1 gene in the mouse genome—see sequences A and B below and denoted as BAC Arms A and B respectively in FIG. 1B). The cassette contains ampicillin and streptomycin genes between the homology arms. This cassette is able to select clones that have been correctly targeted, FIGS. 1A and 1B. The selection cassette will be inserted and targeted using homologous recombination to replace the endogenous mouse VpreB1 gene. Positive clones will be checked using positive selection, ampicillin, followed by PCR based confirmation (denoted by the arrows on the second schematic in FIG. 1A and by means of PRIMER1 to PRIMER4 in FIG. 1B). As shown, the PCR based confirmation will be performed using specific primers situated within the inserted DNA sequence whereas, other primers will be outside the targeted region. A positive amplification product can only be achieved if the newly inserted DNA is targeted correctly to the desired locus. Using 50 bp homology arms (sequences A and B below) that are added to flank the human VPREB1 gene, a vector will be constructed and used to target and replace the positive/negative selection cassette specifically using homologous recombination (bottom schematics in FIGS. 1A and B). Correctly targeted clones containing human VPREB1 (targeted mouse BACs) will be screened using a negative selection, streptomycin and PCR based method. A source of human DNA for the human VPREB1 gene is RP11-373H24 BAC (Invitrogen; Roswell Park Cancer Institute).

```
Sequence A: 5' Arm
acctggccaaactgagcatgacctttgacctagccagctcttaaa
cttgttctgagatcacaaaccagccagaccaaatt Sequence B: 3' Arm
tcctcccagaatgcttccctgggtcaaacccagagccacaaaggc
ttccattagaccattctggtaagtgacagagtcac
```

Retrieval of 19 kb DNA from Mouse BAC

Next, the 19 kb of DNA (see Sabbattini references cited supra) containing human VPREB1, mouse λ5 and the mouse regulatory elements will be removed from the BAC using homologous recombination in *E. coli*. The region will be retrieved from the previously targeted mouse BAC into a smaller vector containing 5' and 3' mouse homology arms (FIG. 2; Mouse Arms 1 and 2). The arms are constructed using mouse BAC as a DNA template to maintain high nucleotide homology. Amplified arms are digested with specific restriction enzymes and cloned into targeting vector (the resulting targeting vector is shown in the top schematic in FIG. 2). The targeting vector is linearised between two homology arms and electroporated into *E. coli* which contains the previously targeted human VPREB1 gene.

```
Mouse Arm 1 Sequence:
AAAAAAAAAAAAGCCCAGCTAGCTTAGTTGGTAGAGCATGAGACT

CTTAATCTCAGAGTCATGGGTTCAGGCCTCATGTTTGGCACCATC

TATAGTGTGCAGTTATAAATCAAACAGTTCACGATGTGGCTGGCT

AGGCACTGGCAACTGCAGTCTCACCTGCTCCCATGGTTCCCAGTT

CCCACAGCTAGTTTGCTGCCAGGCTGTTCACACTTCCCAGGTCAT

CTACCCACTGTGGCAAGCCTGCAGAAAGCCTGCTATTGCTAGCTC

AGATTCCCTTAGCCCTATAAAATGATAACACCACAGACTTTTACT

ATACCATCCAGATTTATAACAGTAATTCTCCAACCC

Mouse Arm 2 Sequence:
CAGGAGTACACCAAAATGTCTAGCCAAAATTTTTATATATGATCA

CTTAAATAAGACTCCTTAACATAAACCTACATGATATACCAAGTC

TTTTCTGCCAAGGCTCTGACACTATAGTTTGTCCTATTCTGGAGT

TAGGTAAGCAAAGGGCTATTTAGGTGTGGATTGCAAAGAGAGAAT

AGCAAGACAACCTGCCCATTCTTTGCCACACCTCACTAATCAGTG

TCCCTTGGAAAGCACTGTAAATATGGAGGTTTCTTTTTGTATTAT

GTAGTAGTGGATTTAACTTGAGGAGCCCCAAAAGGGGTCAGCAAA

GCATGGGAAATCTAAGAATTTAACACTTCAGTGACTTTTAATCAC

CTACAGATCCAGGAAAATAAGCCTGTCTCTT
```

Figure 2:
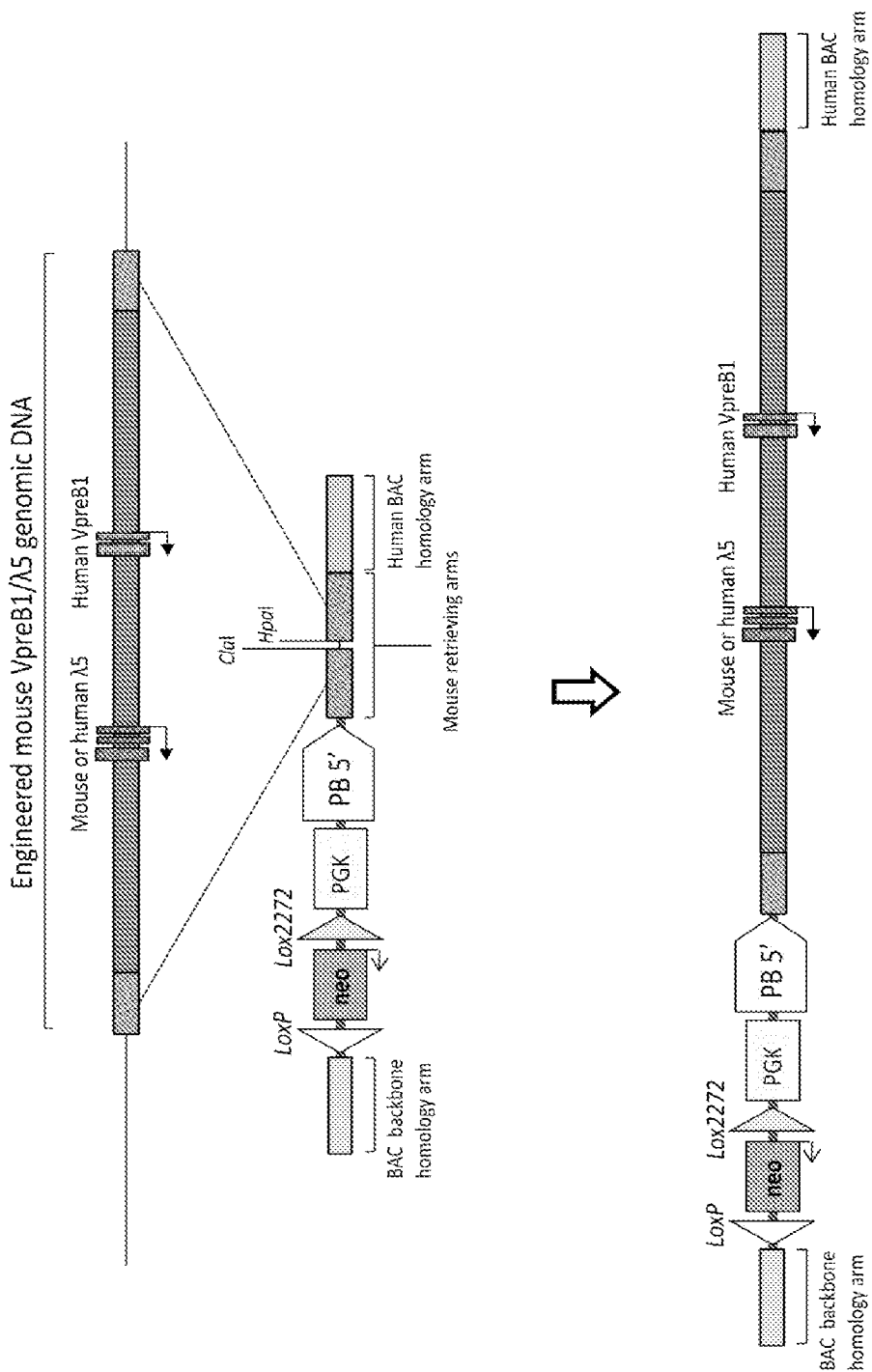
FIG. 2: Upper Schematic: representation of vector for retrieval of the 19 kb mouse DNA sequence containing the human VpreB1 gene; Lower Schematic: representation of the vector containing the retrieved 19 kb mouse DNA sequence containing the human VpreB1 gene. Black rectangular boxes represent homology arms. Black arrows represent the coding sequences of VpreB1 and mouse λ5.
Figure 3:
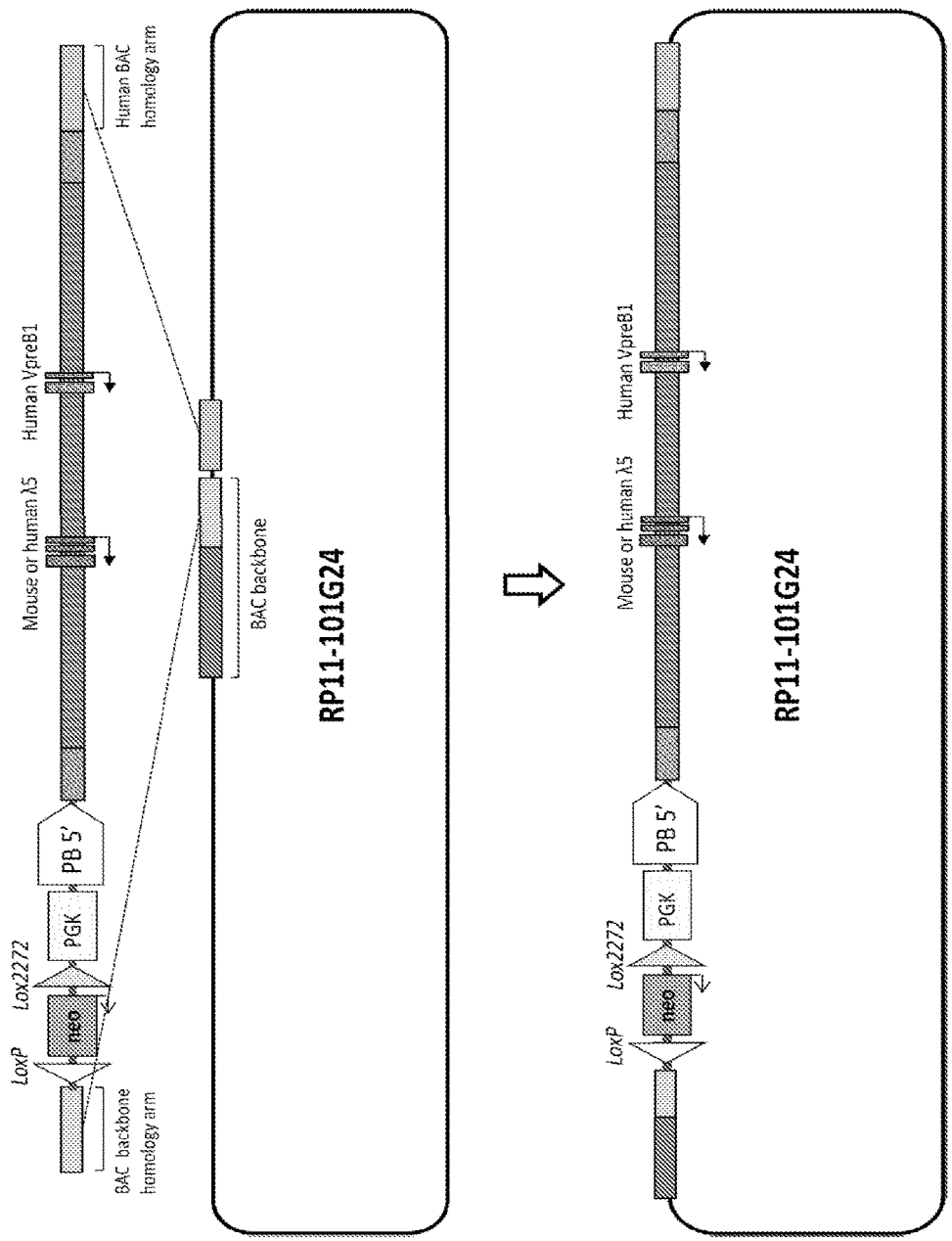
FIGS. 3A & B: Schematic maps of insert (FIG. 3A) a human BAC (FIG. 3B) containing correctly targeted human VpreB1, λ5 and mouse regulatory elements.
Figure 4:
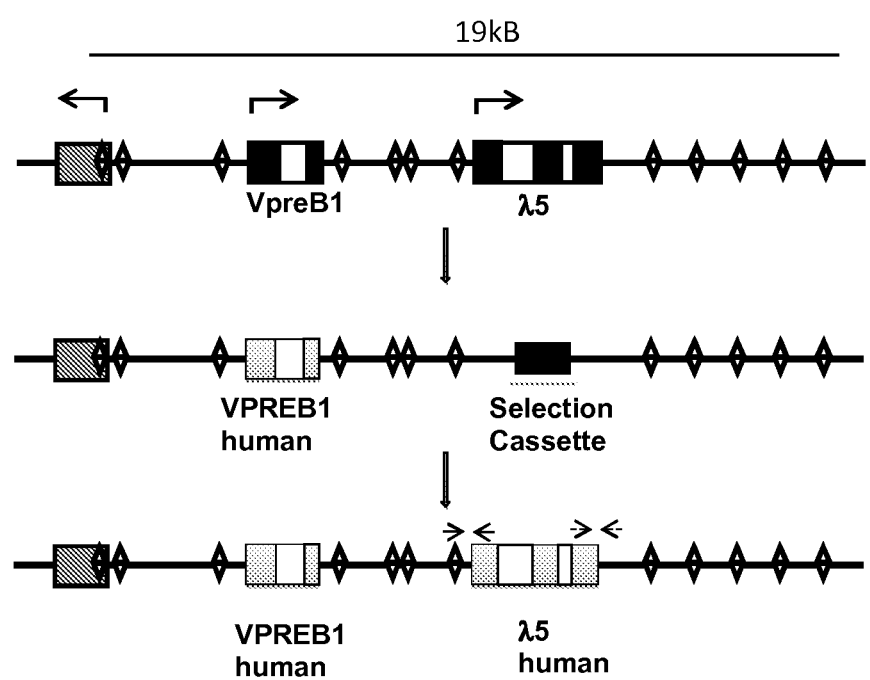
FIG. 4: Schematic representation of the steps involved in replacement of the mouse λ5 with human λ5.

The resulting vector contains the 19 kb sequence containing mouse λ5 and human VPREB1 genes (second schematic in FIG. 2). This vector will allow for amplification of the retrieved 19 kb sequence and use for further insertion into a human BAC of choice (eeg, a BAC containing human antibody gene segments, such as a BAC obtainable from the RPCl-11 library available from Invitrogen). The insertion of the 19 kb DNA fragment will be targeted into a BAC containing human IgH V gene segments (FIGS. 3A and 3B; which can be read in conjunction with the disclosure of WO2011004192, the disclosure of which is incorporated herein by reference), eg, to target the 19 kb sequence directly 5' of the most distal 5' end of the human IgH locus to avoid any possible interference with normal IgH rearrangement subsequently in a mouse or B-cell progeny. To this end, using a series of BACs, human Ig gene segments (VDJ) are inserted in a series of steps into the genome of a mouse ES cell (eg, an AB2.1 cell) using sequential recombinase mediated cassette exchange (sRMCE) or homologous recombination as is known in the art. The 19 kb sequence can be inserted directly 5' of the 5' VH in the last BAC to be used, thus providing the 19 kb sequence immediately 5' of the first human VH in a transgenic IgH locus after insertion of the 19 kb sequence and human VH sequences into the mouse ES cell genome. Thus, a human VPREB1/mouse λ5 gene insert is provided for expression of chimaeric surrogate light chain (SLC) in a subsequent progeny mouse or B-cell.

Humanisation of λ5

Similar procedures of targeting and genetic engineering steps will be used to modify the second gene of SLC, namely the λ5 (FIG. 4), in order to replace mouse λ5 with human λ5.

Correctly targeted ES will be used to generate a transgenic mouse. Analyses will be performed using animals which harbour (i) the human VPREB1 and mouse λ5 (humanVB1/mouse λ5) or (ii) human VPREB1 and human λ5 (human VB1/λ5). Differences in populations of expressed antibodies between a control wild type (WT) mouse and (i) or (ii) will be recorded using Fluorescence-Activated Cell Sorting (FACS). The end point data will be generated using mice spleen to analyse the contribution of human VPREB1 only or in conjunction with human λ5 in expansion of B cell population harbouring human sequences and the generation of more diverse antibody repertoires.

Example 6: Engineering of Non-Human Vertebrate Genome

Chimaeric Surrogate Light Chains Significantly Change Human Variable Region Repertoires In Vivo Construction of Transgenic IgH Loci Insertion of human heavy gene segments from a 1st IGH BAC (RP11-1065N8) into the IGH locus of mouse AB2.1 ES cells (Baylor College of Medicine) was performed to create a heavy chain allele denoted the 51 allele. The inserted human sequence corresponds to the sequence of human chromosome 14 from position 106494908 to position 106328951 and comprises functional heavy gene segments $V_H2-5$, $V_H7-4-1$, $V_H4-4$, $V_H1-3$, $V_H1-2$, $V_H6-1$, D1-1, D2-2, D3-9, D3-10, D4-11, D5-12, D6-13, D1-14, D2-15, D3-16, D4-17, D5-18, D6-19, D1-20, D2-21, D3-22, D4-23, D5-24, D6-25, D1-26, D7-27, $J_H1$, $J_H2$, $J_H3$, $J_H4$, $J_H5$ and $J_H6$ (in 5' to 3' order), wherein the JH6 was chosen to be the human JH6*02 variant. The insertion was made between positions 114666435 and 114666436 on mouse chromosome 12, which is upstream of the mouse Cu region. The mouse $V_H$, D and $J_H$ gene segments were retained in the locus, immediately upstream of (5' of) the inserted human heavy chain DNA.

A second allele, S2 was constructed in which more human functional $V_H$ gene segments were inserted upstream (5') of the 5'-most $V_H$ inserted in the 51 allele by the sequential insertion of human DNA from a second BAC (BAC2). The inserted human sequence from BAC2 corresponds to the sequence of human chromosome 14 from position 106601551 to position 106494909 and comprises functional heavy chain gene segments $V_H3-13$, $V_H3-11$, $V_H3-9$, $V_H1-8$, $V_H3-7$. The mouse $V_H$, D and $J_H$ gene segments were retained in the locus, immediately upstream of (5' of) the inserted human heavy chain DNA.

Mice bearing the S2 insertion into an endogenous heavy chain locus were generated from the ES cells using standard procedures. The other endogenous heavy chain locus was inactivated in the mice by insertion of an inactivating sequence comprising neo$^R$ into the mouse J$_H$-Cμ intron (to produce the "HA" allele). The mice retained mouse VpreB and λ5, but no human VpreB gene (control, S2 mouse) or a human VpreB gene was included in the genome (S2/hVpreB mouse, ie, chimaeric surrogate light chain mouse according to the invention comprising a human VpreB1 gene with mouse VpreB1 promoter-driven expression). The human VpreB was inserted from a BAC using recombinase mediated cassette exchange (RMCE) upon construction of the S2/hVpreB mouse according to the invention. The latter mouse was a chimaeric mouse having around 30% Agouti coat colour, which is indicative of the potential fraction of B cells derived from the injected ES cells bearing the human VpreB gene. Thus, in the chimaeric mouse of the invention most B-cells do not have the human VpreB. This provides for a more challenging test versus control, as explained below. An alternative would be to breed a mouse of the invention where all cells harbour a human VpreB gene, and this is expected to show the advantage of the invention in producing a different repertoire as demonstrated below for the chimaeric test mouse.

Specifically, the following human gene segments were included (in 5' to 3' order):—
 human VH gene segments VH3-13, 3-11, 3-9, 1-8, 3-7, 2-5, 7-4-1, 4-4, 1-3, 1-2 and 6-1;
 human D gene segments D1-1, 2-2, 3-9, 3-10, 4-11, 5-12, 6-13, 1-14, 2-15, 3-16, 4-17, 5-18, 6-19, 1-20, 2-21, 3-22, 4-23, 5-24, 6-25, 1-26 and 7-27; and
 Human JH gene segments J1, J2, J3, J4, J5 and J6.

RNA was extracted from the spleens of both the control and S2/hVpreB mouse of the invention. RT-PCR was performed as described in the VDJ sequencing methodology below. The mouse Cμ transcripts were captured and sequenced, and only human JH transcripts were used for usage analysis to ensure use of transcripts only derived from the transgenic IgH loci bearing human variable region gene segments.

VDJ-Sequencing Methodology

The following methodology was performed to sequence human IgH variable regions from RNA samples obtained from the mouse of the invention comprising a transgenic IgH locus and a human VpreB gene. Comparison of the control with a chimaeric mouse of the invention is more challenging than comparison with a mouse of the invention that is 100% transgenic (ie, where all cells bear the transgenic IgH locus and human VpreB gene). In the chimaeric mouse, only a proportion of the cells comprise the transgenic IgH locus and human VpreB gene, and in those cells the IgH is present in one copy (heterozygous). Thus, the comparison in this example surprisingly was still able to show a difference in repertoires produced in the control and invention mice despite the chimaeric nature of the latter.

Sequences were filtered so that the resulting data set related to human variable regions only (and not variable regions having mouse sequence).

V gene usage frequency was assessed by next generation sequencing of VDJ recombined transcripts using the Illumina Miseq platform (see, eg, Nature. 2008 Nov. 6; 456 (7218): 53-9; "Accurate whole human genome sequencing using reversible terminator chemistry"; Bentley D R et al). Libraries of VDJ sequences were generated with standard adapter sequences at either end that were compatible with Illumina sequencers. The Illumina adapter sequences are termed P5 and P7 permit the binding of DNA fragments to the Illumina flowcell and are the initiation sites of the sequencing reactions. The VDJ libraries were generated using the following methodology: 5' RACE was performed on 5 μg of total RNA to generate cDNA with a known sequence at the 5' end using the ExactSTART Eukaryotic mRNA 5'- & 3' RACE kit (Epicentre) using the manufacturer's protocol with the following modifications: The 5' RACE acceptor oligo was replaced with an RNA oligo (P7 RNA oligo: AGACGUGUGCUCUUCCGAUCU) specific to a 21 bp portion of the Illumina P7 adapter. The first-strand cDNA was synthesised using a reverse primer (IgM RT primer: GAAGACATTTGGGAAGGACTG) specific to the first exon of the IgM constant region. Second strand synthesis, and enrichment of VDJ sequences was achieved by performing 15 cycles of PCR using a primer specific to the ligated RNA oligo (P7 PCR 1: [GTGACTGGAGTTC]A-GACGTGTGCTCTTCCGATCT) that also included additional Illumina P7 sequence at the 5' end (shown by square brackets). Paired with a primer specific to the IgM constant region/J segment splice junction (IgM P5 PCR 1: [ACACTCTTTCCCTACACGACGCTCTTCCGATCTNN] GGGAAGGACTGACTCTCTGA) that also included additional Illumina P5 sequence, and two bases of random nucleotides, at the 5' end (shown by square brackets).

The PCR reaction was purified using gel electrophoresis and the major PCR product that corresponded to VDJ transcripts (~600 bp) was excised and purified using a Qiagen gel extraction kit according to the manufacturer's protocol. A second round of 15-cycle PCR was performed to add the remaining portions of the Illumina P5 & P7 adapter sequence and to incorporate a barcode, so multiple samples could be pooled and sequenced together in a single run. The forward primer was specific to the P5 sequence with the additional P5 flowcell binding sequence shown within square brackets (P5 PCR 2: [AATGATACGGCGACCAC-CGAGATCT]ACACTCTTTCCCTACACGACGCTCTT). The reverse primer was specific to the P7 sequence and incorporated a 6 bp barcode and the P7 flowcell binding sequence shown within square brackets (P7 PCR 2 index X: [CAAGCAGAAGACGGCATACGAGAT******]GT-GACTGGAGTTCAGACGTGT). The 6 bp barcodes were standard Illumina 6 bp indexes, 4 different indexes were used in this case and the sequences were: CGTGAT, GCCTAA, GATCTG, & TCAAGT. The final PCR products were purified using AMPure XP beads (Beckman Coulter) and were pooled together and sequenced on the consisted of a VDJ transcribed gene with a complete P5 and P7 Illumina adapter on either end. This construct was suitable for next generation sequencing on the Illumina Mi-Seq system using the TruSeq DNA sequencing program 2×150 bp paired end sequencing program.

Bioinformatics & Statistical Analysis

The sequences from the Illumina MiSeq were obtained as a set of 4 BAM files from the machine, each file corresponding to a different barcode. Barcodes 1 and 3 were from the surrogate light chain samples, while barcodes 7 and 8 were from the control samples. These BAM files were converted into fastq using bam2fastq using the command: bam2fastq<file>.bam-o<file>#.fastq which splits the paired reads into two different fastq files.

These fastq files were then converted into fasta using fastq_to_fasta-I<file>.fastq-o<file>.fasta-Q33. This yielded a set of 8 fasta files.

The fasta files were then analysed with Basic Local Alignment Search Tool (BLAST) (http://blast.ncbi.nlm.nih.gov/) to find J and V segments from mice and humans.

The paired reads were used to identify the J and V used, with the read from the constant region end being used to find the J and the read from the 5' end of the RNA being used to identify the V gene used. As the transcription occurred before the start of the V segment, 5' UTR sequence from Ensemble (http://www.ensembl.org) was used to search against to find the V genes used.

An InforSense workflow was used to then combine the results from the paired reads by matching their unique identifier to the results from the two Blast searches. These combined results were then filtered for sequences which used a Human J gene and a Human V gene. Because the sample with the chimaeric surrogate light chain was a wild type/transgenic chimaera, there were far fewer samples with a Human J than in the control, which is expected.

To avoid any errors due to PCR duplication events sequences with identical CDR3 regions, as determined by the IMGT numbering scheme, were treated as one sequence. This reduced the number of sequences in the control sample from 2,632,503 to 168,551 and in the surrogate light chain sample from 2,543,248 to 590,462.

The final counts after filtering for Human J, Human V and treating each CDR3 string as single sequence gave 10,781 sequences for the control, and 267 for the surrogate light chain sample. The low percentage of sequences with an identified Human V is due to the 150 bp reads from the Illumina MiSeq not extending very far into the variable part of the V genes. The results are shown in Table 3. In the table, the mouse of the invention is labelled "Chimaeric SLC" and significant changes in gene segment usage are underlined.

TABLE 3

| | Control Total | Chimaeric SLC Total | Control % | Chimaeric SLC % |
|---|---|---|---|---|
| V6-1 | 587 | 38 | 5.44% | 14.23% |
| V1-2 | 155 | 3 | 1.44% | 1.12% |
| V1-3 | 1167 | 43 | 10.82% | 16.10% |
| V4-4 | 984 | 33 | 9.13% | 12.36% |
| V2-5 | 409 | 7 | 3.79% | 2.62% |
| V3-7 | 4095 | 66 | 37.98% | 24.72% |
| V1-8 | 1315 | 21 | 12.20% | 7.87% |
| V3-9 | 893 | 40 | 8.28% | 14.98% |
| V3-11 | 443 | 3 | 4.11% | 1.12% |
| V3-13 | 733 | 13 | 6.80% | 4.87% |
| sum | 10781 | 267 | | |

TABLE 3-continued

| | Control Total | Chimaeric SLC Total | Control % | Chimaeric SLC % |
|---|---|---|---|---|
| IGHJ1*01 | 131 | 13 | 1.21% | 4.87% |
| IGHJ2*01 | 260 | 13 | 2.41% | 4.87% |
| IGHJ3*02 | 1011 | 34 | 9.37% | 12.73% |
| IGHJ4*02 | 5467 | 153 | 50.69% | 57.30% |
| IGHJ5*02 | 867 | 12 | 8.04% | 4.49% |
| IGHJ6*02 | 3050 | 42 | 28.28% | 15.73% |
| sum | 10786 | 267 | | |

The usage between the two samples was compared using a standard Pearson's chi-squared test (see eg, NIST/SEMATECH e-Handbook of Statistical Methods, http://www.itl.nist.gov/div898/handbook/, April 2012). This gave the probabilities that the distribution of the surrogate light chain sample and the control sample being the same was 5.8 E-15 for the V genes and 8.2 E-12 for the J genes. These are below the standard 5% (ie, 0.05) probability cut off and thus are significant.

The individual V and J genes which showed the most significant differences between the two are summarised in the Table 4 below. The probability shown is the probability of obtaining by chance that number or more in the case of an increase or that number or less in the cast of a decrease, using a binomial distribution using the probabilities from the ratios obtained from the control sample. The individual V and J genes in the table have a probability score below the standard 5% (ie, 0.05) probability cut off and thus are significant.

TABLE 4

| Gene | Usage | Chimaeric SLC Count | Expected from Control | Probability |
|---|---|---|---|---|
| IGHV6-1 | Increased | 38 | 14.5 | 2.38E−08 |
| IGHJ1 | Increased | 13 | 3.2 | 6.31E−06 |
| IGHV3-9 | Increased | 40 | 22.1 | 9.80E−05 |
| IGHV1-3 | Increased | 43 | 28.9 | 3.21E−03 |
| IGHJ6 | Decreased | 42 | 75.5 | 1.09E−06 |
| IGHV3-7 | Decreased | 66 | 101.4 | 2.94E−06 |
| IGHV3-11 | Decreased | 3 | 11.0 | 4.42E−03 |
| IGHV1-8 | Decreased | 21 | 32.574 | 1.52E−02 |

SEQUENCE LISTING

Human VpreB1 nucleotide sequence (GenBank Accession No = NG_029387.1)

SEQ ID NO: 1 gagtcagagctctgcatgtctgcaccatgtcctgggctcctgtcctgctcatgctgtttgtctactgcacaggtgaggga accccagatcccaaagactcctgcccctcttcatcctgcctgcccccacggcccacatgcatctgtgtcaccaggt tgtggtcctcagccggtgctgcatcagccgcggccatgtcctcggcccttggaaccacaatccgcctcacctgcaccct gaggaacgaccatgacatcggtgtgtacagcgtctactggtaccagcagaggccgggccaccctcccaggttcctgctga gatatttctcacaatcagacaagagccagggcccccaggtcccccctcgcttctctggatccaaagatgtggccaggaac aggggtatttgagcatctctgagctgcagcctgaggacgaggctatgtattactgtgctatgggggcccgcagctcgga gaaggaggagagggagagggagtgggaggaagaaatggaacccactgcagccaggacacgtgtcccttgaactgaagaca gcagaggcacgcatccccttggagagactgtcatggaagagggtggagccgccgcccgaagcgccgaggaggctgagcca ctcagcatctcctggtcctgcagtgttgctgtaaatccccattggagactgcattagggaattaaagctgcttgtcactt tttgctg

SEQUENCE LISTING

Human VpreB1 amino acid sequence (GenBank Accession No = NP_009059.1)

SEQ ID NO: 2 mswapvllmlfvyctgcgpqpvlhqppamssalgttirltctlrndhdigvysvywyqqrpghpprfllryfsqsdksqg pqvpprfsgskdvarnrgylsiselqpedeamyycamgarssekeerereweeemeptaartrvp Human VpreB3 nucleotide sequence (GenBank Accession No = NC_000022.10)

SEQ ID NO: 3 cttcccagccctgtgccccaaagcacctggagcatatagccttgcagaacttctacttgcctgcctccctgcctctggcc atggcctgccggtgcctcagcttccttctgatggggaccttcctgtcaggtgaatctttcctgggcctcagtcacctggg tgtggggtggggaacagtactggccccagaaggcccctgcaaggaggcaaatcgatggggacagtagggcaggtcctggg aggggtatttttttttttttgagacggagttttgctcttgttgcccaggctggagtgcaacggtgcaatctcggctcac tgcacctctgcctcccaggttcaagcgattcttctgcctcagcgtcctgagtagctgggattacaggcatgcgccaccac gcctggctaattttgtattttagtagagacaaggtttcttcatgttggtcaggctggtctcaaactcctgacctcaggt gatccgcccacctcagcttcccaaagtgctaggattacaggcttgagccactgcacctggctgggaggcgtattcaggta gaggggtgacctggcttcagacagctctgcccttgacctgggcaaatcacttccctgtgtgggccttggttttctcatt cgtgaatgaccagatcactagagccctggactctgactttgggtctccttcttagttttttcacaggggaagctattgtgg gttggtccctaccccacagggcctgaggcaatctaacctccctgagagggtccctgcagccagttgcctgaggctgagtt gatgtgtgggacagcccaggaggttcctgggggtggttagtctgtattcagggtttggaagagctgaagtgaagtgggcg gggaagtgggggagaggggtgcagttctgcagagaaacgtgggtgggtagcagagggacctagaggctgctagtccaacc ttctgagctctgggcctttaactgaacacagatccttgaggatatggcactaatggagatttgggggctaactccaaacc cctcactcacaaagggagatggaggtccagatagggcaccctaagtcacacagaaccaggcctcctgcaccccgttcatt gctaatcccatagcactgggctatgagcccctttgggactgggagtctccatggagtccaaccaagccttcacagggcagg ggtggagggaaggggctcaggctgagtgggtttgtgtctcgcagtttcccagacagtcctggcccagctggatgcactg ctggtcttcccaggccaagtggctcaactctcctgcacgctcagccccagcacgtcaccatcagggactacggtgtgtc ctggtaccagcagcgggcaggcagtgcccctcgatatctcctctactaccgctcggaggaggatcaccaccggcctgctg acatccccgatcgattctcggcagccaaggatgaggcccacaatgcctgtgtcctcaccattagtcccgtgcagcctgaa gacgacgcggattactactgctctgttggctacggctttagtccctaggggtggggtgtgagatgggtgcctcccctctg cctcccatttctgcccctgaccttgggtcccttttaaactttctctgagccttgcttcccctctgtaaaatgggttaata atattcaacatgtcaacaaca Human VpreB3 amino acid sequence (GenBank Accession No = NP_037510)

SEQ ID NO: 4 macrclsfllmgtflsvsqtclaqldallvfpgqvaqlsctlspqhvtirdygvswyqqragsapryllyyrseedhhrp adipdrfsaakdeahnacvltispvqpeddadyycsvgygfsp Mouse VpreB1 nucleotide sequence (GenBank Accession No = NC_000082.5)

SEQ ID NO: 5 agagcccagaaagcctgggagggtggtgagcaggaaccaggggtgcagtgaccctctccccaaagcagggaggagagtgc ttcccagctggtcagggcccaggagcagtggctgtaggggggcagggtgctgcaggtctggagccatggcctggacgtctg tcctgctcatgctgctggcctatctcacaggtaaggaaactcttgggggcccagggcttctttgctcctcctatggccttg ctctgccccagtgatggacatgcttctatcttctcaggttgtggccctcagcccatggtgcatcagccaccattagcatc ttcttcccttggagccaccatccgcctctcctgtaccctgagcaacgaccataacattggcatttacagcatttactggt accagcagaggccgggccaccctcccaggttcctgctgagatacttctcacactcagacaagcaccagggtcccgatatc ccacctcgcttctccgggtccaaagatacgaccaggaacctggggtatctgagcatctctgaactgcagcctgaggacga ggctgtgtattactgtgccgtgggggctccggagccaggaaaagaagaggatggagagggagtgggaaggagaaaagtcgt atacagatttgggatcttaggctctggagacattcagaccctgaactgaagacagagtttgctttgctcggctagtctgg

```
tatgggaaggaggggtagaacgtgaggttttgcagagcctagaagatggaattatgcagcttttccttgttctgcggtgt tgctatgagcccccattggaggctggattgtagaattaaagctgttttactgaa
```

Mouse VpreB1 amino acid sequence (GenBank Accession No = NP_058678)

SEQ ID NO: 6

```
mawtsvllmllayltgcgpqpmvhqpplasssslgatirlsctlsndhnigiysiywyqqrpghpprfllryfshsdkhqg pdipprfsgskdttrnlgylsiselqpedeavyycavglrsqekkrmerewegeksytdlgs
```

Mouse VpreB2 nucleotide sequence (GenBank Accession No = NC_000082)

SEQ ID NO: 7

```
atggcctggacgtctgtcctgctcatgctgctggcccacctcacaggtaagggaactcttggggtccagggcttccttgc tcctcctgtggccttgctctgccccagtgatggacatgcttctatcttctcaggttgtggccctcagcccatggtgcatc agccaccatcagcatcttcttcccttggagccaccatccgcctctcctgtaccctgagcaacgaccataacattggcatt tacagcatttactggtaccagcagaggccgggccaccctcccaggttcctgctgagatacttctcacactcagacaagca cccagggtcccgatatcccacctcgcttctccgggtccaaagatacggccaggaacctggggtatctgagcatctctgaac tgcagcctgaggacgaggctgtgtattactgcgctgtggggctccggagccacgaaaagaagagaatggagagagagtgg gaaggagaaaagtcgtatacagatttgggatcttag
```

Mouse VpreB2 amino acid sequence (GenBank Accession No = NP_058679.1)

SEQ ID NO: 8

```
mawtsvllmllahltgcgpqpmvhqppsasssslgatirlsctlsndhnigiysiywyqqrpghpprfllryfshsdkhqg pdipprfsgskdtarnlgylsiselqpedeavyycavglrshekkrmerewegeksytdlgs
```

Rat VpreB1 nucleotide sequence (GenBank Accession No = NM_001108845.1)

SEQ ID NO: 9

```
ccagaaagcctgggagggtggtgagcaggaaccagtggtgcaaagcagggcgagactgcttcctagctggtcagggcac cggagcagtggctgtagggtcagggtgctgcaggtctggaaccatggcctggacgtctgccctgctcatactgctggcc catctcacaggtacgggaactcttggggcccagagcctccttgctcctcctcttgccttgctctgccgcagtgatgggca cgcttctatttcctcaggttgtggccctcagcccgtgctgcatcagccaccatcggcctcttccttccttggaacctcca tccgcctcacctgtgccctgagcagcaaccataacattggcatttacagcatttactggtaccagcagaggccgggccac cctcccacgttcctgctgagattcttctcacactcagacaagctccagggtcccaagatccccctcgcttctccggatc caaagatacagccaggaacctggggtacctgagcatctctgacctgcagccagaggacgaggctgtgtattactgcgccg tggggcttcggagctggaaaaggagaagaggatggagagggagtgggaagaagaaaagtagcggacagattcgggatct taggctctggagacattcagacctagaaccgaagacggagtttgctttgctcggctaggctggtttggggaggaggggta gaacaccgggcttcgcagagccaggaaggtggagccagccgcttttccttgtattgcagtgttgctatgcgccccatcgg aggctggattgtagaattaaagctgttttttttttttttgttttgttttttgtttttgttctttttcttaactg
```

Rat VpreB1 amino acid sequence (GenBank Accession No = NP_001102315.1)

SEQ ID NO: 10

```
mawtsallillahltgcgpqpvlhqppsassflgtsirltcalssnhnigiysiywyqqrpghpptfllrffshsdklqg pkipprfsgskdtarnlgylsisdlqpedeavyycavglrswekekrmereweeek
```

Rat VpreB2 nucleotide sequence (GenBank Accession No = NC_005110)

SEQ ID NO: 11

```
atggcctggacgtctgccctgctcatactgctggcccatctcacaggtacgggaactcttggggcccagagcctccttgc tcctcctcttgccttgctctgccgcagtgatgggcacgcttctatttctcaggttgtggccctcagcccgtgctgcatc agccaccatcggcctcttccttccttggaacctccatccgcctcacctgtgccctgagcagcaaccataacattggcatt tacagcatttactggtaccagcagaggccgggccaccctcccacgttcctgctgagattcttctcacactcagacaagct ccagggtcccaagatccccctcgcttctccggatccaaagatatagccaggaacctggggtacctgagcatctctgacc tgcagccagaggacgaggctgtgtattactgcgccgtggggcttcggagctggaaaaggagaagaggatggagagggag
```

SEQUENCE LISTING

```
tgggaagaagaaaagtagcggacagattcgggatcttaggctctggagacattcagacctagaaccgaagacggagtttg ctttgctcggctaggctggtttggggaggaggggtagaacaccgggcttcgcagagccaggaaggtggagccagccgctt ttccttgtattgcagtgttgctatgcgcccatcggaggctggattgtagaattaaagctgttttttactg
```

Rat VpreB2 amino acid sequence (GenBank Accession No = NP_001128260)

SEQ ID NO: 12

```
mawtsallillahltgcgpqpvlhqppsassflgtsirltcalssnhnigiysiywyqqrpghpptfllrffshsdklqg pkipprfsgskdiarnlgylsisdlqpedeavyycavglrswekekrmereweeek
```

Human λ5 nucleotide sequence (GenBank Accession No = NG_009791)

SEQ ID NO: 13

```
ggccacatggactggggtgcaatgggacagctgctgccagcgagagggaccagggcaccactctctagggagcccacact gcaagtcaggccacaaggacctctgaccctgagggccgatgaggccagggacaggccaggggggccttgaggcccctggt gagccaggccccaacctcaggcagcgctggcccctgctgctgctgggtctggccgtggtaacccatggcctgctgcgccc aacagctgcatcgcagagcagggccctgggccctggagcccctggaggaagcagccggtccagcctgaggagccggtggg gcaggtaaggggtgagagattccagggatgtgggggctggtggcagaggcgggaaaggatgaccaagggggagacgag ccagaggggtgaggaggaaggttaatccctggaggggagccacagacactgactttaactaaagtgtcaagattttgtcc atctttgaattaattttttattgcttaatgtcatattaaaatattatttatcttgattcctgagatttcttcccccactta catttggcaccaaggccaatgtctccctcacctccccctagtccttggggtagggcaggactggaggcaggggcaggacg tccacaggagtggtggccgctatccctgaaggatgcccaggcctctccctcctcctcctccactcctcctccccccct cctcttttccccttggcctatgtcacctgtccactcccaccctcactgggcaggggccactccctggagctccagctaag gtgtgaggggcctttcctggagtccctgggtcactagacctcagccagcatcgcctcctgaaaccagcccctaggagaca caagcttatccagggtgcaagtgcctccaaagaagaagcccaggagaggctctagggaggccacaactccctgtgtgacc tcagccattgccaccactctgcgtgtggtgggaggtcccagacaaagcaccaagcatcggggtccatttatgagcattt gggacacaacagcctgttcactggtgcatgttatacccacaggcgataatcatttcaggggcagaacctccctctcggtg gccccataggcaggtcctgctgtgatccccttgtgcagacggggatagagcccggagaggtgaggtgaccgtccgagt cactcagctcatgggcacagattctaaggcccaagctatccctctagctctcccctgtcccatcctctaagctgatcga gcggacacgtgcatctctgggacctgagtttccctttttctctcttttttttcttttcaaataaagtttcacagagttt cactcttgtcgcccagtctggagtgcaatggcgagatcttggctcattgaaacctccgtctcccaggttcaagacattct cctgcctcagcttccggagtagctgggattacaggcatctgccaccacacctggctaattttgtgtatttttttttagta aagacagagtttcaccatgttggccaggctggtctcaaactcctgacctcaggtgatccaccacctcagcctcccaaag tgctgggattacaggcatgagacaccacaccgggcctgagtttccccttctgcaatctgaggggccctgactggtgaggg ccttcagcgtcccacccacccagaggatgctggggtggctgtggtgagagctccagcagtggcagccgacctgacccaca ccaggagcccggccatggaggcggggtcagcatggtggcaggccgggaccgggtgtcagtgtcctgcacggacttctgag caaggagtcccatcagggtcaggctctgtgctggggctgaggtcccagaggatctagatttgcccccaattcaagtccac aaggagcggggccgggtgaggagacagccacatgcagggtgatgcctacagaacagagactgggatggggaaggcccga ggggtctccacaagggacgggtgacaggtggagggagacacagataataaaaaatggtattatgttgggggctattaat gtaagttttttatattagaatctttagaaatcttatagaaatactatgggccgggtgctgtgtctcatgcctgtaatccca gcactttaggacgccaagatgggcagatcacgaggtcaggagattgagaccatcctggccaacatggcaaaactccgtct ctactaaaaatacaaaaactagctgggcgtggtggcgcgagcctatagtcccagctactcgggaggggaggcaggagaat cgcttgaatcagggaggtggaggttgcagtgagctgagattgcaccgctgcactccagcctggacgacagaacgagactc ccactcaaaaaaaaaaaaaggtattatgctggggggggatatgaatatgagttttttataatctttagaaatactatgggcc aggtgcagtggctcatgcctgtaatcccacaactttgggaggctgaggcgggattgtttgagcccaggagtttgagatca
```

-continued

SEQUENCE LISTING

```
gcctgagcaacatagcaagaccccatttctacaaaacatataaaaactagctagtcatggtggcacttgcctgtggtccc agctacttaggaggctggtgagaggattgcttaagcctcggaggttgaggatgcagtaagctgagatcccaccactgcac tccagcctgggtgacagaaggagaccctgtctcaaaaaaaaaaaaaaaaaaaagactgattattcctgtagaattctg gtaaatatctcctatcaaataaatgacttttctattcatagcttattaaaagatattttcattgttttaagaaataggt tgtgtatcacttttatatttagttgtaaatttatttgttttattttttttagagatgggggtctcactatgttgcc tgggctggcctccaactgctgggctcaagcaatatccctgcctcagcgtcccagtagctgggactacaagcatgcgcta ccacaccggcataatttttgtagagatgaggtttcgccatgttgcctgggctggtcttgaaccctgggctcaagccat ccacccgcctcggcctcctaaagtgctgagattacagacgtgagccaccctacctagcctgtactattttaataggtct taataggttttgaatgttaattatttttaaattaatttcaaaaatcttctacaacatggatgaaacctgaagacattata cttagtgaaataagccagacacaaaaggacaaatgtcatttgaatccacttctatgaggtacctagaataggcaaattca cttggacaaaaagtagatttgaggttagcagggtgaggggagggaagaatgggggactgtagttaacgggtttagagtt tctgtttgggaagatgaaagagttctggagatggatggtggtgaaggttcccaacggtgtgaatgtacttagtgccacg gagctgtacgtttaaaaatagttaaagtggaaatattgatgctatgtataaaaatggagcggggtgtggtggctcacacc tataatcccagcactttgagaggccaaggtgggcagatcacctgaggtcgggagttcgagaccagcctgacaaacatgga gaaacaccgtctctactgaaaatacaaaaaattagccaagtgtgctggcacatgcctgtaatcccagctactcgggaggc tgaagcaggagaatcgcttgaacccaggatgtggaggttgcggtgagccaaggtggcaccattgcactccagcctgggcg acaagggtgaaattccatttcaaaaaaataaaaggaaatgggactgtacatagcaggagagagagggagagatcaatatg acacttcttttttttttttttttttgggacagtcttgctctgttgccaggctgcactccagcctgggcaacagagcg agactctgtctcaaaaaaaaaagaatgtctagatgcagtagctaagttcgcagaagccatttcagtgtgggaggcgagg tgactgagtccagggactccaggtttctggctgaggggttgagaccgcccatggtcattgtgatgagatgaagacagaaa atgagctgggctggggaaggtggtcatctcctctggacgtgattagtttgaggctcctgttgggtagcccactgggcaa ggtcagtaggcaattgaggagctgagagggtttggagctgggatagactccagcctcaccatgtgggcaatagtgggggt cacagagtgtgaaaatggctaagaaagaggtctgggtggggtctggggagtcagcagccaggcatgggccatggagaaac agatgccaggggaagaggaaagggggagtctcagaccccaaggggaaaagagtcactggaaagaggggccagccctgtgtc gcatccagcggagacaccaggtacagcagaaggaccttggacatgaccatgaggagggccttgttgaccatggcctggga gagatggggtgagagcctgggggaccacaccatgtccccagcacacagtgcctggtagacaggatggatttatggatgg acggacaggtagatggatggacgaatggacagatgatagatggatgcaaagacagatgaatagatggacagatgcataga tggacagatggacagatggatggacggacggatggaatgaatgatcagaaaaggcttcatgaacaaagtgagactgagct gcatctccatgggtagatataaaagcagaggactctcctcttgagtcaggaatgacccaatgtcctggtccagggaggaa gtcagcctcctttgactggggacacttgtggcagatttcagaggcccttaaaatgaggccaagtgaggtggacaggtccga gccagctgaggactcctcagccacacggcacagctgcctgagggatgtgtcactcagggagttgctgggacctactggg cccagcgttgccatcagcaccaacagtttcagagaggggacacacgctgggcagcacctgcctcagagaagggacagg cacagagacactactggggacactactgggacactggccaccccctaccctgtgcctgggtcacagcctacacactgc agccctgtgcccctcactcccagcaggttcctgctccagcgcggctcctggactggcccaggtgctggccccgggggtt tcaatccaagcataactcagtgacgcatgtgtttggcagcgggacccagctcaccgttttaagtaagtggctctaacttc ccaggctgtcccaccctctcctgtctctggaaaatgtgttttctctctctgggcttcttccctctgccctcccagcct taagcactgaccctacctttgtccatggggcctggaggagatgtgttagtctcagggtaatggcaggaagggcccccac agtgggagcagccgccttcaggttccaacagcaggacacagcctggtcccagggcctgggctgggattgggcggggtcag
```

-continued

SEQUENCE LISTING

```
ggctcctcccctctcccagggcagatgtctgagtgagggacagaggctggttctgatgaggggccctgcagtggcttag
agacagtccctgggaccccaggttctaggctgagggctggatgcccatccagcctggagggccacacgggggcctgggg
acacaggggtcaccccaggggagaccaatggagggcacagagagggctctgggtctaggctgcagctctgtggcctctg
ctgggtcttcagggcatggggacacagaggaacggatgaggtcccagagcccagccctccaggacagtcaccagaaagg
agagggtctcttagtgcagagatgtgcctgtccctggagccctgtcatctctggggcctggtgtctctctgttcatggt
cgacctcccaccttcatttgaggaagggcaccttagactcagaaggtgactagcggggagtaaacgggagtgcagagaac
tccatggctgccaggtgaagtccaggggcatcagaggctgctggggtgggcatgggggctgcggtgcccaaagtctggg
ggagcagccccaagaacccagccgatgtgaagggtcctgtggtcgggctggtggggacagggcgacggcagagcccag
ggtgtgtctgggtggagcccacgcttcaccaggagagctgagtgggccaggctggggcacagcctggtgccccaggggat
gggaagctccaggccatgccaggcttgggtctccccacatcctgccagtatagttttgtgtgctgtgagggagacccta
gattccaaactcagactccagaaaccaggaaggagggagcacagcctgccctgggtgcacacggggaaaccgaggctgca
gaggaaagggctgggccaggacacctgggaaaggtgacttgggaagggctcctaggaaggcacagggctgtctgctctcc
agagggctccagtggaaaggagggaatgaggaggggaaggagaggccctgggtggaccaggcggccacaccatgaaccctc
ccagagactttagacagagagaggcgctccacaacaccccacactccctctgccatctctcacccctcctctgtccaca
caggtcagcccaaggccaccccctcggtcactctgttcccgccgtcctctgaggagctccaagccaacaaggctacactg
gtgtgtctcatgaatgacttttatccgggaatcttgacggtgacctggaaggcagatggtaccccatcacccagggcgt
ggagatgaccacgcccctccaaacagagcaacaacaagtacgcggccagcagctacctgagcctgacgcccgagcagtgga
ggtcccgcagaagctacagctgccaggtcatgcacgaagggagcaccgtggagaagacggtggcccctgcagaatgttca
taggttcccagccccgaccccacccaaaggggcctggagctgcaggatcccaggggaagggtctctctctgcatcccaag
ccatccagcccttctccctgtacccagtaaaccctaaataataccctctttgtcaaccagaaa
```

Human λ5 amino acid sequence (GenBank Accession No = NP_064455)

SEQ ID NO: 14

```
mrpgtgqggleapgepgpnlrqrwpllllglavvthgllrptaasqsralgpgapggssrsslrsrwgrfllqrgswtgp
rcwprgfqskhnsvthvfgsgtqltvlsqpkatpsvtlfppsseelqankatlvclmndfypgiltvtwkadgtpitqgv
emttpskqsnnkyaassylsltpeqwrsrrsyscqvmhegstvektvapaecs
```

Mouse λ5 nucleotide sequence (GenBank Accession No = AC_000038)

SEQ ID NO: 15

```
ctggaatagcttttggccaccagaggaggaacaatccttttgccgggagatctacactgcaagtgaggctagagttgact
ttggacttgagggtcaatgaagctcagagtaggacagactctgggcactatcccaggcagtgtgaagttctcctcctgc
tgctgctgtttgggtctagtggatggtgtccaccacatactttccccaagctcagcagaaaggagcagagctgtgggccct
ggagcttcagtgggaagcaacaggcctagcctatgggcccttcccggcaggtaagagacttgcttttggggaaggtacg
cgtgtaggtccacggactagaggctagaatgagtgactgggaaggaaggtggctattgaggccatgggtgtgagaaggaa
ggatctgcctaagaggagggggctgtgcaaatgctagcttaaacttggtacctcgatcattgcaaggccagtgttctacc
aatgaaccacatccatagcccacctccattttccatttattttgagaagaggtcttgctaggtttcccaggctgatctta
ctctctgtagcctatgcaagatttgaacgtcctatagctttcctagatccttcctccttcctaagtcctctttagtagct
agaattaagactgtggtggcgcgtttgttttgtttttgttttttgtttttttgtgtgtgtgtgtgtgtgtcatggt
cctagttcatttagaattaaatgtgtgtgtttatcgtagtcaggtagttgcagttctagaagtttattcttaggtaatta
ttaaaacatccattaaatattgtgagggtgtcttgggttgggaggaggagacaccatggccatggagatcacccagtcaa
gaagaccttgcctgtaaagcatgaggacttaattcagactctcagcaaccattcatctactatcaagatgttttactca
gataaatagaaaaaaaaaaaaaaggtttggtgtggtggcacacctttttatatcccagcagttgggaggcagaggcagg
cagatctttgtgagtttgaggccagcctggtctacatagtagtctcatgatagaaataaaaacaaaagaatccttgcaat
```

```
atagtgtgcatgggtcctggggaggaagcatagggccagtaggaactgatgcacacacgcatgtatgcacacacgcacaag
cacatatgcacacacaaatattcaccagagattcctggttccaccacacccaccagagaagatataccacccaggaattt
ctgagaatctgctgggcctgatattgccatcaacactgaaaaaattcagagatggaagtaagagatggatagatggactt
gtcgggatactggctgctcatctattttctgccaaggacatagtttatttcctgaagttctgtgtctgactcacccaaca
ggctcctgttccagatcatcccacggggagcaggtcccaggtgctcgccccataggcttccatctaagcccagttttgg
tatgtctttggtggtgggacccagctcacaatcctaggtaagtggttctcatggtctcatgatccagctggctcagggaa
gtccatttttgctctggggaattcttactatctgcctttcctagccttgcagtctgaactgtaaaggcagtagtaattct
aaggtaaatcacagggaaaggccctaacagcttcatctactcttctgaggcagatgcccaaaaagagatcaaggaatgag
attttttcaggccatagagaccactacacctcagcatctaaaccgaggcccagatgcccatccagactaagaagaccacat
agtaggtgcagggacatggctggtgccatgaaccccaccttcaaagattcaggccaccctagatagaaaaccacagaggc
tgagagagaaatttggttcaatttaatcttctgctggcccatgaggtcacagagacacacaaaaggctcagagtgatcag
gttactagaaccaggtcctcccaggatgattactagaaaagaaatgtagactgtctattgttcctgagggctggagcctg
ttgtctaacttgtccatcttcctcaaatatccttagacttagatgaggaatgaaggagcaaatggggccaagtgaaatca
ggagtaaccagagacttcctggatggtcaggggtttgctatccttcctagtctgggagatggagcctcaggaacacagcc
agtataggtcttgtgattactgtggacaaagcagtaggtccttggaggagttggaggattttttctggatggaatctaatc
ctcggtgagataactaaatggaatctggagcacaggccccgaagcccttatacagcaggcacacctcaagaccaactctc
caggaccagtcttgcagaataaatgagcagcaattctcagaggagtctctgagcactggagaagcaattcaggttgggga
gctgccctctgcctcaccagaaggccagggtcagatcccaattcactaccaggaggcctgggttagatcccaaatcaggt
tccagcttcaagggggctagagaattcagctggtcttagtctcagcggggggaactgagattgcaagggtctgggtctgggt
cattttatctggaagaggaacatgttctaatgggatgctaggctgtctgctctccaggggactcaagtggtcagaggaga
agaaggaagcatccctggatggaagactgatgctgtagtgaatggccacagagctcctgataagagaaggacgcttcctt
atcacgtgggctctcctatgctaactcttatctccttctctatctgcgcaggtcagcccaagtctgaccccttggtcact
ctgttcctgccttccttaaagaatcttcaggccaacaaggccacactagtgtgtttggtgagcgaattctacccaggtac
tttggtggtggactggaaggtagatgggggtccctgtcactcagggtgtagagacaacccaaccctccaaacagaccaaca
acaaatacatggtcagcagctacctgacactgatatctgaccagtggatgcctcacagtagatacagctgccgggtcact
catgaaggaaacactgtggagaagagtgtgtcacctgctgagtgttcttagaccacaatcctccctgaagcctcaggggc
ctggatctgaagtgccagaaaaagttgttttttgtttttgtttttttgtttttttttcccattaaccatctcactgtctttcc
tgtgcctaatactcaataaatatcttaccaccaac
```
Mouse λ5 amino acid sequence (GenBank Accession No = NP_001177254)
                                                                    SEQ ID NO: 16
mklrvgqtlgtiprqcevlllllllglvdgvhhilspssaersravgpgasvgsnrpslwalpgrllfqiiprgagprcs phrlpskpqfwyvfgggtqltilgqpksdplvtlflpslknlqankatlvclvsefypgtlvvdwkvdgvpvtqgvettq pskqtnnkymvssyltlisdqwmphsryscrvthegntveksvspaecs Rat λ5 nucleotide sequence (GenBank Accession No = NC_005110)
                                                                    SEQ ID NO: 17
```
atgaagctcagggcaggacagacactgggcactatccccaggcaatgtgaaattctccttctgttgctgctgttgggcct
ggtggatggtgtccaccatatactttccccaagctcagcacaaaggggcagagctgtgggccctggagcctcagtgggaa
gcagcaggtctagcctgtggacccttccaggcaggtaagagactttcttataggggaatgtatgtgtgtgggtccatgga
ctggaggctgaaatgggtgactgggaaggaaggtaaccattgaggccataggtgtgagaaggaaggatctgcctaagagg
agggggctgggcaaatgctagcttaaacttagtacctaactcatgcaaggccagtattctatcaatgagccatatccata
```

-continued

SEQUENCE LISTING

```
gcccacctcccttttccatttatttagagaagagggcttgcctgattgcctaggctgatcttactttctgtagcctatgc aagatttgacctcctagatccttcctccttcctaagtcctctttagtagctggaattaaggctggtaccaggttatttta gtgtgtcatggtcctagttcattcagaattgtgtgtgctcatcttagtcaaatagttgcagttttagaagtttattctta ggcaattatcaaaacatccattaaatattctaagagtgtcttgggctgggaagagtagacactggggacatggagaccac ccagtgaagaagactttgactgtcaagcatgaggacctagttcagactctcagcactcatgcatctgctatcaagataca atcacatgttttttactcagataaatagaaaaaaattaaggtttggtgtggtggcacatcccttatatcccagcagttg gcaggcagaggcagatagacctttgtgagtttgaggccagtctggtttacatagtggcctcatgacagaaataaaacaaa agaattctcacaaaatatagtgtgcatgggtcctgggatgaagcacaggaccaggaggaatacacacacacacacacaca cacacacacacacacacacacacacaaatacacatcagagattcctggttccaccacactcaccagagaagatata ccacccagaacttttctgagaatcagttgggcctggtgttgccatcaactggatggaaataggagatggatagatggact tattttctgccaaggacacagttcatttcctgaagtccggtgcctacctcacccaacaggttcctgttccagatcatccc acggggagcaggtcccaggtgctggcccataggcttccatccaagtcccagttatggtacgtctttggtagtgggaccc agctcacaatcctaggtaagcgattcccatggtctcatgatccagctgtcttagggaagtccttttcctctggggagt tcttctcacctgcctttcctagtcttgtagtctgaatggtacctttttctgtgagtgaggggaaggcaagtagttctaag gtaaaccacaggaaaggtcccaatagcttcagctactcttccgaggcagatgtccaaaaagggatcaggggctgaggttt tcaggctgtagagaccactgcacttcagcatctaaactgaggcccagatgcccatccagattaagaaggccacatagtag gtgcagggatatgactggtgccatgattcctgcctttaaagattcaggtaaccctagatagaaaaccacagaggctgaga gaagaatctggcccagtttaatcttctgctggccaatgaggtcatagagacacagaaaaggcttagagtgaccaggtaac tagaaccagctcctcccaggatgattactagaaaaaaaatgtagactgtctattgttcctggggtttctcaggcctggag cctgttgtctaacttgtccatctccctcaaatgtccttagagttagatgaggaatgagggagcaaatggcgccaagtgaa atcaggagtcaccagagacttcctgggtggtcaggggtttgctatccttcctagtctgggagacggagccccaggagcac agtcagagtaggtcttgtgattactgtggacaaagcatcaggcccttggaggagttcctaggacttttcaggatggaatc taatccttggtgagataactaaatagaatctggagcacaggcccgggagcccttatacagcaggcacacctcaagaccaa ctccccaggaccagtcttgcagaataaatgagcagtaattctcagaggaggctctgacactggagaagcaatgggggttg gggagctgctccctgaactcccccaccccataggaggccagcgtcagatcccaattcagattccagctcctagtggcta gagagtacagatggccttggtcttagtggggaaactgagattgcaaggggcagggtgtgggtcatttcacctggaagagg aacacggtctaatggggcaccaggctgtctgctctccaggggactcaggtgggcagaggaaaagaaggaagcatccttga tggaacactctgagctgtagtgaatggctacagggctcctgataagaggaggatgcttccctgtcatgtgggctctccta tgccaactcttatccccttctctatctgcacagggcagcccaagtctgaccccttggtcactctgttcctgccttcctta aagaatctccaggttaagaaggcgacactagtgtgtctggtgagcgaattctacccaggtactttggtggtggactggaa ggtagatgggatccctgtcactcagggtgtggagacaacccaaccctccaaacagaccaacaacaagtacgtggccagca gctacctgacactgatgtctgaccaatggatgcctcacagtagatacacctgccaggtcactcatgaaggaaacactgtg gagaagagtgtgtcacctgctgaatgttcttag
```

Rat λ5amino acid sequence (GenBank Accession No = NP_001177270)

SEQ ID NO: 18

```
mklragqtlgtiprqceillllllllglvdgvhhilspssaqrgravgpgasvgssrsslwtlpgrflfqiiprgagprcw phrlpsksqlwyvfgsgtqltilgqpksdplvtlflpslknlqvkkatlvclvsefypgtlvvdwkvdgipvtqgvettq pskqtnnkyvassyltlmsdqwmphsrytcqvthegntveksvspaecs
```

SEQUENCE LISTING

5' homology arm

SEQ ID NO: 19 acctggccaaactgagcatgacctttgacctagccagctcttaaacttgttctgagatcacaaaccagccagaccaaatt 3' homology arm

SEQ ID NO: 20 tcctcccagaatgcttccctgggtcaaacccagagccacaaaggcttccattagaccattctggtaagtgacagagtcac 5' homology arm

SEQ ID NO: 21

AAAAAAAAAAAGCCCAGCTAGCTTAGTTGGTAGAGCATGAGACTCTTAATCTCAGAGTCATGGGTTCAGGC

CTCATGTTTGGCACCATCTATAGTGTGCAGTTATAAATCAAACAGTTCACGATGTGGCTGGCTAGGCACTGG

CAACTGCAGTCTCACCTGCTCCCATGGTTCCCAGTTCCCACAGCTAGTTTGCTGCCAGGCTGTTCACACTTC

CCAGGTCATCTACCCACTGTGGCAAGCCTGCAGAAAGCCTGCTATTGCTAGCTCAGATTCCCTTAGCCCTAT

AAAATGATAACACCACAGACTTTTACTATACCATCCAGATTTATAACAGTAATTCTCCAACCC

3' homology arm

SEQ ID NO: 22

CAGGAGTACACCAAAATGTCTAGCCAAAATTTTTATATATGATCACTTAAATAAGACTCCTTAACATAAACC

TACATGATATACCAAGTCTTTTCTGCCAAGGCTCTGACACTATAGITTGICCTATTCTGGAGTTAGGTAAGC

AAAGGGCTATTTAGGTGTGGATTGCAAAGAGAGAATAGCAAGACAACCTGCCCATTCTTTGCCACACCTCAC

TAATCAGTGTCCCTTGGAAAGCACTGTAAATATGGAGGTTTCTTTTTGTATTATGTAGTAGTGGATTTAACT

TGAGGAGCCCCAAAAGGGGTCAGCAAAGCATGGGAAATCTAAGAATTTAACACTTCAGTGACTTTTAATCAC

CTACAGATCCAGGAAAATAAGCCTGTCTCTT

---

The invention claimed is:

1. A mouse whose genome comprises an antibody heavy chain transgene, the transgene comprising
   (a) one or more human VH gene segments, one or more human D gene segments and one or more human JH gene segments operably connected upstream of a constant region gene so that the transgene is capable of undergoing VDJ recombination in vivo to produce an antibody gene comprising a rearranged VDJC encoding an antibody heavy chain having a human variable region and a constant region;

the genome further comprising
   (i) a human VpreB gene capable of expressing a human VpreB, and
   (ii) a mouse or rat λ5 gene;
wherein the mouse is capable of expressing a chimaeric surrogate light chain comprising human VpreB and mouse or rat λ5 for pairing with the heavy chain.

2. The mouse of claim 1, wherein the constant region is a mouse constant region.

3. The mouse of claim 1, wherein the constant region and the λ5 gene are mouse constant region and mouse λ5 gene, respectively.

4. The mouse of claim 2, wherein the mouse is a strain selected from the group consisting of a 129-derived mouse strain, a C57Bl/6 derived mouse strain and a JM8 derived mouse strain.

5. The mouse of claim 2, wherein the constant region is of a mouse 129 strain constant region or of a mouse C57Bl/6 strain constant region, and the λ5 gene is a mouse 129 strain or a mouse C57Bl/6 strain.

6. The mouse of claim 1, wherein said constant region gene and λ5 gene are endogenous genes of said mouse.

7. The mouse of claim 1, wherein said genome is homozygous for said transgene, human VpreB gene and mouse or rat λ5 gene.

8. The mouse of claim 1, wherein endogenous antibody heavy chain expression in said mouse is inactive.

9. The mouse of claim 1, wherein endogenous antibody light chain expression in said mouse is inactive.

10. The mouse of claim 1, wherein the heavy chain transgene is devoid of a CHI gene segment and the genome comprises no functional antibody light chain locus.

11. The mouse of claim 1, wherein the heavy chain transgene is devoid of a gamma CHI gene segment and the genome comprises no functional antibody light chain locus.

12. The mouse of claim 1, wherein the heavy chain transgene is devoid of a mu CHI gene segment and the genome comprises no functional antibody light chain locus.

13. The mouse of claim 1, wherein said constant region is a mu constant region.

14. The mouse of claim 1, wherein the human VpreB gene has a nucleotide sequence that is at least 85% identical to SEQ ID NO: 1.

15. The mouse of claim 1, wherein said genome does not comprise a non-human vertebrate species VpreB1 and/or VpreB2 gene.

16. The mouse of claim 1, wherein the genome comprises an insertion of human lambda V region or lambda VJ region comprising all of the V regions and intervening sequences, wherein the lambda V region or VJ region comprises a human VpreB gene.

17. The mouse of claim 16, wherein non-functional V and/or J gene segments are omitted.

18. The mouse of claim 16, wherein the lambda V region or lambda VJ region comprises a human VpreB gene and its associated human promoter.

19. The mouse of claim 16, wherein the insertion is an insertion into an antibody light chain locus.

20. The mouse of claim 16, wherein the insertion replaces endogenous vλ in whole or in part.

21. The mouse of claim 1, wherein the human VpreB gene is not within the endogenous VpreB-λ5 locus.

22. The mouse of claim 1, wherein expression of the human VpreB gene is under endogenous control.

23. The mouse of claim 1, wherein the human VpreB gene is operably linked to one or more DNase I hypersensitive sites.

24. The mouse of claim 1, wherein the human VpreB gene is present in the genome in 2, 3, 4, 5, 6, 7, 8, 9 or 10 copies.

25. The mouse of claim 1, wherein all λ5 sequences in the genome are mouse λ5 sequences.

26. The mouse according to claim 22, wherein the human VpreB gene is operably linked to an endogenous promoter.

27. A mouse according to claim 1, which expresses a repertoire of Ig heavy chain variable regions that significantly differs from the heavy chain variable region repertoire of a control vertebrate in the proportion as a percentage of use of heavy chain variable gene segments, wherein the control and said mouse genomes are of the same background strain and both comprise said antibody heavy chain transgene, the transgenes being identical in the control and said mouse, and wherein the control does not express a human VpreB.

28. A mouse according to claim 1, which expresses a repertoire of Ig heavy chain variable regions that significantly differs from the IgH heavy chain variable region repertoire of a control in the proportion expressed as a percentage of use of heavy chain JH gene segments, wherein the control and said mouse genomes are of the same background mouse strain and both comprise said antibody heavy chain transgene, the transgenes being identical in the control and said mouse, and wherein the control does not express a human VpreB.

29. A mouse according to claim 1, which expresses a repertoire of Ig heavy chain variable regions that significantly differs from the IgH heavy chain variable region repertoire of a control in the proportion expressed as a percentage, of one, more or all heavy chain variable gene segments selected from VH6-1, VH1-3, VH3-7, VH1-8, VH3-9, VH3-11, JH1 and JH6, wherein the control and said mouse genomes are of the same background vertebrate strain and both comprise said antibody heavy chain transgene, the transgenes being identical in the control and said mouse, and wherein the control does not express a human VpreB.

30. The mouse of claim 27, wherein use of one, more or all of VH6-1, VH1-3, VH3-9 and JH1 is higher in the repertoire of said mouse than in the repertoire of the control.

31. The mouse of claim 27, wherein use of one, more or all of VH3-7, VH1-8, VH3-11 and JH6 is lower in the repertoire of said mouse than in the repertoire of the control.

32. The mouse of claim 3, wherein the mouse constant region and said mouse λ5 gene are of the same mouse strain.

33. The mouse of claim 4, wherein said strain is a C57BL/6-129/Sv hybrid strain.

34. The mouse of claim 13, wherein said mu constant region is an endogenous mu constant region.

35. The mouse of claim 16, wherein the genome comprises an insertion of human lambda V region or lambda VJ region comprising all of the V regions and all the J regions, and intervening sequences, wherein the lambda V region or VJ region comprises a human VpreB gene.

36. The mouse of claim 19, wherein the insertion is an insertion into an endogenous lambda locus upstream of the endogenous lambda constant region.

37. The mouse of claim 26, wherein said endogenous promoter is an-endogenous VpreB promoter (e.g., a VpreB1 promoter).

38. The mouse of claim 28, which expresses a repertoire of Ig heavy chain variable regions that differs by a probability of less than 0.05 in a binomial distribution test, from the IgH heavy chain variable region repertoire of a control vertebrate in the proportion expressed as a percentage of use of heavy chain JH gene segments, wherein the control and said mouse genomes are of the same background mouse strain and both comprise said antibody heavy chain transgene, the transgenes being identical in the control and said mouse, and wherein the control does not express a human VpreB.

* * * * *

SEQUENCE LISTING

<160> NUMBER OF SEQ ID NOS: 26

<210> SEQ ID NO 1
<211> LENGTH: 727
<212> TYPE: DNA
<213> ORGANISM: Homo sapiens

<400> SEQUENCE: 1

```
gagtcagagc tctgcatgtc tgcaccatgt cctgggctcc tgtcctgctc atgctgtttg        60
tctactgcac aggtgaggga accccccagat cccaaagact cctgcccctt ccttcatcct       120
gccctgcccc cacggcccac atgcatctgt gtcaccaggt tgtggtcctc agccggtgct       180
gcatcagccg ccggccatgt cctcggccct tggaaccaca atccgcctca cctgcaccct       240
gaggaacgac catgacatcg gtgtgtacag cgtctactgg taccagcaga ggcccgggcca       300 cccctcccagg ttcctgctga gatatttctc acaatcagac aagagccagg ccccccaggt       360 ccccctcgc ttctctggat ccaaagatgt ggccaggaac aggggtatt tgagcatctc        420 tgagctgcag cctgaggacg aggctatgta ttactgtgct atgggggccc gcagctcgga       480
gaaggaggag agggagaggg agtgggagga agaaatggaa cccactgcag ccaggacacg       540
tgtcccttga actgaagaca gcagaggcac gcatcccctt ggagagactg tcatggaaga       600
gggtggagcc gccgcccgaa gcgccgagga ggctgagcca ctcagcatct cctggtcctg       660
cagtgttgct gtaaatcccc attggagact gcattaggga attaaagctg cttgtcactt       720
tttgctg                                                                727
```

-continued

```
<210> SEQ ID NO 2
<211> LENGTH: 145
<212> TYPE: PRT
<213> ORGANISM: homo sapiens

<400> SEQUENCE: 2

Met Ser Trp Ala Pro Val Leu Leu Met Leu Phe Val Tyr Cys Thr Gly
1               5                   10                  15

Cys Gly Pro Gln Pro Val Leu His Gln Pro Ala Met Ser Ser Ala
                20                  25                  30

Leu Gly Thr Thr Ile Arg Leu Thr Cys Thr Leu Arg Asn Asp His Asp
            35                  40                  45

Ile Gly Val Tyr Ser Val Tyr Trp Tyr Gln Gln Arg Pro Gly His Pro
        50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala Arg Ser Ser Glu Lys Glu Glu Arg Glu
        115                 120                 125

Arg Glu Trp Glu Glu Glu Met Glu Pro Thr Ala Ala Arg Thr Arg Val
    130                 135                 140

Pro
145

<210> SEQ ID NO 3
<211> LENGTH: 1701
<212> TYPE: DNA
<213> ORGANISM: homo sapiens

<400> SEQUENCE: 3
cttcccagcc ctgtgcccca agcacctgg agcatatagc cttgcagaac ttctacttgc      60
ctgcctccct gcctctggcc atggcctgcc ggtgcctcag cttccttctg atggggacct    120
tcctgtcagg tgaatctttc ctgggcctca gtcacctggg tgtggggtgg ggaacagtac    180
tggccccaga aggcccctgc aaggaggcaa atcgatgggg acagtagggc aggtcctggg    240
agggtatttt tttttttttt tgagacggag ttttgctctt gttgcccagg ctggagtgca    300
acggtgcaat ctcggctcac tgcacctctg cctcccaggt tcaagcgatt cttctgcctc    360
agcgtcctga gtagctggga ttacaggcat gcgccaccac gcctggctaa ttttgtattt    420
ttagtagaga caaggtttct tcatgttggt caggctggtc tcaaactcct gacctcaggt    480
gatccgccca cctcagcttc ccaaagtgct aggattacag gcttgagcca ctgcacctgg    540
ctgggaggcg tattcaggta gaggggtgac ctggcttcag acagctctgc ccttgacctg    600
gggcaaatca cttccctgtg tgggccttgg ttttctcatt cgtgaatgac cagatcacta    660
gagccctgga ctctgacttt gggtctcctt cttagttttt cacaggggaa gctattgtgg    720
gttggtccct accccacagg gcctgaggca atctaacctc cctgagaggg tccctgcagc    780
cagttgcctg aggctgagtt gatgtgtggg acagcccagg aggttcctgg gggtggttag    840
tctgtattca gggtttggaa gagctgaagt gaagtgggcg gggaagtggg ggagagggt     900 gcagttctgc agagaaacgt gggtgggtag cagagggacc tagaggctgc tagtccaacc    960
ttctgagctc tgggcctta actgaacaca gatccttgag gatatggcac taatggagat    1020
```

-continued

| | |
|---|---|
| ttgggggcta actccaaacc cctcactcac aaagggagat ggaggtccag atagggcacc | 1080 |
| ctaagtcaca cagaaccagg cctcctgcac cccgttcatt gctaatccca tagcactggg | 1140 |
| ctatgagccc tttgggactg ggagtctcca tggagtccaa ccaagccttc acagggcagg | 1200 |
| ggtgggaggg aagggggctca ggctgagtgg gtttgtgtct cgcagttttcc cagacagtcc | 1260 |
| tggcccagct ggatgcactg ctggtcttcc caggccaagt ggctcaactc tcctgcacgc | 1320 |
| tcagccccca gcacgtcacc atcagggact acggtgtgtc ctggtaccag cagcgggcag | 1380 |
| gcagtgcccc tcgatatctc ctctactacc gctcggagga ggatcaccac cggcctgctg | 1440 |
| acatccccga tcgattctcg gcagccaagg atgaggccca caatgcctgt gtcctcacca | 1500 |
| ttagtcccgt gcagcctgaa gacgacgcgg attactactg ctctgttggc tacggcttta | 1560 |
| gtccctaggg gtggggtgtg agatgggtgc ctcccctctg cctcccattt ctgcccctga | 1620 |
| ccttgggtcc cttttaaact ttctctgagc cttgcttccc ctctgtaaaa tgggttaata | 1680 |
| atattcaaca tgtcaacaac a | 1701 |

<210> SEQ ID NO 4
<211> LENGTH: 123
<212> TYPE: PRT
<213> ORGANISM: homo sapiens

<400> SEQUENCE: 4

Met Ala Cys Arg Cys Leu Ser Phe Leu Leu Met Gly Thr Phe Leu Ser
1               5                   10                  15

Val Ser Gln Thr Val Leu Ala Gln Leu Asp Ala Leu Leu Val Phe Pro
                20                  25                  30

Gly Gln Val Ala Gln Leu Ser Cys Thr Leu Ser Pro Gln His Val Thr
            35                  40                  45

Ile Arg Asp Tyr Gly Val Ser Trp Tyr Gln Gln Arg Ala Gly Ser Ala
        50                  55                  60

Pro Arg Tyr Leu Leu Tyr Tyr Arg Ser Glu Glu Asp His His Arg Pro
65                  70                  75                  80

Ala Asp Ile Pro Asp Arg Phe Ser Ala Ala Lys Asp Glu Ala His Asn
                85                  90                  95

Ala Cys Val Leu Thr Ile Ser Pro Val Gln Pro Glu Asp Asp Ala Asp
            100                 105                 110

Tyr Tyr Cys Ser Val Gly Tyr Gly Phe Ser Pro
        115                 120

<210> SEQ ID NO 5
<211> LENGTH: 855
<212> TYPE: DNA
<213> ORGANISM: Mus musculus

<400> SEQUENCE: 5

| | |
|---|---|
| agagcccaga aagcctggga gggtggtgag caggaaccag gggtgcagtg accctctccc | 60 |
| caaagcaggg aggagagtgc ttcccagctg gtcagggccc aggagcagtg gctgtagggg | 120 |
| gcagggtgct gcaggtctgg agccatggcc tggacgtctg tcctgctcat gctgctggcc | 180 |
| tatctcacag gtaaggaaac tcttgggggcc cagggcttct tgctcctcc tatgccttg | 240 |
| ctctgcccca gtgatggaca tgcttctatc ttctcaggtt gtggccctca gcccatggtg | 300 |
| catcagccac cattagcatc ttcttccctt ggagccacca tccgcctctc ctgtaccctg | 360 |
| agcaacgacc ataacattgg catttacagc atttactggt accagcagag gccgggccac | 420 |
| cctcccaggt tcctgctgag atacttctca cactcagaca agcaccaggg tcccgatatc | 480 |

```
ccacctcgct tctccgggtc caaagatacg accaggaacc tggggtatct gagcatctct    540
gaactgcagc ctgaggacga ggctgtgtat tactgtgccg tggggctccg gagccaggaa    600
aagaagagga tggagaggga gtgggaagga gaaaagtcgt atacagattt gggatcttag    660
gctctggaga cattcagacc ctgaactgaa gacagagttt gctttgctcg ctagtctgg     720 tatgggaagg aggggtagaa cgtgaggttt tgcagagcct agaagatgga attatgcagc    780
ttttccttgt tctgcggtgt tgctatgagc ccccattgga ggctggattg tagaattaaa    840
gctgttttta ctgaa                                                    855
```

<210> SEQ ID NO 6
<211> LENGTH: 142
<212> TYPE: PRT
<213> ORGANISM: Mus musculus

<400> SEQUENCE: 6

```
Met Ala Trp Thr Ser Val Leu Leu Met Leu Leu Ala Tyr Leu Thr Gly
1               5                   10                  15

Cys Gly Pro Gln Pro Met Val His Gln Pro Pro Leu Ala Ser Ser Ser
            20                  25                  30

Leu Gly Ala Thr Ile Arg Leu Ser Cys Thr Leu Ser Asn Asp His Asn
        35                  40                  45

Ile Gly Ile Tyr Ser Ile Tyr Trp Tyr Gln Gln Arg Pro Gly His Pro
    50                  55                  60

Pro Arg Phe Leu Leu Arg Tyr Phe Ser His Ser Asp Lys His Gln Gly
65                  70                  75                  80

Pro Asp Ile Pro Pro Arg Phe Ser Gly Ser Lys Asp Thr Thr Arg Asn
                85                  90                  95

Leu Gly Tyr Leu Ser Ile Ser Glu Leu Gln Pro Glu Asp Glu Ala Val
            100                 105                 110

Tyr Tyr Cys Ala Val Gly Leu Arg Ser Gln Glu Lys Lys Arg Met Glu
        115                 120                 125

Arg Glu Trp Glu Gly Glu Lys Ser Tyr Thr Asp Leu Gly Ser
    130                 135                 140
```

<210> SEQ ID NO 7
<211> LENGTH: 516
<212> TYPE: DNA
<213> ORGANISM: Mus musculus

<400> SEQUENCE: 7

```
atggcctgga cgtctgtcct gctcatgctg ctggcccacc tcacaggtaa gggaactctt     60
ggggtccagg gcttccttgc tcctcctgtg gccttgctct gccccagtga tggacatgct    120
tctatcttct caggttgtgg ccctcagccc atggtgcatc agccaccatc agcatcttct    180
tcccttggag ccaccatccg cctctcctgt accctgagca acgaccataa cattggcatt    240
tacagcattt actggtacca gcagaggccg gccacccctc caggttcct gctgagatac     300 ttctcacact cagacaagca ccagggtccc gatatcccac ctcgcttctc cgggtccaaa    360
gatacggcca gaacctgggg gtatctgagc atctctgaac tgcagcctga ggacgaggct    420
gtgtattact gcgctgtggg gctccggagc acgaaaaga agagaatgga gagagtgg      480 gaaggagaaa agtcgtatac agatttggga tcttag                             516
```

<210> SEQ ID NO 8
<211> LENGTH: 142

<212> TYPE: PRT
<213> ORGANISM: Mus musculus

<400> SEQUENCE: 8

```
Met Ala Trp Thr Ser Val Leu Leu Met Leu Leu Ala His Leu Thr Gly
1               5                   10                  15

Cys Gly Pro Gln Pro Met Val His Gln Pro Ser Ala Ser Ser Ser
            20                  25                  30

Leu Gly Ala Thr Ile Arg Leu Ser Cys Thr Leu Ser Asn Asp His Asn
        35                  40                  45

Ile Gly Ile Tyr Ser Ile Tyr Trp Tyr Gln Gln Arg Pro Gly His Pro
    50                  55                  60

Pro Arg Phe Leu Leu Arg Tyr Phe Ser His Ser Asp Lys His Gln Gly
65                  70                  75                  80

Pro Asp Ile Pro Pro Arg Phe Ser Gly Ser Lys Asp Thr Ala Arg Asn
                85                  90                  95

Leu Gly Tyr Leu Ser Ile Ser Glu Leu Gln Pro Glu Asp Glu Ala Val
            100                 105                 110

Tyr Tyr Cys Ala Val Gly Leu Arg Ser His Glu Lys Lys Arg Met Glu
        115                 120                 125

Arg Glu Trp Glu Gly Glu Lys Ser Tyr Thr Asp Leu Gly Ser
    130                 135                 140
```

<210> SEQ ID NO 9
<211> LENGTH: 878
<212> TYPE: DNA
<213> ORGANISM: Rattus norvegicus

<400> SEQUENCE: 9

```
ccagaaagcc tgggagggtg gtgagcagga accagtggtg caaagcaggg gcgagactgc      60
ttcctagctg gtcagggcac cggagcagtg gctgtagggg tcagggtgct gcaggtctgg     120
aaccatggcc tggacgtctg ccctgctcat actgctggcc catctcacag gtacgggaac     180
tcttggggcc cagagcctcc ttgctcctcc tcttgccttg ctctgccgca gtgatgggca     240
cgcttctatt ttctcaggtt gtggccctca gcccgtgctg catcagccac catcggcctc     300
ttccttcctt ggaacctcca tccgcctcac ctgtgccctg agcagcaacc ataacattgg     360
catttacagc atttactggt accagcagag gccgggccac cctcccacgt tcctgctgag     420
attcttctca cactcagaca agctccaggg tcccaagatc ccccctcgct ctccggatc      480
caaagataca gccaggaacc tggggtacct gagcatctct gacctgcagc cagaggacga     540
ggctgtgtat tactgcgccg tggggcttcg gagctgggaa aaggagaaga ggatggagag     600
ggagtgggaa gaagaaaagt agcggacaga ttcgggatct taggctctgg agacattcag     660
acctagaacc gaagacggag tttgctttgc tcggctaggc tggtttgggg aggagggta      720
gaacaccggg cttcgcagag ccaggaaggt ggagccagcc gcttttcctt gtattgcagt     780
gttgctatgc gccccatcgg aggctggatt gtagaattaa agctgttttt ttttttttg     840
ttttgttttt tgttttttg tttctttttt cttaactg                              878
```

<210> SEQ ID NO 10
<211> LENGTH: 136
<212> TYPE: PRT
<213> ORGANISM: Rattus norvegicus

<400> SEQUENCE: 10

```
Met Ala Trp Thr Ser Ala Leu Leu Ile Leu Leu Ala His Leu Thr Gly
```

```
            1               5              10              15

Cys Gly Pro Gln Pro Val Leu His Gln Pro Pro Ser Ala Ser Ser Phe
                20              25              30

Leu Gly Thr Ser Ile Arg Leu Thr Cys Ala Leu Ser Ser Asn His Asn
                35              40              45

Ile Gly Ile Tyr Ser Ile Tyr Trp Tyr Gln Gln Arg Pro Gly His Pro
        50              55              60

Pro Thr Phe Leu Leu Arg Phe Phe Ser His Ser Asp Lys Leu Gln Gly
65              70              75              80

Pro Lys Ile Pro Pro Arg Phe Ser Gly Ser Lys Asp Thr Ala Arg Asn
                85              90              95

Leu Gly Tyr Leu Ser Ile Ser Asp Leu Gln Pro Glu Asp Glu Ala Val
                100             105             110

Tyr Tyr Cys Ala Val Gly Leu Arg Ser Trp Glu Lys Glu Lys Arg Met
            115             120             125

Glu Arg Glu Trp Glu Glu Lys
        130             135

<210> SEQ ID NO 11
<211> LENGTH: 711
<212> TYPE: DNA
<213> ORGANISM: Rattus norvegicus

<400> SEQUENCE: 11
atggcctgga cgtctgccct gctcatactg ctggcccatc tcacaggtac gggaactctt      60
ggggcccaga gctccttgc tcctcctctt gccttgctct gccgcagtga tgggcacgct     120 tctatttct caggttgtgg ccctcagccc gtgctgcatc agccaccatc ggcctcttcc     180
ttccttggaa cctccatccg cctcacctgt gccctgagca gcaaccataa cattggcatt     240
tacagcattt actggtacca gcagaggccg gccacccctc ccacgttcct gctgagattc     300
ttctcacact cagacaagct ccagggtccc aagatccccc ctcgcttctc cggatccaaa     360
gatatagcca ggaacctggg gtacctgagc atctctgacc tgcagccaga ggacgaggct     420
gtgtattact gcgccgtggg gcttcggagc tgggaaaagg agaagaggat ggagagggag     480
tgggaagaag aaaagtagcg gacagattcg ggatcttagg ctctggagac attcagacct     540
agaaccgaag acggagtttg ctttgctcgg ctaggctggt ttggggagga ggggtagaac     600
accgggcttc gcagagccag gaaggtggag ccagccgctt ttccttgtat tgcagtgttg     660
ctatgcgccc catcggaggc tggattgtag aattaaagct gttttttact g             711

<210> SEQ ID NO 12
<211> LENGTH: 136
<212> TYPE: PRT
<213> ORGANISM: Rattus norvegicus

<400> SEQUENCE: 12

Met Ala Trp Thr Ser Ala Leu Leu Ile Leu Leu Ala His Leu Thr Gly
1               5              10              15

Cys Gly Pro Gln Pro Val Leu His Gln Pro Pro Ser Ala Ser Ser Phe
                20              25              30

Leu Gly Thr Ser Ile Arg Leu Thr Cys Ala Leu Ser Ser Asn His Asn
                35              40              45

Ile Gly Ile Tyr Ser Ile Tyr Trp Tyr Gln Gln Arg Pro Gly His Pro
        50              55              60

Pro Thr Phe Leu Leu Arg Phe Phe Ser His Ser Asp Lys Leu Gln Gly
```

```
            65                  70                  75                  80
Pro Lys Ile Pro Pro Arg Phe Ser Gly Ser Lys Asp Ile Ala Arg Asn
                    85                  90                  95

Leu Gly Tyr Leu Ser Ile Ser Asp Leu Gln Pro Glu Asp Glu Ala Val
                100                 105                 110

Tyr Tyr Cys Ala Val Gly Leu Arg Ser Trp Glu Lys Glu Lys Arg Met
                115                 120                 125

Glu Arg Glu Trp Glu Glu Glu Lys
    130                 135
```

<210> SEQ ID NO 13
<211> LENGTH: 7184
<212> TYPE: DNA
<213> ORGANISM: Homo sapiens

<400> SEQUENCE: 13

```
ggccacatgg actggggtgc aatgggacag ctgctgccag cgagagggac cagggcacca    60
ctctctaggg agcccacact gcaagtcagg ccacaaggac ctctgaccct gagggccgat   120
gaggccaggg acaggccagg ggggccttga ggccctggt gagccaggcc ccaacctcag    180
gcagcgctgg cccctgctgc tgctgggtct ggccgtggta acccatggcc tgctgcgccc   240
aacagctgca tcgcagagca gggccctggg ccctggagcc cctggaggaa gcagccggtc   300
cagcctgaga agccggtggg gcaggtaagg ggtgagagat tccaggggat gtggggtct    360
gggtggcaga ggcgggaaag gatgaccaag gggagacgag ccagaggggt gaggaggaag   420
gttaatccct ggaggggagc cacagacact gactttaact aaagtgtcaa gattttgtcc   480
atctttgaat taattttta tgcttaatgt catattaaaa tattatttat cttgattcct    540
gagatttctt cccccactta catttggcac caaggccaat gtctccctca cctcccccta   600
gtccttgggg tagggcagga ctggaggcag gggcaggacg tccacaggag tggtggccgc   660
tatccctgaa ggatgcccag gcctctccct cctcctcctc ccactcctcc tcccccccct   720
cctcttttcc ccttggccta tgtcacctgt ccactccac cctcactggg caggggccac    780
tccctggagc tccagctaag gtgtgagggg ccttttcctgg agtccctggg tcactagacc   840
tcagccagca tcgcctcctg aaaccagccc ctaggagaca caagcttatc cagggtgcaa   900
gtgcctccaa agaagaagcc caggagaggc tctagggagg ccacaactcc ctgtgtgacc    960
tcagccattg ccaccactct gcgtgtggtg ggaggtcccc agacaaagca ccaagcatcg   1020
gggtccattt atgagcattt gggacacaac agcctgttca ctggtgcatg ttatacccac   1080
aggcgataat catttcaggg gcagaacctc cctctcggtg gccccatagg caggtcctgc   1140
tgtgatcccc tttgtgcaga cggggataga gcccggagag gtgaggtgac ccgtccgagt   1200
cactcagctc atgggcacag attctaaggc ccaagctatc ccctctagct ctccctgtc    1260
ccatcctcta agctgatcga gcggacacgt gcatctctgg gacctgagtt tccctttttc   1320
tctctttttt ttcttttttca ataaagtttt cacagagttt cactcttgtc gcccagtctg   1380
gagtgcaatg gcgagatctt ggctcattga aacctccgtc tcccaggttc aagacattct   1440
cctgcctcag cttccggagt agctgggatt acaggcatct gccaccacac ctggctaatt   1500
ttgtgtattt ttttttagta aagacagagt ttcaccatgt tggccaggct ggtctcaaac    1560
tcctgacctc aggtgatcca cccacctcag cctcccaaag tgctgggatt acaggcatga   1620
gacaccacac cggcctgag tttccccttc tgcaatctga ggggccctga ctggtgaggg    1680
cctttcagcgt cccacccacc cagaggatgc tggggtggct gtggtgagag ctccagcagt   1740
```

```
ggcagccgac ctgacccaca ccaggagccc ggccatggag gcggggtcag catggtggca   1800
ggccgggacc gggtgtcagt gtcctgcacg gacttctgag caaggagtcc ccatcagggt   1860
caggctctgt gctggggctg aggtcccaga ggatctagat ttgccccaat tcaagtccac   1920
aaggagcggg ggccgggtga ggagacagcc acatgcaggg tgatgcctac agaacagaga   1980
ctgggatggg gaaggcccga ggggtctcca caagggacgg gtgacaggtg gagggagaca   2040
cagataataa aaaatggtat tatgttgggg ggctattaat gtaagttttt atattagaat   2100
ctttagaaat cttatagaaa tactatgggc cgggtgctgt gtctcatgcc tgtaatccca   2160
gcactttagg acgccaagat gggcagatca cgaggtcagg agattgagac catcctggcc   2220
aacatggcaa aactccgtct ctactaaaaa tacaaaaact agctgggcgt ggtggcgcga   2280
gcctatagtc ccagctactc gggagggag gcaggagaat cgcttgaatc agggaggtgg   2340
aggttgcagt gagctgagat tgcaccgctg cactccagcc tggacgacag aacgagactc   2400
ccactcaaaa aaaaaaaaag gtattatgct ggggggggata tgaatatgag tttttataat   2460
ctttagaaat actatgggcc aggtgcagtg gctcatgcct gtaatcccac aactttggga   2520
ggctgaggcg ggattgtttg agcccaggag tttgagatca gcctgagcaa catagcaaga   2580
ccccatttct acaaaacata taaaaactag ctagtcatgg tggcacttgc ctgtggtccc   2640
agctacttag gaggctggtg agaggattgc ttaagcctcg gaggttgagg atgcagtaag   2700
ctgagatccc accactgcac tccagcctgg gtgacagaag gagaccctgt ctcaaaaaaa   2760
aaaaaaaaaa aaaagactg attattcctg tagaattctg gtaaatatct cctatcaaat   2820
aaatgacttt tctattcata gcttattaaa agatattttc attgttttta agaaataggt   2880
tgtgtatcac ttttatatt tagttgtaaa tttatttgtt ttatttattt ttttagagat   2940
gggggtctca ctatgttgcc tgggctggcc tccaactgct gggctcaagc aatatccctg   3000
cctcagcgtc cccagtagct gggactacaa gcatgcgcta ccacaccggc ataattttt   3060 gtagagatga ggtttcgcca tgttgcctgg gctggtcttg aacccctggg ctcaagccat   3120
ccacccgcct cggcctccta aagtgctgag attacagacg tgagccaccc tacctagcct   3180
gtactatttt taataggtct taataggttt tgaatgttaa ttattttaa attaatttca   3240 aaaatcttct acaacatgga tgaaacctga agacattata cttagtgaaa taagccagac   3300
acaaaaggac aaatgtcatt tgaatccact tctatgaggt acctagaata ggcaaattca   3360
cttggacaaa aagtagattt gaggttagca gggtgagggg gagggaagaa tggggactg   3420 tagttaacgg gtttagagtt tctgtttggg aagatgaaag agttctggag atggatggtg   3480
gtgaaggttg cccaacggtg tgaatgtact tagtgccacg gagctgtacg tttaaaaata   3540
gttaaagtgg aaatattgat gctatgtata aaaatggagc ggggtgtggt ggctcacacc   3600
tataatccca gcactttgag aggccaaggt gggcagatca cctgaggtcg ggagttcgag   3660
accagcctga caaacatgga gaaacaccgt ctctactgaa aatacaaaaa attagccaag   3720
tgtgctggca catgcctgta atcccagcta ctcgggaggc tgaagcagga gaatcgcttg   3780
aacccaggat gtggaggttg cggtgagcca aggtggcacc attgcactcc agcctgggcg   3840
acaagggtga aattccattt caaaaaaata aaaggaaatg ggactgtaca tagcaggaga   3900
gagagggaga gatcaatatg acacttcttt ttttttttt ttttttttgg gacagtcttg   3960
ctctgttgcc aggctgcact ccagcctggg caacagagcg agactctgtc tcaaaaaaaa   4020
aaagaatgtc tagatgcagt agctaagttc gcagaagcca tttcagtgtg ggaggcgagg   4080
```

```
tgactgagtc cagggactcc aggtttctgg ctgaggggtt gagaccgccc atggtcattg    4140
tgatgagatg aagacagaaa atgagctggg ctggggaag gtggtcatct cctctggacg    4200
tgattagttt gaggctcctg ttgggtagcc cactgggcaa ggtcagtagg caattgagga    4260
gctgagaggg tttggagctg ggatagactc cagcctcacc atgtgggcaa tagtgggggt    4320
cacagagtgt gaaaatggct aagaaagagg tctgggtggg gtctgggag tcagcagcca    4380 ggcatgggcc atgagaaac agatgccagg ggaagaggaa aggggagtct cagaccccaa    4440
ggggaaaaga gtcactggaa agaggggcca gccctgtgtc gcatccagcg agacaccag    4500 gtacagcaga aggaccttgg acatgaccat gaggagggcc ttgttgacca tggcctggga    4560
gagatggggg tgagagcctg ggggaccaca ccatgtcccc agcacacagt gcctggtaga    4620
caggatggat ttatgatgg acggacaggt agatggatgg acgaatggac agatgataga    4680
tggatgcaaa gacagatgaa tagatggaca gatgcataga tggacagatg gacagatgga    4740
tggacggacg gatggaatga atgatcagaa aaggcttcat gaacaaagtg agactgagct    4800
gcatctccat gggtagatat aaaagcagag gactctcctc ttgagtcagg aatgacccaa    4860
tgtcctggtc cagggaggaa gtcagcctcc ttgactgggg acacttgtgg cagatttcag    4920
aggcccttaa aatgaggcca agtgaggtgg acaggtccga gccagctgag gactcctcag    4980
ccacacggca cagctgcctg aggggatgtg tcactcaggg agttgctggg acctactggg    5040
cccagcgttg ccatcagcac caacagtttc agagaggggg acacacgctg gggcagcacc    5100
tgcctcagag aagggacagg cacagagaca ctactggggg acactactgg gacactggcc    5160
acccccctac cctgtgcctg ggtcacagcc tacacactgc agccctgtgc ccctcactcc    5220
cagcaggttc ctgctccagc gcggctcctg gactggcccc aggtgctggc ccgggggtt    5280 tcaatccaag cataactcag tgacgcatgt gtttggcagc gggacccagc tcaccgtttt    5340
aagtaagtgg ctctaacttc ccaggctgtc ccaccctctc ctgtctctgg aaaatgtgtt    5400
ttctctctct ggggcttctt cccctctgcc ctcccagcct taagcactga cccctacctt    5460
tgtccatggg gcctggagga gatgtgttag tctcagggta atggcaggaa gggcccccac    5520
agtgggagca gccgccttca ggttccaaca gcaggacaca gcctggtccc agggcctggg    5580
ctgggattgg gcggggtcag ggctcctccc ctctcccagg gcagatgtct gagtgaggga    5640
cagaggctgt ttctgatgag gggccctgca gtggccttag agacagtccc tgggacccca    5700
ggttctaggc tgagggctgg atgcccatcc agcctgggag ggccacacgg gggcctgggg    5760
acacaggggt caccccagg ggagaccaat ggagggcaca gagagggctc tgggtctagg    5820
ctgcagctct gtggcctctg ctgggtcttc agggcatggg gacacagagg aacggatgag    5880
gtcccagagc ccagccctcc caggacagtc accagaaagg agagggtctc ttagtgcaga    5940
gatgtgcctg tccctggagc cctgtcatct ctggggcctg gtgtctctct gttcatgggt    6000
cgacctccca ccttcatttg aggaagggca ccttagactc agaaggtgac tagcggggag    6060
taaacgggag tgcagagaac tccatggctg ccaggtgaag tccaggggca tcagaggctg    6120
ctggggtggg catgggggct gcggtgcccc aaagtctggg ggagcagccc caagaaccca    6180
gccgatgtga agggtcctgt ggtcgggctg gtggggacag gggcgacggc agagcccag    6240 ggtgtgtctg ggtggagccc acgcttcacc aggagagctg agtgggccag gctggggcac    6300
agcctggtgc cccaggggat gggaagctcc aggccatgcc aggcttgggt ctccccacat    6360
cctgccagta tagtttttgtg tgctgtgagg gagacccta gattccaaac tcagactcca    6420
gaaaccagga aggagggagc acagcctgcc ctgggtgcac acggggaaac cgaggctgca    6480
```

-continued

```
gaggaaaggg ctgggccagg acacctggga aaggtgactt gggaagggct cctaggaagg    6540
cacagggctg tctgctctcc agagggctcc agtggaaagg agggaatgag gagggaagga    6600
gaggccctgg gtggaccagg cggccacacc atgaaccctc ccagagactt tagacagaga    6660
gaggcgctcc acaacacccc acactccctc tgccatctct caccccctcc tctgtccaca    6720
caggtcagcc caaggccacc ccctcggtca ctctgttccc gccgtcctct gaggagctcc    6780
aagccaacaa ggctacactg tgtgtctca tgaatgactt ttatccggga atcttgacgg     6840
tgacctggaa ggcagatggt accccatca cccagggcgt ggagatgacc acgccctcca     6900
aacagagcaa caacaagtac gcggccagca gctacctgag cctgacgccc gagcagtgga    6960
ggtcccgcag aagctacagc tgccaggtca tgcacgaagg gagcaccgtg gagaagacgg    7020
tggcccctgc agaatgttca taggttccca gccccgaccc cacccaaagg ggcctggagc    7080
tgcaggatcc caggggaagg gtctctctct gcatcccaag ccatccagcc cttctccctg    7140
tacccagtaa accctaaata aataccctct tgtcaaccac gaaa                    7184
```

<210> SEQ ID NO 14
<211> LENGTH: 213
<212> TYPE: PRT
<213> ORGANISM: Homo sapiens

<400> SEQUENCE: 14

```
Met Arg Pro Gly Thr Gly Gln Gly Gly Leu Glu Ala Pro Gly Glu Pro
1               5                  10                  15

Gly Pro Asn Leu Arg Gln Arg Trp Pro Leu Leu Leu Gly Leu Ala
            20                  25                  30

Val Val Thr His Gly Leu Leu Arg Pro Thr Ala Ala Ser Gln Ser Arg
        35                  40                  45

Ala Leu Gly Pro Gly Ala Pro Gly Gly Ser Ser Arg Ser Ser Leu Arg
    50                  55                  60

Ser Arg Trp Gly Arg Phe Leu Leu Gln Arg Gly Ser Trp Thr Gly Pro
65                  70                  75                  80

Arg Cys Trp Pro Arg Gly Phe Gln Ser Lys His Asn Ser Val Thr His
                85                  90                  95

Val Phe Gly Ser Gly Thr Gln Leu Thr Val Leu Ser Gln Pro Lys Ala
            100                 105                 110

Thr Pro Ser Val Thr Leu Phe Pro Pro Ser Ser Glu Glu Leu Gln Ala
        115                 120                 125

Asn Lys Ala Thr Leu Val Cys Leu Met Asn Asp Phe Tyr Pro Gly Ile
    130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175

Ser Tyr Leu Ser Leu Thr Pro Glu Gln Trp Arg Ser Arg Arg Ser Tyr
            180                 185                 190

Ser Cys Gln Val Met His Glu Gly Ser Thr Val Glu Lys Thr Val Ala
        195                 200                 205

Pro Ala Glu Cys Ser
    210
```

<210> SEQ ID NO 15
<211> LENGTH: 3315
<212> TYPE: DNA

<213> ORGANISM: Mus musculus

<400> SEQUENCE: 15

| | | | | | |
|---|---|---|---|---|---|
| ctggaatagc | ttttggccac | cagaggagga | acaatccttt | tgccgggaga | tctacactgc | 60 |
| aagtgaggct | agagttgact | ttggacttga | gggtcaatga | agctcagagt | aggacagact | 120 |
| ctgggcacta | tccccaggca | gtgtgaagtt | ctcctcctgc | tgctgctgtt | gggtctagtg | 180 |
| gatggtgtcc | accacatact | ttccccaagc | tcagcagaaa | ggagcagagc | tgtgggccct | 240 |
| ggagcttcag | tgggaagcaa | caggcctagc | ctatgggccc | ttcccggcag | gtaagagact | 300 |
| tgcttttttgg | ggaaggtacg | cgtgtaggtc | cacggactag | aggctagaat | gagtgactgg | 360 |
| gaaggaaggt | ggctattgag | gccatgggtg | tgagaaggaa | ggatctgcct | aagaggaggg | 420 |
| ggctgtgcaa | atgctagctt | aaacttggta | cctcgatcat | tgcaaggcca | gtgttctacc | 480 |
| aatgaaccac | atccatagcc | cacctccatt | ttccatttat | tttgagaaga | ggtcttgcta | 540 |
| ggtttcccag | gctgatctta | ctctctgtag | cctatgcaag | atttgaacgt | cctatagctt | 600 |
| tcctagatcc | ttcctccttc | ctaagtcctc | tttagtagct | agaattaaga | ctgtggtggc | 660 |
| gcgtttgttt | ttgttttttg | tttttttgttt | ttttgtgtgt | gtgtgtgtgt | gtgtcatggt | 720 |
| cctagttcat | ttagaattaa | atgtgtgtgt | ttatcgtagt | caggtagttg | cagttctaga | 780 |
| agtttattct | taggtaatta | ttaaaacatc | cattaaatat | tgtgagggtg | tcttgggttg | 840 |
| ggaggaggag | acaccatggc | catggagatc | acccagtcaa | gaagaccttg | cctgtaaagc | 900 |
| atgaggactt | aattcagact | ctcagcaacc | attcatctac | tatcaagatg | tttttactca | 960 |
| gataaataga | aaaaaaaaaa | aaaaaggttt | ggtgtggtgg | cacacctttt | atatcccagc | 1020 |
| agttgggagg | cagaggcagg | cagatctttg | tgagtttgag | gccagcctgg | tctacatagt | 1080 |
| agtctcatga | tagaaataaa | aacaaaagaa | tccttgcaat | atagtgtgca | tgggtcctgg | 1140 |
| gaggaagcat | agggccagta | ggaactgatg | cacacacgca | tgtatgcaca | cacgcacaag | 1200 |
| cacatatgca | cacacaaata | ttcaccagag | attcctggtt | ccaccacacc | caccagagaa | 1260 |
| gatataccac | ccaggaattt | ctgagaatct | gctgggcctg | atattgccat | caacactgaa | 1320 |
| aaaattcaga | gatggaagta | agagatggat | agatggactt | gtcgggatac | tggctgctca | 1380 |
| tctattttct | gccaaggaca | tagtttattt | cctgaagttc | tgtgtctgac | tcacccaaca | 1440 |
| ggctcctgtt | ccagatcatc | ccacggggag | caggtcccag | gtgctcgccc | cataggcttc | 1500 |
| catctaagcc | ccagttttgg | tatgtctttg | gtggtgggac | ccagctcaca | atcctaggta | 1560 |
| agtggttctc | atggtctcat | gatccagctg | gctcagggaa | gtccattttt | gctctgggga | 1620 |
| attcttacta | tctgcctttc | ctagccttgc | agtctgaact | gtaaaggcag | tagtaattct | 1680 |
| aaggtaaatc | acagggaaag | gccctaacag | cttcatctac | tcttctgagg | cagatgccca | 1740 |
| aaaagagatc | aaggaatgag | attttttcagg | ccatagagac | cactacacct | cagcatctaa | 1800 |
| accgaggccc | agatgcccat | ccagactaag | aagaccacat | agtaggtgca | gggacatggc | 1860 |
| tggtgccatg | aaccccacct | tcaaagattc | aggccaccct | agatagaaaa | ccacagaggc | 1920 |
| tgagagagaa | atttggttca | atttaatctt | ctgctggccc | atgaggtcac | agagacacac | 1980 |
| aaaaggctca | gagtgatcag | gttactagaa | ccaggtcctc | ccaggatgat | tactagaaaa | 2040 |
| gaaatgtaga | ctgtctattg | ttcctgaggg | ctggagcctg | ttgtctaact | tgtccatctt | 2100 |
| cctcaaatat | ccttagactt | agatgaggaa | tgaaggagca | atggggcca | agtgaaatca | 2160 |
| ggagtaacca | gagacttcct | ggatggtcag | gggtttgcta | tccttcctag | tctgggagat | 2220 |
| ggagcctcag | gaacacagcc | agtataggtc | ttgtgattac | tgtggacaaa | gcagtaggtc | 2280 |

```
cttggaggag ttggaggatt tttctggatg gaatctaatc ctcggtgaga taactaaatg    2340
gaatctggag cacaggcccc gaagcccta tacagcaggc acacctcaag accaactctc    2400
caggaccagt cttgcagaat aaatgagcag caattctcag aggagtctct gagcactgga    2460
gaagcaattc aggttgggga gctgccctct gcctcaccag aaggccaggg tcagatccca    2520
attcactacc aggaggcctg ggttagatcc caaatcaggt tccagcttca aggggctaga    2580
gaattcagct ggtcttagtc tcagcggggg aactgagatt gcaagggtct gggtctgggt    2640
cattttatct ggaagaggaa catgttctaa tgggatgcta ggctgtctgc tctccagggg    2700
actcaagtgg tcagaggaga agaaggaagc atccctggat ggaagactga tgctgtagtg    2760
aatggccaca gagctcctga taagagaagg acgcttcctt atcacgtggg ctctcctatg    2820
ctaactctta tctccttctc tatctgcgca ggtcagccca agtctgaccc cttggtcact    2880
ctgttcctgc cttccttaaa gaatcttcag ccaacaagg ccacactagt gtgtttggtg    2940
agcgaattct acccaggtac tttggtggtg gactggaagg tagatggggt ccctgtcact    3000
cagggtgtag agacaaccca accctccaaa cagaccaaca acaaatacat ggtcagcagc    3060
tacctgacac tgtatatctga ccagtggatg cctcacagta gatacagctg ccgggtcact    3120
catgaaggaa acactgtgga gaagagtgtg tcacctgctg agtgttctta gaccacaatc    3180
ctccctgaag cctcagggc ctggatctga agtgccagaa aaagttgttt tttgttttgt    3240
tttttgtttt ttttcccatt aaccatctca ctgtctttcc tgtgcctaat actcaataaa    3300
tatcttacca ccaac                                                   3315

<210> SEQ ID NO 16
<211> LENGTH: 209
<212> TYPE: PRT
<213> ORGANISM: Mus musculus

<400> SEQUENCE: 16

Met Lys Leu Arg Val Gly Gln Thr Leu Gly Thr Ile Pro Arg Gln Cys
1               5                   10                  15

Glu Val Leu Leu Leu Leu Leu Leu Gly Leu Val Asp Gly Val His
            20                  25                  30

His Ile Leu Ser Pro Ser Ala Glu Arg Ser Arg Ala Val Gly Pro
        35                  40                  45

Gly Ala Ser Val Gly Ser Asn Arg Pro Ser Leu Trp Ala Leu Pro Gly
    50                  55                  60

Arg Leu Leu Phe Gln Ile Ile Pro Arg Gly Ala Gly Pro Arg Cys Ser
65                  70                  75                  80

Pro His Arg Leu Pro Ser Lys Pro Gln Phe Trp Tyr Val Phe Gly Gly
                85                  90                  95

Gly Thr Gln Leu Thr Ile Leu Gly Gln Pro Lys Ser Asp Pro Leu Val
            100                 105                 110

Thr Leu Phe Leu Pro Ser Leu Lys Asn Leu Gln Ala Asn Lys Ala Thr
        115                 120                 125

Leu Val Cys Leu Val Ser Glu Phe Tyr Pro Gly Thr Leu Val Val Asp
    130                 135                 140

Trp Lys Val Asp Gly Val Pro Val Thr Gln Gly Val Glu Thr Thr Gln
145                 150                 155                 160

Pro Ser Lys Gln Thr Asn Asn Lys Tyr Met Val Ser Ser Tyr Leu Thr
                165                 170                 175

Leu Ile Ser Asp Gln Trp Met Pro His Ser Arg Tyr Ser Cys Arg Val
```

| | 180 | | | | 185 | | | | 190 | | | |
|---|---|---|---|---|---|---|---|---|---|---|---|---|
Thr His Glu Gly Asn Thr Val Glu Lys Ser Val Ser Pro Ala Glu Cys
            195                 200                 205
Ser

<210> SEQ ID NO 17
<211> LENGTH: 2993
<212> TYPE: DNA
<213> ORGANISM: Rattus norvegicus

<400> SEQUENCE: 17

```
atgaagctca gggcaggaca gacactgggc actatcccca ggcaatgtga aattctcctt     60
ctgttgctgc tgttgggcct ggtggatggt gtccaccata tactttcccc aagctcagca    120
caaaggggca gagctgtggg ccctggagcc tcagtgggaa gcagcaggtc tagcctgtgg    180
acccttccag gcaggtaaga gactttctta taggggaatg tatgtgtgtg gtccatgga    240
ctggaggctg aaatgggtga ctgggaagga aggtaaccat tgaggccata ggtgtgagaa    300
ggaaggatct gcctaagagg aggggctgg gcaaatgcta gcttaaactt agtacctaac    360
tcatgcaagg ccagtattct atcaatgagc catatccata gcccacctcc cttttccatt    420
tatttagaga gagggcttg cctgattgcc taggctgatc ttactttctg tagcctatgc     480
aagatttgac ctcctagatc cttcctcctt cctaagtcct ctttagtagc tgaattaag    540
gctggtacca ggttatttta gtgtgtcatg gtcctagttc attcagaatt gtgtgtgctc    600
atcttagtca aatagttgca gttttagaag tttattctta ggcaattatc aaaacatcca    660
ttaaatattc taagagtgtc ttgggctggg aagagtagac actggggaca tggagaccac    720
ccagtgaaga agactttgac tgtcaagcat gaggacctag ttcagactct cagcactcat    780
gcatctgcta tcaagataca atcacatgtt ttttactca gataaataga aaaaaattaa    840
ggtttggtgt ggtggcacat cccttatatc ccagcagttg gcaggcagag cagatagac    900
ctttgtgagt ttgaggccag tctggtttac atagtggcct catgacagaa ataaaacaaa    960
agaattctca caaatatag tgtgcatggg tcctgggatg aagcacagga ccaggaggaa   1020
tacacacaca cacacacaca cacacacaca cacacacaca cacacacaca aatacacatc   1080
agagattcct ggttccacca cactccaccag agaagatata ccacccagaa cttttctgag  1140
aatcagttgg gcctggtgtt gccatcaact ggatggaaat aggagatgga tagatggact   1200
tattttctgc caaggacaca gttcatttcc tgaagtccgg tgcctacctc acccaacagg   1260
ttcctgttcc agatcatccc acggggagca ggtcccaggt gctggcccca taggcttcca   1320
tccaagtccc agttatggta cgtctttggt agtgggaccc agctcacaat cctaggtaag   1380
cgattcccat ggtctcatga tccagctgtc ttagggaagt cccttttcc tctggggagt    1440
tcttctcacc tgccttttcct agtcttgtag tctgaatggt accttttct gtgagtgagg    1500
ggaaggcaag tagttctaag gtaaaccaca ggaaaggtcc caatagcttc agctactctt    1560
ccgaggcaga tgtccaaaaa gggatcaggg gctgaggttt tcaggctgta gagaccactg    1620
cacttcagca tctaaactga ggcccagatg cccatccaga ttaagaaggc cacatagtag    1680
gtgcagggat atgactggtg ccatgattcc tgcctttaaa gattcaggta accctagata    1740
gaaaaccaca gaggctgaga aagaatctg gcccagttta atcttctgct ggccaatgag   1800
gtcatagaga cacagaaaag gcttagagtg accaggtaac tagaaccagc tcctcccagg    1860
atgattacta gaaaaaaaat gtagactgtc tattgttcct ggggtttctc aggcctggag    1920
```

```
cctgttgtct aacttgtcca tctccctcaa atgtccttag agttagatga ggaatgaggg    1980
agcaaatggc gccaagtgaa atcaggagtc accagagact tcctgggtgg tcagggtttt    2040
gctatccttc ctagtctggg agacggagcc ccaggagcac agtcagagta ggtcttgtga    2100
ttactgtgga caaagcatca ggcccttgga ggagttccta ggacttttca ggatggaatc    2160
taatccttgg tgagataact aaatagaatc tggagcacag gcccgggagc ccttatacag    2220
caggcacacc tcaagaccaa ctccccagga ccagtcttgc agaataaatg agcagtaatt    2280
ctcagaggag gctctgacac tggagaagca atggggttg gggagctgct ccctgaactc     2340
ccccaccccc ataggaggcc agcgtcagat cccaattcag attccagctc ctagtggcta    2400
gagagtacag atggccttgg tcttagtggg gaaactgaga ttgcaagggg cagggtgtgg    2460
gtcatttcac ctggaagagg aacacggtct aatggggcac caggctgtct gctctccagg    2520
ggactcaggt gggcagagga aaagaaggaa gcatccttga tggaacactc tgagctgtag    2580
tgaatggcta cagggctcct gataagagga ggatgcttcc ctgtcatgtg ggctctccta    2640
tgccaactct tatcccttc tctatctgca cagggcagcc caagtctgac cccttggtca     2700
ctctgttcct gccttcctta aagaatctcc aggttaagaa ggcgacacta gtgtgtctgg    2760
tgagcgaatt ctacccaggt actttggtgg tggactggaa ggtagatggg atccctgtca    2820
ctcagggtgt ggagacaacc caaccctcca aacagaccaa caacaagtac gtggccagca    2880
gctacctgac actgatgtct gaccaatgga tgcctcacag tagatacacc tgccaggtca    2940
ctcatgaagg aaacactgtg gagaagagtg tgtcacctgc tgaatgttct tag           2993
```

<210> SEQ ID NO 18
<211> LENGTH: 209
<212> TYPE: PRT
<213> ORGANISM: Rattus norvegicus

<400> SEQUENCE: 18

```
Met Lys Leu Arg Ala Gly Gln Thr Leu Gly Thr Ile Pro Arg Gln Cys
1               5                   10                  15

Glu Ile Leu Leu Leu Leu Leu Leu Gly Leu Val Asp Gly Val His
            20                  25                  30

His Ile Leu Ser Pro Ser Ser Ala Gln Arg Gly Arg Ala Val Gly Pro
        35                  40                  45

Gly Ala Ser Val Gly Ser Ser Arg Ser Ser Leu Trp Thr Leu Pro Gly
    50                  55                  60

Arg Phe Leu Phe Gln Ile Ile Pro Arg Gly Ala Gly Pro Arg Cys Trp
65                  70                  75                  80

Pro His Arg Leu Pro Ser Lys Ser Gln Leu Trp Tyr Val Phe Gly Ser
                85                  90                  95

Gly Thr Gln Leu Thr Ile Leu Gly Gln Pro Lys Ser Asp Pro Leu Val
            100                 105                 110

Thr Leu Phe Leu Pro Ser Leu Lys Asn Leu Gln Val Lys Lys Ala Thr
        115                 120                 125

Leu Val Cys Leu Val Ser Glu Phe Tyr Pro Gly Thr Leu Val Val Asp
    130                 135                 140

Trp Lys Val Asp Gly Ile Pro Val Thr Gln Gly Val Glu Thr Thr Gln
145                 150                 155                 160

Pro Ser Lys Gln Thr Asn Asn Lys Tyr Val Ala Ser Ser Tyr Leu Thr
                165                 170                 175

Leu Met Ser Asp Gln Trp Met Pro His Ser Arg Tyr Thr Cys Gln Val
            180                 185                 190
```

```
Thr His Glu Gly Asn Thr Val Glu Lys Ser Val Ser Pro Ala Glu Cys
        195                 200                 205

Ser

<210> SEQ ID NO 19
<211> LENGTH: 80
<212> TYPE: DNA
<213> ORGANISM: Artificial Sequence
<220> FEATURE:
<223> OTHER INFORMATION: 5 homology arm

<400> SEQUENCE: 19
acctggccaa actgagcatg acctttgacc tagccagctc ttaaacttgt tctgagatca      60
caaaccagcc agaccaaatt                                                  80

<210> SEQ ID NO 20
<211> LENGTH: 80
<212> TYPE: DNA
<213> ORGANISM: Artificial Sequence
<220> FEATURE:
<223> OTHER INFORMATION: 3 homology arm

<400> SEQUENCE: 20
tcctcccaga atgcttccct gggtcaaacc cagagccaca aaggcttcca ttagaccatt      60
ctggtaagtg acagagtcac                                                  80

<210> SEQ ID NO 21
<211> LENGTH: 348
<212> TYPE: DNA
<213> ORGANISM: Artificial Sequence
<220> FEATURE:
<223> OTHER INFORMATION: 5 homology arm

<400> SEQUENCE: 21
aaaaaaaaaa aagcccagct agcttagttg gtagagcatg agactcttaa tctcagagtc      60
atgggttcag gcctcatgtt tggcaccatc tatagtgtgc agttataaat caaacagttc     120
acgatggctg gctaggcact ggcaactgca gtctcacctg ctcccatggt tcccagttcc     180
cacagctagt ttgctgccag gctgttcaca cttcccaggt catctaccca ctgtggcaag     240
cctgcagaaa gcctgctatt gctagctcag ttcccttagc cctataaaat gataacacca     300
cagactttta ctataccatc cagatttata acagtaattc tccaaccc                  348

<210> SEQ ID NO 22
<211> LENGTH: 389
<212> TYPE: DNA
<213> ORGANISM: Artificial Sequence
<220> FEATURE:
<223> OTHER INFORMATION: 3 homology arm

<400> SEQUENCE: 22
caggagtaca ccaaaatgtc tagccaaaat ttttatatat gatcacttaa ataagactcc      60
ttaacataaa cctacatgat ataccaagtc ttttctgcca aggctctgac actatagttt     120
gtcctatctg gagttaggta agcaaagggc tatttaggtg tggattgcaa agagagaata     180
gcaagacaac ctgcccattc tttgccacac ctcactaatc agtgtccctt ggaaagcact     240
gtaaatatgg aggtttcttt ttgtattatg tagtgtggat ttaacttgag gagccccaaa     300
aggggtcagc aaagcatggg aaatctaaga atttaacact tcagtgactt ttaatcacct     360
acagatccag gaaaataagc ctgtctctt                                       389
```

```
<210> SEQ ID NO 23
<211> LENGTH: 21
<212> TYPE: RNA
<213> ORGANISM: artificial
<220> FEATURE:
<223> OTHER INFORMATION: RNA oligo

<400> SEQUENCE: 23 agacguguge ucuuccgauc u                                              21

<210> SEQ ID NO 24
<211> LENGTH: 21
<212> TYPE: DNA
<213> ORGANISM: artificial
<220> FEATURE:
<223> OTHER INFORMATION: primer

<400> SEQUENCE: 24
gaagacattt gggaaggact g                                              21

<210> SEQ ID NO 25
<211> LENGTH: 34
<212> TYPE: DNA
<213> ORGANISM: artificial
<220> FEATURE:
<223> OTHER INFORMATION: primer

<400> SEQUENCE: 25
gtgactggag ttcagacgtg tgctcttccg atct                                34

<210> SEQ ID NO 26
<211> LENGTH: 55
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (34)..(35)
<223> OTHER INFORMATION: n is a, c, g, or t

<400> SEQUENCE: 26
acactctttc cctacacgac gctcttccga tctnnggaa ggactgactc tctga         55
```